(12) United States Patent
Madge et al.

(10) Patent No.: US 9,290,511 B2
(45) Date of Patent: Mar. 22, 2016

(54) THIENO-PYRIMIDINES, USEFUL AS POTASSIUM CHANNEL INHIBITORS

(71) Applicant: XENTION LIMITED, Cambridge (GB)

(72) Inventors: David Madge, Cambridge (GB); Fiona Chan, Cambridge (GB); Derek Edward John, Cambridge (GB); Simon D. Edwards, Cambridge (GB); Richard Blunt, Cambridge (GB); Basil Hartzoulakis, Cambridge (GB); Lindsay Brown, Cambridge (GB)

(73) Assignee: Xention Limited, Cambridge (GB)

( * ) Notice: Subject to any disclaimer, the term of this patent is extended or adjusted under 35 U.S.C. 154(b) by 0 days.

(21) Appl. No.: 14/358,722

(22) PCT Filed: Nov. 15, 2012

(86) PCT No.: PCT/GB2012/052842
§ 371 (c)(1),
(2) Date: May 15, 2014

(87) PCT Pub. No.: WO2013/072694
PCT Pub. Date: May 23, 2013

(65) Prior Publication Data
US 2014/0371203 A1 Dec. 18, 2014

(30) Foreign Application Priority Data

Nov. 15, 2011 (GB) .................................. 1119703.5
Aug. 9, 2012 (GB) .................................. 1214250.1

(51) Int. Cl.
C07D 495/04 (2006.01)
A61K 31/519 (2006.01)
A61P 9/06 (2006.01)
C07D 491/048 (2006.01)

(52) U.S. Cl.
CPC ............ C07D 495/04 (2013.01); A61K 31/519 (2013.01); C07D 491/048 (2013.01)

(58) Field of Classification Search
CPC ..... C07D 495/04; A61K 31/519; A61K 45/06
USPC ................. 544/278, 276; 514/260.1
See application file for complete search history.

(56) References Cited

U.S. PATENT DOCUMENTS

| | | | | |
|---|---|---|---|---|
| 7,259,168 B2* | 8/2007 | Jonas et al. | ............... | 514/260.1 |
| 7,427,623 B2* | 9/2008 | Adams et al. | ............... | 514/260.1 |
| 8,022,076 B2* | 9/2011 | Ford et al. | ............... | 514/260.1 |
| 8,193,178 B2* | 6/2012 | Edwards et al. | ............... | 514/218 |
| 2003/0153556 A1 | 8/2003 | Levy et al. | | |
| 2004/0138238 A1* | 7/2004 | Dhanoa et al. | ............... | 514/260.1 |
| 2006/0089370 A1 | 4/2006 | Brewster et al. | | |
| 2007/0213305 A1* | 9/2007 | Cai et al. | ............... | 514/151 |
| 2008/0234482 A1* | 9/2008 | Han et al. | ............... | 544/278 |
| 2009/0163545 A1 | 6/2009 | Goldfarb et al. | | |
| 2010/0053047 A1* | 3/2010 | Chen et al. | ............... | 345/84 |
| 2010/0056548 A1* | 3/2010 | Aicher et al. | ............... | 514/260.1 |
| 2010/0063047 A1 | 3/2010 | Borchardt et al. | | |
| 2010/0143341 A1* | 6/2010 | Taylor et al. | ............... | 424/133.1 |
| 2010/0227853 A1 | 9/2010 | Hoffman et al. | | |
| 2012/0065200 A1* | 3/2012 | Barbosa et al. | ............... | 514/234.2 |
| 2012/0128686 A1* | 5/2012 | Austen et al. | ............... | 424/158.1 |

FOREIGN PATENT DOCUMENTS

| | | | |
|---|---|---|---|
| EP | 0452002 | * | 3/1991 |
| EP | 0 447 891 | | 9/1991 |
| EP | 1 947 103 | | 7/2008 |
| JP | 2001-097979 | | 4/2001 |
| WO | WO 98/08845 | | 3/1998 |
| WO | WO 01/27107 | | 4/2001 |
| WO | WO 01/46200 | | 6/2001 |
| WO | WO 2004/014850 | | 2/2004 |
| WO | WO 2004/065391 | | 8/2004 |
| WO | WO 2004/111057 | | 12/2004 |
| WO | WO 2006/030031 | | 3/2006 |
| WO | WO 2006/061642 | | 6/2006 |
| WO | WO 2006/071988 | | 7/2006 |
| WO | WO 2006/100591 | | 9/2006 |
| WO | WO 2006/103545 | | 10/2006 |
| WO | WO 2007/066127 | | 6/2007 |
| WO | WO 2009/007115 | | 1/2009 |
| WO | WO 2011/029054 | | 3/2011 |
| WO | WO 2011/082268 | | 7/2011 |
| WO | WO 2012/080727 | | 6/2012 |
| WO | WO 2012/097013 | | 7/2012 |

OTHER PUBLICATIONS

Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Cecil Textbook of Medicine, edited by Bennet, J.C., and Plum F., 20th edition, vol. 1, 1004-101 O, 1996.*
Bhave et al. Future Med Chem. May 1, 2010; 2(5): 757-774.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
International Search Report for PCT/GB12/052842, dated Dec. 18, 2012.
Hozein, et al., "Synthesis and application of some new thienopyrimidine derivatives as antimicrobial agents", Synthetic Communications: An International Journal for Rapid Communication of Synthetic Organic chemistry, 26(20):3733-3755 (1996).

(Continued)

*Primary Examiner* — Venkataraman Balasubramanian
(74) *Attorney, Agent, or Firm* — Baker Botts L.L.P.

(57) ABSTRACT

The present invention provides compounds of formula (I): (Formula (I); wherein A, $R^1$, $R^2$, $R^3_I$, V, X, and Z are defined herein, which are potassium channel inhibitors. The invention further provides pharmaceutical compositions comprising the compounds of formula (I) and their use in therapy, in particular in treatment of diseases or conditions that are mediated by $K_{ir}3.1$ and/or $K_{ir}3.4$ or any heteromultimers thereof, or that require inhibition of $K_{ir}3.1$ and/or $K_{ir}3.4$ or any heteromultimers thereof.

17 Claims, No Drawings

(56) References Cited

OTHER PUBLICATIONS

Alqasoumi et al., "Radioprotective and antitumor activity of some novel amino acids and imidazoles containing thieno [2,3-d]pyrimidine moiety", *Phosphorus, Sulfur, and Silicon*, 184:3241-3257 (2009).

Clark et al., "Heterocyclic studies. Part 43. Thieno [2,3-d:4,5-d]dipyrimidines", *J. Chem. Soc. Perkin Trans.*, pp. 2005-2008 (1984).

Gorja et al., "C—C (alkynylation) vs C—O (ether) bond formation under Pd/C—CU catalysis: synthesis and pharmacological evaluation of 4-alkynylthieno [2,3-d] pyrimidines", *Belstein Journal of Organic Chemistry*, 7:338-345 (2011).

Lack et al., "Targeting the binding function3 (BF3) site of the human androgen receptor through virtual screening", *Journal of Medicinal Chemistry*, 54:8563-8573 (2011).

Robba et al., "5-Methyl-Thieno-[2.3-d] Pyrimidine and Derivatives", *G. R. Acad. Sci.* Paris, pp. 1706-1708 (1968) (English Machine Translation of the Abstract).

Tasler et al., "Thienopyrimidines as β3-adrenoceptor agonists: Hit-to-lead optimization", *Bioorganic & Medicinal Chemistry Letters*, 20:6108-6115 (2010).

\* cited by examiner

THIENO-PYRIMIDINES, USEFUL AS POTASSIUM CHANNEL INHIBITORS

CROSS-REFERENCE TO RELATED APPLICATIONS

The present application is a U.S. national stage application under 35 U.S.C. §371 of International Application No. PCT/GB2012/052842, filed Nov. 15, 2012, and published as WO/2013/072694 on May 23, 2013, which claims priority to GB Application No. 1119703.5, filed Nov. 15, 2011, and to GB Application No. 1214250.1, filed Aug. 9, 2012, the contents of each of which are incorporated by reference in their entireties, and to each of which priority is claimed.

TECHNICAL FIELD

The present invention relates to compounds of formula (i) which are potassium channel inhibitors. Pharmaceutical compositions comprising the compounds, their use in therapy and methods of treatment employing the compounds are also provided.

BACKGROUND ART

Ion channels are proteins that span the lipid bilayer of the cell membrane and provide an aqueous pathway through which specific ions such as $Na^+$, $K^+$, $Ca^{2+}$ and $Cl^-$ can pass (Hille et al., 1999). Potassium channels represent the largest and most diverse sub-group of ion channels and they play a central role in regulating the membrane potential, cell volume, signal transduction controlling cellular excitability (Armstrong & Hille, 1998). Potassium channels have been categorized into gene families based on their amino acid sequence and their biophysical properties (for nomenclature see (Gutman et al., 2003) and http://www.iuphar-db.org/DATABASE/ReceptorFamiliesForward?type=IC).

Compounds which modulate potassium channels have multiple therapeutic applications in a number of areas/disorders including cardiovascular, neuronal, renal, metabolic, endocrine, auditory, pain, respiratory, immunological, inflammation, gastrointestinal, reproduction, cancer and cell proliferation, (for reviews see (Ehrlich, 2008; Wulff & Zhorov, 2008; Kobayashi & Ikeda, 2006; Mathie & Veale, 2007; Wulff et al., 2009; Camerino et al., 2008; Shieh et al., 2000; Ford et al., 2002; Geibel, 2005). More specifically potassium channels such as those formed by Kir3.x, Kv4.x, Kir2.x, Kir6.x, Kv11.x, Kv7.x, $K_{Ca}$, $K_{2P}$, and Kv1.x along with their ancillary subunit are involved in the repolarisation phase of the action potential in cardiac myocytes (Tamargo et al., 2004). These potassium channels subtypes have been associated with cardiovascular diseases and disorders including atrial arrhythmias, ventricular arrhythmias, cardiomyopathy, hypertrophy long QT syndrome, short QT syndrome, Brugada syndrome; and all of which can cause cardiac failure and fatality (Marban, 2002;Novelli et al., 2010; Tamargo et al., 2004).

Inwardly rectifying potassium channels are members of a large superfamily comprised of Kir1.x to Kir7.x. The Kir3.x subfamily are G-protein coupled inwardly rectifying potassium ion channels comprised of 4 mammalian subunit members Kir3.1 to Kir3.4. These subunits form homo- or heterotetrameric ion channels involved in potassium flux across the membrane. Kir3.x ion channels are expressed in the cardiovascular system (Kir3.1 and Kir3.4), central nervous system (Kir3.1, Kir3.2, Kir3.3>Kir3.4), gastrointestinal tract (Kir3.1 and Kir3.2) and have been implicated in a number of disease areas including cardiac arrhythmias, pain, Parkinson's disease, Down's Syndrome, epilepsy/seizure, addiction, depression and ataxia (Luscher & Slesinger, 2010; Tamargo et al., 2004) The human G-protein coupled inwardly-rectifying potassium channel subunits Kir3.1 and Kir3.4 are predominantly expressed in the supraventricular regions (including atria, nodal tissue, pulmonary sleeve) and conduction system of the heart and are believed to offer therapeutic opportunities for the management of atrial fibrillation for several different reasons (see review of (Ehrlich, 2008):

(1) Kir3.1/3.4 underlies IKACh: There is evidence that a tetrameric assembly of Kir3.1 and/or Kir3.4 subunits underlies the cardiac acetylcholine/adenosine activated inwardly-rectifying potassium current (hereto referred to as IKACh) in the heart due to similar biophysical (Krapivinsky et al., 1995; Duprat et al., 1995; Corey & CLAPHAM, 1998; Corey et al., 1998) and pharmacological (Jin & Lu, 1998; Jin et al., 1999; Jin & Lu, 1999; Drici et al., 2000; Cha et al., 2006; Dobrev et al., 2005; Voigt et al., 2010b) properties (for review see (Hibino et al., 2010; Belardinelli et al., 1995)).

(2) IKACh is involved in AF: The Kir3.1 subunit cannot form a functional homotetramer or cannot traffic to the membrane (Philipson et al., 1995; Hedin et al., 1996; Woodward et al., 1997) and as such genetic knockout of Kir3.4 gene in the mouse results in the lack of a functional IKACh in the atria (Wickman et al., 1998). This genetic ablation of IKACh results in resistance to atrial fibrillation (Kovoor et al., 2001). These data support the notion of an assembly of Kir3.1/3.4 and the importance of IKACh in the initiation and sustaining of AF. Furthermore, single nucleotide polymorphisms of Kir3.4 gene have been correlated with paroxysmal lone AF in a Chinese population (Zhang et al., 2009). However, no function has been ascribed to these polymorphisms.

(3) IKACh is an atrial-specific target: High levels of Kir3.1 and Kir3.4 gene expression (Gaborit et al., 2007b) and large IKACh are found in both the left and right human atria (Dobrev et al., 2001; Dobrev et al., 2005; Voigt et al., 2010b; Wettwer et al., 2004; Bosch et al., 1999; Voigt et al., 2010a). This contrasts with the human ventricle, where mRNA (Gaborit et al., 2007b) and current expression are considerable smaller, and the number of cells expressing IKACh and the ACh sensitivity is small compared to the atria (Koumi & Wasserstrom, 1994; Koumi et al., 1994). In conjunction with a lower density of parasympathetic innervations (Kent et al., 1974), this argues against a functional role of $I_{KACh}$ in human ventricles (Brodde & Michel, 1999; Belardinelli et al., 1995). This is further supported by the lack of effect of selective IKACh inhibitors on ventricular repolarisation in in vitro (Cha et al., 2006) and in vivo dog studies (Hashimoto et al., 2006; Hashimoto et al., 2008; Machida et al., 2011). The predominant expression of IKACh in the atria cf. the ventricle provides a mechanism to modulate atrial repolarisation without interfering with ventricular repolarisation and potentially inducing fatal ventricular arrhythmia (Hashimoto et al., 2006).

(4) Constitutive-activation of IKACh in chronic AF: The carbachol-induced IKACh recorded from atrial myocytes from patients with chronic AF is smaller than those from patients in sinus rhythm, a phenomenon initially thought to be due to decreased Kir3.4 mRNA and protein levels (Bosch et al., 1999; Brundel et al., 2001a; Brundel et al., 2001b; Dobrev et al., 2001). However, it was later demonstrated that the blunted response to carbachol is due to IKACh being constitutively active in the absence of agonist (Dobrev et al., 2005). Similar observations have also been reported in the atria and pulmonary vein in the tachypaced-dog model of AF (Cha et al., 2006; Ehrlich et al., 2004; Voigt et al., 2008; Makary et al., 2011). Ionic remodeling (for review see (Schotten et al., 2011; Workman et al., 2008), including the constitutive-activation of IKACh, contributes to the shortening of action potential duration observed in chronic AF human patients (Dobrev et al., 2001; Dobrev et al., 2005; Bosch et al., 1999; Wettwer et al., 2004) and tachypaced dog atrial myocytes (Ehrlich et al., 2004; Ehrlich et al., 2007; Cha et al., 2006), which, in turn, causes a reduction in the atrial effective refractory period (Brundel et al., 2002b; Brundel et al., 2002a; Workman et al., 2008) predisposing to the generation of arrhythmias. In addition, the heterogeneous distribution (Gaborit et al., 2007a; Lomax et al., 2003; Sarmast et al., 2003; Voigt et al., 2010b) of constitutively active IKACh (Dobrev et al., 2005; Cha et al., 2006; Ehrlich et al., 2004) across the atria is expected to increase the dispersion of atrial repolarization/refractoriness (Liu & Nattel, 1997; Kabell et al., 1994; Schauerte et al., 2000; Chiou et al., 1997) and in turn increase vulnerability to transient atrial arrhythmias (Liu & Nattel, 1997; Kabell et al., 1994). Pharmacological studies have shown that selective inhibition of IKACh has as a more pronounced prolonging effect on action potential duration in the remodeled dog atria (Cha et al., 2006; Ehrlich et al., 2007). Prolonging the action potential duration by inhibiting IKACh or the constitutive IKACh could present safer pharmacological interventions for protecting against atrial arrhythmias such as chronic atrial fibrillation and atrial flutter compared to traditional class III antiarrhythmics by prolonging the atrial refractory period while leaving ventricular refractoriness unaltered (Cha et al., 2006; Tanaka & Hashimoto, 2007; Hashimoto et al., 2007; Machida et al., 2011).

(5) IKACh Inhibitors in AF: Class III antiarrhythmics have been widely reported as a preferred method for treating cardiac arrhythmias (Colatsky et al., 1990). Traditional and novel class III antiarrhythmic potassium channel blockers have been reported to have a mechanism of action that includes the direct modulation of Kir3.1/3.4 or IKACh. The known antiarrhythmics dronedarone (Altomare et al., 2000; Guillemare et al., 2000), amiodarone (Watanabe et al., 1996; Guillemare et al., 2000), propafenone (Voigt et al., 2010a) and flecamide (Voigt et al., 2010a), ibutilide (Borchard et al., 2005) quinidine (Kurachi et al., 1987; Hara & Kizaki, 2002), verapamil (Hibino et al., 2010), AVE0118 (Gögelein et al., 2004; Voigt et al., 2010a) NIP-142 (Matsuda et al., 2006; Hashimoto et al., 2007; Tanaka & Hashimoto, 2007), NIP-151 (Hashimoto et al., 2008), NTC-801 (Machida et al., 2011) have all been reported as potassium channel blockers of Kir3.1/3.4 or IKACh in atrial myocytes. A benzopyran derivative, NIP-142, preferentially blocks Kir3.1/3.4 with selectivity over other cardiac channels, prolongs the atrial refractory period and terminates atrial fibrillation and flutter in in vivo canine models (Nagasawa et al., 2002; Tanaka & Hashimoto, 2007). From the same chemical class, both NIP-151 and NTC-801 are highly selective IKACh inhibitors and have been shown to be effective in terminating AF in the vagal-induced and aconitine-induced canine models of AF (Hashimoto et al., 2008; Machida et al., 2011). The latter, NTC-801, has also been shown to prevent the induction of AF in an atrial-tachypacing dog model of persistent AF (AT-AF) (Machida et al., 2011) in which the atria exhibit electrical remodeling akin to chronic AF in man (Cha et al., 2006; Ehrlich et al., 2004; Voigt et al., 2008; Makary et al., 2011). The selective IKACh inhibitor peptide tertiapin (Jin & Lu, 1998; Drici et al., 2000) has also been shown to be effective in terminating AF in both vagal-induced and acontine-induced canine models of AF (Hashimoto et al., 2006). None of the agents were shown to affect ventricular repolarisation (QTc or VERP) at therapeutically relevant doses. These data support the utility of IKACh inhibitors for the cardioversion and prevention of recurrence of supraventricular arrhythmias such as AF and atrial flutter without effecting ventricular function. A combination of anti-arrhythmics with other ion channel modulating drugs may also provide greater (synergistic) benefit in the treatment of atrial arrhythmias as shown for the non-selective anti-arrhythmics drugs amiodarone/dronedarone and ranolozine (Burashnikov et al., 2010; Sicouri et al., 2009) and the combination of the IKr inhibitor sotalol with an IKur inhibitor BMS-394136 (Sun et al., 2010). As such, the combination of a selective IKACh inhibitor with other ion channel or ion exchanger modulating drugs could provide added clinical benefit.

(6) IKACh inhibition in stroke prevention in AF: Atrial fibrillation is associated with a 5-fold increased risk for stroke and in the United States approximately 15% to 25% of all strokes can be attributed to AF (Steinberg, 2004). Regardless of the approach to arrhythmias treatment (rate, rhythm, ablation), the prevention of thromboembolism is a cornerstone of clinical treatment of atrial arrhythmias. Constitutive activation of IKACh has been reported to contribute to the contractile deficit associated with AF in the tachy-paced-atrial dog model of AF. Inhibition of IKACh could be a novel target to prevent hypocontractility-related thrombo-embolic complications (Koo et al., 2010). IKACh inhibitors alone or in combination with other anti-platelet or anti-coagulant therapies may significant reduce the risk of stroke and thromboembolism in AF.

(7) Role of autonomic system in AF: Clinical (Coumel, 1994; Coumel, 1996; Pappone et al., 2004; Tan et al., 2006; Yamashita et al., 1997; Huang et al., 1998) and experimental (Liu & Nattel, 1997; Ogawa et al., 2007; Sharifov et al., 2004; Jayachandran et al., 2000; Scherlag et al., 2005; Horikawa-Tanami et al., 2007; Po et al., 2006) observations highlight the importance of the autonomic nervous system and in particular parasymthpathetic/vagal activation in AF. The electrophysiologic substrate of AF is often latent until vagal activation which is sufficient to induce and maintain AF via IKACh activation. IKACh inhibitors are expected to be effective in the treatment of paroxysmal AF with a neurogenic (vagal) component.

(8) Autonomic system in the initiation of AF: Ectopic activity arising from the pulmonary veins and sleeves (PV) has been shown to play a prominent role in the initiation and maintenance of AF (Haissaguerre et al., 1998; Pappone et al., 2000). Pulmonary vein isolation is a procedure used frequently to eliminate the triggers arising from the pulmonary veins. Electrical activity, originating from PV sleeves following parasympathetic and/or sympathetic stimulation, has been proposed as a potential trigger in the initiation of AF (Burashnikov & Antzelevitch, 2006; Patterson et al., 2005; Patterson et al., 2006; Wongcharoen et al., 2007; Lo et al., 2007). Studies in animal models have shown an increase in the time-dependent IKACh in the pulmonary sleeve of the AT-AF dog (Ehrlich et al., 2004). Autonomic nerve stimulation reduces PV-sleeve action potential duration and causes triggered PV firing that is suppressed by muscarinic cholinergic receptor blockade (Patterson et al., 2005). Fibrillatory cycle length shortening in response to vagal stimulation points to ACh effects on PV drivers (Takahashi et al., 2006). Thus, inhibition of IKACH could remove vagally enhanced PV drivers that initiate and maintain AF.

(9) Autonomic nervous system in atrial remodeling: Autoantibodies to the muscarinic M2 receptor have been shown to increase expression of Kir3.1 and Kir3.4 mRNA and Kir3.4 protein in the rabbit heart, resulting in both electrical and structural remodeling creating a substrate for AF (Hong et al., 2009). Increased vagal-nerve activity has been shown to promote atrial electrical remodeling in atrial tachypaced dogs; this effect was partially revered by atropine and fully reversed by a combination of cholinergic block and a vasoactive intestinal polypeptide (VIP) antagonist (Yang et al., 2011). Clinical studies have also shown that parasympathetic block may promote the recovery from AERP shortening associated with rapid atrial pacing (Miyauchi et al., 2004). Although the mechanism that underlies these observations is not fully elucidated, inhibition of IKACH alone or in combination with other agents could prevent or reverse atrial remodeling associated with AF.

Beyond use in the treatment of atrial arrhythmias, Kir3.1/3.4 inhibitors may have utility in a number of other indications:

(1) IKACh and sinoatrial and atrioventricular node function: Acetylcholine (ACh) is an important neuromodulator of cardiac function that is released upon stimulation of the vagus nerve. Negative chronotropic and dromotropic effects are cardiovascular features associated with ACh release upon parasympathetic stimulation. In the mammalian heart, cholinergic parasympathetic fibres are extensively distributed to the sinus node, to the atria and to the atrioventricular (AV) node. Vagal stimulation produces a negative chronotropic and dromotropic effect on the heart and can induce or predispose to atrial arrhythmias due to shortening of the atrial ERP. Vagal stimulation increases AV-ERP (ALANIS et al., 1958; ALANIS et al., 1959), prolongs atrial conduction time (Martin, 1977) and produces a negative dromotropic effect. Selective inhibition of IKACh with tertiapin has been shown to inhibit the dromotropic and blunts the chronotropic effects of ACh on the heart and relieve AV block (Drici et al., 2000). The abundance of Kir3.1 and Kir3.4, is reported to be equal in the sinus node and atrial muscle (Tellez et al., 2006). Activation of IKACh causes decreased spontaneous activity, hyperpolarization of the maximum diastolic potential, and a decrease in the diastolic depolarization rate of the SA node contributing to the negative chronotropic effect of ACh (Dobrzynski et al., 2007; Han & Bolter, 2011; Rodriguez-Martinez et al., 2011). Atrial fibrillation is associated with structure and ionic remodelling in the atria (for review see (Schotten et al., 2011; Workman et al., 2008) and damage to the SAN (Thery et al., 1977). Clinical studies have shown that sick sinus syndrome is frequently associated with AF and atrial flutter (Ferrer, 1968; Gomes et al., 1981). Sinoatrial node dysfunction is a heterogeneous disorder of unknown etiology characterized by a variety of supraventricular arrhythmias with symptoms of persistent bradycardia, tachycardia, syncope, palpitations, and dizziness. The mechanism underlying the abnormal rhythm is incompletely understood. However, atropine, a muscarinic antagonist, is used in the treatment of sick sinus syndrome. However, side-effects preclude its long term use (1973). Taken together, these data highlight both the presence and functional importance of IKACh in the SAN and AVN and indicate the potential of an IKACh inhibitor to modulate AV conduction in setting of hypervagotony or early inferior myocardial infarctions (Drici et al., 2000) and provide a novel mechanism in the treatment of sinus node dysfunction.

(2) Kir3.1/3.4 inhibitors and prevention of thromboembolism: Current approaches to the prevention of thromboembolism include the use of anti-platelet therapy (e.g. aspirin) or anticoagulation therapy including the use vitamin K antagonist warfarin, and oral agents, including direct thrombin inhibitors such as dabigatran, ximelagatran and factor Xa inhibitors such as apixaban, rivaroxaban, and edoxaban, betrixaban and YM150 (for review see (Ezekowitz et al., 2010)). Damaged blood vessels, red blood cells and platelets release ADP and induce platelet aggregation. Pathological thrombosis formation can lead to vascular occlusion, resulting in ischemic insults. The platelet ADP receptor designated P2Y12, the target of the antithrombotic agents like clopidogrel, activates Kir3.x channels via Gi/o proteins (Hollopeter et al., 2001). Human platelets have been shown to express both Kir3.1 and Kir3.4 protein by Western blot (Shankar et al., 2004). Kir3.1/3.4 inhibitors, such as SCH23390 and ethosuximide, can inhibit ADP- and thrombin-mediated platelet aggregation (Shankar et al., 2004; Kobayashi et al., 2009). Therefore, Kir3.1/3.4 inhibitors may be effective for preventing thrombosis and thromboembolic diseases including stroke, myocardial infarction and peripheral vascular diseases (Kobayashi & Ikeda, 2006).

(3) Kir3.4 and pancreatic function: Although predominantly expressed in the heart Kir3.4 has been cloned from the human pancreas (Chan et al., 1996) and has been detected in α, β, δ cells of the mouse pancreas (Yoshimoto et al., 1999; Ferrer et al., 1995; Iwanir & Reuveny, 2008). Electrophysiological studies have shown that somatostatin and α2-adrenoceptor agonists activate sulfonylurea-insensitive $K^{30}$ channels by a G protein-dependent mechanisms, and thereby inhibit activity of Kir3.4-expressing β-cells (Rorsman et al., 1991), (Yoshimoto et al., 1999), suggesting that activation of Kir3 channels may inhibit insulin secretion. Additionally, somatostatin released from 6 cells activates Kir3 channels in glucagon-expressing α cells (Yoshimoto et al., 1999). The adrenaline-induced hyperpolarisation of mouse pancreatic cells has been shown to be a tertiapin-sensitive inwardly-rectifying potassium current (Iwanir & Reuveny, 2008). Therefore, pancreatic Kir3.4 channels may be related to control of pancreatic hormone secretion and have utility in the treatment of diabetes mellitus alone or in combination with sulfonylureas and other oral agents (Kobayashi & Ikeda, 2006).

(4) Kir3.1/3.4 in the central nervous system: In addition to expression in the heart, Kir3.1 and Kir3.4 mRNA have been detected in the parts of the brain (Wickman et al., 2000; Mark & Herlitze, 2000; Hibino et al., 2010). A number of psychotropic and antidepressant drugs have been shown to inhibit the Kir3.1/3.4 channels including paroxetine (Kobayashi et al., 2006), fluoxetine (Kobayashi et al., 2003), reboxetine (Kobayashi et al., 2010), atomoxetine (Kobayashi et al., 2010), mipramine, desipramine, amitriptyline, nortriptyline, clomipramine, maprotiline, citalopram (Kobayashi et al., 2004), and ethosuximide (Kobayashi et al., 2009). This suggests that the Kir3.x inhibition may underlie some of the therapeutic effects related to the CNS. As such, Kir3.1/3.4 inhibits may have utility in the treatment of neurological and neuropsychiatric disorders diseases including pain, depression, anxiety, attention-deficit/hyperactivity disorder, and epilepsy.

(5) Kir3.1/3.4 and pituitary function: Kir3.1 and Kir3.4 have been detected in the pituitary cells of the rat (Gregerson et al., 2001; Wulfsen et al., 2000) where they potentially play a critical role in excitation-secretion coupling. As such, Kir3.1/3.4 inhibitors could be used to modulate neuroendocrine function and the secretion of pituitary hormones. However, corroborative data in man is currently lacking.

(6) Kir3.1/3.4 and cancer: In addition, other reports have cloned Kir3.1 and Kir3.4 from human breast cancer cell line (Wagner et al., 2010) and suggest they may be involved in cellular signaling and cancer (Dhar & Plummer, III, 2006; Plummer, III et al., 2004). Although additional data are required to establish a causal link, targeting Kir3.1/3.4 could be useful in the treatment of breast cancer.

Nissan Chemical Industries have reported a series of substituted benzopyrans as atrial-specific antiarrythmics.

In WO 01/21610 Nissan discloses a series of benzopyran derivatives which are claimed to increase the functional refractory period in an ex vivo preparation of guinea pig atrial tissue with potential use as atrial-specific antiarrythmics.

In WO 02/064581, WO 03/000675 and WO 2005/080368 Nissan discloses a series of 4-amino substituted benzopyran derivatives which are claimed to selectively prolong the atrial refractory period in an in vivo dog model of vagal-induced atrial fibrillation with potential use as atrial-specific antiarrythmics.

In WO 2008/0004262 Nissan discloses a series of fused tricyclic benzopyran derivatives which are claimed to selectively prolong the atrial refractory period in an in vivo dog model of vagal-induced atrial fibrillation with potential use as atrial-specific antiarrythmics.

The above Nissan patents do not specify a biological target, but in subsequent publications (Hashimoto et al, 2008) compounds of these documents have been disclosed as blockers of the Kir3.1/3.4 channel and the IKACh cardiac current.

WO 2010/0331271 discloses a series of derivatives of the flavone acacetin which are claimed inter alia as blockers of the cardiac acetylcholine-activated current (IKACh) with potential use as atrial-specific antiarrythmics.

In WO 2009/104819 Otsuka Pharmaceuticals discloses a series of benzodiazepine derivatives which are claimed as blockers of the Kir3.1/3.4 channel with potential use as atrial-specific antiarrythmics.

Thienopyrimidines, furanopyrimidines and thienopyridines have been shown to modulate ligand-gated and voltage-gated ion channels as well as GPCRs.

US2005/0222175 and US2005/022176 disclose 4-piperidylamino substituted thieno[2,3-d]pyrimidines which modulate the 5-HT receptor, in particular, the 5-HT$_{2b}$ receptor for the treatment of pulmonary arterial hypertension, heart failure, and hypertension.

US2007/0287717 (Vertex) discloses 2-phenyl substituted thieno[2,3-d]pyrimidines which modulate voltage-gated sodium and calcium channels for the treatment of various disorders including epilepsy and neuropathic pain.

US2009/0270405 and WO2011/053292 disclose quinuclidine substituted thieno[2,3-d]pyrimidines which modulate the alpha-2-nicotinic acetylcholine receptor for the treatment of affective and neurodegenerative disorders.

WO2004/11057 (Xention) discloses 4-alkylamino and 4-alkoxy thieno[2,3-d]pyrimidines as blockers of the Kv1.5 voltage-gated potassium channel for the treatment of Atrial Fibrillation.

WO2005/121149 (Xention) discloses furano[2,3-d]pyrimidines as blockers of the Kv1.5 voltage-gated potassium channel for the treatment of Atrial Fibrillation.

WO2007/066127 (Xention) discloses 4-aminoalkyl and 4-alkoxy substituted thieno[3,2-c]pyridines as blockers of the Kv1.5 voltage-gated potassium channel for the treatment of Atrial Fibrillation and also as blockers of the Kv1.3 voltage-gated potassium channel for the treatment of autoimmune disorders.

WO2006/061642 (Xention) discloses 4-alkylamino substituted thieno[2,3-b]pyridines as blockers of the Kv1.5 voltage-gated potassium channel for the treatment of Atrial Fibrillation and also as blockers of the Kv1.3 voltage-gated potassium channel for the treatment of autoimmune disorders.

Ramakrishna et al disclose fused thieno[2,3-d]pyrimidines and 4-alkoxythieno[2,3-d]pyrimidines which act as antagonists of the 5-HT$_6$ receptor.

Modica et al (2004) disclose 4-piperazinyl thieno[2,3-d] pyrimidines which behave as competitive antagonists of the 5-HT$_3$ receptor.

Thienopyrimidines have also been shown to be useful against other biological targets. US2003/0153556 discloses 4-piperazinyl and 4-homopiperazinyl substituted thieno[2,3-d]pyrimidines for the treatment of thrombosis.

WO2006/079916, WO2006/103555, WO2006/103545, WO2006/103544, and WO2006/100591 (Pharmacia and Upjohn) discose 2-amino-4-piperidyl substituted thieno[2,3-d]pyrimidines for the inhibition of ADP-mediated platelet aggregation.

US2011/0166121 (LG Lifesciences) discloses fused 4-piperidinyl and 4-piperazinyl thieno[2,3-d]pyrimidines for the inhibition of platelet aggregation.

WO2011/029054 (University of Michigan) discloses 4-piperazinyl and 4-homopiperazinyl theino[2,3-d]pyrimidines which inhibit the interaction of menin with the proto-oncogene Mixed Lineage Leukemia (MLL).

WO2004/014850 (Predix Pharmaceuticals) discloses 4-(aminopiperidyl) substituted thieno[2,3-d]pyrimidines as Neurokinin antagonists.

WO2004/065391 (Almirall Prodespharma) discloses 4-amino-6-carbonitrile substituted thieno[2,3-d]pyrimidines as inhibitors of PDE7 for the treatment of T-cell mediated immune disorders.

WO2006/030031 (Janssen/Addex) discloses 4-alkylamino substituted thieno[2,3-d]pyrimidines as positive allosteric modulators of the mGluR2 receptor.

WO2006/071988 (Memory Pharmaceuticals) discloses 4-alkoxy, 4-alkyl, and 4-aminoalkyl thieno[2,3-d]pyrimidines as inhibitors of PDE 10.

WO2009/007115 (Syngenta) discloses 4-tropanyl substituted thieno[2,3-d]pyrimidines that are claimed to have usefulness as pesticides.

Gorja et al (2011) disclose 4-alkynyl substituted tricyclic thieno[2,3-d]pyrimidines which were tested for cytotoxic activity against the chronic myelogenous leukemia (CML) cell line.

Jang et al (2010) disclose a series of 4-N-piperazinyl thieno [2,3-d]pyrimidines which were tested for immunosuppressive activity in a mixed lymphocyte reaction (MLR) assay.

Tasler et al (2010) disclose a series of 4-(4-aminopiperidyl) substituted thieno[2,3-d]pyrimidines which act as agonists for the 33-adrenoreceptor.

DISCLOSURE OF THE INVENTION

A first aspect of the invention provides a compound of formula (i)

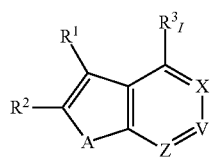

(I)

or a pharmaceutically acceptable derivative thereof, wherein:

A is O or S;
X is N or $CR^3_{II}$;
V is N or $CR^3_{III}$;
Z is N or $CR^3_{IV}$;
wherein one or two of V, X and Z are N;

$R^1$ is selected from optionally substituted alkyl, optionally substituted cycloalkyl, optionally substituted aryl, and optionally substituted heteroaryl;

$R^2$ is selected from H, halo, —CN, trifluoromethyl, optionally substituted alkyl, optionally substituted alkoxy, —$NR^4R^5$, —$NR^6C(O)R^7$, —$NR^6S(O)_2R^7$, —$S(O)_2NR^4R^5$, —$CONR^4R^5$, —$CO_2R^7$, optionally substituted oxazolinyl, —$SR^{14}$, —$S(O)R^{14}$ and —$S(O)_2R^{14}$;

$R^3_I$ is selected from H, halo, —CN, trifluoromethyl, optionally substituted alkyl, optionally substituted alkoxy, optionally substituted heterocycloalkoxy, —$NR^6C(O)R^7$, —$NR^6S(O)_2R^7$, —$S(O)_2NR^4R^5$, —$CONR^4R^5$, —$CO_2R^7$, —$NR^8R^9$, —C≡C-J, optionally substituted cycloalkyl-J and —($NR^aR^b$)-J;

Each of $R^3_{II}$, $R^3_{III}$, and $R^3_{IV}$ is independently selected from H, halo, —CN, trifluoromethyl, optionally substituted alkyl, optionally substituted alkoxy, optionally substituted heterocycloalkoxy, optionally substituted heterocycloalkylalkyl, —$NR^6C(O)R^7$, —$NR^6S(O)_2R^7$, —$S(O)_2NR^4R^5$, —$CONR^4R^5$, optionally substituted -alkylene-$CONR^4R^5$, —$CO_2R^7$, —$NR^{10}R^{11}$, —C≡C-J, optionally substituted cycloalkyl-J and —($NR^cR^d$)-J, provided that $R^3_I$ is —C≡C-J, optionally substituted cycloalkyl-J or —($NR^aR^b$)-J, and/or at least one of $R^3_{II}$, $R^3_{III}$, and $R^3_{IV}$ is present as —C≡C-J, optionally substituted cycloalkyl-J or —($NR^cR^d$)-J;

wherein $R^a$ and $R^b$ are linked to form an optionally substituted 4 to 7 membered heterocycloalkyl ring, which is optionally bridged by a bond, optionally substituted $C_{1-2}$alkylene, —$NR^6$—, —O—, or —$S(O)_z$—, wherein the optionally bridged, optionally substituted heterocycloalkyl ring is selected from the group consisting of azetidinyl, pyrrolidinyl, piperidinyl, morpholinyl, tetrahydro-1,3-oxazinyl, hexahydropyrimidinyl, 1,4-thiazanyl, azepanyl, 1,4-oxaazepanyl, and 1,4-thieazepanyl;

wherein $R^c$ and $R^d$ are linked to form an optionally substituted 4 to 7 membered heterocycloalkyl ring, which is optionally bridged by a bond, optionally substituted $C_{1-2}$alkylene, —$NR^6$—, —O—, or —$S(O)_z$—;

J is selected from H and —$(CR^{12}R^{13})_q$L-M-W,
wherein
q is 0, 1 or 2;
L is —O— or —N(G)-; and
G is selected from hydrogen, optionally substituted alkyl and optionally substituted cycloalkyl;
M is —$(CR^{12}R^{13})_t$—;
t is 0, 1, 2 or 3;
W is selected from the group consisting of optionally substituted alkyl, optionally substituted alkoxy, optionally substituted alkenyl, optionally substituted cycloalkyl, optionally substituted heterocycloalkyl, optionally substituted aryl, optionally substituted heteroaryl and —$NR^8R^9$, wherein when W is optionally substituted cycloalkyl it may optionally be bridged by a bond or optionally substituted $C_{1-2}$alkylene, and wherein when W is optionally substituted heterocycloalkyl it may optionally be bridged by a bond, optionally substituted $C_{1-2}$alkylene, —$NR^6$—, —O—, or —$S(O)_z$—;

alternatively, when L=—N(G)-, L, G, M and W may be linked to form an optionally substituted heterocycloalkyl, an optionally substituted hetercycloalkenyl, or an optionally substituted heteroaryl;

z is 0, 1 or 2;

$R^4$ and $R^5$ are, at each instance, independently selected from H, optionally substituted alkyl, optionally substituted aryl, optionally substituted heteroaryl, and optionally substituted cycloalkyl, or are linked to form an optionally substituted heterocycloalkyl;

$R^6$ and $R^7$ are, at each instance, independently selected from H and optionally substituted alkyl, or are linked to form an optionally substituted heterocycloalkyl;

$R^8$ and $R^9$ are, at each instance, independently selected from optionally substituted alkyl, optionally substituted aryl, optionally substituted heteroaryl, optionally substituted heteroaryl, and optionally substituted cycloalkyl;

$R^{10}$ and $R^{11}$ are, at each instance, independently selected from H, optionally substituted alkyl, optionally substituted aryl, optionally substituted heterocycloalkyl, optionally substituted heteroaryl, and optionally substituted cycloalkyl;

$R^{12}$ and $R^{13}$ are, at each instance, independently selected from H, hydroxy, and optionally substituted alkyl, or may be linked to form an optionally substituted cycloalkyl ring, or may together form =O; and $R^{14}$ is optionally substituted alkyl, wherein the optional substituents are independently selected from halo, trihalomethyl, trihaloethyl, trihalomethoxy, trihaloethoxy, —OH, —$NO_2$, —CN, —$CO_2H$, —$CO_2C_{1-6}$alkyl, —$SO_3H$, —$SOC_{1-6}$alkyl, —$SO_2C_{1-6}$alkyl, —$NHSO_2C_{1-6}$alkyl, —$NC_{1-6}$alkyl$SO_2C_{1-6}$alkyl, —$SO_2NH_2$, —$SO_2NHC_{1-6}$alkyl, —$SO_2N(C_{1-6}$alkyl$)_2$, —$NHSO_2NH_2$, —$NHSO_2NHC_{1-6}$alkyl, —$NHSO_2N(C_{1-6}$alkyl$)_2$, —$NC_{1-6}$alkyl$SO_2NH_2$, —$NC_{1-6}$alkyl$SO_2NHC_{1-6}$alkyl, —$NC_{1-6}$alkyl$SO_2N(C_{1-6}$alkyl$)_2$, —$C(=O)H$, —$C(=O)C_{1-6}$alkyl, —$NHC(=O)C_{1-6}$alkyl, —$NC_{1-6}$alkyl$C(=O)C_{1-6}$alkyl, $C_{1-6}$alkylenedioxy, =O, —$N(C_{1-6}$alkyl$)_2$, —$C(=O)NH_2$, —$C(=O)NHC_{1-6}$alkyl, —$C(=O)N(C_{1-6}$alkyl$)_2$, —$NHC(=O)NH_2$, —$NHC(=O)NHC_{1-6}$alkyl, —$NHC(=O)N(C_{1-6}$alkyl$)_2$, —$NC_{1-6}$alkyl$C(=O)NH_2$, —$NC_{1-6}$alkyl$C(=O)NHC_{1-6}$alkyl, —$NC_{1-6}$alkyl$C(=O)N(C_{1-6}$alkyl$)_2$, —$C(=NH)NH_2$, —$C(=NH)NHC_{1-6}$alkyl, —$C(=NH)N(C_{1-6}$alkyl$)_2$, —$C(=NC_{1-6}$alkyl$)NH_2$, —$C(=NC_{1-6}$alkyl$)NHC_{1-6}$alkyl, —$C(=NC_{1-6}$alkyl$)N(C_{1-6}$alkyl$)_2$, —$C_{1-6}$alkyl, —$C_{3-6}$cycloalkyl, —$C_{3-6}$heterocycloalkyl, 2-imidazolidinon-3-yl, 1-$C_{1-6}$alkyl-2-imidazolidinon-3-yl, $C_{1-6}$alkyl$C_{3-6}$heterocycloalkyl, aryl, haloaryl, $C_{1-6}$alkoxyaryl, —$C_{1-6}$alkylene-$NHSO_2C_{1-6}$alkyl, —$C_{1-6}$alkylene-$NC_{1-6}$alkyl$SO_2C_{1-6}$alkyl, —$C_{1-6}$alkylene-$SO_2NH_2$, —$C_{1-6}$alkylene-$SO_2NHC_{1-6}$alkyl, —$C_{1-6}$alkylene-$SO_2N(C_{1-6}$alkyl$)_2$, —$Z^tH$, —$Z^t$—$C_{1-6}$alkyl, —$C_{1-6}$alkylene-$Z^tH$, —$Z^t$—$C_{3-6}$cycloalkyl, or —$C(=O)NHC_{1-6}$alkylene-$Z^tH$ wherein $Z^t$ is independently O, S, NH or $N(C_{1-6}$alkyl).

In one embodiment, A is S, Z is N and V is $CR^3_{III}$. In a further embodiment, X is N. In a further embodiment, $R^1$ is phenyl. In a further embodiment, $R^2$ is selected from H, trifluoromethyl, substituted alkyl, optionally substituted alkoxy, —$NR^4R^5$, —$NR^6C(O)R^7$, —$S(O)_2NR^4R^5$, —$CONR^4R^5$, —$CO_2R^7$, optionally substituted oxazolinyl, —$SR^{14}$, —$S(O)R^{14}$ and —$S(O)_2R^{14}$. In a further embodiment, $R^3{}_I$ is selected from trifluoromethyl, optionally substituted alkyl, optionally substituted alkoxy, optionally substituted heterocycloalkoxy, —$NR^6C(O)R^7$, —$NR^6S(O)_2R^7$, —$S(O)_2NR^4R^5$, —$CONR^4R^5$, —$CO_2R^7$, —$NR^8R^9$ optionally substituted cycloalkyl-J and —$(NR^aR^b)$-J. In a further embodiment, $R^3{}_{III}$, is selected from H, halo, —CN, trifluoromethyl, optionally substituted alkyl, optionally substituted alkoxy, optionally substituted heterocycloalkoxy, optionally substituted heterocycloalkylalkyl, —$NR^6C(O)R^7$, —$NR^6S(O)_2R^7$, —$S(O)_2NR^4R^5$, —$CONR^4R^5$, optionally substituted -alkylene-$CONR^4R^5$, —$CO_2R^7$, —$NR^{10}R^{11}$, optionally substituted cycloalkyl-J and —$(NR^aR^d)$-J. In a further embodiment, $R^3{}_I$ is —$(NR^aR^b)$-J. In a further embodiment, $R^3{}_I$ is —$(NR^aR^b)$-J, V is $CR^3{}_{III}$ and $R^3{}_{III}$ is H or —$(NR^cR^d)$-J and, in at least one instance, J is —$(CR^{12}R^{13})_q$-L-M-W. In a further embodiment, q is 0 or 1. In a further embodiment, q is 1. In a further embodiment, t is 0, 1 or 2. In a further embodiment, t is 2. In a further embodiment, L is O, or, in an alternative embodiment, L is —N(G)-. In a further embodiment, $R^{12}$ and $R^{13}$ are, at each instance, H. In a further embodiment, W is optionally substituted heterocycloalkyl.

A second aspect of the invention provides a pharmaceutical composition comprising at least one compound of formula (i) and, optionally, one or more pharmaceutically acceptable excipients.

A third aspect of the invention provides a compound of formula (i) or a composition comprising at least one compound of formula (i) for use in therapy.

A fourth aspect of the invention provides a method for the treatment of a disease or condition that is mediated by Kir3.1 and/or Kir3.4 or any heteromultimers thereof, or that requires inhibition of Kir3.1 and/or Kir3.4 or any heteromultimers thereof, comprising administering to a subject an effective amount of at least one compound of formula (i) or composition comprising at least one compound of formula (i).

A fifth aspect of the invention provides a compound of formula (i) or a composition comprising at least one compound of formula (i) for use in a method for the treatment of a disease or condition that is mediated by Kir3.1 and/or Kir3.4 or any heteromultimers thereof, or that requires inhibition of Kir3.1 and/or Kir3.4 or any heteromultimers thereof, comprising administering to a subject an effective amount of at least one compound of formula (i) or composition comprising at least one compound of formula (i).

A sixth aspect of the invention provides the use of a compound of formula (i) for the manufacture of a medicament for use in the treatment of a disease or condition that is mediated by Kir3.1 and/or Kir3.4 or any heteromultimers thereof, or that requires inhibition of Kir3.1 and/or Kir3.4 or any heteromultimers thereof.

In the first, second and third aspects of the invention, the compound of formula (i) is not:
2-Benzyl-5-methyl-4-morpholin-4-yl-thieno[2,3-d]pyrimidine-6-carbonitrile,
[1-(5-phenyl-thieno[2,3-d]pyrimidin-4-yl)-piperidin-4-yl]-carbamic acid tert-butyl ester,
[1-(6-methyl-5-phenyl-thieno[2,3-d]pyrimidin-4-yl)-piperidin-4-yl]-carbamic acid tert-butyl ester,
{1-[5-(4-bromo-phenyl)-thieno[2,3-d]pyrimidin-4-yl]-piperidin-4-yl}-carbamic acid tert-butyl ester,
[1-(5-p-tolyl-thieno[2,3-d]pyrimidin-4-yl)-piperidin-4-yl]-carbamic acid tert-butyl ester,
[1-(5-methyl-thieno[2,3-d]pyrimidin-4-yl)-piperidin-4-yl]-carbamic acid tert-butyl ester,
1-(5-phenyl-thieno[2,3-d]pyrimidine-4-yl)-piperidin-4-ylamine,
1-(6-methyl-5-phenyl-thieno[2,3-d]pyrimidine-4-yl)-piperidin-4-ylamine,
1-(5-(4-bromo-phenyl)-thieno[2,3-d]pyrimidine-4-yl)-piperidin-4-ylamine,
1-(5-p-tolyl-thieno[2,3-d]pyrimidine-4-yl)-piperidin-4-ylamine,
1-(5-methyl-thieno[2,3-d]pyrimidine-4-yl)-piperidin-4-ylamine,
1-(5-phenyl-thieno[2,3-d]pyrimidin-4-yl)-piperidin-4-one,
1-[5-(4-bromo-phenyl)-thieno[2,3-d]pyrimidin-4-yl]-piperidin-4-one,
1-(5-p-tolyl-thieno[2,3-d]pyrimidin-4-yl)-piperidin-4-one,
1-(6-methyl-5-phenyl-thieno[2,3-d]pyrimidin-4-yl)-piperidin-4-one,
2-{1-[5-(4-bromo-phenyl)-thieno[2,3-d]pyrimidin-4-yl]-piperidin-4-ylamino}-cyclohexanol,
2-{1-(5-p-tolyl-thieno[2,3-d]pyrimidin-4-yl)-piperidin-4-ylamino}-cyclohexanol,
2-{1-(6-methyl-5-phenyl-thieno[2,3-d]pyrimidin-4-yl)-piperidin-4-ylamino}-cyclohexanol,
1-benzyloxy-3-[1-(5-phenyl-thieno[2,3-d]pyrimidin-4-yl)-piperidin-4-ylamino]-propan-2-ol,
2-[1-(5-phenyl-thieno[2,3-d]pyrimidin-4-yl)-piperidin-4-ylamino]-cyclohexanol,
5-methoxy-2-{[1-(5-phenyl-thieno[2,3-d]pyrimidin-4-yl)-piperidin-4-ylamino]methyl}-phenol,
bis-(2-fluoro-benzyl)-[1-(5-phenyl-thieno[2,3-d]pyrimidin-4-yl)-piperidin-4-yl]-amine,
2-fluoro-6-{[1-(6-methyl-5-phenyl-thieno[2,3-d]pyrimidin-4-yl)-piperidin-4-ylamino]methyl}-phenol,
2-({1-[5-(4-bromo-phenyl)-thieno[2,3-d]pyrimidin-4-yl]-piperidin-4-ylamino}methyl)-6-fluoro-phenol,
2-fluoro-6-{[1-(5-p-tolyl-thieno[2,3-d]pyrimidin-4-yl)-piperidin-4-ylamino]methyl}-phenol (3-Benzyloxy-2-hydroxy-propyl)-[1-(5-phenyl-thieno[2,3-d]pyrimidin-4-yl)-piperidin-4-yl]-ammonium; chloride,
4-{4-[2-(4-Fluoro-phenoxymethyl-morpholin-4-yl]-piperidin-1-yl}-5-phenyl-thieno[2,3-d]pyrimidine,
4-{4-[2-(Benzo[1,3]dioxol-5-yloxymethyl)-morpholin-4-yl]-piperidin-1-yl}-5-phenyl-thieno[2,3-d]pyrimidine, or
6-(Benzo[1,3]dioxol-5-yloxymethyl)-4-[1-(5-phenyl-thieno[2,3-d]pyrimidin-4-yl)-piperidin-4-yl]-morpholin-3-one.

As discussed above, inhibition of $K_{ir}3.1$ and/or $K_{ir}3.4$ (or heteromultimers thereof) has implications in:
the diagnosis and treatment of cardiovascular diseases, such as atrial fibrillation (AF), atrial flutter (AFL), atrioventricular (AV) dysfunction and sinoatrial node (SAN) dysfunction;
the prevention of recurrence of supraventriclar arrhythmias including AF and AFL;
the maintenance of sinus rhythm;
the termination and cardioversion of supraventriclar arrhythmias;
the treatment of sinus node dysfunction;
the treatment of AV node dysfunction, including AV block;
the treatment of conduction dysfunction;
the prevention or reversal of atrial structural and ionic remodeling;
the prevention of thrombosis, thromboembolism and thromboembolic diseases, such as stroke, myocardial infarction, and peripheral vascular diseases;
the improvement of cardiac contractility;
the treatment of metabolic diseases, such as diabetes mellitus;
the modulation of neuro-endocrine function;
the modulation of the secretion of pituitary hormones;

the treatment of neurological and neuropsychiatric disorders, such as pain, depression, anxiety, attention deficit/hyperactivity disorder and epilepsy; and the treatment of cancer, such as breast cancer.

DETAILED DESCRIPTION OF THE INVENTION

At various places in the present specification, substituents of compounds of the invention are disclosed in groups or in ranges. It is specifically intended that the invention include each and every individual subcombination of the members of such groups and ranges. For example, the term "$C_{1-6}$alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

However, combinations of features are permissible only if such combinations result in stable compounds. Compounds of the invention are typically stable and isolatable at room temperature and pressure. A "stable" compound is sufficiently robust to survive isolation to a useful degree of purity from a reaction mixture, and formulation into an efficacious therapeutic agent.

In one embodiment, A is S. In another embodiment, A is O.

In one embodiment, Z is N. In another embodiment, X is N. In one embodiment, Z is N, and V is $CR^3_{III}$. In another embodiment, Z is N, X is N, and V is $CR^3_{III}$. In another embodiment, Z is N, X is $CR^3_{II}$, and V is $CR^3_{III}$.

In one embodiment, V is N, X is $CR^3_{II}$, and Z is $CR^3_{IV}$. In another embodiment, X is N, V is $CR^3_{III}$, and Z is $CR^3_{IV}$. In another embodiment, Z is N, V is N, and X is $CR^3_{II}$. In another embodiment, V is N, X is N, and Z is $CR^3_{IV}$.

In a specific embodiment, A is S, Z is N, X is N, and V is $CR^3_{III}$, i.e. the compounds are thienopyrimidines.

In one embodiment, $R^3_I$ is —C≡C-J or —(NR$^a$R$^b$)-J, and/or at least one of $R^3_{II}$, $R^3_{III}$, and $R^{31}_{IV}$ is present as —C≡C-J or —(NR$^c$R$^d$)-J. In another embodiment, $R^3_I$ is optionally substituted cycloalkyl-J or —(NR$^a$R$^b$)-J, and/or at least one of $R^3_{II}$, $R^3_{III}$, and $R^3_{IV}$ is present as optionally substituted cycloalkyl-J or —(NR$^c$R$^d$)-J. In another embodiment, $R^3_I$ is —(NR$^a$R$^b$)-J and/or at least one of $R^3_{II}$, $R^3_{III}$, and $R^3_{IV}$ is present as —(NR$^c$R$^d$)-J.

In one embodiment, $R^3_I$ is selected from H, halo, —CN, trifluoromethyl, optionally substituted alkyl, optionally substituted alkoxy, —NR$^6$C(O)R$^7$, —NR$^6$S(O)$_2$R$^7$, —S(O)$_2$NR$^4$R$^5$, —CONR$^4$R$^5$, —CO$_2$R$^7$, —NR$^8$R$^9$, —C≡C-J, optionally substituted cycloalkyl-J and —(NR$^a$R$^b$)-J. In another embodiment, $R^3_I$ is selected from trifluoromethyl, optionally substituted alkyl, optionally substituted alkoxy, optionally substituted heterocycloalkoxy, —NR$^6$C(O)R$^7$, —NR$^6$S(O)$_2$R$^7$, —S(O)$_2$NR$^4$R$^5$, —CONR$^4$R$^5$, —CO$_2$R$^7$, —NR$^8$R$^9$, optionally substituted cycloalkyl-J and —(NR$^a$R$^b$)-J. In another embodiment, $R^3_I$ is selected from H, —(NR$^a$R$^b$)-J, optionally substituted cycloalkyl-J and —C≡C-J. In another embodiment, $R^3_I$ is selected from —(NR$^a$R$^b$)-J, and —C≡C-J. In another embodiment, $R^3_I$ is selected from —(NR$^a$R$^b$)-J, and optionally substituted cycloalkyl-J. In another embodiment, $R^3_I$ is —(NR$^a$R$^b$)-J. In another embodiment, $R^3_I$ is —(NR$^a$R$^b$)-J and J is (CR$^{12}$R$^{13}$)$_q$-L-M-W.

In one embodiment, each of $R^3_{II}$, $R^3_{III}$, and $R^3_{IV}$ is independently selected from H, halo, —CN, trifluoromethyl, optionally substituted alkyl, optionally substituted alkoxy, —NR$^6$C(O)R$^7$, —NR$^6$S(O)$_2$R$^7$, —S(O)$_2$NR$^4$R$^5$, —CONR$^4$R$^5$, —CO$_2$R$^7$, —NR$^{10}$R$^{11}$, —C≡C-J, optionally substituted cycloalkyl-J and —(NR$^c$R$^d$)-J. In another embodiment, each of $R^3_{II}$, $R^3_{III}$, and $R^3_{IV}$ is independently selected from H, halo, —CN, trifluoromethyl, optionally substituted alkyl, optionally substituted alkoxy, optionally substituted heterocycloalkoxy, optionally substituted heterocycloalkylalkyl, —NR$^6$C(O)R$^7$, —NR$^6$S(O)$_2$R$^7$, —S(O)$_2$NR$^4$R$^5$, —CONR$^4$R$^5$, optionally substituted -alkylene-CONR$^4$R$^5$, —CO$_2$R$^7$, —NR$^{10}$R$^{11}$, optionally substituted cycloalkyl-J and —(NR$^c$R$^d$)-J. In another embodiment, each of $R^3_{II}$, $R^3_{III}$, and $R^3_{IV}$ is independently selected from H, halo, —CN, trifluoromethyl, optionally substituted alkoxy, —NR$^6$C(O)R$^7$, —NR$^6$S(O)$_2$R$^7$, —S(O)$_2$NR$^4$R$^5$, —CONR$^4$R$^5$, —CO$_2$R$^7$, —NR$^{10}$R$^{11}$, —C≡C-J, optionally substituted cycloalkyl-J and —(NR$^c$R$^d$)-J. In another embodiment, each of $R^3_{II}$, $R^3_{III}$, and $R^3_{IV}$ is independently selected from H, —NR$^{10}$R$^{11}$, —C≡C-J, optionally substituted cycloalkyl-J and —(NR$^c$R$^d$)-J. In one embodiment, each of $R^3_{II}$, $R^3_{III}$, and $R^3_{IV}$ is independently selected from H, —NR$^{10}$R$^{11}$, —C≡C-J and —(NR$^c$R$^d$)-J. In another embodiment, $R^3_{II}$ and $R^3_{IV}$ are H. In another embodiment, $R^3_{II}$, $R^3_{III}$ and $R^3_{IV}$, are independently selected from —C≡C-J, optionally substituted cycloalkyl-J and —(NR$^c$R$^d$)-J. In another embodiment, $R^3_{III}$ is selected from H, halo, —CN, trifluoromethyl, optionally substituted alkyl, optionally substituted alkoxy, optionally substituted heterocycloalkoxy, optionally substituted heterocycloalkylalkyl, —NR$^6$C(O)R$^7$, —NR$^6$S(O)$_2$R$^7$, —S(O)$_2$NR$^4$R$^5$, —CONR$^4$R$^5$, optionally substituted -alkylene-CONR$^4$R$^5$, —CO$_2$R$^7$, —NR$^{10}$R$^{11}$, optionally substituted cycloalkyl-J and —(NR$^c$R$^d$)-J. In another embodiment, $R^3_{III}$ is independently selected from H, —NR$^{10}$R$^{11}$, —C≡C-J, optionally substituted cycloalkyl-J and —(NR$^c$R$^d$)-J. In another embodiment, $R^3_{III}$ is selected from —C≡C-J, optionally substituted cycloalkyl-J and —(NR$^c$R$^d$)-J. In another embodiment, $R^3_{III}$ is selected from optionally substituted cycloalkyl-J and —(NR$^c$R$^d$)-J. In another embodiment, $R^3_{III}$ is —(NR$^c$R$^d$)-J.

In another embodiment, $R^3_I$ is —(NR$^a$R$^b$)-J, V is $CR^3_{III}$ and $R^3_{III}$ is —(NR$^c$R$^d$)-J. In another embodiment, $R^3_I$ is —(NR$^a$R$^b$)-J, V is $CR^3_{III}$ and $R^3_{III}$ is —(NR$^c$R$^d$)-J and, in at least one instance, J is —(CR$^{12}$R$^{13}$)$_q$-L-M-W. In another embodiment, $R^3_I$ is —(NR$^a$R$^b$)—(CR$^{12}$R$^{13}$)$_q$ L-M-W, V is $CR^3_{III}$ and $R^3_{III}$ is —(NR$^c$R$^d$)—H.

In one embodiment, if X is N, then $R^3_I$ is not —NR$^8$R$^9$. In another embodiment, if X is $CR^3_{II}$ and Z is N, then $R^3_I$ is not H, halo or —NR$^8$R$^9$.

In one embodiment, each of $R^3_{II}$, $R^3_{III}$, and $R^3_{IV}$ is independently selected from —NR$^6$S(O)$_2$R$^7$, —S(O)$_2$NR$^4$R$^5$, —C≡C-J, and optionally substituted cycloalkyl-J. In another embodiment, if V is N, then $R^3_{II}$ and $R^3_{IV}$ are independently selected from H, halo, —CN, trifluoromethyl, optionally substituted alkyl, optionally substituted alkoxy, —NR$^6$C(O)R$^7$, —NR$^6$S(O)$_2$R$^7$, —S(O)$_2$NR$^4$R$^5$, —CONR$^4$R$^5$, —CO$_2$R$^7$, —NR$^{10}$R$^{11}$, —C≡C-J, optionally substituted cycloalkyl-J and —(NR$^c$R$^d$)-J.

In one embodiment, $R^1$ is selected from optionally substituted alkyl, optionally substituted heteroaryl and optionally substituted aryl. In another embodiment, $R^1$ is selected from optionally substituted alkyl and optionally substituted aryl. In another embodiment, $R^1$ is selected from optionally substituted heteroaryl and optionally substituted aryl. In another embodiment, $R^1$ is selected from optionally substituted alkyl and optionally substituted phenyl. In another embodiment, $R^1$ is selected from optionally substituted methyl, optionally substituted ethyl, optionally substituted i-propyl, and optionally substituted phenyl. In another embodiment, $R^1$ is selected from methyl, ethyl, i-propyl, and phenyl, wherein phenyl is optionally substituted by one or more of halo, $-NO_2$ and $-SO_2N(C_{1-6}alkyl)_2$. In another embodiment, $R^1$ is selected from methyl, ethyl, i-propyl, and phenyl, wherein phenyl is optionally substituted by one or more of F, $-NO_2$ and $-SO_2NMe_2$. In another embodiment, $R^1$ is optionally substituted phenyl. In another embodiment, $R^1$ is phenyl. In another embodiment, $R^1$ is substituted phenyl. In another embodiment, $R^1$ is selected from methyl, ethyl and i-propyl. In embodiments in which $R^1$ is substituted phenyl, it may be substituted at the 2-, 3-, 4-, 5- and/or 6-position(s). In one embodiment, $R^1$ is 2-substituted phenyl and in a further embodiment, the 2-substituent is methoxy.

In one embodiment, $R^2$ is selected from halo, —CN, trifluoromethyl, optionally substituted alkyl, optionally substituted alkoxy, $-NR^4R^5$, $-NR^6C(O)R^7$, $-NR^6S(O)_2R^7$, $-S(O)_2NR^4R^5$, $-CONR^4R^5$, $-CO_2R^7$, optionally substituted oxazolinyl, $-SR^{14}$, $-S(O)R^{14}$ and $-S(O)_2R^{14}$. In another embodiment, $R^2$ is selected from H, halo, —CN, trifluoromethyl, optionally substituted alkyl, optionally substituted alkoxy, $-NR^4R^5$, $-NR^6C(O)R^7$, $-S(O)_2NR^4R^5$, $-CONR^4R^5$, $-CO_2R^7$, optionally substituted oxazolinyl, $-SR^{14}$, $-S(O)R^{14}$ and $-S(O)_2R^{14}$. In another embodiment, $R^2$ is selected from H, trifluoromethyl, substituted alkyl, optionally substituted alkoxy, $-NR^4R^5$, $-NR^6C(O)R^7$, $-S(O)_2NR^4R^5$, $-CONR^4R^5$, $-CO_2R^7$, optionally substituted oxazolinyl, $-SR^{14}$, $-S(O)R^{14}$ and $-S(O)_2R^{14}$. In another embodiment, $R^2$ is selected from H, halo, —CN, optionally substituted alkyl, $-NR^4R^5$, $-NR^6C(O)R^7$, and $-CONR^4R^5$. In another embodiment, $R^2$ is selected from H, halo, —CN, optionally substituted methyl, ethyl, and i-propyl, $-NR^4R^5$, $-NR^6C(O)R^7$, and $-CONR^4R^5$. In another embodiment, $R^2$ is selected from H, bromo, —CN, methyl, ethyl, i-propyl, $-NR^4R^5$, $-NR^6C(O)R^7$, and $-CONR^4R^5$. In another embodiment, $R^2$ is selected from H, $-NR^6C(O)R^7$, and $-CONR^4R^5$. In another embodiment, $R^2$ is selected from H and $-CONR^4R^5$. In another embodiment, $R^2$ is H. In one embodiment, optionally substituted oxazolinyl is optionally substituted 2-oxazolinyl.

In one embodiment, $R^2$ is not —CN. In another embodiment, if $R^2$ is —CN then $R^3_{III}$ is not substituted alkyl.

In a specific embodiment, $R^1$ is phenyl and $R^2$ is H.

In one embodiment, $NR^aR^b$ forms an optionally bridged, optionally substituted ring of formula (II):

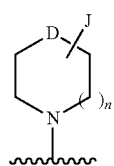

(II)

wherein
n is 0, 1 or 2;
D is selected from $-CH_2-$, —CHJ-, and —O—.

In one embodiment, D is —CHJ-. In one embodiment, n is 0 or 1. In another embodiment, n is 1. In another embodiment, n is 0.

In one embodiment, $NR^aR^b$ is optionally bridged by bond, $-CH_2-$, $-C_2H_4-$ or —CHJ-. In another embodiment, $NR^aR^b$ is optionally bridged by bond, $-CH_2-$ or —CHJ-. In another embodiment, $NR^aR^b$ is bridged by bond, $-CH_2-$, $-C_2H_4-$ or —CHJ-. In another embodiment, $NR^aR^b$ is bridged by bond, $-CH_2-$ or —CHJ-. In another embodiment, $NR^aR^b$ is not bridged.

In one embodiment, $NR^aR^b$ is selected from optionally substituted pyrrolidinyl, optionally substituted piperidinyl, optionally substituted morpholinyl, optionally substituted azabicyclohexanyl, optionally substituted azabicycloheptanyl, and optionally substituted azabicyclooctanyl. In another embodiment, $NR^aR^b$ is selected from optionally substituted pyrrolidinyl, optionally substituted piperidinyl, optionally substituted morpholinyl, optionally substituted azabicyclo[3.1.0]hexanyl, optionally substituted azabicyclo[2.2.1]heptanyl, and optionally substituted azabicyclo[3.2.1]octanyl. In another embodiment, $NR^aR^b$ is selected from optionally substituted pyrrolidinyl, optionally substituted piperidinyl, optionally substituted morpholinyl, optionally substituted 3-azabicyclo[3.1.0]hexanyl, optionally substituted 2-azabicyclo[2.2.1]heptanyl, and optionally substituted 8-azabicyclo[3.2.1]octanyl. In another embodiment, $NR^aR^b$ is selected from pyrrolidinyl, piperidinyl, and 3-azabicyclo[3.1.0]hexanyl. In another embodiment, $NR^aR^b$ is selected from pyrrolidinyl, and piperidinyl. In one embodiment, $NR^aR^b$ is pyrrolidinyl. In another embodiment, $NR^aR^b$ is piperidinyl.

In one embodiment, if $R^3_I$ is cycloalkyl-J or $-(NR^aR^b)$-J, wherein $NR^aR^b$ is piperidinyl, q is 0, and L is —N(G)-, then $R^3_{III}$ is not H, optionally substituted $C_{1-4}$alkyl or optionally substituted cycloalkyl-J. In another embodiment, if $R^3_{III}$ is $-(NR^aR^b)$-J, wherein $NR^aR^b$ is piperidinyl, q is 0, and L is —N(G)-, then $R^3_{III}$ is not H, optionally substituted $C_{1-4}$alkyl or optionally substituted cycloalkyl-J. In another embodiment, if $R^3_I$ is $-(NR^aR^b)$-J, wherein $NR^aR^b$ is piperidinyl, q is 0, and L is —N(G)-, then $R^3_{III}$ is not H. In another embodiment, if $R^3_I$ is $-(NR^aR^b)$-J, wherein $NR^aR^b$ is substituted piperidinyl and J is H, then $R^3_{III}$ is not H.

J may be attached to any atom on the ring or, if present, the bridge. In one embodiment, $NR^aR^b$ is pyrrolidinyl and J is present at the 3-position. In another embodiment, $NR^aR^b$ is piperidinyl and J is present at the 4-position.

$R^c$ and $R^d$ are linked to form an optionally substituted 4 to 7 membered heterocycloalkyl ring, which is optionally bridged by a bond, optionally substituted $C_{1-2}$alkylene, $-NR^6-$, $-O-$, or $-S(O)_z-$. J may be attached to any atom on the ring or, if present, the bridge. In one embodiment, $NR^cR^d$ forms an optionally bridged, optionally substituted heterocycloalkyl selected from the group consisting of azetidinyl, pyrrolidinyl, piperidinyl, morpholinyl, tetrahydro-1,3-oxazinyl, piperazinyl, hexahydropyrimidinyl, 1,4-thiazanyl, azepanyl, 1,4-oxaazepanyl, 1,4-thieazepanyl and 1,4-diazepanyl. In one embodiment, $NR^cR^d$ forms an optionally bridged, optionally substituted ring of formula (II):

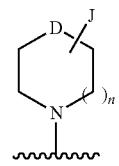

(II)

wherein
n is 0, 1 or 2;
D is selected from $-CH_2-$, —CHJ-, —O—, —N(H)— and —N(J)-.

In one embodiment, D is selected from —CHJ- and —N(J)-. In one embodiment, n is 0 or 1.

In one embodiment, n is 1. In another embodiment, n is 0.

In one embodiment, $NR^cR^d$ is optionally bridged by bond, —CH$_2$—, —C$_2$H$_4$— or —CHJ-. In another embodiment, $NR^cR^d$ is optionally bridged by bond, —CH$_2$— or —CHJ-. In another embodiment, $NR^cR^d$ is bridged by bond, —CH$_2$—, —C$_2$H$_4$— or —CHJ-. In another embodiment, $NR^cR^d$ is bridged by bond, —CH$_2$— or —CHJ-. In another embodiment, $NR^cR^d$ is not bridged.

In one embodiment, $NR^cR^d$ is selected from optionally substituted pyrrolidinyl, optionally substituted piperidinyl, optionally substituted morpholinyl, optionally substituted piperazinyl, optionally substituted azabicyclohexanyl, optionally substituted azabicycloheptanyl, and optionally substituted azabicyclooctanyl. In another embodiment, $NR^cR^d$ is selected from optionally substituted pyrrolidinyl, optionally substituted piperidinyl, optionally substituted morpholinyl, optionally substituted piperazinyl, optionally substituted azabicyclo[3.1.0]hexanyl, optionally substituted azabicyclo[2.2.1]heptanyl, and optionally substituted azabicyclo[3.2.1]octanyl. In another embodiment, $NR^cR^d$ is selected from optionally substituted pyrrolidinyl, optionally substituted piperidinyl, optionally substituted morpholinyl, optionally substituted piperazinyl, optionally substituted 3-azabicyclo[3.1.0]hexanyl, optionally substituted 2-azabicyclo[2.2.1]heptanyl, and optionally substituted 8-azabicyclo[3.2.1]octanyl. In another embodiment, $NR^cR^d$ is selected from optionally substituted pyrrolidinyl, piperidinyl, morpholinyl, piperazinyl, and 3-azabicyclo[3.1.0]hexanyl. In another embodiment, $NR^cR^d$ is selected from pyrrolidinyl, piperidinyl, piperazinyl, and 3-azabicyclo[3.1.0]hexanyl. In another embodiment, $NR^cR^d$ is selected from pyrrolidinyl, piperidinyl, and piperazinyl. In another embodiment, $NR^cR^d$ is selected from pyrrolidinyl and piperidinyl. In one embodiment, $NR^cR^d$ is pyrrolidinyl. In another embodiment, $NR^cR^d$ is piperidinyl.

J may be attached to any atom on the ring or, if present, the bridge. In one embodiment, $NR^cR^d$ is pyrrolidinyl and J is present at the 3-position. In another embodiment, $NR^cR^d$ is piperidinyl and J is present at the 4-position.

In one embodiment, J is —(CR$^{12}$R$^{13}$)$_q$-L-M-W. In another embodiment, J is H. In another embodiment, if more than one J group is present, then, in at least one instance J is present as —(CR$^{12}$R$^{13}$)$_q$-L-M-W.

In one embodiment, q is 0 or 1. In another embodiment, q is 1 or 2. In another embodiment, q is 0 or 2. In another embodiment, q is 0. In another embodiment, q is 1. In another embodiment, q is 2. In another embodiment, q is 1 or 2 and R$^{12}$ and R$^{13}$ are independently selected from H and alkyl. In another embodiment, q is 1 or 2 and R$^{12}$ and R$^{13}$ are both H. In another embodiment, q is 1 and R$^{12}$ and R$^{13}$ are both H.

In one embodiment, L is O. In another embodiment, L is —N(G)-.

In one embodiment, L is —N(G)- and L, G, M and W may be linked to form an optionally substituted heterocycloalkyl. In one embodiment, L is —N(G)- and L, G, M and W are linked to form an optionally substituted heterocycloalkyl. In another embodiment, L is —N(G)- and L, G, M and W are linked to form optionally substituted azetidinyl, optionally substituted pyrrolidinyl, optionally substituted piperidinyl or optionally substituted morpholinyl. In another embodiment, L is —N(G)- and L, G, M and W are linked to form azetidinyl, pyrrolidinyl, piperidinyl or morpholinyl, wherein each of pyrrolidinyl, piperidinyl and morpholinyl is optionally substituted by one or more groups selected from halo, trihalomethyl, —OH, —C$_{1-6}$alkyl, —O—C$_{1-6}$alkyl, —N(C$_{1-6}$alkyl)$_2$, —C$_{1-6}$alkylene-OH, aryl, haloaryl, —C(=O)NH$_2$ and —C$_{3-6}$heterocycloalkyl. In another embodiment, L is —N(G)- and L, G, M and W are linked to form pyrrolidinyl, piperidinyl or morpholinyl substituted by one or more groups selected from pyrrolidinyl, —OH, —F, -Me, —OMe, —CH$_2$OH, —CF$_3$, —NMe$_2$, phenyl, F-phenyl, —CONH$_2$.

In one embodiment, G is selected from hydrogen, and optionally substituted alkyl. In another embodiment, G is selected from H, optionally substituted methyl and optionally substituted ethyl. In another embodiment, G is selected from H, methyl and ethyl, wherein ethyl is optionally substituted by —OH or —O—C$_{1-6}$alkyl. In another embodiment, G is selected from H, methyl and ethyl, wherein ethyl is optionally substituted by —OH or —O-Me. In another embodiment, G is selected from H and methyl.

In one embodiment, t is 0, 1 or 2. In another embodiment, t is 0. In another embodiment, t is 1. In another embodiment, t is 2. In another embodiment, t is 3. In another embodiment, M is selected from bond, —(CH$_2$)—, —(CH$_2$)$_2$—, —(CH$_2$)$_3$—, -cycloalkyl-, —CHOH—CH$_2$—, CH$_2$—CHOH—, —CH$_2$—C(alkyl)$_2$-, —(CH$_2$)—C(=O)—, —C(=O)—(CH$_2$)—. In another embodiment, M is selected from bond, —(CH$_2$)—, —(CH$_2$)$_2$—, —(CH$_2$)$_3$—, -cyclopentyl-, —CHOH—CH$_2$—, CH$_2$—C(Me)$_2$-, —(CH$_2$)—C(=O)—. In another embodiment, M is selected from bond, —(CH$_2$)—, —(CH$_2$)$_2$— and —(CH$_2$)$_3$—.

In one embodiment, W is selected from the group consisting of substituted alkyl, alkoxy, alkenyl, cycloalkyl, optionally substituted heterocycloalkyl, aryl, heteroaryl. In another embodiment, W is selected from substituted alkyl, alkoxy, cyclopropyl, cyclobutyl, optionally substituted pyrrolidinyl, optionally substituted piperidinyl, optionally substituted piperazinyl, optionally substituted morpholinyl, tetrahydrofuran, furan, thiophene, phenyl, and pyridine. In another embodiment, W is selected from alkyl substituted by one or more groups selected from halo, —OH, —NH$_2$, and —N(C$_{1-6}$alkyl)$_2$, alkoxy, cyclopropyl, cyclobutyl, pyrrolidinyl, piperidinyl, piperazinyl, morpholinyl, tetrahydrofuran, furan, thiophene, phenyl, and pyridine, wherein each of pyrrolidinyl, piperidinyl, piperazinyl, and morpholinyl is optionally substituted by one or more groups selected from halo, C$_{1-6}$alkyl, —C(=O)C$_{1-6}$alkyl, —CO$_2$C$_{1-6}$alkyl, —N(C$_{1-6}$alkyl)$_2$, —NHC(=O)C$_{1-6}$alkyl, —C(=O)NH$_2$, and =O. In another embodiment, W is selected from alkyl substituted by one or more groups selected from —F, —OH, —NH$_2$, and —N(Me)$_2$, alkoxy, cyclopropyl, cyclobutyl, pyrrolidinyl, piperidinyl, piperazinyl, morpholinyl, tetrahydrofuran, furan, thiophene, phenyl, and pyridine, wherein each of pyrrolidinyl, piperidinyl, piperazinyl, and morpholinyl is optionally substituted by one or more groups selected from —F, -Me, -Et, -iPr, —C(=O)Me, —CO$_2$tBu, —NHC(=O)Me, —C(=O)NH$_2$, and =O. In another embodiment, W is selected from cyclopropyl, cyclobutyl, pyrrolidinyl, and piperidinyl, wherein each of pyrrolidinyl and piperidinyl is optionally substituted by one of -Me, -Et and -iPr. In another embodiment, W is selected from pyrrolidinyl, and piperidinyl, wherein each of pyrrolidinyl and piperidinyl is optionally substituted by one of -Me, -Et and -iPr. In one embodiment, W is 1-methylpyrrolidin-2-yl.

In one embodiment, z is 0. In another embodiment, z is 1. In another embodiment, z is 2.

In one embodiment, R$^4$ and R$^5$ are, at each instance, independently selected from H and optionally substituted alkyl, or are linked to form an optionally substituted heterocycloalkyl. In another embodiment, R$^4$ and R$^5$ are, at each instance, independently selected from H, optionally substituted methyl, optionally substituted ethyl, optionally substituted i-propyl, and optionally substituted pyrrolidinyl. In another embodiment, $R^4$ and $R^5$ are, at each instance, independently selected from H, methyl, ethyl, i-propyl, and pyrrolidinyl optionally substituted by =O.

$R^6$ and $R^7$ are, at each instance, independently selected from H and optionally substituted alkyl, or, in the groups —$NR^6C(O)R^7$, —$NR^6S(O)_2R^7$, may be linked to form an optionally substituted heterocycloalkyl.

In one embodiment, $R^6$ is, at each instance, independently selected from H and optionally substituted alkyl. In another embodiment, $R^6$ is H.

In one embodiment, $R^7$ is, at each instance, independently selected from H and optionally substituted alkyl. In another embodiment, $R^7$ is alkyl. In another embodiment, $R^7$ is methyl.

In one embodiment, $R^8$ and $R^9$ are, at each instance, independently selected from optionally substituted alkyl, optionally substituted aryl, optionally substituted heteroaryl, and optionally substituted cycloalkyl. In one embodiment, $R^8$ and $R^9$ are, at each instance, independently selected from optionally substituted alkyl, and optionally substituted cycloalkyl. In another embodiment, $R^8$ and $R^9$ are, at each instance, independently selected from optionally substituted aryl, optionally substituted heteroaryl, and optionally substituted cycloalkyl.

In one embodiment, $R^{10}$ and $R^{11}$ are, at each instance, independently selected from H, optionally substituted alkyl, optionally substituted aryl, optionally substituted heteroaryl, and optionally substituted cycloalkyl. In one embodiment, $R^{10}$ and $R^{11}$ are, at each instance, independently selected from H, optionally substituted alkyl, and optionally substituted cycloalkyl. In another embodiment, $R^{10}$ and $R^{11}$ are, at each instance, independently selected from H, optionally substituted methyl, optionally substituted ethyl, and optionally substituted i-propyl. In another embodiment, $R^{10}$ and $R^{11}$ are, at each instance, independently selected from optionally substituted methyl, optionally substituted ethyl, and optionally substituted i-propyl. In another embodiment, $R^{10}$ and $R^{11}$ are, at each instance, independently selected from H, methyl, ethyl, and i-propyl, wherein each of methyl, ethyl, and i-propyl is optionally substituted by one or more of —OH, —O—$C_{1-6}$ alkyl, —$C_{3-6}$cycloalkyl, —$C_{3-6}$heterocycloalkyl and —C(=O)$NH_2$. In another embodiment, $R^{10}$ and $R^{11}$ are, at each instance, independently selected from H, methyl, ethyl, and i-propyl, wherein each of methyl, ethyl, and i-propyl is optionally substituted by one or more of —OH, —OMe, cyclopropyl, pyrrolidinyl and —C(=O)$NH_2$. In another embodiment, $R^{10}$ and $R^{11}$ are, at each instance, independently selected from H, methyl, ethyl, and i-propyl, wherein each of methyl, ethyl, and i-propyl is substituted by one or more of —OH, —OMe, cyclopropyl, pyrrolidinyl and —C(=O) $NH_2$. In one embodiment, $R^{10}$ is H.

In one embodiment, $R^{12}$ is H and $R^{13}$ is, at each instance, independently selected from hydroxy, and optionally substituted alkyl, or $R^{12}$ and $R^{13}$ are linked to form an optionally substituted cycloalkyl ring, or together form =O. In another embodiment, $R^{12}$ and $R^{13}$ are, at each instance, independently selected from H, hydroxy, and optionally substituted alkyl. In another embodiment, $R^{12}$ and $R^{13}$ are, at each instance, independently selected from H, hydroxy, optionally substituted methyl, and optionally substituted ethyl. In another embodiment, $R^{12}$ and $R^{13}$ are, at each instance, H.

In one embodiment, $R^{14}$ is alkyl. In another embodiment, $R^{14}$ is methyl.

In one embodiment, the compound is not a compound of WO 2004/014850 or WO 2004/065391.

In one embodiment, the compound is not

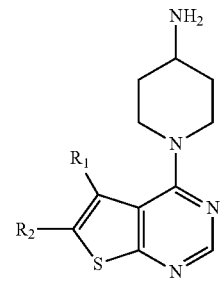

or a hydrochloride salt thereof,

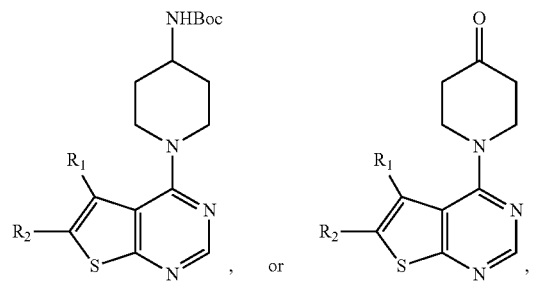

wherein $R_1$ is optionally substituted aryl and $R_2$ is H or optionally substituted alkyl.

Specific Embodiments

In one embodiment:
A is S;
X is N;
V is $CR^3{}_{III}$;
Z is N;
$R^1$ is selected from optionally substituted alkyl, optionally substituted cycloalkyl, optionally substituted aryl, and optionally substituted heteroaryl;
$R^2$ is selected from H, halo, —CN, trifluoromethyl, optionally substituted alkyl, optionally substituted alkoxy, —$NR^4R^5$, —$NR^6C(O)R^7$, —$NR^6S(O)_2R^7$, —$S(O)_2NR^4R^5$, —$CONR^4R^5$, —$CO_2R^7$, optionally substituted oxazolinyl, —$SR^{14}$, —$S(O)R^{14}$ and —$S(O)_2R^{14}$;
$R^3{}_I$ is selected from H, halo, —CN, trifluoromethyl, optionally substituted alkyl, optionally substituted alkoxy, optionally substituted heterocycloalkoxy, —$NR^6C(O)R^7$, —$NR^6S(O)_2R^7$, —$S(O)_2NR^4R^5$, —$CONR^4R^5$, —$CO_2R^7$, —$NR^8R^9$, —C≡C-J, optionally substituted cycloalkyl-J and —($NR^aR^b$)-J;
$R^3{}_{III}$ is selected from H, halo, —CN, trifluoromethyl, optionally substituted alkyl, optionally substituted alkoxy, optionally substituted heterocycloalkoxy, optionally substituted heterocycloalkylalkyl, —$NR^6C(O)R^7$, —$NR^6S(O)_2R^7$, —$S(O)_2NR^4R^5$, —$CONR^4R^5$, optionally substituted -alkylene-$CONR^4R^5$, —$CO_2R^7$, —$NR^{10}R^{11}$, —C≡C-J, optionally substituted cycloalkyl-J and —($NR^cR^d$)-J,
provided that $R^3{}_I$ is —C≡C-J, optionally substituted cycloalkyl-J or —($NR^aR^b$)-J, and/or $R^3{}_{III}$ is —C≡C-J, optionally substituted cycloalkyl-J or —($NR^cR^d$)-J;
wherein $R^a$ and $R^b$ are linked to form an optionally substituted 4 to 7 membered heterocycloalkyl ring, which is optionally bridged by a bond, optionally substituted $C_{1-2}$alkylene, —NR$^6$—, —O—, or —S(O)$_z$—, wherein the optionally bridged, optionally substituted heterocycloalkyl ring is selected from the group consisting of azetidinyl, pyrrolidinyl, piperidinyl, morpholinyl, tetrahydro-1,3-oxazinyl, hexahydropyrimidinyl, 1,4-thiazanyl, azepanyl, 1,4-oxaazepanyl, and 1,4-thieazepanyl;

wherein R$^c$ and R$^d$ are linked to form an optionally substituted 4 to 7 membered heterocycloalkyl ring, which is optionally bridged by a bond, optionally substituted C$_{1-2}$alkylene, —NR$^6$—, —O—, or —S(O)$_z$—;

J is selected from H and —(CR$^{12}$R$^{13}$)$_q$L-M-W,
wherein
q is 0, 1 or 2;
L is —O— or —N(G)-; and
G is selected from hydrogen, optionally substituted alkyl and optionally substituted cycloalkyl;
M is —(CR$^{12}$R$^{13}$)$_t$—;
t is 0, 1, 2 or 3;
W is selected from the group consisting of optionally substituted alkyl, optionally substituted alkoxy, optionally substituted alkenyl, optionally substituted cycloalkyl, optionally substituted heterocycloalkyl, optionally substituted aryl, optionally substituted heteroaryl and —NR$^8$R$^9$, wherein when W is optionally substituted cycloalkyl it may optionally be bridged by a bond or optionally substituted C$_{1-2}$alkylene, and wherein when W is optionally substituted heterocycloalkyl it may optionally be bridged by a bond, optionally substituted C$_{1-2}$alkylene, —NR$^6$—, —O—, or —S(O)$_z$—;

alternatively, when L=—N(G)-, L, G, M and W may be linked to form an optionally substituted heterocycloalkyl, an optionally substituted hetercycloalkenyl, or an optionally substituted heteroaryl;

z is 0, 1 or 2;

R$^4$ and R$^5$ are, at each instance, independently selected from H, optionally substituted alkyl, optionally substituted aryl, optionally substituted heteroaryl, and optionally substituted cycloalkyl, or are linked to form an optionally substituted heterocycloalkyl;

R$^6$ is, at each instance, independently selected from H and optionally substituted alkyl;

R$^7$ is, at each instance, independently selected from H and optionally substituted alkyl;

R$^8$ and R$^9$ are, at each instance, independently selected from optionally substituted alkyl, optionally substituted aryl, optionally substituted heterocycloalkyl, optionally substituted heteroaryl, and optionally substituted cycloalkyl;

R$^{10}$ and R$^{11}$ are, at each instance, independently selected from H, optionally substituted alkyl, optionally substituted aryl, optionally substituted heterocycloalkyl, optionally substituted heteroaryl, and optionally substituted cycloalkyl;

R$^{12}$ and R$^{13}$ are, at each instance, independently selected from H, hydroxy, and optionally substituted alkyl, or may be linked to form an optionally substituted cycloalkyl ring, or may together form =O; and R$^{14}$ is optionally substituted alkyl,
wherein the optional substituents are independently selected from halo, trihalomethyl, trihaloethyl, trihalomethoxy, trihaloethoxy, —OH, —NO$_2$, —CN, —CO$_2$H, —CO$_2$C$_{1-6}$alkyl, —SO$_3$H, —SOC$_{1-6}$alkyl, —SO$_2$C$_{1-6}$alkyl, —NHSO$_2$C$_{1-6}$alkyl, —NC$_{1-6}$alkylSO$_2$C$_{1-6}$alkyl, —SO$_2$NH$_2$, —SO$_2$NHC$_{1-6}$alkyl, —SO$_2$N(C$_{1-6}$alkyl)$_2$, —NHSO$_2$NH$_2$, —NHSO$_2$NHC$_{1-6}$alkyl, —NHSO$_2$N(C$_{1-6}$alkyl)$_2$, —NC$_{1-6}$alkylSO$_2$NH$_2$, —NC$_{1-6}$alkylSO$_2$NHC$_{1-6}$alkyl, —NC$_{1-6}$alkylSO$_2$N(C$_{1-6}$alkyl)$_2$, —C(=O)H, —C(=O)C$_{1-6}$alkyl, —NHC(=O)C$_{1-6}$alkyl, —NC$_{1-6}$alkylC(=O)C$_{1-6}$alkyl, C$_{1-6}$alkylenedioxy, =O, —N(C$_{1-6}$alkyl)$_2$, —C(=O)NH$_2$, —C(=O)NHC$_{1-6}$alkyl, —C(=O)N(C$_{1-6}$alkyl)$_2$, —NHC(=O)NH$_2$, —NHC(=O)NHC$_{1-6}$alkyl, —NHC(=O)N(C$_{1-6}$alkyl)$_2$, —NC$_{1-6}$alkylC(=O)NH$_2$, —NC$_{1-6}$alkylC(=O)NHC$_{1-6}$alkyl, —NC$_{1-6}$alkylC(=O)N(C$_{1-6}$alkyl)$_2$, —C(=NH)NH$_2$, —C(=NH)NHC$_{1-6}$alkyl, —C(=NH)N(C$_{1-6}$alkyl)$_2$, —C(=NC$_{1-6}$alkyl)NH$_2$, —C(=NC$_{1-6}$alkyl)NHC$_{1-6}$alkyl, —C(=NC$_{1-6}$alkyl)N(C$_{1-6}$alkyl)$_2$, —C$_{1-6}$alkyl, —C$_{3-6}$cycloalkyl, —C$_{3-6}$heterocycloalkyl, 2-imidazolidinon-3-yl, 1-C$_{1-6}$alkyl-2-imidazolidinon-3-yl, C$_{1-6}$alkylC$_{3-6}$heterocycloalkyl, aryl, haloaryl, C$_{1-6}$alkoxyaryl, —Z$^t$H, —Z$^t$—C$_{1-6}$alkyl, —C$_{1-6}$alkylene-Z$^t$H, —Z$^t$—C$_{3-6}$cycloalkyl, or —C(=O)NHC$_{1-6}$alkylene-Z$^t$H wherein Z$^t$ is independently O, S, NH or N(C$_{1-6}$alkyl).

In one embodiment:
A is S;
X is N;
V is CR$^3{}_{III}$;
Z is N;
R$^1$ is selected from optionally substituted alkyl, optionally substituted cycloalkyl, optionally substituted aryl, and optionally substituted heteroaryl;
R$^2$ is selected from H, trifluoromethyl, substituted alkyl, optionally substituted alkoxy, —NR$^4$R$^5$, —NR$^6$C(O)R$^7$, —S(O)$_2$NR$^4$R$^5$, —CONR$^4$R$^5$, —CO$_2$R$^7$, optionally substituted oxazolinyl, —SR$^{14}$, —S(O)R$^{14}$ and —S(O)$_2$R$^{14}$;
R$^3{}_I$ is selected from H, halo, —CN, trifluoromethyl, optionally substituted alkyl, optionally substituted alkoxy, optionally substituted heterocycloalkoxy, —NR$^6$C(O)R$^7$, —NR$^6$S(O)$_2$R$^7$, —S(O)$_2$NR$^4$R$^5$, —CONR$^4$R$^5$, —CO$_2$R$^7$, —NR$^8$R$^9$, —C≡C-J, optionally substituted cycloalkyl-J and —(NR$^a$R$^b$)-J;
R$^3{}_{III}$ is selected from H, halo, —CN, trifluoromethyl, optionally substituted alkyl, optionally substituted alkoxy, optionally substituted heterocycloalkoxy, optionally substituted heterocycloalkylalkyl, —NR$^6$C(O)R$^7$, —NR$^6$S(O)$_2$R$^7$, —S(O)$_2$NR$^4$R$^5$, —CONR$^4$R$^5$, optionally substituted -alkylene-CONR$^4$R$^5$, —CO$_2$R$^7$, —NR$^{10}$R$^{11}$, —C≡C-J, optionally substituted cycloalkyl-J and —(NR$^c$R$^d$)-J,
provided that R$^3{}_I$ is —C≡C-J, optionally substituted cycloalkyl-J or —(NR$^a$R$^b$)-J, and/or R$^3{}_{III}$ is —C≡C-J, optionally substituted cycloalkyl-J or —(NR$^c$R$^d$)-J;

wherein R$^a$ and R$^b$ are linked to form an optionally substituted 4 to 7 membered heterocycloalkyl ring, which is optionally bridged by a bond, optionally substituted C$_{1-2}$alkylene, —NR$^6$—, —O—, or —S(O)$_z$—, wherein the optionally bridged, optionally substituted heterocycloalkyl ring is selected from the group consisting of azetidinyl, pyrrolidinyl, piperidinyl, morpholinyl, tetrahydro-1,3-oxazinyl, hexahydropyrimidinyl, 1,4-thiazanyl, azepanyl, 1,4-oxaazepanyl, and 1,4-thieazepanyl;

wherein R$^c$ and R$^d$ are linked to form an optionally substituted 4 to 7 membered heterocycloalkyl ring, which is optionally bridged by a bond, optionally substituted C$_{1-2}$alkylene, —NR$^6$—, —O—, or —S(O)$_z$—;

J is selected from H and —(CR$^{12}$R$^{13}$)$_q$L-M-W,
wherein
q is 0, 1 or 2;
L is —O— or —N(G)-; and
G is selected from hydrogen, optionally substituted alkyl and optionally substituted cycloalkyl;
M is —(CR$^{12}$R$^{13}$)$_t$—;
t is 0, 1, 2 or 3;
W is selected from the group consisting of optionally substituted alkyl, optionally substituted alkoxy, optionally substituted alkenyl, optionally substituted cycloalkyl, optionally substituted heterocycloalkyl, optionally substituted aryl, optionally substituted heteroaryl and —NR$^8$R$^9$, wherein when W is optionally substituted cycloalkyl it may optionally be bridged by a bond or optionally substituted $C_{1-2}$alkylene, and wherein when W is optionally substituted heterocycloalkyl it may optionally be bridged by a bond, optionally substituted $C_{1-2}$alkylene, $-NR^6-$, $-O-$, or $-S(O)_z-$;

alternatively, when $L=-N(G)-$, L, G, M and W may be linked to form an optionally substituted heterocycloalkyl, an optionally substituted hetercycloalkenyl, or an optionally substituted heteroaryl;

z is 0, 1 or 2;

$R^4$ and $R^5$ are, at each instance, independently selected from H, optionally substituted alkyl, optionally substituted aryl, optionally substituted heteroaryl, and optionally substituted cycloalkyl, or are linked to form an optionally substituted heterocycloalkyl;

$R^6$ is, at each instance, independently selected from H and optionally substituted alkyl;

$R^7$ is, at each instance, independently selected from H and optionally substituted alkyl;

$R^8$ and $R^9$ are, at each instance, independently selected from optionally substituted alkyl, optionally substituted aryl, optionally substituted heterocycloalkyl, optionally substituted heteroaryl, and optionally substituted cycloalkyl;

$R^{10}$ and $R^{11}$ are, at each instance, independently selected from H, optionally substituted alkyl, optionally substituted aryl, optionally substituted heterocycloalkyl, optionally substituted heteroaryl, and optionally substituted cycloalkyl;

$R^{12}$ and $R^{13}$ are, at each instance, independently selected from H, hydroxy, and optionally substituted alkyl, or may be linked to form an optionally substituted cycloalkyl ring, or may together form =O; and $R^{14}$ is optionally substituted alkyl, wherein the optional substituents are independently selected from halo, trihalomethyl, trihaloethyl, trihalomethoxy, trihaloethoxy, $-OH$, $-NO_2$, $-CN$, $-CO_2H$, $-CO_2C_{1-6}$alkyl, $-SO_3H$, $-SOC_{1-6}$alkyl, $-SO_2C_{1-6}$alkyl, $-NHSO_2C_{1-6}$alkyl, $-NC_{1-6}$alkyl$SO_2C_{1-6}$alkyl, $-SO_2NH_2$, $-SO_2NHC_{1-6}$alkyl, $-SO_2N(C_{1-6}$alkyl$)_2$, $-NHSO_2NH_2$, $-NHSO_2NHC_{1-6}$alkyl, $-NHSO_2N(C_{1-6}$alkyl$)_2$, $-NC_{1-6}$alkyl$SO_2NH_2$, $-NC_{1-6}$alkyl$SO_2NHC_{1-6}$alkyl, $-NC_{1-6}$alkyl$SO_2N(C_{1-6}$alkyl$)_2$, $-C(=O)H$, $-C(=O)C_{1-6}$alkyl, $-NHC(=O)C_{1-6}$alkyl, $-NC_{1-6}$alkyl$C(=O)C_{1-6}$alkyl, $C_{1-6}$alkylenedioxy, =O, $-N(C_{1-6}$alkyl$)_2$, $-C(=O)NH_2$, $-C(=O)NHC_{1-6}$alkyl, $-C(=O)N(C_{1-6}$alkyl$)_2$, $-NHC(=O)NH_2$, $-NHC(=O)NHC_{1-6}$alkyl, $-NHC(=O)N(C_{1-6}$alkyl$)_2$, $-NC_{1-6}$alkyl$C(=O)NH_2$, $-NC_{1-6}$alkyl$C(=O)NHC_{1-6}$alkyl, $-NC_{1-6}$alkyl$C(=O)N(C_{1-6}$alkyl$)_2$, $-C(=NH)NH_2$, $-C(=NH)NHC_{1-6}$alkyl, $-C(=NH)N(C_{1-6}$alkyl$)_2$, $-C(=NC_{1-6}$alkyl$)NH_2$, $-C(=NC_{1-6}$alkyl$)NHC_{1-6}$alkyl, $-C(=NC_{1-6}$alkyl$)N(C_{1-6}$alkyl$)_2$, $-C_{1-6}$alkyl, $-C_{3-6}$cycloalkyl, $-C_{3-6}$heterocycloalkyl, 2-imidazolidinon-3-yl, 1-$C_{1-6}$alkyl-2-imidazolidinon-3-yl, $C_{1-6}$alkyl$C_{3-6}$heterocycloalkyl, aryl, haloaryl, $C_{1-6}$alkoxyaryl, $-Z^tH$, $-Z^t-C_{1-6}$alkyl, $-C_{1-6}$alkylene-$Z^tH$, $-Z^t-C_{3-6}$cycloalkyl, or $-C(=O)NHC_{1-6}$alkylene-$Z^tH$ wherein $Z^t$ is independently O, S, NH or N($C_{1-6}$alkyl).

In one embodiment:

A is S;

X is N;

V is $CR^3_{III}$;

Z is N;

$R^1$ is selected from optionally substituted alkyl, optionally substituted cycloalkyl, optionally substituted aryl, and optionally substituted heteroaryl;

$R^2$ is selected from H, trifluoromethyl, substituted alkyl, optionally substituted alkoxy, $-NR^4R^5$, $-NR^6C(O)R^7$, $-S(O)_2NR^4R^5$, $-CONR^4R^5$, $-CO_2R^7$, optionally substituted oxazolinyl, $-SR^{14}$, $-S(O)R^{14}$ and $-S(O)_2R^{14}$;

$R^3_I$ is selected from trifluoromethyl, optionally substituted alkyl, optionally substituted alkoxy, optionally substituted heterocycloalkoxy, $-NR^6C(O)R^7$, $-NR^6S(O)_2R^7$, $-S(O)_2NR^4R^5$, $-CONR^4R^5$, $-CO_2R^7$, $-NR^8R^9$, optionally substituted cycloalkyl-J and $-(NR^aR^b)$-J;

$R^3_{III}$ is selected from H, halo, $-CN$, trifluoromethyl, optionally substituted alkyl, optionally substituted alkoxy, optionally substituted heterocycloalkoxy, optionally substituted heterocycloalkylalkyl, $-NR^6C(O)R^7$, $-NR^6S(O)_2R^7$, $-S(O)_2NR^4R^5$, $-CONR^4R^5$, optionally substituted -alkylene-$CONR^4R^5$, $-CO_2R^7$, $-NR^{10}R^{11}$, optionally substituted cycloalkyl-J and $-(NR^cR^d)$-J, provided that $R^3_I$ is optionally substituted cycloalkyl-J or $-(NR^aR^b)$-J, and/or $R^3_{III}$ is optionally substituted cycloalkyl-J or $-(NR^cR^d)$-J;

wherein $R^a$ and $R^b$ are linked to form an optionally substituted 4 to 7 membered heterocycloalkyl ring, which is optionally bridged by a bond, optionally substituted $C_{1-2}$alkylene, $-NR^6-$, $-O-$, or $-S(O)_z-$, wherein the optionally bridged, optionally substituted heterocycloalkyl ring is selected from the group consisting of azetidinyl, pyrrolidinyl, piperidinyl, morpholinyl, tetrahydro-1,3-oxazinyl, hexahydropyrimidinyl, 1,4-thiazanyl, azepanyl, 1,4-oxaazepanyl, and 1,4-thieazepanyl;

wherein $R^c$ and $R^d$ are linked to form an optionally substituted 4 to 7 membered heterocycloalkyl ring, which is optionally bridged by a bond, optionally substituted $C_{1-2}$alkylene, $-NR^6-$, $-O-$, or $-S(O)_z-$;

J is selected from H and $-(CR^{12}R^{13})_q$L-M-W, wherein q is 0 or 1;

L is $-O-$ or $-N(G)-$; and

G is selected from hydrogen, optionally substituted alkyl and optionally substituted cycloalkyl;

M is $-(CR^{12}R^{13})_t-$;

t is 0, 1, or 2;

W is selected from the group consisting of optionally substituted alkyl, optionally substituted alkoxy, optionally substituted alkenyl, optionally substituted cycloalkyl, optionally substituted heterocycloalkyl, optionally substituted aryl, optionally substituted heteroaryl and $-NR^8R^9$, wherein when W is optionally substituted cycloalkyl it may optionally be bridged by a bond or optionally substituted $C_{1-2}$alkylene, and wherein when W is optionally substituted heterocycloalkyl it may optionally be bridged by a bond, optionally substituted $C_{1-2}$alkylene, $-NR^6-$, $-O-$, or $-S(O)_z-$;

alternatively, when $L=-N(G)-$, L, G, M and W may be linked to form an optionally substituted heterocycloalkyl, an optionally substituted hetercycloalkenyl, or an optionally substituted heteroaryl;

z is 0, 1 or 2;

$R^4$ and $R^5$ are, at each instance, independently selected from H, optionally substituted alkyl, optionally substituted aryl, optionally substituted heteroaryl, and optionally substituted cycloalkyl, or are linked to form an optionally substituted heterocycloalkyl;

$R^6$ is, at each instance, independently selected from H and optionally substituted alkyl;

$R^7$ is, at each instance, independently selected from H and optionally substituted alkyl;

$R^8$ and $R^9$ are, at each instance, independently selected from optionally substituted alkyl, optionally substituted aryl, optionally substituted heterocycloalkyl, optionally substituted heteroaryl, and optionally substituted cycloalkyl;

$R^{10}$ and $R^{11}$ are, at each instance, independently selected from H, optionally substituted alkyl, optionally substituted aryl, optionally substituted heterocycloalkyl, optionally substituted heteroaryl, and optionally substituted cycloalkyl;

$R^{12}$ and $R^{13}$ are, at each instance, independently selected from H, hydroxy, and optionally substituted alkyl, or may be linked to form an optionally substituted cycloalkyl ring, or may together form =O; and $R^{14}$ is optionally substituted alkyl, wherein the optional substituents are independently selected from halo, trihalomethyl, trihaloethyl, trihalomethoxy, trihaloethoxy, —OH, —NO$_2$, —CN, —CO$_2$H, —CO$_2$C$_{1-6}$alkyl, —SO$_3$H, —SOC$_{1-6}$alkyl, —SO$_2$C$_{1-6}$alkyl, —NHSO$_2$C$_{1-6}$alkyl, —NC$_{1-6}$alkylSO$_2$C$_{1-6}$alkyl, —SO$_2$NH$_2$, —SO$_2$NHC$_{1-6}$alkyl, —SO$_2$N(C$_{1-6}$alkyl)$_2$, —NHSO$_2$NH$_2$, —NHSO$_2$NHC$_{1-6}$alkyl, —NHSO$_2$N(C$_{1-6}$alkyl)$_2$, —NC$_{1-6}$alkylSO$_2$NH$_2$, —NC$_{1-6}$alkylSO$_2$NHC$_{1-6}$alkyl, —NC$_{1-6}$alkylSO$_2$N(C$_{1-6}$alkyl)$_2$, —C(=O)H, —C(=O)C$_{1-6}$alkyl, —NHC(=O)C$_{1-6}$alkyl, —NC$_{1-6}$alkylC(=O)C$_{1-6}$alkyl, C$_{1-6}$alkylenedioxy, =O, —N(C$_{1-6}$alkyl)$_2$, —C(=O)NH$_2$, —C(=O)NHC$_{1-6}$alkyl, —C(=O)N(C$_{1-6}$alkyl)$_2$, —NHC(=O)NH$_2$, —NHC(=O)NHC$_{1-6}$alkyl, —NHC(=O)N(C$_{1-6}$alkyl)$_2$, —NC$_{1-6}$alkylC(=O)NH$_2$, —NC$_{1-6}$alkylC(=O)NHC$_{1-6}$alkyl, —NC$_{1-6}$alkylC(=O)N(C$_{1-6}$alkyl)$_2$, —C(=NH)NH$_2$, —C(=NH)NHC$_{1-6}$alkyl, —C(=NH)N(C$_{1-6}$alkyl)$_2$, —C(=NC$_{1-6}$alkyl)NH$_2$, —C(=NC$_{1-6}$alkyl)NHC$_{1-6}$alkyl, —C(=NC$_{1-6}$alkyl)N(C$_{1-6}$alkyl)$_2$, —C$_{1-6}$alkyl, —C$_{3-6}$cycloalkyl, —C$_{3-6}$heterocycloalkyl, 2-imidazolidinon-3-yl, 1-C$_{1-6}$alkyl-2-imidazolidinon-3-yl, C$_{1-6}$alkylC$_{3-6}$heterocycloalkyl, aryl, haloaryl, C$_{1-6}$alkoxyaryl, —Z$^t$H, —Z$^t$—C$_{1-6}$alkyl, —C$_{1-6}$alkylene-Z$^t$H, —Z$^t$—C$_{3-6}$cycloalkyl, or —C(=O)NHC$_{1-6}$alkylene-Z$^t$H wherein Z$^t$ is independently O, S, NH or N(C$_{1-6}$alkyl).

In one embodiment:

A is S;

X is N;

V is CR$^3_{III}$;

Z is N;

$R^1$ is selected from optionally substituted alkyl, optionally substituted cycloalkyl, optionally substituted aryl, and optionally substituted heteroaryl;

$R^2$ is selected from H, trifluoromethyl, substituted alkyl, optionally substituted alkoxy, —NR$^4$R$^5$, —NR$^6$C(O)R$^7$, —S(O)$_2$NR$^4$R$^5$, —CONR$^4$R$^5$, —CO$_2$R$^7$, optionally substituted oxazolinyl, —SR$^{14}$, —S(O)R$^{14}$ and —S(O)$_2$R$^{14}$;

$R^3_I$ is —(NR$^a$R$^b$)-J;

$R^3_{III}$ is selected from H, halo, —CN, trifluoromethyl, optionally substituted alkyl, optionally substituted alkoxy, optionally substituted heterocycloalkoxy, optionally substituted heterocycloalkylalkyl, —NR$^6$C(O)R$^7$, —NR$^6$S(O)$_2$R$^7$, —S(O)$_2$NR$^4$R$^5$, —CONR$^4$R$^5$, optionally substituted -alkylene-CONR$^4$R$^5$, —CO$_2$R$^7$, —NR$^{10}$R$^{11}$, optionally substituted cycloalkyl-J and —(NR$^c$R$^d$)-J, wherein R$^a$ and R$^b$ are linked to form an optionally substituted 4 to 7 membered heterocycloalkyl ring, which is optionally bridged by a bond, optionally substituted C$_{1-2}$alkylene, —NR$^6$—, —O—, or —S(O)$_z$—, wherein the optionally bridged, optionally substituted heterocycloalkyl ring is selected from the group consisting of azetidinyl, pyrrolidinyl, piperidinyl, morpholinyl, tetrahydro-1,3-oxazinyl, hexahydropyrimidinyl, 1,4-thiazanyl, azepanyl, 1,4-oxaazepanyl, and 1,4-thieazepanyl;

wherein R$^c$ and R$^d$ are linked to form an optionally substituted 4 to 7 membered heterocycloalkyl ring, which is optionally bridged by a bond, optionally substituted C$_{1-2}$alkylene, —NR$^6$—, —O—, or —S(O)$_z$—;

J is selected from H and —(CR$^{12}$R$^{13}$)$_q$L-M-W, wherein q is 0 or 1;

L is —O— or —N(G)-; and

G is selected from hydrogen, optionally substituted alkyl and optionally substituted cycloalkyl;

M is —(CR$^{12}$R$^{13}$)$_t$—;

t is 0, 1, or 2;

W is selected from the group consisting of optionally substituted alkyl, optionally substituted alkoxy, optionally substituted alkenyl, optionally substituted cycloalkyl, optionally substituted heterocycloalkyl, optionally substituted aryl, optionally substituted heteroaryl and —NR$^8$R$^9$, wherein when W is optionally substituted cycloalkyl it may optionally be bridged by a bond or optionally substituted C$_{1-2}$alkylene, and wherein when W is optionally substituted heterocycloalkyl it may optionally be bridged by a bond, optionally substituted C$_{1-2}$alkylene, —NR$^6$—, —O—, or —S(O)$_z$—;

alternatively, when L=—N(G)-, L, G, M and W may be linked to form an optionally substituted heterocycloalkyl, an optionally substituted hetercycloalkenyl, or an optionally substituted heteroaryl;

z is 0, 1 or 2;

$R^4$ and $R^5$ are, at each instance, independently selected from H, optionally substituted alkyl, optionally substituted aryl, optionally substituted heteroaryl, and optionally substituted cycloalkyl, or are linked to form an optionally substituted heterocycloalkyl;

$R^6$ is, at each instance, independently selected from H and optionally substituted alkyl;

$R^7$ is, at each instance, independently selected from H and optionally substituted alkyl;

$R^8$ and $R^9$ are, at each instance, independently selected from optionally substituted alkyl, optionally substituted aryl, optionally substituted heterocycloalkyl, optionally substituted heteroaryl, and optionally substituted cycloalkyl;

$R^{10}$ and $R^{11}$ are, at each instance, independently selected from H, optionally substituted alkyl, optionally substituted aryl, optionally substituted heterocycloalkyl, optionally substituted heteroaryl, and optionally substituted cycloalkyl;

$R^{12}$ and $R^{13}$ are, at each instance, independently selected from H, hydroxy, and optionally substituted alkyl, or may be linked to form an optionally substituted cycloalkyl ring, or may together form =O; and $R^{14}$ is optionally substituted alkyl, wherein the optional substituents are independently selected from halo, trihalomethyl, trihaloethyl, trihalomethoxy, trihaloethoxy, —OH, —NO$_2$, —CN, —CO$_2$H, —CO$_2$C$_{1-6}$alkyl, —SO$_3$H, —SOC$_{1-6}$alkyl, —SO$_2$C$_{1-6}$alkyl, —NHSO$_2$C$_{1-6}$alkyl, —NC$_{1-6}$alkylSO$_2$C$_{1-6}$alkyl, —SO$_2$NH$_2$, —SO$_2$NHC$_{1-6}$alkyl, —SO$_2$N(C$_{1-6}$alkyl)$_2$, —NHSO$_2$NH$_2$, —NHSO$_2$NHC$_{1-6}$alkyl, —NHSO$_2$N(C$_{1-6}$alkyl)$_2$, —NC$_{1-6}$alkylSO$_2$NH$_2$, —NC$_{1-6}$alkylSO$_2$NHC$_{1-6}$alkyl, —NC$_{1-6}$alkylSO$_2$N(C$_{1-6}$alkyl)$_2$, —C(=O)H, —C(=O)C$_{1-6}$alkyl, —NHC(=O)C$_{1-6}$alkyl, —NC$_{1-6}$alkylC(=O)C$_{1-6}$alkyl, C$_{1-6}$alkylenedioxy, =O, —N(C$_{1-6}$alkyl)$_2$, —C(=O)NH$_2$, —C(=O)NHC$_{1-6}$alkyl, —C(=O)N(C$_{1-6}$alkyl)$_2$, —NHC(=O)NH$_2$, —NHC(=O)NHC$_{1-6}$alkyl, —NHC(=O)N(C$_{1-6}$alkyl)$_2$, —NC$_{1-6}$alkylC(=O)NH$_2$, —NC$_{1-6}$alkylC(=O)NHC$_{1-6}$alkyl, —NC$_{1-6}$alkylC(=O)N(C$_{1-6}$alkyl)$_2$, —C(=NH)NH$_2$, —C(=NH)NHC$_{1-6}$alkyl, —C(=NH)N(C$_{1-6}$alkyl)$_2$, —C(=NC$_{1-6}$alkyl)NH$_2$, —C(=NC$_{1-6}$alkyl)NHC$_{1-6}$alkyl, —C(=NC$_{1-6}$alkyl)N(C$_{1-6}$alkyl)$_2$, —C$_{1-6}$alkyl, —C$_{3-6}$cycloalkyl, —C$_{3-6}$heterocycloalkyl, 2-imidazolidinon-3-yl, 1-C$_{1-6}$alkyl-2-imidazolidinon-3-yl, C$_{1-6}$alkylC$_{3-6}$heterocycloalkyl, aryl, haloaryl, C$_{1-6}$alkoxyaryl, —Z$^t$H, —Z$^t$—C$_{1-6}$alkyl, —C$_{1-6}$alkylene-Z$^t$H, —Z$^t$—C$_{3-6}$cycloalkyl, or —C(=O)NHC$_{1-6}$alkylene-Z$^t$H wherein Z$^t$ is independently O, S, NH or N(C$_{1-6}$alkyl).

In one embodiment:

A is S;

Z is N and V is $CR^3{}_{III}$;

$R^3{}_I$ is selected from H, —$(NR^aR^b)$-J, optionally substituted cycloalkyl-J and —C≡C-J;

Each of $R^3{}_{II}$, $R^3{}_{III}$, and $R^3{}_{IV}$ is independently selected from H, —$NR^{10}R^{11}$, —C≡C-J, optionally substituted cycloalkyl-J and —$(NR^cR^d)$-J;

$R^1$ is selected from optionally substituted alkyl and optionally substituted phenyl;

$R^2$ is selected from H, halo, —CN, optionally substituted alkyl, —$NR^4R^5$, —$NR^6C(O)R^7$, —$CONR^4R^5$;

$NR^aR^b$ and $NR^cR^d$ each form an optionally bridged, optionally substituted ring of formula (II):

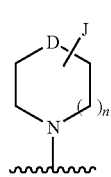

(II)

wherein n and D are defined in each case above;

J is present in at least one instance as —$(CR^{12}R^{13})_q$-L-M-W;

q is 1 or 2;

G is selected from H, optionally substituted methyl and optionally substituted ethyl;

M is selected from bond, —$(CH_2)$—, —$(CH_2)_2$—, —$(CH_2)_3$—, -cycloalkyl-, —CHOH—$CH_2$—, $CH_2$—CHOH—, —$CH_2$—$C(alkyl)_2$-, —$(CH_2)$—$C(=O)$—, —$C(=O)$—$(CH_2)$—;

W is selected from substituted alkyl, alkoxy, cyclopropyl, cyclobutyl, optionally substituted pyrrolidinyl, optionally substituted piperidinyl, optionally substituted piperazinyl, optionally substituted morpholinyl, tetrahydrofuran, furan, thiophene, phenyl, and pyridine; alternatively, when L=N (G)-, L, G, M and W may be linked to form an optionally substituted heterocycloalkyl;

$R^4$ and $R^5$ are, at each instance, independently selected from H and optionally substituted alkyl, or are linked to form an optionally substituted heterocycloalkyl;

$R^6$ is H;

$R^7$ is alkyl; and $R^{10}$ and $R^{11}$ are, at each instance, independently selected from H, optionally substituted methyl, optionally substituted ethyl, and optionally substituted i-propyl, wherein the optional substituents are independently selected from halo, trihalomethyl, trihaloethyl, trihalomethoxy, trihaloethoxy, —OH, —$NO_2$, —CN, —$CO_2H$, —$CO_2C_{1-6}$alkyl, —$SO_3H$, —$SOC_{1-6}$alkyl, —$SO_2C_{1-6}$alkyl, —$NHSO_2$ $C_{1-6}$alkyl, —$NC_{1-6}$alkyl$SO_2C_{1-6}$alkyl, —$SO_2NH_2$, —$SO_2NHC_{1-6}$alkyl, —$SO_2N(C_{1-6}$alkyl$)_2$, —$NHSO_2NH_2$, —$NHSO_2NHC_{1-6}$alkyl, —$NHSO_2N(C_{1-6}$alkyl$)_2$, —$NC_{1-6}$alkyl$SO_2NH_2$, —$NC_{1-6}$alkyl$SO_2NHC_{1-6}$alkyl, —$NC_{1-6}$alkyl$SO_2N(C_{1-6}$alkyl$)_2$, —$C(=O)H$, —$C(=O)C_{1-6}$alkyl, —$NHC(=O)C_{1-6}$alkyl, —$NC_{1-6}$alkyl$C(=O)C_{1-6}$alkyl, $C_{1-6}$alkylenedioxy, =O, —$N(C_{1-6}$alkyl$)_2$, —$C(=O)NH_2$, —$C(=O)NHC_{1-6}$alkyl, —$C(=O)N(C_{1-6}$alkyl$)_2$, —NHC (=O)$NH_2$, —$NHC(=O)NHC_{1-6}$alkyl, —NHC(=O) $N(C_{1-6}$alkyl$)_2$, —$NC_{1-6}$alkyl$C(=O)NH_2$, —$NC_{1-6}$alkyl$C(=O)NHC_{1-6}$alkyl, —$NC_{1-6}$alkyl$C(=O)N(C_{1-6}$alkyl$)_2$, —C(=NH)$NH_2$, —C(=NH)$NHC_{1-6}$alkyl, —C(=NH)N $(C_{1-6}$alkyl$)_2$, —$C(=NC_{1-6}$alkyl$)NH_2$, —$C(=NC_{1-6}$alkyl$)$ $NHC_{1-6}$alkyl, —$C(=NC_{1-6}$alkyl$)N(C_{1-6}$alkyl$)_2$, —$C_{1-6}$ alkyl, —$C_{3-6}$cycloalkyl, —$C_{3-6}$heterocycloalkyl, 2-imidazolidinon-3-yl, 1-$C_{1-6}$alkyl-2-imidazolidinon-3-yl, $C_{1-6}$alkyl$C_{3-6}$heterocycloalkyl, aryl, haloaryl, $C_{1-6}$alkoxyaryl, —$Z^tH$, —$Z^t$—$C_{1-6}$alkyl, —$C_{1-6}$alkylene-$Z^tH$, —$Z^t$—$C_{3-6}$cycloalkyl, or —$C(=O)NHC_{1-6}$alkylene-$Z^tH$ wherein $Z^t$ is independently O, S, NH or N($C_{1-6}$alkyl).

In one embodiment:

A is S;

Z is N and V is $CR^3{}_{III}$;

$R^3{}_I$ is selected from —$(NR^aR^b)$-J, and —C≡C-J;

$R^3{}_{II}$ and $R^3{}_{IV}$ are H;

$R^3{}_{III}$ is independently selected from H, —$NR^cR^{11}$, —C≡C-J, optionally substituted cycloalkyl-J and —$(NR^cR^d)$-J;

$R^1$ is selected from methyl, ethyl, i-propyl, and phenyl, wherein phenyl is optionally substituted by one or more of halo, —$NO_2$ and —$SO_2N(C_{1-6}$alkyl$)_2$;

$R^2$ is selected from H, bromo, —CN, methyl, ethyl, i-propyl, —$NR^4R^5$, —$NR^6C(O)R^7$, —$CONR^4R^5$;

$NR^aR^b$ is selected from optionally substituted pyrrolidinyl, piperidinyl, morpholinyl, and 3-azabicyclo[3.1.0]hexanyl;

$NR^cR^d$ is selected from optionally substituted pyrrolidinyl, piperidinyl, morpholinyl, piperazinyl, and 3-azabicyclo [3.1.0]hexanyl;

J is present in at least one instance as —$(CR^{12}R^{13})_q$-L-M-W;

q is 1;

G is selected from H, methyl and ethyl, wherein ethyl is optionally substituted by —OH or —O—$C_{1-6}$alkyl;

M is selected from bond, —$(CH_2)$—, —$(CH_2)_2$—, —$(CH_2)_3$—, -cyclopentyl-, —CHOH—$CH_2$—, —$CH_2$—C $(Me)_2$-, —$(CH_2)$—$C(=O)$—;

W is selected from alkyl substituted by one or more groups selected from halo, —OH, —$NH_2$, and —$N(C_{1-6}$alkyl$)_2$, alkoxy, cyclopropyl, cyclobutyl, pyrrolidinyl, piperidinyl, piperazinyl, morpholinyl, tetrahydrofuran, furan, thiophene, phenyl, and pyridine, wherein each of pyrrolidinyl, piperidinyl, piperazinyl, and morpholinyl is optionally substituted by one or more groups selected from halo, $C_{1-6}$alkyl, —$C(=O)$ $C_{1-6}$alkyl, —$CO_2C_{1-6}$alkyl, —$N(C_{1-6}$alkyl$)_2$, —$NHC(=O)$ $C_{1-6}$alkyl, —$C(=O)NH_2$, and =O;

alternatively, when L is —N(G)-, L, G, M and W may be linked to form azetidinyl, pyrrolidinyl, piperidinyl or morpholinyl, wherein each of pyrrolidinyl, piperidinyl and morpholinyl is optionally substituted by one or more groups selected from halo, trihalomethyl, —OH, —$C_{1-6}$alkyl, —O—$C_{1-6}$alkyl, —$N(C_{1-6}$alkyl$)_2$, —$C_{1-6}$alkylene-OH, aryl, haloaryl, —$C(=O)NH_2$ and —$C_{3-6}$heterocycloalkyl;

$R^4$ and $R^5$ are, at each instance, independently selected from H, methyl, ethyl, i-propyl, and pyrrolidinyl optionally substituted by =O;

$R^6$ is H;

$R^7$ is methyl; and $R^{10}$ and $R^{11}$ are, at each instance, independently selected from H, methyl, ethyl, and i-propyl, wherein each of methyl, ethyl, and i-propyl is optionally substituted by one or more of —OH, —O—$C_{1-6}$alkyl, —$C_{3-6}$cycloalkyl, —$C_{3-6}$heterocycloalkyl and —$C(=O)NH_2$, wherein the optional substituents are independently selected from halo, trihalomethyl, trihaloethyl, trihalomethoxy, trihaloethoxy, —OH, —$NO_2$, —CN, —$CO_2H$, —$CO_2C_{1-6}$alkyl, —$SO_3H$, —$SOC_{1-6}$alkyl, —$SO_2C_{1-6}$alkyl, —$NHSO_2$ $C_{1-6}$alkyl, —$NC_{1-6}$alkyl$SO_2C_{1-6}$alkyl, —$SO_2NH_2$, —$SO_2NHC_{1-6}$alkyl, —$SO_2N(C_{1-6}$alkyl$)_2$, —$NHSO_2NH_2$, —$NHSO_2NHC_{1-6}$alkyl, —$NHSO_2N(C_{1-6}$alkyl$)_2$, —$NC_{1-6}$ alkyl$SO_2NH_2$, —$NC_{1-6}$alkyl$SO_2NHC_{1-6}$alkyl, —$NC_{1-6}$ alkyl$SO_2N(C_{1-6}$alkyl$)_2$, —$C(=O)H$, —$C(=O)C_{1-6}$alkyl, —$NHC(=O)C_{1-6}$alkyl, —$NC_{1-6}$alkyl$C(=O)C_{1-6}$alkyl, $C_{1-6}$alkylenedioxy, =O, —$N(C_{1-6}$alkyl$)_2$, —$C(=O)NH_2$, —C(=O)NHC$_{1-6}$alkyl, —C(=O)N(C$_{1-6}$alkyl)$_2$, —NHC(=O)NH$_2$, —NHC(=O)NHC$_{1-6}$alkyl, —NHC(=O)N(C$_{1-6}$alkyl)$_2$, —NC$_{1-6}$alkylC(=O)NH$_2$, —NC$_{1-6}$alkylC(=O)NHC$_{1-6}$alkyl, —NC$_{1-6}$alkylC(=O)N(C$_{1-6}$alkyl)$_2$, —C(=NH)NH$_2$, —C(=NH)NHC$_{1-6}$alkyl, —C(=NH)N(C$_{1-6}$alkyl)$_2$, —C(=NC$_{1-6}$alkyl)NH$_2$, —C(=NC$_{1-6}$alkyl)NHC$_{1-6}$alkyl, —C(=NC$_{1-6}$alkyl)N(C$_{1-6}$alkyl)$_2$, —C$_{1-6}$alkyl, —C$_{3-6}$cycloalkyl, —C$_{3-6}$heterocycloalkyl, 2-imidazolidinon-3-yl, 1-C$_{1-6}$alkyl-2-imidazolidinon-3-yl, C$_{1-6}$alkylC$_{3-6}$heterocycloalkyl, aryl, haloaryl, C$_{1-6}$alkoxyaryl, —Z$^t$H, —Z$^t$—C$_{1-6}$alkyl, —C$_{1-6}$alkylene-Z$^t$H, —Z$^t$—C$_{3-6}$cycloalkyl, or —C(=O)NHC$_{1-6}$alkylene-Z$^t$H wherein Z$^t$ is independently O, S, NH or N(C$_{1-6}$alkyl).

In one embodiment:

A is S;
Z is N and X is N;
R$^3_I$ is —(NR$^a$R$^b$)-J and J is (CR$^{12}$R$^{13}$)$_q$L-M-W;
R$^3_{II}$ and R$^3_{IV}$ are H;
R$^3_{III}$ is —(NR$^c$R$^d$)-J;
R$^1$ is phenyl;
R$^2$ is H;
NR$^a$R$^b$ and NR$^c$R$^d$ are each selected from pyrrolidinyl and piperidinyl;
J is present in at least one instance as —(CR$^{12}$R$^{13}$)$_q$-L-M-W;
q is 1;
G is selected from H and methyl;
M is selected from bond, —(CH$_2$)—, —(CH$_2$)$_2$— and —(CH$_2$)$_3$—; and
W is selected from pyrrolidinyl, and piperidinyl, wherein each of pyrrolidinyl and piperidinyl is optionally substituted by one of -Me, -Et and -iPr;
alternatively, when L is —N(G)-, L, G, M and W may be linked to form pyrrolidinyl, piperidinyl or morpholinyl substituted by one or more groups selected from pyrrolidinyl, —OH, —F, -Me, —OMe, —CH$_2$OH, —CF$_3$, —NMe$_2$, phenyl, F-phenyl, —CONH$_2$.

In one embodiment, the compound of the invention is selected from:

4-[4-[2-(1-methylpyrrolidin-2-yl)ethoxymethyl]-1-piperidyl]-5-phenyl-thieno[2,3-d]pyrimidine
5-methyl-4-[4-[2-(1-methylpyrrolidin-2-yl)ethoxymethyl]-1-piperidyl]thieno[2,3-d]pyrimidine
4-[4-[2-(1-methylpyrrolidin-2-yl)ethoxymethyl]-1-piperidyl]thieno[2,3-d]pyrimidine
5,6-dimethyl-4-[4-[2-(1-methylpyrrolidin-2-yl)ethoxymethyl]-1-piperidyl]thieno[2,3-d]pyrimidine
5-phenyl-4-[4-(2-pyrrolidin-1-ylethoxymethyl)-1-piperidyl]thieno[2,3-d]pyrimidine
4-[2-[[1-(5-phenylthieno[2,3-d]pyrimidin-4-yl)-4-piperidyl]methoxy]ethyl]morpholine
4-[4-[(1-methylpyrrolidin-2-yl)methoxymethyl]-1-piperidyl]-5-phenyl-thieno[2,3-d]pyrimidine
N,N-dimethyl-3-[[1-(5-phenylthieno[2,3-d]pyrimidin-4-yl)-4-piperidyl]methoxy]propan-1-amine
4-[4-(cyclobutoxymethyl)-1-piperidyl]-5-phenyl-thieno[2,3-d]pyrimidine
4-[4-[2-(1-methyl-2-piperidyl)ethoxymethyl]-1-piperidyl]-5-phenyl-thieno[2,3-d]pyrimidine
N,N-dimethyl-2-[[1-(5-phenylthieno[2,3-d]pyrimidin-4-yl)-4-piperidyl]methoxy]ethanamine
4-[4-[(1-methylpyrrolidin-3-yl)oxymethyl]-1-piperidyl]-5-phenyl-thieno[2,3-d]pyrimidine
4-[4-[(1-methyl-4-piperidyl)oxymethyl]-1-piperidyl]-5-phenyl-thieno[2,3-d]pyrimidine
1-[4-[4-(2-dimethylaminoethyloxymethyl)-1-piperidyl]-5-phenyl-thieno[2,3-d]pyrimidin-2-yl]pyrrolidine-3-carboxamide
4-[4-(isopropoxymethyl)-1-piperidyl]-5-phenyl-thieno[2,3-d]pyrimidine
5-phenyl-4-[4-(tetrahydrofuran-3-yloxymethyl)-1-piperidyl]thieno[2,3-d]pyrimidine
5-(3-fluorophenyl)-4-[4-(2-pyrrolidin-1-ylethoxymethyl)-1-piperidyl]thieno[2,3-d]pyrimidine
5-ethyl-6-methyl-4-[4-(2-pyrrolidin-1-ylethoxymethyl)-1-piperidyl]thieno[2,3-d]pyrimidine
4-[2-[[1-(6-isopropylthieno[2,3-d]pyrimidin-4-yl)-4-piperidyl]methoxy]ethyl]morpholine
5-(4-fluorophenyl)-4-[4-(2-pyrrolidin-1-ylethoxymethyl)-1-piperidyl]thieno[2,3-d]pyrimidine
4-[2-[[1-[5-(4-fluorophenyl)thieno[2,3-d]pyrimidin-4-yl]-4-piperidyl]methoxy]ethyl]morpholine
4-[4-[2-(3-fluoropyrrolidin-1-yl)ethoxymethyl]-1-piperidyl]-5-phenyl-thieno[2,3-d]pyrimidine
4-[2-[[1-(5-ethyl-6-methyl-thieno[2,3-d]pyrimidin-4-yl)-4-piperidyl]methoxy]ethyl]morpholine
5-ethyl-6-methyl-4-[4-[2-(1-methylpyrrolidin-2-yl)ethoxymethyl]-1-piperidyl]thieno[2,3-d]pyrimidine
6-isopropyl-4-[4-[2-(1-methyl-2-piperidyl)ethoxymethyl]-1-piperidyl]thieno[2,3-d]pyrimidine
4-[4-[2-(3,3-difluoropyrrolidin-1-yl)ethoxymethyl]-1-piperidyl]-5-phenyl-thieno[2,3-d]pyrimidine
5-[2-[[1-(5-phenylthieno[2,3-d]pyrimidin-4-yl)-4-piperidyl]methoxy]ethyl]-2-oxa-5-azabicyclo[2.2.1]heptane
4-[2-[[1-(5-phenylthieno[2,3-d]pyrimidin-4-yl)-4-piperidyl]methoxy]ethyl]piperazin-2-one
1-[2-[[1-(5-phenylthieno[2,3-d]pyrimidin-4-yl)-4-piperidyl]methoxy]ethyl]pyrrolidine-3-carboxamide
N-[1-[2-[[1-(5-phenylthieno[2,3-d]pyrimidin-4-yl)-4-piperidyl]methoxy]ethyl]pyrrolidin-3-yl]acetamide
1-[2-[[1-(5-phenylthieno[2,3-d]pyrimidin-4-yl)-4-piperidyl]methoxy]ethyl]pyrrolidine-2-carboxamide
4-[4-[2-[(3R)-3-fluoropyrrolidin-1-yl]ethoxymethyl]-1-piperidyl]-5-phenyl-thieno[2,3-d]pyrimidine
4-[4-[2-[(3S)-3-fluoropyrrolidin-1-yl]ethoxymethyl]-1-piperidyl]-5-phenyl-thieno[2,3-d]pyrimidine
5-ethyl-6-methyl-4-[4-[2-(1-methyl-2-piperidyl)ethoxymethyl]-1-piperidyl]thieno[2,3-d]pyrimidine
5-(3-fluorophenyl)-4-[4-[2-(1-methylpyrrolidin-2-yl)ethoxymethyl]-1-piperidyl]thieno[2,3-d]pyrimidine
5-(3-fluorophenyl)-4-[4-[2-(1-methyl-2-piperidyl)ethoxymethyl]-1-piperidyl]thieno[2,3-d]pyrimidine
5-phenyl-4-[6-(2-pyrrolidin-1-ylethoxymethyl)-3-azabicyclo[3.1.0]hexan-3-yl]thieno[2,3-d]pyrimidine
4-[2-[[3-(5-phenylthieno[2,3-d]pyrimidin-4-yl)-3-azabicyclo[3.1.0]hexan-6-yl]methoxy]ethyl]morpholine
4-[6-[2-(1-methylpyrrolidin-2-yl)ethoxymethyl]-3-azabicyclo[3.1.0]hexan-3-yl]-5-phenyl-thieno[2,3-d]pyrimidine
4-[6-[2-[(3S)-3-fluoropyrrolidin-1-yl]ethoxymethyl]-3-azabicyclo[3.1.0]hexan-3-yl]-5-phenyl-thieno[2,3-d]pyrimidine
4-[6-[2-[(3R)-3-fluoropyrrolidin-1-yl]ethoxymethyl]-3-azabicyclo[3.1.0]hexan-3-yl]-5-phenyl-thieno[2,3-d]pyrimidine
(2R)-1-[2-[[3-(5-phenylthieno[2,3-d]pyrimidin-4-yl)-3-azabicyclo[3.1.0]hexan-6-yl]methoxy]ethyl]pyrrolidine-2-carboxamide
(2S)-1-[2-[[3-(5-phenylthieno[2,3-d]pyrimidin-4-yl)-3-azabicyclo[3.1.0]hexan-6-yl]methoxy]ethyl]pyrrolidine-2-carboxamide
N,N-dimethyl-4-[4-[4-(2-pyrrolidin-1-ylethoxymethyl)-1-piperidyl]thieno[2,3-d]pyrimidin-5-yl]benzenesulfonamide (2R)-1-[2-[[3-[5-(4-fluorophenyl)thieno[2,3-d]pyrimidin-4-yl]-3-azabicyclo[3.1.0]hexan-6-yl]methoxy]ethyl]pyrrolidine-2-carboxamide
5-(4-nitrophenyl)-4-[4-(2-pyrrolidin-1-ylethoxymethyl)-1-piperidyl]thieno[2,3-d]pyrimidine
5-(4-fluorophenyl)-4-[6-[2-[(3S)-3-fluoropyrrolidin-1-yl]ethoxymethyl]-3-azabicyclo[3.1.0]hexan-3-yl]thieno[2,3-d]pyrimidine
5-[2-[[3-[5-(4-fluorophenyl)thieno[2,3-d]pyrimidin-4-yl]-3-azabicyclo[3.1.0]hexan-6-yl]methoxy]ethyl]-2-oxa-5-azabicyclo[2.2.1]heptane
1-cyclopropyl-N—[[1-(5-phenylthieno[2,3-d]pyrimidin-4-yl)-4-piperidyl]methyl]methanamine
4-[4-[(3-methylpyrrolidin-1-yl)methyl]-1-piperidyl]-5-phenyl-thieno[2,3-d]pyrimidine
N—[[1-(5-phenylthieno[2,3-d]pyrimidin-4-yl)-4-piperidyl]methyl]propan-1-amine
2,2-difluoro-N—[[1-(5-phenylthieno[2,3-d]pyrimidin-4-yl)-4-piperidyl]methyl]ethanamine
2-methoxy-N-(2-methoxyethyl)-N—[[1-(5-phenylthieno[2,3-d]pyrimidin-4-yl)-4-piperidyl]methyl]ethanamine
[1-[[1-(5-phenylthieno[2,3-d]pyrimidin-4-yl)-4-piperidyl]methylamino]cyclopentyl]methanol
1-[[1-(5-phenylthieno[2,3-d]pyrimidin-4-yl)-4-piperidyl]methyl]piperidin-3-ol
2-phenyl-4-[[1-(5-phenylthieno[2,3-d]pyrimidin-4-yl)-4-piperidyl]methyl]morpholine
3-phenyl-2-[[1-(5-phenylthieno[2,3-d]pyrimidin-4-yl)-4-piperidyl]methylamino]propan-1-ol
2-(1-methylpyrrolidin-2-yl)-N—[[1-(5-phenylthieno[2,3-d]pyrimidin-4-yl)-4-piperidyl]methyl]ethanamine
2-methyl-2-morpholino-N—[[1-(5-phenylthieno[2,3-d]pyrimidin-4-yl)-4-piperidyl]methyl]propan-1-amine
N,N-dimethyl-1-[[1-(5-phenylthieno[2,3-d]pyrimidin-4-yl)-4-piperidyl]methyl]piperidin-3-amine
1-(2-furyl)-N—[[1-(5-phenylthieno[2,3-d]pyrimidin-4-yl)-4-piperidyl]methyl]methanamine
N',N'-diisopropyl-N—[[1-(5-phenylthieno[2,3-d]pyrimidin-4-yl)-4-piperidyl]methyl]ethane-1,2-diamine
N'-[[1-(5-phenylthieno[2,3-d]pyrimidin-4-yl)-4-piperidyl]methyl]ethane-1,2-diamine
N—[[1-(5-phenylthieno[2,3-d]pyrimidin-4-yl)-4-piperidyl]methyl]cyclobutanamine
[1-[[1-(5-phenylthieno[2,3-d]pyrimidin-4-yl)-4-piperidyl]methyl]pyrrolidin-2-yl]methanol
N—[[1-(5-phenylthieno[2,3-d]pyrimidin-4-yl)-4-piperidyl]methyl]-1-(2-pyridyl)methanamine
(3S,4S)-1-[[1-(5-phenylthieno[2,3-d]pyrimidin-4-yl)-4-piperidyl]methyl]-4-pyrrolidin-1-yl-pyrrolidin-3-ol
4-[4-[(3-methoxypyrrolidin-1-yl)methyl]-1-piperidyl]-5-phenyl-thieno[2,3-d]pyrimidine
N—[[1-(5-phenylthieno[2,3-d]pyrimidin-4-yl)-4-piperidyl]methyl]-1-(2-thienyl)methanamine
4-[4-[[3-(4-fluorophenyl)pyrrolidin-1-yl]methyl]-1-piperidyl]-5-phenyl-thieno[2,3-d]pyrimidine
N,N,N'-trimethyl-N'-[[1-(5-phenylthieno[2,3-d]pyrimidin-4-yl)-4-piperidyl]methyl]ethane-1,2-diamine
N,N,N'-trimethyl-N'-[[1-(5-phenylthieno[2,3-d]pyrimidin-4-yl)-4-piperidyl]methyl]propane-1,3-diamine
4-[4-(azetidin-1-ylmethyl)-1-piperidyl]-5-phenyl-thieno[2,3-d]pyrimidine
N—[[1-(5-phenylthieno[2,3-d]pyrimidin-4-yl)-4-piperidyl]methyl]cyclopropanamine
N,N-dimethyl-1-[[1-(5-phenylthieno[2,3-d]pyrimidin-4-yl)-4-piperidyl]methyl]piperidin-4-amine
5-phenyl-4-[4-[(3-pyrrolidin-1-ylpyrrolidin-1-yl)methyl]-1-piperidyl]thieno[2,3-d]pyrimidine
N—[[1-[5-(4-fluorophenyl)thieno[2,3-d]pyrimidin-4-yl]-4-piperidyl]methyl]cyclopropanamine
N—[[1-[5-(4-fluorophenyl)thieno[2,3-d]pyrimidin-4-yl]-4-piperidyl]methyl]cyclobutanamine
1-[[1-[5-(4-fluorophenyl)thieno[2,3-d]pyrimidin-4-yl]-4-piperidyl]methyl]-N,N-dimethyl-piperidin-3-amine
2-(1-methyl-2-piperidyl)-N—[[1-(5-phenylthieno[2,3-d]pyrimidin-4-yl)-4-piperidyl]methyl]ethanamine
(3R)—N,N-dimethyl-1-[[1-(5-phenylthieno[2,3-d]pyrimidin-4-yl)-4-piperidyl]methyl]pyrrolidin-3-amine
tert-butyl2-[2-[[1-(5-phenylthieno[2,3-d]pyrimidin-4-yl)-4-piperidyl]methylamino]ethyl]pyrrolidine-1-carboxylate
N-methyl-1-[1-(5-phenylthieno[2,3-d]pyrimidin-4-yl)-4-piperidyl]-N-(pyrrolidin-2-ylmethyl)methanamine
N-[(1-methylpyrrolidin-2-yl)methyl]-1-[1-(5-phenylthieno[2,3-d]pyrimidin-4-yl)-4-piperidyl]methanamine
N—[[1-(5-phenylthieno[2,3-d]pyrimidin-4-yl)-4-piperidyl]methyl]-2-pyrrolidin-2-yl-ethanamine
N-methyl-N—[[1-(5-phenylthieno[2,3-d]pyrimidin-4-yl)-4-piperidyl]methyl]-2-pyrrolidin-2-yl-ethanamine
2-(1-ethylpyrrolidin-2-yl)-N-methyl-N—[[1-(5-phenylthieno[2,3-d]pyrimidin-4-yl)-4-piperidyl]methyl]ethanamine
2-(1-isopropylpyrrolidin-2-yl)-N-methyl-N—[[1-(5-phenylthieno[2,3-d]pyrimidin-4-yl)-4-piperidyl]methyl]ethanamine
1-[2-[2-[methyl-[[1-(5-phenylthieno[2,3-d]pyrimidin-4-yl)-4-piperidyl]methyl]amino]ethyl]pyrrolidin-1-yl]ethanone
(3S)-1-[[1-(5-phenylthieno[2,3-d]pyrimidin-4-yl)-4-piperidyl]methyl]piperidin-3-amine
1-methyl-4-[[1-(5-phenylthieno[2,3-d]pyrimidin-4-yl)-4-piperidyl]methylamino]pyrrolidin-2-one
4-[4-[[(3S)-3-fluoropyrrolidin-1-yl]methyl]-1-piperidyl]-5-phenyl-thieno[2,3-d]pyrimidine
2-[methyl-[[1-(5-phenylthieno[2,3-d]pyrimidin-4-yl)-4-piperidyl]methyl]amino]-1-pyrrolidin-1-yl-ethanone
N—[[1-(5-phenylthieno[2,3-d]pyrimidin-4-yl)-4-piperidyl]methyl]prop-2-en-1-amine
[1-[[1-(5-phenylthieno[2,3-d]pyrimidin-4-yl)-4-piperidyl]methyl]pyrrolidin-3-yl]methanol
N-[1-[1-(5-phenylthieno[2,3-d]pyrimidin-4-yl)-4-piperidyl]ethyl]cyclopropanamine
1-methyl-N—[[1-(5-phenylthieno[2,3-d]pyrimidin-4-yl)-4-piperidyl]methyl]piperidin-4-amine
4-[4-[(2,5-dimethylpyrrolidin-1-yl)methyl]-1-piperidyl]-5-phenyl-thieno[2,3-d]pyrimidine
5-phenyl-4-[4-[[4-(trifluoromethyl)-1-piperidyl]methyl]-1-piperidyl]thieno[2,3-d]pyrimidine
2-[(2S)-1-methylpyrrolidin-2-yl]-N—[[1-(5-phenylthieno[2,3-d]pyrimidin-4-yl)-4-piperidyl]methyl]ethanamine
N-methyl-2-(1-methylpyrrolidin-2-yl)-N—[[1-(5-phenylthieno[2,3-d]pyrimidin-4-yl)-4-piperidyl]methyl]ethanamine
N—[[1-(5-phenylthieno[2,3-d]pyrimidin-4-yl)-4-piperidyl]methyl]-2-tetrahydrofuran-2-yl-ethanamine
2-cyclopropyl-N—[[1-(5-phenylthieno[2,3-d]pyrimidin-4-yl)-4-piperidyl]methyl]ethanamine
2-(1-methylpyrrolidin-3-yl)-N—[[1-(5-phenylthieno[2,3-d]pyrimidin-4-yl)-4-piperidyl]methyl]ethanamine
2-[[1-(5-phenylthieno[2,3-d]pyrimidin-4-yl)-4-piperidyl]methylamino]-1-pyrrolidin-1-yl-ethanone
(2S)-1-[[1-(5-phenylthieno[2,3-d]pyrimidin-4-yl)-4-piperidyl]methyl]pyrrolidine-2-carboxamide
2-[2-hydroxyethyl-[[1-[2-(4-methylpiperazin-1-yl)-5-phenyl-thieno[2,3-d]pyrimidin-4-yl]-4-piperidyl]methyl]amino]ethanol 4-[4-[(isopropylamino)methyl]-1-piperidyl]-5-phenyl-N-(2-pyrrolidin-1-ylethyl)thieno[2,3-d]pyrimidin-2-amine 4-[4-[(2-methoxyethylamino)methyl]-1-piperidyl]-5-phenyl-N-(2-pyrrolidin-1-ylethyl)thieno[2,3-d]pyrimidin-2-amine 4-[4-[[methyl-(1-methylpyrrolidin-3-yl)amino]methyl]-1-piperidyl]-5-phenyl-N-(2-pyrrolidin-1-ylethyl)thieno[2,3-d]pyrimidin-2-amine N,1-dimethyl-N—[[1-[2-(4-methylpiperazin-1-yl)-5-phenyl-thieno[2,3-d]pyrimidin-4-yl]-4-piperidyl]methyl]pyrrolidin-3-amine N,1-dimethyl-N—[[1-(5-phenyl-2-piperazin-1-yl-thieno[2,3-d]pyrimidin-4-yl)-4-piperidyl]methyl]pyrrolidin-3-amine

[1-[[1-[2-(4-methylpiperazin-1-yl)-5-phenyl-thieno[2,3-d]pyrimidin-4-yl]-4-piperidyl]methylamino]cyclopentyl]methanol N—[[1-[2-(4-methylpiperazin-1-yl)-5-phenyl-thieno[2,3-d]pyrimidin-4-yl]-4-piperidyl]methyl]-2-(1-methylpyrrolidin-2-yl)ethanamine N,N-dimethyl-1-[[1-[2-(4-methylpiperazin-1-yl)-5-phenyl-thieno[2,3-d]pyrimidin-4-yl]-4-piperidyl]methyl]piperidin-3-amine N—[[1-[2-(4-methylpiperazin-1-yl)-5-phenyl-thieno[2,3-d]pyrimidin-4-yl]-4-piperidyl]methyl]cyclobutanamine 4-[4-[[3-(dimethylamino)-1-piperidyl]methyl]-1-piperidyl]-5-phenyl-N-(2-pyrrolidin-1-ylethyl)thieno[2,3-d]pyrimidin-2-amine N-(2-methoxyethyl)-4-[4-[[methyl-(1-methylpyrrolidin-3-yl)amino]methyl]-1-piperidyl]-5-phenyl-thieno[2,3-d]pyrimidin-2-amine N-(cyclopropylmethyl)-4-[4-[[methyl-(1-methylpyrrolidin-3-yl)amino]methyl]-1-piperidyl]-5-phenyl-thieno[2,3-d]pyrimidin-2-amine 1-[4-[4-[[methyl-(1-methylpyrrolidin-3-yl)amino]methyl]-1-piperidyl]-5-phenyl-thieno[2,3-d]pyrimidin-2-yl]pyrrolidine-3-carboxamide 2-[methyl-[4-[4-[[methyl-(1-methylpyrrolidin-3-yl)amino]methyl]-1-piperidyl]-5-phenyl-thieno[2,3-d]pyrimidin-2-yl]amino]acetamide N—[[1-[2-[4-(2-methoxyethyl)piperazin-1-yl]-5-phenyl-thieno[2,3-d]pyrimidin-4-yl]-4-piperidyl]methyl]-N,1-dimethyl-pyrrolidin-3-amine 1-[4-[4-[[3-(dimethylamino)-1-piperidyl]methyl]-1-piperidyl]-5-phenyl-thieno[2,3-d]pyrimidin-2-yl]pyrrolidine-3-carboxamide 4-[4-[[3-(dimethylamino)-1-piperidyl]methyl]-1-piperidyl]-N-(2-methoxyethyl)-5-phenyl-thieno[2,3-d]pyrimidin-2-amine 4-[4-[4-[(cyclobutylamino)methyl]-1-piperidyl]-5-phenyl-thieno[2,3-d]pyrimidin-2-yl]piperazin-2-one 4-[4-[(cyclobutylamino)methyl]-1-piperidyl]-N-(2-methoxyethyl)-5-phenyl-thieno[2,3-d]pyrimidin-2-amine 4-[4-[(cyclobutylamino)methyl]-1-piperidyl]-5-phenyl-N-(2-pyrrolidin-1-ylethyl)thieno[2,3-d]pyrimidin-2-amine 1-[4-[4-[(cyclobutylamino)methyl]-1-piperidyl]-5-phenyl-thieno[2,3-d]pyrimidin-2-yl]pyrrolidine-3-carboxamide 1-[4-[4-[[methyl-(1-methylpyrrolidin-3-yl)amino]methyl]-1-piperidyl]-5-phenyl-thieno[2,3-d]pyrimidin-2-yl]piperidine-2-carboxamide 1-[4-[4-[[methyl-(1-methylpyrrolidin-3-yl)amino]methyl]-1-piperidyl]-5-phenyl-thieno[2,3-d]pyrimidin-2-yl]pyrrolidine-2-carboxamide N-methyl-4-[4-[[methyl-(1-methylpyrrolidin-3-yl)amino]methyl]-1-piperidyl]-5-phenyl-thieno[2,3-d]pyrimidine-6-carboxamide N-isopropyl-4-[4-[[methyl-(1-methylpyrrolidin-3-yl)amino]methyl]-1-piperidyl]-5-phenyl-thieno[2,3-d]pyrimidine-6-carboxamide 5-isopropyl-N,N-dimethyl-4-[4-(2-pyrrolidin-1-ylethoxymethyl)-1-piperidyl]thieno[2,3-d]pyrimidine-6-carboxamide 5-isopropyl-N-methyl-4-[4-(2-pyrrolidin-1-ylethoxymethyl)-1-piperidyl]thieno[2,3-d]pyrimidine-6-carboxamide N,N-dimethyl-5-phenyl-4-[4-(2-pyrrolidin-1-ylethoxymethyl)-1-piperidyl]thieno[2,3-d]pyrimidine-6-carboxamide N,N-dimethyl-4-[4-[[methyl-(1-methylpyrrolidin-3-yl)amino]methyl]-1-piperidyl]-5-phenyl-thieno[2,3-d]pyrimidine-6-carboxamide 5-(3-fluorophenyl)-N-isopropyl-4-[4-(2-pyrrolidin-1-ylethoxymethyl)-1-piperidyl]thieno[2,3-d]pyrimidine-6-carboxamide 5-(3-fluorophenyl)-N,N-dimethyl-4-[4-(2-pyrrolidin-1-ylethoxymethyl)-1-piperidyl]thieno[2,3-d]pyrimidine-6-carboxamide

[5-phenyl-4-[4-(2-pyrrolidin-1-ylethoxymethyl)-1-piperidyl]thieno[2,3-d]pyrimidin-6-yl]-pyrrolidin-1-yl-methanone N-isopropyl-5-phenyl-4-[4-(2-pyrrolidin-1-ylethoxymethyl)-1-piperidyl]thieno[2,3-d]pyrimidine-6-carboxamide N-methyl-5-phenyl-4-[4-(2-pyrrolidin-1-ylethoxymethyl)-1-piperidyl]thieno[2,3-d]pyrimidine-6-carboxamide 3-phenyl-4-[4-(2-pyrrolidin-1-ylethoxymethyl)-1-piperidyl]thieno[2,3-b]pyridine 2-bromo-3-phenyl-4-[4-(2-pyrrolidin-1-ylethoxymethyl)-1-piperidyl]thieno[2,3-b]pyridine 3-phenyl-4-[4-(2-pyrrolidin-1-ylethoxymethyl)-1-piperidyl]thieno[2,3-b]pyridine-2-carbonitrile 5-phenyl-2-[4-(2-pyrrolidin-1-ylethyl)piperazin-1-yl]thieno[2,3-d]pyrimidine 2-(1-methylpyrrolidin-2-yl)-N—[[1-(5-phenylthieno[2,3-d]pyrimidin-2-yl)-4-piperidyl]methyl]ethanamine (2R)-1-[2-[4-(5-phenylthieno[2,3-d]pyrimidin-2-yl)piperazin-1-yl]ethyl]pyrrolidine-2-carboxamide 5-phenyl-2-[4-(2-pyrrolidin-1-ylethoxymethyl)-1-piperidyl]thieno[2,3-d]pyrimidine 5-phenyl-2-[3-(2-pyrrolidin-1-ylethoxymethyl)pyrrolidin-1-yl]thieno[2,3-d]pyrimidine (3R)-1-[2-[4-(5-phenylthieno[2,3-d]pyrimidin-2-yl)piperazin-1-yl]ethyl]pyrrolidine-3-carboxamide 2-[4-[2-[(3R)-3-fluoropyrrolidin-1-yl]ethoxymethyl]-1-piperidyl]-5-phenyl-thieno[2,3-d]pyrimidine 5-(4-fluorophenyl)-2-[4-(2-pyrrolidin-1-ylethoxymethyl)-1-piperidyl]thieno[2,3-d]pyrimidine 1-[2-[[1-(5-phenylthieno[2,3-d]pyrimidin-2-yl)-4-piperidyl]methoxy]ethyl]pyrrolidine-3-carboxamide 5-[2-[[1-(5-phenylthieno[2,3-d]pyrimidin-2-yl)-4-piperidyl]methoxy]ethyl]-2-oxa-5-azabicyclo[2.2.1]heptane N-[5-phenyl-2-[4-(2-pyrrolidin-1-ylethoxymethyl)-1-piperidyl]thieno[2,3-d]pyrimidin-6-yl]acetamide 1-[5-phenyl-2-[4-(2-pyrrolidin-1-ylethoxymethyl)-1-piperidyl]thieno[2,3-d]pyrimidin-6-yl]pyrrolidin-2-one 5-isopropyl-2-[4-(2-pyrrolidin-1-ylethoxymethyl)-1-piperidyl]thieno[2,3-d]pyrimidine 1-[5-phenyl-2-[4-(2-pyrrolidin-1-ylethoxymethyl)-1-piperidyl]thieno[2,3-d]pyrimidin-6-yl]pyrrolidin-2-one 5-isopropyl-2-[4-(2-pyrrolidin-1-ylethoxymethyl)-1-piperidyl]thieno[2,3-d]pyrimidine 4-[3-[(1-methylpyrrolidin-3-yl)methoxy]prop-1-ynyl]-5-phenyl-thieno[2,3-d]pyrimidine 5-phenyl-4-[3-(2-pyrrolidin-1-ylethoxy)prop-1-ynyl]thieno[2,3-d]pyrimidine
N-[5-phenyl-4-[4-(2-pyrrolidin-1-ylethoxymethyl)-1-piperidyl]thieno[2,3-d]pyrimidin-6-yl]acetamide
1-[5-phenyl-4-[4-(2-pyrrolidin-1-ylethoxymethyl)-1-piperidyl]thieno[2,3-d]pyrimidin-6-yl]pyrrolidin-2-one
5-phenyl-4-[(1S,5R)-3-(2-pyrrolidin-1-ylethoxymethyl)-8-azabicyclo[3.2.1]octan-8-yl]thieno[2,3-d]pyrimidine
[8-(4-morpholino-5-phenyl-thieno[2,3-d]pyrimidin-2-yl)-8-azabicyclo[3.2.1]octan-3-yl]methanol
N-[2-(1-methylpyrrolidin-2-yl)ethyl]-1-(5-phenylthieno[2,3-d]pyrimidin-4-yl)piperidine-4-carboxamide
5-phenyl-4-[4-(2-pyrrolidin-1-ylethoxymethyl)-1-piperidyl]thieno[2,3-d]pyrimidine-6-carbonitrile
N-benzyl-5-phenyl-4-[4-(2-pyrrolidin-1-ylethoxymethyl)-1-piperidyl]thieno[2,3-d]pyrimidin-6-amine
N,N-dimethyl-1-(5-phenylthieno[2,3-d]pyrimidin-4-yl)piperidin-4-amine
1-(2-ethyl-5-phenyl-thieno[2,3-d]pyrimidin-4-yl)-N,N-dimethyl-piperidin-4-amine
2-[1-[5-(4-fluorophenyl)-2-(2-hydroxyethylamino)thieno[2,3-d]pyrimidin-4-yl]-4-piperidyl]ethanol
4-[4-(methoxymethyl)-1-piperidyl]-5-phenyl-thieno[2,3-d]pyrimidine
N-[4-[4-(methoxymethyl)-1-piperidyl]-5-phenyl-thieno[2,3-d]pyrimidin-2-yl]-N',N'-dimethyl-ethane-1,2-diamine
4-[4-(methoxymethyl)-1-piperidyl]-2-(4-methylpiperazin-1-yl)-5-phenyl-thieno[2,3-d]pyrimidine
4-[4-(methoxymethyl)-1-piperidyl]-5-phenyl-N-(2-pyrrolidin-1-ylethyl)thieno[2,3-d]pyrimidin-2-amine
4-[4-(4-methoxyphenyl)-1-piperidyl]-5-phenyl-thieno[2,3-d]pyrimidine
5-cyclohexyl-4-[4-(methoxymethyl)-1-piperidyl]-N-[2-(1-methylpyrrolidin-2-yl)ethyl]thieno[2,3-d]pyrimidin-2-amine
4-(3-benzyloxypyrrolidin-1-yl)-5-phenyl-thieno[2,3-d]pyrimidine
4-[4-(dimethylamino)-1-piperidyl]-5-phenyl-N-(2-pyrrolidin-1-ylethyl)thieno[2,3-d]pyrimidin-2-amine
5-phenyl-4-[4-(3-pyridyloxymethyl)-1-piperidyl]thieno[2,3-d]pyrimidine
5-phenyl-4-[3-(1-piperidyl)pyrrolidin-1-yl]thieno[2,3-d]pyrimidine
2-[4-[4-(methoxymethyl)-1-piperidyl]-5-phenyl-thieno[2,3-d]pyrimidin-2-yl]-N-(2-pyrrolidin-1-ylethyl)acetamide
2-[4-[4-(methoxymethyl)-1-piperidyl]-5-phenyl-thieno[2,3-d]pyrimidin-2-yl]-1-pyrrolidin-1-yl-ethanone
5-(4-fluorophenyl)-4-[4-(methoxymethyl)-1-piperidyl]-2-(2-pyrrolidin-1-ylethyl)thieno[2,3-d]pyrimidine
2-[[4-[4-(methoxymethyl)-1-piperidyl]-5-phenyl-thieno[2,3-d]pyrimidin-2-yl]-(2-pyrrolidin-1-ylethyl)amino]ethanol
2-[2-hydroxyethyl-[[1-(5-phenylthieno[2,3-d]pyrimidin-4-yl)-4-piperidyl]methyl]amino]ethanol
N—[[1-(5-phenylthieno[2,3-d]pyrimidin-4-yl)-4-piperidyl]methyl]propan-2-amine
1-[4-[4-(dimethylamino)-1-piperidyl]-5-phenyl-thieno[2,3-d]pyrimidin-2-yl]pyrrolidin-3-ol
1-[5-phenyl-2-(2-pyrrolidin-1-ylethylamino)thieno[2,3-d]pyrimidin-4-yl]pyrrolidin-3-ol
(3S)-1-[[1-(5-phenylthieno[2,3-d]pyrimidin-4-yl)-4-piperidyl]methyl]pyrrolidin-3-ol
[1-[4-[4-(methoxymethyl)-1-piperidyl]-5-phenyl-thieno[2,3-d]pyrimidin-2-yl]-4-piperidyl]methanol
2-methoxy-N—[[1-[4-[4-(methoxymethyl)-1-piperidyl]-5-phenyl-thieno[2,3-d]pyrimidin-2-yl]-4-piperidyl]methyl]ethanamine
4-[4-(methoxymethyl)-1-piperidyl]-N-methyl-N-(1-methylpyrrolidin-3-yl)-5-phenyl-thieno[2,3-d]pyrimidin-2-amine
5-cyclohexyl-4-[4-(methoxymethyl)-1-piperidyl]-2-piperazin-1-yl-thieno[2,3-d]pyrimidine
1-(5-phenylthieno[2,3-d]pyrimidin-4-yl)-4-(pyrrolidin-1-ylmethyl)piperidin-4-ol
N—[[1-(5-cyclohexylthieno[2,3-d]pyrimidin-4-yl)-4-piperidyl]methyl]propan-2-amine
4-[[1-(5-cyclohexylthieno[2,3-d]pyrimidin-4-yl)-4-piperidyl]methyl]-2,6-dimethyl-morpholine
4-[4-[(3-methylpyrrolidin-1-yl)methyl]-2-phenyl-pyrrolidin-1-yl]-5-phenyl-thieno[2,3-d]pyrimidine
2-[5-(4-fluorophenyl)-4-(2-phenylpyrrolidin-1-yl)thieno[2,3-d]pyrimidin-2-yl]-N-(2-pyrrolidin-1-ylethyl)acetamide
1-[[1-(5-cyclohexylthieno[2,3-d]pyrimidin-4-yl)-4-piperidyl]methyl]pyrrolidin-3-ol
2-[[1-(5-cyclohexylthieno[2,3-d]pyrimidin-4-yl)-4-piperidyl]methyl-(2-hydroxyethyl)amino]ethanol
N,1-dimethyl-N—[[1-(5-phenylthieno[2,3-d]pyrimidin-4-yl)-4-piperidyl]methyl]pyrrolidin-3-amine
N-methyl-N—[[1-(5-phenylthieno[2,3-d]pyrimidin-4-yl)-4-piperidyl]methyl]tetrahydrofuran-3-amine
2-(1-methylpyrrolidin-2-yl)-N—[[1-(5-phenylthieno[2,3-d]pyrimidin-4-yl)pyrrolidin-3-yl]methyl]ethanamine
N,1-dimethyl-N—[[1-(5-phenylthieno[2,3-d]pyrimidin-4-yl)pyrrolidin-3-yl]methyl]pyrrolidin-3-amine
N—[[1-(5-phenylthieno[2,3-d]pyrimidin-4-yl)-4-piperidyl]methyl]-2-pyrrolidin-1-yl-ethanamine
N—[[1-(5-phenylthieno[2,3-d]pyrimidin-4-yl)-3-piperidyl]methyl]cyclobutanamine
N,N-dimethyl-1-[[1-(5-phenylthieno[2,3-d]pyrimidin-4-yl)-3-piperidyl]methyl]piperidin-3-amine
N—[[5-methyl-1-(5-phenylthieno[2,3-d]pyrimidin-4-yl)pyrrolidin-3-yl]methyl]-2-(1-methylpyrrolidin-2-yl)ethanamine
2-(1-methylpyrrolidin-2-yl)-N—[[1-(5-methylthieno[2,3-d]pyrimidin-4-yl)-5-phenyl-pyrrolidin-3-yl]methyl]ethanamine
1-[[1-(5-phenylthieno[2,3-d]pyrimidin-4-yl)-4-piperidyl]methyl]piperidin-3-amine
5-phenyl-4-[4-[[3-(trifluoromethyl)-1-piperidyl]methyl]-1-piperidyl]thieno[2,3-d]pyrimidine
4-[[1-(5-phenylthieno[2,3-d]pyrimidin-4-yl)-4-piperidyl]methyl]piperazin-2-one
4-[4-[(4-methylpiperazin-1-yl)methyl]-1-piperidyl]-5-phenyl-thieno[2,3-d]pyrimidine
(3S)—N,N-dimethyl-1-[[1-(5-phenylthieno[2,3-d]pyrimidin-4-yl)-4-piperidyl]methyl]piperidin-3-amine
(3R)—N,N-dimethyl-1-[[1-(5-phenylthieno[2,3-d]pyrimidin-4-yl)-4-piperidyl]methyl]piperidin-3-amine
N',N'-dimethyl-N—[[1-(5-phenylthieno[2,3-d]pyrimidin-4-yl)-4-piperidyl]methyl]propane-1,3-diamine
5-phenyl-4-[4-[[3-(1-piperidyl)pyrrolidin-1-yl]methyl]-1-piperidyl]thieno[2,3-d]pyrimidine
2-(1-methylpyrrolidin-2-yl)-N—[[1-(5-phenylthieno[2,3-d]pyrimidin-4-yl)azetidin-3-yl]methyl]ethanamine
N—[[1-(5,6-dimethylthieno[2,3-d]pyrimidin-4-yl)-4-piperidyl]methyl]-2-(1-methylpyrrolidin-2-yl)ethanamine
2-(1-methylimidazol-2-yl)-N—[[1-(5-phenylthieno[2,3-d]pyrimidin-4-yl)-4-piperidyl]methyl]ethanamine
N,N-dimethyl-1-[1-(5-phenylthieno[2,3-d]pyrimidin-4-yl)-4-piperidyl]piperidin-4-amine
1-methyl-N-[1-(5-phenylthieno[2,3-d]pyrimidin-4-yl)-4-piperidyl]piperidin-4-amine
N-[2-(1-methylpyrrolidin-2-yl)ethyl]-1-(5-phenylthieno[2,3-d]pyrimidin-4-yl)piperidine-4-carboxamide 1-[4-[4-[[2-dimethylaminoethyl(methyl)amino]methyl]-1-piperidyl]-5-phenyl-thieno[2,3-d]pyrimidin-2-yl]pyrrolidine-3-carboxamide N-[1-[4-[4-[[methyl-(1-methylpyrrolidin-3-yl)amino]methyl]-1-piperidyl]-5-phenyl-thieno[2,3-d]pyrimidin-2-yl]pyrrolidin-3-yl]acetamide N-methyl-1-[4-[4-[[methyl-(1-methylpyrrolidin-3-yl)amino]methyl]-1-piperidyl]-5-phenyl-thieno[2,3-d]pyrimidin-2-yl]piperidine-3-carboxamide N,N-diethyl-1-[4-[4-[[methyl-(1-methylpyrrolidin-3-yl)amino]methyl]-1-piperidyl]-5-phenyl-thieno[2,3-d]pyrimidin-2-yl]piperidine-3-carboxamide (2R)-1-[4-[4-[[methyl-(1-methylpyrrolidin-3-yl)amino]methyl]-1-piperidyl]-5-phenyl-thieno[2,3-d]pyrimidin-2-yl]pyrrolidine-2-carboxamide 4-[4-(4-methylpiperazin-1-yl)-1-piperidyl]-5-phenyl-thieno[2,3-d]pyrimidine N-methyl-N-(1-methylpyrrolidin-3-yl)-1-(5-phenylthieno[2,3-d]pyrimidin-4-yl)piperidin-4-amine N—[[1-(5,6-dimethylthieno[2,3-d]pyrimidin-4-yl)-4-piperidyl]methyl]-1-methyl-piperidin-4-amine N—[[1-(5,6-dimethylthieno[2,3-d]pyrimidin-4-yl)-4-piperidyl]methyl]-2-(1-methyl-2-piperidyl)ethanamine 1-[[1-(5,6-dimethylthieno[2,3-d]pyrimidin-4-yl)-4-piperidyl]methyl]-N,N-dimethyl-piperidin-3-amine 1-[4-[4-[[4-(dimethylamino)-1-piperidyl]methyl]-1-piperidyl]-5-phenyl-thieno[2,3-d]pyrimidin-2-yl]pyrrolidine-3-carboxamide 1-[4-[4-[[(3R)-3-(dimethylamino)pyrrolidin-1-yl]methyl]-1-piperidyl]-5-phenyl-thieno[2,3-d]pyrimidin-2-yl]pyrrolidine-3-carboxamide 1-[4-[4-[[methyl-(1-methylpyrrolidin-3-yl)amino]methyl]-1-piperidyl]-5-phenyl-thieno[2,3-d]pyrimidin-2-yl]azetidine-3-carboxamide 1-[4-[4-[[methyl-(1-methylpyrrolidin-3-yl)amino]methyl]-1-piperidyl]-5-phenyl-thieno[2,3-d]pyrimidin-2-yl]piperidine-3-carboxamide 1-[4-[4-[[methyl-(1-methylpyrrolidin-3-yl)amino]methyl]-1-piperidyl]-5-phenyl-thieno[2,3-d]pyrimidin-2-yl]piperidine-4-carboxamide 1-[5,6-dimethyl-4-[4-[[2-(1-methyl-2-piperidyl)ethylamino]methyl]-1-piperidyl]thieno[2,3-d]pyrimidin-2-yl]pyrrolidine-3-carboxamide N-methyl-N-[1-[4-[4-[[methyl-(1-methylpyrrolidin-3-yl)amino]methyl]-1-piperidyl]-5-phenyl-thieno[2,3-d]pyrimidin-2-yl]-4-piperidyl]acetamide N—[[1-(5-isopropylthieno[2,3-d]pyrimidin-4-yl)-4-piperidyl]methyl]-2-(1-methylpyrrolidin-2-yl)ethanamine 2-(1-methylpyrrolidin-2-yl)-N—[[1-(5-methylthieno[2,3-d]pyrimidin-4-yl)-4-piperidyl]methyl]ethanamine 1-[[4-[4-[[methyl-(1-methylpyrrolidin-3-yl)amino]methyl]-1-piperidyl]-5-phenyl-thieno[2,3-d]pyrimidin-2-yl]methyl]pyrrolidin-2-one 1-[5-isopropyl-4-[4-[[methyl-(1-methylpyrrolidin-3-yl)amino]methyl]-1-piperidyl]thieno[2,3-d]pyrimidin-2-yl]pyrrolidine-3-carboxamide N,N-diethyl-1-[[1-(5-phenylthieno[2,3-d]pyrimidin-4-yl)-4-piperidyl]methyl]piperidine-3-carboxamide 1-[[1-(5-phenylthieno[2,3-d]pyrimidin-4-yl)-4-piperidyl]methyl]pyrrolidine-2-carboxamide N-methyl-N-[1-[[1-(5-phenylthieno[2,3-d]pyrimidin-4-yl)-4-piperidyl]methyl]pyrrolidin-3-yl]acetamide N-methyl-N-(1-methylpyrrolidin-3-yl)-1-(5-phenylthieno[2,3-d]pyrimidin-4-yl)piperidine-4-carboxamide 1-methyl-4-[methyl-[[1-(5-phenylthieno[2,3-d]pyrimidin-4-yl)-4-piperidyl]methyl]amino]pyrrolidin-2-one N-methyl-N—[[1-(5-phenylthieno[2,3-d]pyrimidin-4-yl)-4-piperidyl]methyl]cyclobutanamine 2-[cyclobutyl-[[1-(5-phenylthieno[2,3-d]pyrimidin-4-yl)-4-piperidyl]methyl]amino]-N-methyl-acetamide N-[1-[[1-(5-phenylthieno[2,3-d]pyrimidin-4-yl)-4-piperidyl]methyl]pyrrolidin-3-yl]acetamide (2S)—N,N-dimethyl-2-[[1-(5-phenylthieno[2,3-d]pyrimidin-4-yl)-4-piperidyl]methoxy]propan-1-amine 1-[4-[4-[2-(1-methylpyrrolidin-2-yl)ethoxymethyl]-1-piperidyl]-5-phenyl-thieno[2,3-d]pyrimidin-2-yl]pyrrolidine-3-carboxamide 1-[5-phenyl-4-[4-(2-pyrrolidin-1-ylethoxymethyl)-1-piperidyl]thieno[2,3-d]pyrimidin-2-yl]pyrrolidine-3-carboxamide N-[1-[5-phenyl-4-[4-(2-pyrrolidin-1-ylethoxymethyl)-1-piperidyl]thieno[2,3-d]pyrimidin-2-yl]pyrrolidin-3-yl]acetamide 1-[4-[4-(2-morpholinoethoxymethyl)-1-piperidyl]-5-phenyl-thieno[2,3-d]pyrimidin-2-yl]pyrrolidine-3-carboxamide N-[1-[4-[4-(2-morpholinoethoxymethyl)-1-piperidyl]-5-phenyl-thieno[2,3-d]pyrimidin-2-yl]pyrrolidin-3-yl]acetamide N-methyl-[[1-(5-phenylthieno[2,3-d]pyrimidin-4-yl)-4-piperidyl]methylamino]cyclobutanecarboxamide 1-[4-[2-[[1-(5-phenylthieno[2,3-d]pyrimidin-4-yl)-4-piperidyl]methoxy]ethyl]piperazin-1-yl]ethanone 5-phenyl-4-[(3R)-3-(2-pyrrolidin-1-ylethoxymethyl)pyrrolidin-1-yl]thieno[2,3-d]pyrimidine 5-phenyl-4-[(3S)-3-(2-pyrrolidin-1-ylethoxymethyl)pyrrolidin-1-yl]thieno[2,3-d]pyrimidine N,5-diisopropyl-4-[4-(2-pyrrolidin-1-ylethoxymethyl)-1-piperidyl]thieno[2,3-d]pyrimidine-6-carboxamide 5-isopropyl-4-[4-(2-pyrrolidin-1-ylethoxymethyl)-1-piperidyl]thieno[2,3-d]pyrimidine N—[[1-(6-bromo-5-phenyl-thieno[2,3-d]pyrimidin-4-yl)-4-piperidyl]methyl]-N,1-dimethyl-pyrrolidin-3-amine 1-(5-phenylthieno[2,3-d]pyrimidin-4-yl)-N-(2-pyrrolidin-1-ylethyl)piperidine-4-carboxamide 1-(5-phenylthieno[2,3-d]pyrimidin-4-yl)-N-(2-pyrrolidin-1-ylethyl)piperidine-3-carboxamide 5-phenyl-4-[3-(2-pyrrolidin-1-ylethoxy)pyrrolidin-1-yl]thieno[2,3-d]pyrimidine 1-(5-phenylthieno[2,3-d]pyrimidin-4-yl)-N-(2-pyrrolidin-1-ylethyl)pyrrolidine-3-carboxamide 5-phenyl-4-[4-(2-pyrrolidin-1-ylethoxy)-1-piperidyl]thieno[2,3-d]pyrimidine 5-phenyl-4-[3-(2-pyrrolidin-1-ylethoxy)-1-piperidyl]thieno[2,3-d]pyrimidine 5-phenyl-4-[3-(2-pyrrolidin-1-ylethoxymethyl)azetidin-1-yl]thieno[2,3-d]pyrimidine 1-[5-phenyl-2-[4-(2-pyrrolidin-1-ylethoxymethyl)-1-piperidyl]thieno[2,3-d]pyrimidin-4-yl]pyrrolidine-3-carboxamide N,N-dimethyl-5-phenyl-2-[4-(2-pyrrolidin-1-ylethoxymethyl)-1-piperidyl]thieno[2,3-d]pyrimidin-4-amine 4-[5-phenyl-2-[4-(2-pyrrolidin-1-ylethoxymethyl)-1-piperidyl]thieno[2,3-d]pyrimidin-4-yl]morpholine (2S)-1-[2-[[3-[5-(4-fluorophenyl)thieno[2,3-d]pyrimidin-4-yl]-3-azabicyclo[3.1.0]hexan-6-yl]methoxy]ethyl]pyrrolidine-2-carboxamide 5-(4-fluorophenyl)-4-[6-[2-[(3R)-3-fluoropyrrolidin-1-yl]ethoxymethyl]-3-azabicyclo[3.1.0]hexan-3-yl]thieno[2,3-d]pyrimidine 2-chloro-5-(4-fluorophenyl)-4-[4-(2-pyrrolidin-1-ylethoxymethyl)-1-piperidyl]thieno[2,3-d]pyrimidine N-(2-hydroxyethyl)-5-phenyl-4-[4-(2-pyrrolidin-1-ylethoxymethyl)-1-piperidyl]thieno[2,3-d]pyrimidine-6-carboxamide

[5-phenyl-4-[4-(2-pyrrolidin-1-ylethoxymethyl)-1-piperidyl]thieno[2,3-d]pyrimidin-6-yl]methanol N-methyl-N-(1-methylpyrrolidin-3-yl)-1-(5-phenylthieno[2,3-d]pyrimidin-4-yl)piperidine-3-carboxamide 5-cyclohexyl-2-[4-(2-pyrrolidin-1-ylethoxymethyl)-1-piperidyl]thieno[2,3-d]pyrimidine 5-phenyl-4-[5-(2-pyrrolidin-1-ylethoxy)-2-azabicyclo[2.2.1]heptan-2-yl]thieno[2,3-d]pyrimidine N-(2-morpholinoethyl)-1-(5-phenylthieno[2,3-d]pyrimidin-4-yl)piperidine-3-carboxamide 5-phenyl-4-[3-(2-pyrrolidin-1-ylethoxymethyl)-8-azabicyclo[3.2.1]octan-8-yl]thieno[2,3-d]pyrimidine 5-isopropyl-4-[3-(2-pyrrolidin-1-ylethoxymethyl)-8-azabicyclo[3.2.1]octan-8-yl]thieno[2,3-d]pyrimidine 5-isopropyl-4-[5-(2-pyrrolidin-1-ylethoxy)-2-azabicyclo[2.2.1]heptan-2-yl]thieno[2,3-d]pyrimidine 5-phenyl-4-[3-(2-pyrrolidin-1-ylethoxy)-8-azabicyclo[3.2.1]octan-8-yl]thieno[2,3-d]pyrimidine 1-[2-[[2-(5-phenylthieno[2,3-d]pyrimidin-4-yl)-2-azabicyclo[2.2.1]heptan-5-yl]oxy]ethyl]pyrrolidine-3-carboxamide 4-[5-[2-[(3S)-3-fluoropyrrolidin-1-yl]ethoxy]-2-azabicyclo[2.2.1]heptan-2-yl]-5-phenyl-thieno[2,3-d]pyrimidine 5-[2-[[2-(5-isopropylthieno[2,3-d]pyrimidin-4-yl)-2-azabicyclo[2.2.1]heptan-5-yl]oxy]ethyl]-2-oxa-5-azabicyclo[2.2.1]heptane (2R)-1-[2-[[2-(5-phenylthieno[2,3-d]pyrimidin-4-yl)-2-azabicyclo[2.2.1]heptan-5-yl]oxy]ethyl]pyrrolidine-2-carboxamide 4-[5-[2-[(3S)-3-fluoropyrrolidin-1-yl]ethoxy]-2-azabicyclo[2.2.1]heptan-2-yl]-5-isopropyl-thieno[2,3-d]pyrimidine 4-[5-[2-[(3R)-3-fluoropyrrolidin-1-yl]ethoxy]-2-azabicyclo[2.2.1]heptan-2-yl]-5-isopropyl-thieno[2,3-d]pyrimidine 5-phenyl-4-[4-(3-pyrrolidin-1-ylpropoxy)-1-piperidyl]thieno[2,3-d]pyrimidine 5-isopropyl-4-[3-(2-pyrrolidin-1-ylethoxy)-8-azabicyclo[3.2.1]octan-8-yl]thieno[2,3-d]pyrimidine

[8-(4-morpholino-5-phenyl-thieno[2,3-d]pyrimidin-2-yl)-8-azabicyclo[3.2.1]octan-3-yl]methanol 8-[4-[4-(methoxymethyl)-1-piperidyl]-5-phenyl-thieno[2,3-d]pyrimidin-2-yl]-8-azabicyclo[3.2.1]octan-3-ol 4-[2-[3-(methoxymethyl)-8-azabicyclo[3.2.1]octan-8-yl]-5-phenyl-thieno[2,3-d]pyrimidin-4-yl]morpholine 8-[2-[4-(2-pyrrolidin-1-ylethoxymethyl)-1-piperidyl]thieno[2,3-d]pyrimidin-4-yl]-3-oxa-8-azabicyclo[3.2.1]octane 3-methyl-N-[5-phenyl-2-[4-(2-pyrrolidin-1-ylethoxymethyl)-1-piperidyl]thieno[2,3-d]pyrimidin-6-yl]butanamide 2-methyl-N-[5-phenyl-2-[4-(2-pyrrolidin-1-ylethoxymethyl)-1-piperidyl]thieno[2,3-d]pyrimidin-6-yl]propanamide 4-[5-phenyl-2-[4-(2-pyrrolidin-1-ylethoxymethyl)-1-piperidyl]thieno[2,3-d]pyrimidin-4-yl]morpholine-2-carboxamide 1-(4-morpholino-5-phenyl-thieno[2,3-d]pyrimidin-2-yl)pyrrolidine-3-carboxamide 2-(2-azabicyclo[2.2.1]heptan-5-yloxy)-4-[4-(methoxymethyl)-1-piperidyl]-5-phenyl-thieno[2,3-d]pyrimidine 5-phenyl-4-[4-(2-pyrrolidin-1-ylethoxymethyl)-1-piperidyl]furo[2,3-d]pyrimidine 1-[4-(2-oxa-5-azabicyclo[2.2.1]heptan-5-yl)-5-phenyl-thieno[2,3-d]pyrimidin-2-yl]pyrrolidine-3-carboxamide 1-[4-[3-(hydroxymethyl)-8-azabicyclo[3.2.1]octan-8-yl]-5-phenyl-thieno[2,3-d]pyrimidin-2-yl]pyrrolidine-3-carboxamide 5-(4-pyridyl)-4-[4-(2-pyrrolidin-1-ylethoxymethyl)-1-piperidyl]thieno[2,3-d]pyrimidine 5-(3-methoxyphenyl)-4-[4-(2-pyrrolidin-1-ylethoxymethyl)-1-piperidyl]thieno[2,3-d]pyrimidine 4-[4-(2-pyrrolidin-1-ylethoxymethyl)-1-piperidyl]-5-[3-(trifluoromethoxy)phenyl]thieno[2,3-d]pyrimidine 5-phenyl-4-[4-(2-pyrrolidin-1-ylethoxymethyl)-1-piperidyl]thieno[2,3-d]pyrimidin-2-amine 5-(3-furyl)-4-[4-(2-pyrrolidin-1-ylethoxymethyl)-1-piperidyl]thieno[2,3-d]pyrimidine 5-(2-methoxy-3-pyridyl)-4-[4-(2-pyrrolidin-1-ylethoxymethyl)-1-piperidyl]thieno[2,3-d]pyrimidine 4-[4-(2-pyrrolidin-1-ylethoxymethyl)-1-piperidyl]-5-(3-thienyl)thieno[2,3-d]pyrimidine N-tert-butyl-2-methyl-4-(5-phenylthieno[2,3-d]pyrimidin-4-yl)but-3-yn-2-amine 5-(1,3-benzodioxol-5-yl)-4-[4-(2-pyrrolidin-1-ylethoxymethyl)-1-piperidyl]thieno[2,3-d]pyrimidine 5-(2-pyridyl)-4-[4-(2-pyrrolidin-1-ylethoxymethyl)-1-piperidyl]thieno[2,3-d]pyrimidine N-cyclobutyl-8-(2-cyclopropyl-5-phenyl-thieno[2,3-d]pyrimidin-4-yl)-8-azabicyclo[3.2.1]octan-3-amine 4-[3-(azetidin-1-yl)-8-azabicyclo[3.2.1]octan-8-yl]-2-cyclopropyl-5-phenyl-thieno[2,3-d]pyrimidine N—[[8-(5-phenylthieno[2,3-d]pyrimidin-4-yl)-8-azabicyclo[3.2.1]octan-3-yl]methyl]cyclobutanamine 5-(3-pyridyl)-4-[4-(2-pyrrolidin-1-ylethoxymethyl)-1-piperidyl]thieno[2,3-d]pyrimidine N-cyclobutyl-8-(5-phenylthieno[2,3-d]pyrimidin-4-yl)-8-azabicyclo[3.2.1]octan-3-amine 4-[3-(azetidin-1-yl)-8-azabicyclo[3.2.1]octan-8-yl]-5-phenyl-thieno[2,3-d]pyrimidine N-isopropyl-8-(5-phenylthieno[2,3-d]pyrimidin-4-yl)-8-azabicyclo[3.2.1]octan-3-amine 5-(2-isopropoxy-3-pyridyl)-4-[4-(2-pyrrolidin-1-ylethoxymethyl)-1-piperidyl]thieno[2,3-d]pyrimidine 5-(2-methoxyphenyl)-4-[4-(2-pyrrolidin-1-ylethoxymethyl)-1-piperidyl]thieno[2,3-d]pyrimidine N,N-dimethyl-2-[4-[4-(2-pyrrolidin-1-ylethoxymethyl)-1-piperidyl]thieno[2,3-d]pyrimidin-5-yl]benzamide 5-(2-ethoxy-3-pyridyl)-4-[4-(2-pyrrolidin-1-ylethoxymethyl)-1-piperidyl]thieno[2,3-d]pyrimidine N,N-dimethyl-3-[4-[4-(2-pyrrolidin-1-ylethoxymethyl)-1-piperidyl]thieno[2,3-d]pyrimidin-5-yl]benzamide 2-methyl-N—[[8-(5-phenylthieno[2,3-d]pyrimidin-4-yl)-8-azabicyclo[3.2.1]octan-3-yl]methyl]propan-2-amine N—[[8-(5-phenylthieno[2,3-d]pyrimidin-4-yl)-8-azabicyclo[3.2.1]octan-3-yl]methyl]propan-2-amine 5-phenyl-4-[3-(pyrrolidin-1-ylmethyl)-8-azabicyclo[3.2.1]octan-8-yl]thieno[2,3-d]pyrimidine 4-[5-phenyl-2-(trifluoromethyl)thieno[2,3-d]pyrimidin-4-yl]morpholine 1-[4-[3-(cyclobutylamino)-8-azabicyclo[3.2.1]octan-8-yl]-5-phenyl-thieno[2,3-d]pyrimidin-2-yl]pyrrolidine-3-carboxamide 4-[3-(cyclobutylamino)-8-azabicyclo[3.2.1]octan-8-yl]-5-phenyl-thieno[2,3-d]pyrimidine-2-carbonitrile 4-[3-(cyclobutylamino)-8-azabicyclo[3.2.1]octan-8-yl]-N,N-dimethyl-5-phenyl-thieno[2,3-d]pyrimidine-6-carboxamide 5-phenyl-4-[4-(2-pyrrolidin-1-ylethoxymethyl)-1-piperidyl]-2-(trifluoromethyl)thieno[2,3-d]pyrimidine N-cyclobutyl-8-[5-[2-(trifluoromethoxy)phenyl]thieno[2,3-d]pyrimidin-4-yl]-8-azabicyclo[3.2.1]octan-3-amine N-cyclobutyl-8-[5-(2-methoxyphenyl)thieno[2,3-d]pyrimidin-4-yl]-8-azabicyclo[3.2.1]octan-3-amine
4-[3-(cyclobutylamino)-8-azabicyclo[3.2.1]octan-8-yl]-N-methyl-5-phenyl-thieno[2,3-d]pyrimidine-6-carboxamide
N-cyclobutyl-8-[5-(o-tolyl)thieno[2,3-d]pyrimidin-4-yl]-8-azabicyclo[3.2.1]octan-3-amine
N-cyclobutyl-8-[5-(2-methoxy-3-pyridyl)thieno[2,3-d]pyrimidin-4-yl]-8-azabicyclo[3.2.1]octan-3-amine
N-cyclobutyl-8-[5-(5-fluoro-2-methoxy-3-pyridyl)thieno[2,3-d]pyrimidin-4-yl]-8-azabicyclo[3.2.1]octan-3-amine
4-[3-[cyclobutyl(methyl)amino]-8-azabicyclo[3.2.1]octan-8-yl]-N,N-dimethyl-5-phenyl-thieno[2,3-d]pyrimidine-6-carboxamide
2-(2-azabicyclo[2.2.1]heptan-5-yloxy)-4-[3-methoxy-8-azabicyclo[3.2.1]octan-8-yl]-5-phenyl-thieno[2,3-d]pyrimidine
8-[2-(2-azabicyclo[2.2.1]heptan-5-yloxy)-5-phenyl-thieno[2,3-d]pyrimidin-4-yl]-3-oxa-8-azabicyclo[3.2.1]octane
N-cyclobutyl-8-[5-(2-methoxyphenyl)thieno[2,3-d]pyrimidin-4-yl]-N-methyl-8-azabicyclo[3.2.1]octan-3-amine
N-cyclobutyl-8-[5-(2-methoxy-3-pyridyl)thieno[2,3-d]pyrimidin-4-yl]-N-methyl-8-azabicyclo[3.2.1]octan-3-amine
2-(2-azabicyclo[2.2.1]heptan-5-yloxy)-4-[3-(methoxymethyl)-8-azabicyclo[3.2.1]octan-8-yl]-5-phenyl-thieno[2,3-d]pyrimidine
N,N-dimethyl-5-phenyl-4-[3-pyrrolidin-1-yl-8-azabicyclo[3.2.1]octan-8-yl]thieno[2,3-d]pyrimidine-6-carboxamide
N-isopropyl-5-phenyl-4-[3-pyrrolidin-1-yl-8-azabicyclo[3.2.1]octan-8-yl]thieno[2,3-d]pyrimidine-6-carboxamide
N-isopropyl-5-phenyl-4-[3-pyrrolidin-1-yl-8-azabicyclo[3.2.1]octan-8-yl]thieno[2,3-d]pyrimidine-6-carboxamide
N,N-dimethyl-5-phenyl-4-[3-(2-pyrrolidin-1-ylethoxymethyl)-8-azabicyclo[3.2.1]octan-8-yl]thieno[2,3-d]pyrimidine-6-carboxamide
N-isopropyl-5-phenyl-4-[3-(2-pyrrolidin-1-ylethoxymethyl)-8-azabicyclo[3.2.1]octan-8-yl]thieno[2,3-d]pyrimidine-6-carboxamide
2-cyclopropyl-5-(2-methoxyphenyl)-4-[4-(2-pyrrolidin-1-ylethoxymethyl)-1-piperidyl]thieno[2,3-d]pyrimidine
N-cyclobutyl-8-[5-phenyl-2-(trifluoromethyl)thieno[2,3-d]pyrimidin-4-yl]-8-azabicyclo[3.2.1]octan-3-amine
2-cyclopropyl-5-phenyl-4-[4-(2-pyrrolidin-1-ylethoxymethyl)-1-piperidyl]thieno[2,3-d]pyrimidine
N-methyl-5-phenyl-4-[3-(2-pyrrolidin-1-ylethoxymethyl)-8-azabicyclo[3.2.1]octan-8-yl]thieno[2,3-d]pyrimidine-6-carboxamide
5-(2-methoxyphenyl)-4-[3-(2-pyrrolidin-1-ylethoxymethyl)-8-azabicyclo[3.2.1]octan-8-yl]thieno[2,3-d]pyrimidine
5-(2-methoxy-3-pyridyl)-4-[3-(2-pyrrolidin-1-ylethoxymethyl)-8-azabicyclo[3.2.1]octan-8-yl]thieno[2,3-d]pyrimidine
N,N-dimethyl-2-[4-[3-(2-pyrrolidin-1-ylethoxymethyl)-8-azabicyclo[3.2.1]octan-8-yl]thieno[2,3-d]pyrimidin-5-yl]benzamide
[8-[5-(2-methoxy-3-pyridyl)thieno[2,3-d]pyrimidin-4-yl]-8-azabicyclo[3.2.1]octan-3-yl]methanol
2-(2-azabicyclo[2.2.1]heptan-5-yloxy)-4-[3-(methoxymethyl)-8-azabicyclo[3.2.1]octan-8-yl]-N,N-dimethyl-5-phenyl-thieno[2,3-d]pyrimidine-6-carboxamide
N—[[8-[5-(2-methoxyphenyl)thieno[2,3-d]pyrimidin-4-yl]-8-azabicyclo[3.2.1]octan-3-yl]methyl]cyclobutanamine
1-[5-phenyl-4-[4-(2-pyrrolidin-1-ylethoxymethyl)-1-piperidyl]thieno[2,3-d]pyrimidin-6-yl]imidazolidin-2-one
2-[5-phenyl-4-[4-(2-pyrrolidin-1-ylethoxymethyl)-1-piperidyl]thieno[2,3-d]pyrimidin-6-yl]-1,2-thiazolidine 1,1-dioxide
1-(2-ethyl-5-phenyl-thieno[2,3-d]pyrimidin-4-yl)-N,N-dimethyl-piperidin-4-amine
[8-[4-(3-methoxy-8-azabicyclo[3.2.1]octan-8-yl)-5-(2-methoxyphenyl)thieno[2,3-d]pyrimidin-2-yl]-8-azabicyclo[3.2.1]octan-3-yl]methanol
8-[4-[3-(methoxymethyl)-8-azabicyclo[3.2.1]octan-8-yl]-5-(2-methoxyphenyl)thieno[2,3-d]pyrimidin-2-yl]-8-azabicyclo[3.2.1]octan-3-ol
1-[5-(2-chlorophenyl)-4-(3-methoxy-8-azabicyclo[3.2.1]octan-8-yl)thieno[2,3-d]pyrimidin-2-yl]piperidine-3-carboxamide
1-[5-(2-chlorophenyl)-2-(3-methoxy-8-azabicyclo[3.2.1]octan-8-yl)thieno[2,3-d]pyrimidin-4-yl]piperidine-3-carboxamide
8-[5-(2-chlorophenyl)-4-(3-methoxy-8-azabicyclo[3.2.1]octan-8-yl)thieno[2,3-d]pyrimidin-2-yl]-8-azabicyclo[3.2.1]octan-3-ol
1-[4-[3-(methoxymethyl)-8-azabicyclo[3.2.1]octan-8-yl]-5-(2-methoxyphenyl)thieno[2,3-d]pyrimidin-2-yl]pyrrolidine-3-carboxamide
8-[4-(3-methoxy-8-azabicyclo[3.2.1]octan-8-yl)-5-(2-methoxyphenyl)thieno[2,3-d]pyrimidin-2-yl]-8-azabicyclo[3.2.1]octan-3-ol
4-[4-[3-(methoxymethyl)-8-azabicyclo[3.2.1]octan-8-yl]-5-(2-methoxyphenyl)thieno[2,3-d]pyrimidin-2-yl]piperazin-2-one
8-[4-(3-methoxy-8-azabicyclo[3.2.1]octan-8-yl)-5-(2-methoxyphenyl)thieno[2,3-d]pyrimidin-2-yl]-3-oxa-8-azabicyclo[3.2.1]octane
4-[4-(3-methoxy-8-azabicyclo[3.2.1]octan-8-yl)-5-(2-methoxyphenyl)thieno[2,3-d]pyrimidin-2-yl]piperazin-2-one
1-[4-(3-methoxy-8-azabicyclo[3.2.1]octan-8-yl)-5-(2-methoxyphenyl)thieno[2,3-d]pyrimidin-2-yl]piperidine-3-carboxamide
4-[5-(2-chlorophenyl)-4-(3-methoxy-8-azabicyclo[3.2.1]octan-8-yl)thieno[2,3-d]pyrimidin-2-yl]piperazin-2-one
4-[5-(2-chlorophenyl)-4-(3-methoxy-8-azabicyclo[3.2.1]octan-8-yl)thieno[2,3-d]pyrimidin-2-yl]piperazine-2-carboxamide
1-[5-(2-chlorophenyl)-2-[3-(hydroxymethyl)-8-azabicyclo[3.2.1]octan-8-yl]thieno[2,3-d]pyrimidin-4-yl]piperidine-3-carboxamide
4-[4-(3-methoxy-8-azabicyclo[3.2.1]octan-8-yl)-5-(2-methoxyphenyl)thieno[2,3-d]pyrimidin-2-yl]piperazine-2-carboxamide
8-[2-[3-(methoxymethyl)-8-azabicyclo[3.2.1]octan-8-yl]-5-(2-methoxyphenyl)thieno[2,3-d]pyrimidin-4-yl]-3-oxa-8-azabicyclo[3.2.1]octane
1-[4-(3-methoxy-8-azabicyclo[3.2.1]octan-8-yl)-5-(2-methoxyphenyl)thieno[2,3-d]pyrimidin-2-yl]pyrrolidine-3-carboxamide
8-[2-(3-methoxy-8-azabicyclo[3.2.1]octan-8-yl)-5-(2-methoxyphenyl)thieno[2,3-d]pyrimidin-4-yl]-3-oxa-8-azabicyclo[3.2.1]octane
4-[5-(2-methoxyphenyl)-4-(3-oxa-8-azabicyclo[3.2.1]octan-8-yl)thieno[2,3-d]pyrimidin-2-yl]piperazine-2-carboxamide
1-[5-(2-methoxyphenyl)-4-(3-oxa-8-azabicyclo[3.2.1]octan-8-yl)thieno[2,3-d]pyrimidin-2-yl]piperidine-3-carboxamide
8-[5-(2-methoxyphenyl)-4-(3-oxa-8-azabicyclo[3.2.1]octan-8-yl)thieno[2,3-d]pyrimidin-2-yl]-8-azabicyclo[3.2.1]octan-3-ol 1-[5-(2-methoxyphenyl)-4-(3-oxa-8-azabicyclo[3.2.1]octan-8-yl)thieno[2,3-d]pyrimidin-2-yl]pyrrolidine-3-carboxamide 8-[5-(2-methoxyphenyl)-2-(3-oxa-8-azabicyclo[3.2.1]octan-8-yl)thieno[2,3-d]pyrimidin-4-yl]-3-oxa-8-azabicyclo[3.2.1]octane 4-[5-(2-methoxyphenyl)-4-(3-oxa-8-azabicyclo[3.2.1]octan-8-yl)thieno[2,3-d]pyrimidin-2-yl]piperazin-2-one 1-[5-(2-methoxyphenyl)-4-(3-oxa-8-azabicyclo[3.2.1]octan-8-yl)thieno[2,3-d]pyrimidin-2-yl]pyrrolidin-3-ol 4-(3-methoxy-8-azabicyclo[3.2.1]octan-8-yl)-5-(2-methoxyphenyl)thieno[2,3-d]pyrimidine-2-carbonitrile 4-[3-(methoxymethyl)-8-azabicyclo[3.2.1]octan-8-yl]-5-(2-methoxyphenyl)thieno[2,3-d]pyrimidine-2-carbonitrile 2,4-bis(3-methoxy-8-azabicyclo[3.2.1]octan-8-yl)-5-(2-methoxyphenyl)thieno[2,3-d]pyrimidine 4-[5-(2-chlorophenyl)-4-(3-methoxy-8-azabicyclo[3.2.1]octan-8-yl)thieno[2,3-d]pyrimidin-2-yl]morpholine-2-carboxamide 4-[4-(3-methoxy-8-azabicyclo[3.2.1]octan-8-yl)-5-(2-methoxyphenyl)thieno[2,3-d]pyrimidin-2-yl]morpholine-2-carboxamide 1-[5-(2-chlorophenyl)-4-(3-oxa-8-azabicyclo[3.2.1]octan-8-yl)thieno[2,3-d]pyrimidin-2-yl]piperidine-3-carboxamide 1-[5-(2-chlorophenyl)-2-(3-oxa-8-azabicyclo[3.2.1]octan-8-yl)thieno[2,3-d]pyrimidin-4-yl]piperidine-3-carboxamide 1-[5-(2-chlorophenyl)-2-(3-hydroxy-8-azabicyclo[3.2.1]octan-8-yl)thieno[2,3-d]pyrimidin-4-yl]pyrrolidine-3-carboxamide 4-[2-[3-(hydroxymethyl)-8-azabicyclo[3.2.1]octan-8-yl]-5-(2-methoxyphenyl)thieno[2,3-d]pyrimidin-4-yl]piperazin-2-one 1-[2-(3-hydroxy-8-azabicyclo[3.2.1]octan-8-yl)-5-(2-methoxyphenyl)thieno[2,3-d]pyrimidin-4-yl]pyrrolidine-3-carboxamide 1-[5-(2-chlorophenyl)-2-(3-oxa-8-azabicyclo[3.2.1]octan-8-yl)thieno[2,3-d]pyrimidin-4-yl]pyrrolidine-3-carboxamide 4-[5-(2-chlorophenyl)-4-(3-oxa-8-azabicyclo[3.2.1]octan-8-yl)thieno[2,3-d]pyrimidin-2-yl]piperazine-2-carboxamide 4-[5-(2-chlorophenyl)-2-(3-oxa-8-azabicyclo[3.2.1]octan-8-yl)thieno[2,3-d]pyrimidin-4-yl]piperazine-2-carboxamide 4-[5-(2-methoxyphenyl)-4-(3-oxa-8-azabicyclo[3.2.1]octan-8-yl)thieno[2,3-d]pyrimidin-2-yl]morpholine-2-carboxamide 4-[5-(2-methoxyphenyl)-2-(3-oxa-8-azabicyclo[3.2.1]octan-8-yl)thieno[2,3-d]pyrimidin-4-yl]morpholine-2-carboxamide 4-[5-(2-chlorophenyl)-4-(3-oxa-8-azabicyclo[3.2.1]octan-8-yl)thieno[2,3-d]pyrimidin-2-yl]morpholine-2-carboxamide 8-[5-(2-chlorophenyl)-4-(3-oxa-8-azabicyclo[3.2.1]octan-8-yl)thieno[2,3-d]pyrimidin-2-yl]-8-azabicyclo[3,2,1]octan-3-ol 1-[5-(2-chlorophenyl)-4-(3-oxa-8-azabicyclo[3.2.1]octan-8-yl)thieno[2,3-d]pyrimidin-2-yl]pyrrolidine-3-carboxamide 8-[5-(2-chlorophenyl)-2-(3-oxa-8-azabicyclo[3.2.1]octan-8-yl)thieno[2,3-d]pyrimidin-4-yl]-3-oxa-8-azabicyclo[3.2.1]octane 4-[5-(2-chlorophenyl)-4-(3-oxa-8-azabicyclo[3.2.1]octan-8-yl)thieno[2,3-d]pyrimidin-2-yl]piperazin-2-one 8-[5-(2-chlorophenyl)-2-morpholino-thieno[2,3-d]pyrimidin-4-yl]-3-oxa-8-azabicyclo[3.2.1]octane, 1-[5-(2-chlorophenyl)-4-(3-oxa-8-azabicyclo[3.2.1]octan-8-yl)thieno[2,3-d]pyrimidin-2-yl]pyrrolidin-3-ol, N—[[8-[5-(2-methoxy-3-pyridyl)thieno[2,3-d]pyrimidin-4-yl]-8-azabicyclo[3.2.1]octan-3-yl]methyl]cyclobutan-amine.

In one embodiment, the compound of the invention is not 2-[5-phenyl-4-[4-(2-pyrrolidin-1-ylethoxymethyl)-1-piperidyl]thieno[2,3-d]pyrimidin-6-yl]-1,2-thiazolidine 1,1-dioxide or 1-(2-ethyl-5-phenyl-thieno[2,3-d]pyrimidin-4-yl)-N,N-dimethyl-piperidin-4-amine.

In one embodiment, the compound of the invention is selected from:

4-[4-[2-(1-methylpyrrolidin-2-yl)ethoxymethyl]-1-piperidyl]-5-phenyl-thieno[2,3-d]pyrimidine 5-methyl-4-[4-[2-(1-methylpyrrolidin-2-yl)ethoxymethyl]-1-piperidyl]thieno[2,3-d]pyrimidine 4-[4-[2-(1-methylpyrrolidin-2-yl)ethoxymethyl]-1-piperidyl]thieno[2,3-d]pyrimidine 5,6-dimethyl-4-[4-[2-(1-methylpyrrolidin-2-yl)ethoxymethyl]-1-piperidyl]thieno[2,3-d]pyrimidine 5-phenyl-4-[4-(2-pyrrolidin-1-ylethoxymethyl)-1-piperidyl]thieno[2,3-d]pyrimidine 4-[2-[[1-(5-phenylthieno[2,3-d]pyrimidin-4-yl)-4-piperidyl]methoxy]ethyl]morpholine 4-[4-[(1-methylpyrrolidin-2-yl)methoxymethyl]-1-piperidyl]-5-phenyl-thieno[2,3-d]pyrimidine N,N-dimethyl-3-[[1-(5-phenylthieno[2,3-d]pyrimidin-4-yl)-4-piperidyl]methoxy]propan-1-amine 4-[4-(cyclobutoxymethyl)-1-piperidyl]-5-phenyl-thieno[2,3-d]pyrimidine 4-[4-[2-(1-methyl-2-piperidyl)ethoxymethyl]-1-piperidyl]-5-phenyl-thieno[2,3-d]pyrimidine N,N-dimethyl-2-[[1-(5-phenylthieno[2,3-d]pyrimidin-4-yl)-4-piperidyl]methoxy]ethanamine 4-[4-[(1-methylpyrrolidin-3-yl)oxymethyl]-1-piperidyl]-5-phenyl-thieno[2,3-d]pyrimidine 4-[4-[(1-methyl-4-piperidyl)oxymethyl]-1-piperidyl]-5-phenyl-thieno[2,3-d]pyrimidine 1-[4-[4-(2-dimethylaminoethyloxymethyl)-1-piperidyl]-5-phenyl-thieno[2,3-d]pyrimidin-2-yl]pyrrolidine-3-carboxamide 4-[4-(isopropoxymethyl)-1-piperidyl]-5-phenyl-thieno[2,3-d]pyrimidine 5-phenyl-4-[4-(tetrahydrofuran-3-yloxymethyl)-1-piperidyl]thieno[2,3-d]pyrimidine 5-(3-fluorophenyl)-4-[4-(2-pyrrolidin-1-ylethoxymethyl)-1-piperidyl]thieno[2,3-d]pyrimidine 5-ethyl-6-methyl-4-[4-(2-pyrrolidin-1-ylethoxymethyl)-1-piperidyl]thieno[2,3-d]pyrimidine 4-[2-[[1-(6-isopropylthieno[2,3-d]pyrimidin-4-yl)-4-piperidyl]methoxy]ethyl]morpholine 5-(4-fluorophenyl)-4-[4-(2-pyrrolidin-1-ylethoxymethyl)-1-piperidyl]thieno[2,3-d]pyrimidine 4-[2-[[1-[5-(4-fluorophenyl)thieno[2,3-d]pyrimidin-4-yl]-4-piperidyl]methoxy]ethyl]morpholine 4-[4-[2-(3-fluoropyrrolidin-1-yl)ethoxymethyl]-1-piperidyl]-5-phenyl-thieno[2,3-d]pyrimidine 4-[2-[[1-(5-ethyl-6-methyl-thieno[2,3-d]pyrimidin-4-yl)-4-piperidyl]methoxy]ethyl]morpholine 5-ethyl-6-methyl-4-[4-[2-(1-methylpyrrolidin-2-yl)ethoxymethyl]-1-piperidyl]thieno[2,3-d]pyrimidine 6-isopropyl-4-[4-[2-(1-methyl-2-piperidyl)ethoxymethyl]-1-piperidyl]thieno[2,3-d]pyrimidine 4-[4-[2-(3,3-difluoropyrrolidin-1-yl)ethoxymethyl]-1-piperidyl]-5-phenyl-thieno[2,3-d]pyrimidine 5-[2-[[1-(5-phenylthieno[2,3-d]pyrimidin-4-yl)-4-piperidyl]methoxy]ethyl]-2-oxa-5-azabicyclo[2.2.1]heptane 4-[2-[[1-(5-phenylthieno[2,3-d]pyrimidin-4-yl)-4-piperidyl]methoxy]ethyl]piperazin-2-one 1-[2-[[1-(5-phenylthieno[2,3-d]pyrimidin-4-yl)-4-piperidyl]methoxy]ethyl]pyrrolidine-3-carboxamide N-[1-[2-[[1-(5-phenylthieno[2,3-d]pyrimidin-4-yl)-4-piperidyl]methoxy]ethyl]pyrrolidin-3-yl]acetamide 1-[2-[[1-(5-phenylthieno[2,3-d]pyrimidin-4-yl)-4-piperidyl]methoxy]ethyl]pyrrolidine-2-carboxamide 4-[4-[2-[(3R)-3-fluoropyrrolidin-1-yl]ethoxymethyl]-1-piperidyl]-5-phenyl-thieno[2,3-d]pyrimidine 4-[4-[2-[(3S)-3-fluoropyrrolidin-1-yl]ethoxymethyl]-1-piperidyl]-5-phenyl-thieno[2,3-d]pyrimidine 5-ethyl-6-methyl-4-[4-[2-(1-methyl-2-piperidyl)ethoxymethyl]-1-piperidyl]thieno[2,3-d]pyrimidine 5-(3-fluorophenyl)-4-[4-[2-(1-methylpyrrolidin-2-yl)ethoxymethyl]-1-piperidyl]thieno[2,3-d]pyrimidine 5-(3-fluorophenyl)-4-[4-[2-(1-methyl-2-piperidyl)ethoxymethyl]-1-piperidyl]thieno[2,3-d]pyrimidine 5-phenyl-4-[6-(2-pyrrolidin-1-ylethoxymethyl)-3-azabicyclo[3.1.0]hexan-3-yl]thieno[2,3-d]pyrimidine 4-[2-[[3-(5-phenylthieno[2,3-d]pyrimidin-4-yl)-3-azabicyclo[3.1.0]hexan-6-yl]methoxy]ethyl]morpholine 4-[6-[2-(1-methylpyrrolidin-2-yl)ethoxymethyl]-3-azabicyclo[3.1.0]hexan-3-yl]-5-phenyl-thieno[2,3-d]pyrimidine 4-[6-[2-[(3S)-3-fluoropyrrolidin-1-yl]ethoxymethyl]-3-azabicyclo[3.1.0]hexan-3-yl]-5-phenyl-thieno[2,3-d]pyrimidine 4-[6-[2-[(3R)-3-fluoropyrrolidin-1-yl]ethoxymethyl]-3-azabicyclo[3.1.0]hexan-3-yl]-5-phenyl-thieno[2,3-d]pyrimidine (2R)-1-[2-[[3-(5-phenylthieno[2,3-d]pyrimidin-4-yl)-3-azabicyclo[3.1.0]hexan-6-yl]methoxy]ethyl]pyrrolidine-2-carboxamide (2S)-1-[2-[[3-(5-phenylthieno[2,3-d]pyrimidin-4-yl)-3-azabicyclo[3.1.0]hexan-6-yl]methoxy]ethyl]pyrrolidine-2-carboxamide N,N-dimethyl-4-[4-[4-(2-pyrrolidin-1-ylethoxymethyl)-1-piperidyl]thieno[2,3-d]pyrimidin-5-yl]benzenesulfonamide (2R)-1-[2-[[3-[5-(4-fluorophenyl)thieno[2,3-d]pyrimidin-4-yl]-3-azabicyclo[3.1.0]hexan-6-yl]methoxy]ethyl]pyrrolidine-2-carboxamide 5-(4-nitrophenyl)-4-[4-(2-pyrrolidin-1-ylethoxymethyl)-1-piperidyl]thieno[2,3-d]pyrimidine 5-(4-fluorophenyl)-4-[6-[2-[(3S)-3-fluoropyrrolidin-1-yl]ethoxymethyl]-3-azabicyclo[3.1.0]hexan-3-yl]thieno[2,3-d]pyrimidine 5-[2-[[3-[5-(4-fluorophenyl)thieno[2,3-d]pyrimidin-4-yl]-3-azabicyclo[3.1.0]hexan-6-yl]methoxy]ethyl]-2-oxa-5-azabicyclo[2.2.1]heptane 1-cyclopropyl-N—[[1-(5-phenylthieno[2,3-d]pyrimidin-4-yl)-4-piperidyl]methyl]methanamine 4-[4-[(3-methylpyrrolidin-1-yl)methyl]-1-piperidyl]-5-phenyl-thieno[2,3-d]pyrimidine N—[[1-(5-phenylthieno[2,3-d]pyrimidin-4-yl)-4-piperidyl]methyl]propan-1-amine 2,2-difluoro-N—[[1-(5-phenylthieno[2,3-d]pyrimidin-4-yl)-4-piperidyl]methyl]ethanamine 2-methoxy-N-(2-methoxyethyl)-N—[[1-(5-phenylthieno[2,3-d]pyrimidin-4-yl)-4-piperidyl]methyl]ethanamine

[1-[[1-(5-phenylthieno[2,3-d]pyrimidin-4-yl)-4-piperidyl]methylamino]cyclopentyl]methanol 1-[[1-(5-phenylthieno[2,3-d]pyrimidin-4-yl)-4-piperidyl]methyl]piperidin-3-ol 2-phenyl-4-[[1-(5-phenylthieno[2,3-d]pyrimidin-4-yl)-4-piperidyl]methyl]morpholine 3-phenyl-2-[[1-(5-phenylthieno[2,3-d]pyrimidin-4-yl)-4-piperidyl]methylamino]propan-1-ol 2-(1-methylpyrrolidin-2-yl)-N—[[1-(5-phenylthieno[2,3-d]pyrimidin-4-yl)-4-piperidyl]methyl]ethanamine 2-methyl-2-morpholino-N—[[1-(5-phenylthieno[2,3-d]pyrimidin-4-yl)-4-piperidyl]methyl]propan-1-amine N,N-dimethyl-1-[[1-(5-phenylthieno[2,3-d]pyrimidin-4-yl)-4-piperidyl]methyl]piperidin-3-amine 1-(2-furyl)-N—[[1-(5-phenylthieno[2,3-d]pyrimidin-4-yl)-4-piperidyl]methyl]methanamine N',N'-diisopropyl-N—[[1-(5-phenylthieno[2,3-d]pyrimidin-4-yl)-4-piperidyl]methyl]ethane-1,2-diamine N'-[[1-(5-phenylthieno[2,3-d]pyrimidin-4-yl)-4-piperidyl]methyl]ethane-1,2-diamine N—[[1-(5-phenylthieno[2,3-d]pyrimidin-4-yl)-4-piperidyl]methyl]cyclobutanamine

[1-[[1-(5-phenylthieno[2,3-d]pyrimidin-4-yl)-4-piperidyl]methyl]pyrrolidin-2-yl]methanol N—[[1-(5-phenylthieno[2,3-d]pyrimidin-4-yl)-4-piperidyl]methyl]-1-(2-pyridyl)methanamine (3S,4S)-1-[[1-(5-phenylthieno[2,3-d]pyrimidin-4-yl)-4-piperidyl]methyl]-4-pyrrolidin-1-yl-pyrrolidin-3-ol 4-[4-[(3-methoxypyrrolidin-1-yl)methyl]-1-piperidyl]-5-phenyl-thieno[2,3-d]pyrimidine N—[[1-(5-phenylthieno[2,3-d]pyrimidin-4-yl)-4-piperidyl]methyl]-1-(2-thienyl)methanamine 4-[4-[[3-(4-fluorophenyl)pyrrolidin-1-yl]methyl]-1-piperidyl]-5-phenyl-thieno[2,3-d]pyrimidine N,N,N'-trimethyl-N'-[[1-(5-phenylthieno[2,3-d]pyrimidin-4-yl)-4-piperidyl]methyl]ethane-1,2-diamine N,N,N'-trimethyl-N'-[[1-(5-phenylthieno[2,3-d]pyrimidin-4-yl)-4-piperidyl]methyl]propane-1,3-diamine 4-[4-(azetidin-1-ylmethyl)-1-piperidyl]-5-phenyl-thieno[2,3-d]pyrimidine N—[[1-(5-phenylthieno[2,3-d]pyrimidin-4-yl)-4-piperidyl]methyl]cyclopropanamine N,N-dimethyl-1-[[1-(5-phenylthieno[2,3-d]pyrimidin-4-yl)-4-piperidyl]methyl]piperidin-4-amine 5-phenyl-4-[4-[(3-pyrrolidin-1-ylpyrrolidin-1-yl)methyl]-1-piperidyl]thieno[2,3-d]pyrimidine N—[[1-[5-(4-fluorophenyl)thieno[2,3-d]pyrimidin-4-yl]-4-piperidyl]methyl]cyclopropanamine N—[[1-[5-(4-fluorophenyl)thieno[2,3-d]pyrimidin-4-yl]-4-piperidyl]methyl]cyclobutanamine 1-[[1-[5-(4-fluorophenyl)thieno[2,3-d]pyrimidin-4-yl]-4-piperidyl]methyl]-N,N-dimethyl-piperidin-3-amine 2-(1-methyl-2-piperidyl)-N—[[1-(5-phenylthieno[2,3-d]pyrimidin-4-yl)-4-piperidyl]methyl]ethanamine (3R)—N,N-dimethyl-1-[[1-(5-phenylthieno[2,3-d]pyrimidin-4-yl)-4-piperidyl]methyl]pyrrolidin-3-amine tert-butyl 2-[2-[[1-(5-phenylthieno[2,3-d]pyrimidin-4-yl)-4-piperidyl]methylamino]ethyl]pyrrolidine-1-carboxylate N-methyl-1-[1-(5-phenylthieno[2,3-d]pyrimidin-4-yl)-4-piperidyl]-N-(pyrrolidin-2-ylmethyl)methanamine N-[(1-methylpyrrolidin-2-yl)methyl]-1-[1-(5-phenylthieno[2,3-d]pyrimidin-4-yl)-4-piperidyl]methanamine N—[[1-(5-phenylthieno[2,3-d]pyrimidin-4-yl)-4-piperidyl]methyl]-2-pyrrolidin-2-yl-ethanamine N-methyl-N—[[1-(5-phenylthieno[2,3-d]pyrimidin-4-yl)-4-piperidyl]methyl]-2-pyrrolidin-2-yl-ethanamine 2-(1-ethylpyrrolidin-2-yl)-N-methyl-N—[[1-(5-phenylthieno[2,3-d]pyrimidin-4-yl)-4-piperidyl]methyl]ethanamine 2-(1-isopropylpyrrolidin-2-yl)-N-methyl-N—[[1-(5-phenylthieno[2,3-d]pyrimidin-4-yl)-4-piperidyl]methyl]ethanamine 1-[2-[2-[methyl-[[1-(5-phenylthieno[2,3-d]pyrimidin-4-yl)-4-piperidyl]methyl]amino]ethyl]pyrrolidin-1-yl]ethanone
(3S)-1-[[1-(5-phenylthieno[2,3-d]pyrimidin-4-yl)-4-piperidyl]methyl]piperidin-3-amine
1-methyl-4-[[1-(5-phenylthieno[2,3-d]pyrimidin-4-yl)-4-piperidyl]methylamino]pyrrolidin-2-one
4-[4-[[(3S)-3-fluoropyrrolidin-1-yl]methyl]-1-piperidyl]-5-phenyl-thieno[2,3-d]pyrimidine
2-[methyl-[[1-(5-phenylthieno[2,3-d]pyrimidin-4-yl)-4-piperidyl]methyl]amino]-1-pyrrolidin-1-yl-ethanone
N—[[1-(5-phenylthieno[2,3-d]pyrimidin-4-yl)-4-piperidyl]methyl]prop-2-en-1-amine
[1-[[1-(5-phenylthieno[2,3-d]pyrimidin-4-yl)-4-piperidyl]methyl]pyrrolidin-3-yl]methanol
N-1-[1-(5-phenylthieno[2,3-d]pyrimidin-4-yl)-4-piperidyl]ethyl]cyclopropanamine
1-methyl-N—[[1-(5-phenylthieno[2,3-d]pyrimidin-4-yl)-4-piperidyl]methyl]piperidin-4-amine
4-[4-[(2,5-dimethylpyrrolidin-1-yl)methyl]-1-piperidyl]-5-phenyl-thieno[2,3-d]pyrimidine
5-phenyl-4-[4-[[4-(trifluoromethyl)-1-piperidyl]methyl]-1-piperidyl]thieno[2,3-d]pyrimidine
2-[(2S)-1-methylpyrrolidin-2-yl]-N—[[1-(5-phenylthieno[2,3-d]pyrimidin-4-yl)-4-piperidyl]methyl]ethanamine
N-methyl-2-(1-methylpyrrolidin-2-yl)-N—[[1-(5-phenylthieno[2,3-d]pyrimidin-4-yl)-4-piperidyl]methyl]ethanamine
N—[[1-(5-phenylthieno[2,3-d]pyrimidin-4-yl)-4-piperidyl]methyl]-2-tetrahydrofuran-2-yl-ethanamine
2-cyclopropyl-N—[[1-(5-phenylthieno[2,3-d]pyrimidin-4-yl)-4-piperidyl]methyl]ethanamine
2-(1-methylpyrrolidin-3-yl)-N—[[1-(5-phenylthieno[2,3-d]pyrimidin-4-yl)-4-piperidyl]methyl]ethanamine
2-[[1-(5-phenylthieno[2,3-d]pyrimidin-4-yl)-4-piperidyl]methylamino]-1-pyrrolidin-1-yl-ethanone
(2S)-1-[[1-(5-phenylthieno[2,3-d]pyrimidin-4-yl)-4-piperidyl]methyl]pyrrolidine-2-carboxamide
2-[2-hydroxyethyl-[[1-[2-(4-methylpiperazin-1-yl)-5-phenyl-thieno[2,3-d]pyrimidin-4-yl]-4-piperidyl]methyl]amino]ethanol
4-[4-[(isopropylamino)methyl]-1-piperidyl]-5-phenyl-N-(2-pyrrolidin-1-ylethyl)thieno[2,3-d]pyrimidin-2-amine
4-[4-[(2-methoxyethylamino)methyl]-1-piperidyl]-5-phenyl-N-(2-pyrrolidin-1-ylethyl)thieno[2,3-d]pyrimidin-2-amine
4-[4-[[methyl-(1-methylpyrrolidin-3-yl)amino]methyl]-1-piperidyl]-5-phenyl-N-(2-pyrrolidin-1-ylethyl)thieno[2,3-d]pyrimidin-2-amine
N,1-dimethyl-N—[[1-[2-(4-methylpiperazin-1-yl)-5-phenyl-thieno[2,3-d]pyrimidin-4-yl]-4-piperidyl]methyl]pyrrolidin-3-amine
N,1-dimethyl-N—[[1-(5-phenyl-2-piperazin-1-yl-thieno[2,3-d]pyrimidin-4-yl)-4-piperidyl]methyl]pyrrolidin-3-amine
[1-[[1-[2-(4-methylpiperazin-1-yl)-5-phenyl-thieno[2,3-d]pyrimidin-4-yl]-4-piperidyl]methylamino]cyclopentyl]methanol
N—[[1-[2-(4-methylpiperazin-1-yl)-5-phenyl-thieno[2,3-d]pyrimidin-4-yl]-4-piperidyl]methyl]-2-(1-methylpyrrolidin-2-yl)ethanamine
N,N-dimethyl-1-[[1-[2-(4-methylpiperazin-1-yl)-5-phenyl-thieno[2,3-d]pyrimidin-4-yl]-4-piperidyl]methyl]piperidin-3-amine
N—[[1-[2-(4-methylpiperazin-1-yl)-5-phenyl-thieno[2,3-d]pyrimidin-4-yl]-4-piperidyl]methyl]cyclobutanamine
4-[4-[[3-(dimethylamino)-1-piperidyl]methyl]-1-piperidyl]-5-phenyl-N-(2-pyrrolidin-1-ylethyl)thieno[2,3-d]pyrimidin-2-amine
N-(2-methoxyethyl)-4-[4-[[methyl-(1-methylpyrrolidin-3-yl)amino]methyl]-1-piperidyl]-5-phenyl-thieno[2,3-d]pyrimidin-2-amine
N-(cyclopropylmethyl)-4-[4-[[methyl-(1-methylpyrrolidin-3-yl)amino]methyl]-1-piperidyl]-5-phenyl-thieno[2,3-d]pyrimidin-2-amine
1-[4-[4-[[methyl-(1-methylpyrrolidin-3-yl)amino]methyl]-1-piperidyl]-5-phenyl-thieno[2,3-d]pyrimidin-2-yl]pyrrolidine-3-carboxamide
2-[methyl-[4-[4-[[methyl-(1-methylpyrrolidin-3-yl)amino]methyl]-1-piperidyl]-5-phenyl-thieno[2,3-d]pyrimidin-2-yl]amino]acetamide
N—[[1-[2-[4-(2-methoxyethyl)piperazin-1-yl]-5-phenyl-thieno[2,3-d]pyrimidin-4-yl]-4-piperidyl]methyl]-N,1-dimethyl-pyrrolidin-3-amine
1-[4-[4-[[3-(dimethylamino)-1-piperidyl]methyl]-1-piperidyl]-5-phenyl-thieno[2,3-d]pyrimidin-2-yl]pyrrolidine-3-carboxamide
4-[4-[[3-(dimethylamino)-1-piperidyl]methyl]-1-piperidyl]-N-(2-methoxyethyl)-5-phenyl-thieno[2,3-d]pyrimidin-2-amine
4-[4-[4-[(cyclobutylamino)methyl]-1-piperidyl]-5-phenyl-thieno[2,3-d]pyrimidin-2-yl]piperazin-2-one
4-[4-[(cyclobutylamino)methyl]-1-piperidyl]-N-(2-methoxyethyl)-5-phenyl-thieno[2,3-d]pyrimidin-2-amine
4-[4-[(cyclobutylamino)methyl]-1-piperidyl]-5-phenyl-N-(2-pyrrolidin-1-ylethyl)thieno[2,3-d]pyrimidin-2-amine
1-[4-[4-[(cyclobutylamino)methyl]-1-piperidyl]-5-phenyl-thieno[2,3-d]pyrimidin-2-yl]pyrrolidine-3-carboxamide
1-[4-[4-[[methyl-(1-methylpyrrolidin-3-yl)amino]methyl]-1-piperidyl]-5-phenyl-thieno[2,3-d]pyrimidin-2-yl]piperidine-2-carboxamide
1-[4-[4-[[methyl-(1-methylpyrrolidin-3-yl)amino]methyl]-1-piperidyl]-5-phenyl-thieno[2,3-d]pyrimidin-2-yl]pyrrolidine-2-carboxamide
N-methyl-4-[4-[[methyl-(1-methylpyrrolidin-3-yl)amino]methyl]-1-piperidyl]-5-phenyl-thieno[2,3-d]pyrimidine-6-carboxamide
N-isopropyl-4-[4-[[methyl-(1-methylpyrrolidin-3-yl)amino]methyl]-1-piperidyl]-5-phenyl-thieno[2,3-d]pyrimidine-6-carboxamide
5-isopropyl-N,N-dimethyl-4-[4-(2-pyrrolidin-1-ylethoxymethyl)-1-piperidyl]thieno[2,3-d]pyrimidine-6-carboxamide
5-isopropyl-N-methyl-4-[4-(2-pyrrolidin-1-ylethoxymethyl)-1-piperidyl]thieno[2,3-d]pyrimidine-6-carboxamide
N,N-dimethyl-5-phenyl-4-[4-(2-pyrrolidin-1-ylethoxymethyl)-1-piperidyl]thieno[2,3-d]pyrimidine-6-carboxamide
N,N-dimethyl-4-[4-[[methyl-(1-methylpyrrolidin-3-yl)amino]methyl]-1-piperidyl]-5-phenyl-thieno[2,3-d]pyrimidine-6-carboxamide
5-(3-fluorophenyl)-N-isopropyl-4-[4-(2-pyrrolidin-1-ylethoxymethyl)-1-piperidyl]thieno[2,3-d]pyrimidine-6-carboxamide
5-(3-fluorophenyl)-N,N-dimethyl-4-[4-(2-pyrrolidin-1-ylethoxymethyl)-1-piperidyl]thieno[2,3-d]pyrimidine-6-carboxamide
[5-phenyl-4-[4-(2-pyrrolidin-1-ylethoxymethyl)-1-piperidyl]thieno[2,3-d]pyrimidin-6-yl]-pyrrolidin-1-yl-methanone N-isopropyl-5-phenyl-4-[4-(2-pyrrolidin-1-ylethoxymethyl)-1-piperidyl]thieno[2,3-d]pyrimidine-6-carboxamide N-methyl-5-phenyl-4-[4-(2-pyrrolidin-1-ylethoxymethyl)-1-piperidyl]thieno[2,3-d]pyrimidine-6-carboxamide 3-phenyl-4-[4-(2-pyrrolidin-1-ylethoxymethyl)-1-piperidyl]thieno[2,3-b]pyridine 2-bromo-3-phenyl-4-[4-(2-pyrrolidin-1-ylethoxymethyl)-1-piperidyl]thieno[2,3-b]pyridine 3-phenyl-4-[4-(2-pyrrolidin-1-ylethoxymethyl)-1-piperidyl]thieno[2,3-b]pyridine-2-carbonitrile 5-phenyl-2-[4-(2-pyrrolidin-1-ylethyl)piperazin-1-yl]thieno[2,3-d]pyrimidine 2-(1-methylpyrrolidin-2-yl)-N—[[1-(5-phenylthieno[2,3-d]pyrimidin-2-yl)-4-piperidyl]methyl]ethanamine (2R)-1-[2-[4-(5-phenylthieno[2,3-d]pyrimidin-2-yl)piperazin-1-yl]ethyl]pyrrolidine-2-carboxamide 5-phenyl-2-[4-(2-pyrrolidin-1-ylethoxymethyl)-1-piperidyl]thieno[2,3-d]pyrimidine 5-phenyl-2-[3-(2-pyrrolidin-1-ylethoxymethyl)pyrrolidin-1-yl]thieno[2,3-d]pyrimidine (3R)-1-[2-[4-(5-phenylthieno[2,3-d]pyrimidin-2-yl)piperazin-1-yl]ethyl]pyrrolidine-3-carboxamide 2-[4-[2-[(3R)-3-fluoropyrrolidin-1-yl]ethoxymethyl]-1-piperidyl]-5-phenyl-thieno[2,3-d]pyrimidine 5-(4-fluorophenyl)-2-[4-(2-pyrrolidin-1-ylethoxymethyl)-1-piperidyl]thieno[2,3-d]pyrimidine 1-[2-[[1-(5-phenylthieno[2,3-d]pyrimidin-2-yl)-4-piperidyl]methoxy]ethyl]pyrrolidine-3-carboxamide 5-[2-[[1-(5-phenylthieno[2,3-d]pyrimidin-2-yl)-4-piperidyl]methoxy]ethyl]-2-oxa-5-azabicyclo[2.2.1]heptane N-[5-phenyl-2-[4-(2-pyrrolidin-1-ylethoxymethyl)-1-piperidyl]thieno[2,3-d]pyrimidin-6-yl]acetamide 1-[5-phenyl-2-[4-(2-pyrrolidin-1-ylethoxymethyl)-1-piperidyl]thieno[2,3-d]pyrimidin-6-yl]pyrrolidin-2-one 5-isopropyl-2-[4-(2-pyrrolidin-1-ylethoxymethyl)-1-piperidyl]thieno[2,3-d]pyrimidine 1-[5-phenyl-2-[4-(2-pyrrolidin-1-ylethoxymethyl)-1-piperidyl]thieno[2,3-d]pyrimidin-6-yl]pyrrolidin-2-one 5-isopropyl-2-[4-(2-pyrrolidin-1-ylethoxymethyl)-1-piperidyl]thieno[2,3-d]pyrimidine 4-[3-[(1-methylpyrrolidin-3-yl)methoxy]prop-1-ynyl]-5-phenyl-thieno[2,3-d]pyrimidine 5-phenyl-4-[3-(2-pyrrolidin-1-ylethoxy)prop-1-ynyl]thieno[2,3-d]pyrimidine N-[5-phenyl-4-[4-(2-pyrrolidin-1-ylethoxymethyl)-1-piperidyl]thieno[2,3-d]pyrimidin-6-yl]acetamide 1-[5-phenyl-4-[4-(2-pyrrolidin-1-ylethoxymethyl)-1-piperidyl]thieno[2,3-d]pyrimidin-6-yl]pyrrolidin-2-one 5-phenyl-4-[(1S,5R)-3-(2-pyrrolidin-1-ylethoxymethyl)-8-azabicyclo[3.2.1]octan-8-yl]thieno[2,3-d]pyrimidine

[8-(4-morpholino-5-phenyl-thieno[2,3-d]pyrimidin-2-yl)-8-azabicyclo[3.2.1]octan-3-yl]methanol N-[2-(1-methylpyrrolidin-2-yl)ethyl]-1-(5-phenylthieno[2,3-d]pyrimidin-4-yl)piperidine-4-carboxamide 5-phenyl-4-[4-(2-pyrrolidin-1-ylethoxymethyl)-1-piperidyl]thieno[2,3-d]pyrimidine-6-carbonitrile and N-benzyl-5-phenyl-4-[4-(2-pyrrolidin-1-ylethoxymethyl)-1-piperidyl]thieno[2,3-d]pyrimidin-6-amine.

Chemical Groups

Halo

The term "halogen" (or "halo") includes fluorine, chlorine, bromine and iodine (or fluoro, chloro, bromo, and iodo).

Alkyl, Alkylene, Alkenyl, Alkynyl, Cycloalkyl Etc.

The terms "alkyl", "alkylene", "alkenyl", or "alkynyl" are used herein to refer to both straight and branched chain acyclic forms. Cyclic analogues thereof are referred to as cycloalkyl, etc.

The term "alkyl" includes monovalent, straight or branched, saturated, acyclic hydrocarbyl groups. Alkyl may be $C_{1-6}$alkyl, or $C_{1-6}$alkyl, or $C_{1-4}$alkyl. Examples include methyl, ethyl, n-propyl, i-propyl, n-butyl, s-butyl, t-butyl, n-pentyl, and s-pentyl.

The term "cycloalkyl" includes monovalent, saturated, cyclic hydrocarbyl groups. Cycloalkyl may be $C_{3-10}$cycloalkyl, or $C_{3-6}$cycloalkyl. Examples include cyclopropyl, cyclobutyl, cyclopentyl and cyclohexyl. A cycloalkyl may optionally be "bridged", which occurs when ring carbon atoms are further linked by a bond, or by one or more carbon atoms. Typical bridges are one or two carbon atoms, e.g. methylene or ethylene groups. When a ring is bridged, the substituents recited for the ring may also be present on the bridge.

The term "alkoxy" means alkyl-O—. Examples include methoxy, ethoxy, n-propoxy, i-propoxy, n-butoxy, s-butoxy, t-butoxy, n-pentoxy, and s-pentoxy.

The term "alkenyl" includes monovalent, straight or branched, unsaturated, acyclic hydrocarbyl groups having at least one carbon-carbon double bond at any point along the carbon chain and, optionally, no carbon-carbon triple bonds. Alkenyl may be $C_{2-10}$alkenyl, or $C_{2-6}$alkenyl, or $C_{2-4}$alkenyl. Examples include ethenyl and propenyl.

The term "cycloalkenyl" includes monovalent, partially unsaturated, cyclic hydrocarbyl groups having at least one carbon-carbon double bond and, optionally, no carbon-carbon triple bonds. Cycloalkenyl may be $C_{3-10}$cycloalkenyl, or $C_{5-10}$cycloalkenyl. Examples include cyclohexenyl and benzocyclohexyl.

The term "alkynyl" includes monovalent, straight or branched, unsaturated, acyclic hydrocarbyl groups having at least one carbon-carbon triple bond at any point along the carbon chain and, optionally, no carbon-carbon double bonds. Alkynyl may be $C_{2-10}$alkynyl, or $C_{2-6}$alkynyl, or $C_{2-4}$alkynyl. Examples include ethynyl and propynyl.

The term "alkylene" includes divalent, straight or branched, saturated, acyclic hydrocarbyl groups. Alkylene may be $C_{1-10}$alkylene, or $C_{1-6}$alkylene, or $C_{1-4}$alkylene, such as methylene, ethylene, n-propylene, i-propylene or t-butylene groups.

The term "alkenylene" includes divalent, straight or branched, acyclic hydrocarbyl groups having at least one carbon-carbon double bond and, optionally, no carbon-carbon triple bonds. Alkenylene may be $C_{2-10}$alkenylene, or $C_{2-6}$alkenylene, or $C_{2-4}$alkenylene.

Heteroalkyl Etc.

The term "heteroalkyl" includes alkyl groups in which up to three carbon atoms, or up to two carbon atoms, or one carbon atom, are each replaced independently by O, $S(O)_z$ (z=0, 1 or 2) or N, provided at least one of the alkyl carbon atoms remains. The heteroalkyl group may be C-linked or hetero-linked, i.e. it may be linked to the remainder of the molecule through a carbon atom or through O, $S(O)_z$ or N.

The term "heterocycloalkyl" includes cycloalkyl groups in which up to three carbon atoms, or up to two carbon atoms, or one carbon atom, are each replaced independently by O, $S(O)_z$ or N, provided at least one of the cycloalkyl carbon atoms remains. Examples of heterocycloalkyl groups include oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, tetrahydro-1,3-oxazinyl, 1,4-dithianyl, piperazinyl, hexahydropyrimidinyl, 1,4-thiazanyl, oxepanyl, thiepanyl, azepanyl, 1,4-dioxepanyl, 1,4-oxathiepanyl, 1,4-oxaazepanyl, 1,4-dithiepanyl, 1,4-thieazepanyl and 1,4-diazepanyl. The heterocycloalkyl group may be C-linked or N-linked, i.e. it may be linked to the remainder of the molecule through a carbon atom or through a nitrogen atom. A heterocycloalkyl may optionally be "bridged", which occurs when ring carbon or nitrogen atoms are further linked by a bond or one or more atoms (e.g. C, O, N, or S). Typical bridges include, but are not limited to, one carbon atom, two carbon atoms, one nitrogen atom, two nitrogen atoms, and a carbon-nitrogen group. When a ring is bridged, the substituents recited for the ring may also be present on the bridge. A cycloalkyl bridged by one or more atoms including a heteroatom (i.e. O, N, or S) may be viewed as a heterocycloalkyl with a carbon bridge. Examples of bridged heterocycloalkyl groups include azabicyclohexanyl, (e.g. 3-azabicyclo[3.1.0]hexanyl), azabicycloheptanyl (e.g. 2-azabicyclo[2.2.1]heptanyl), azabicyclooctanyl (e.g. 8-azabicyclo[3.2.1]octanyl), and 2-oxa-5-azabicyclo[2.2.1] heptane (or 5-aza-2-oxabicyclo[2.2.1]heptane). The values given herein in terms such as "4 to 7 membered heterocycloalkyl ring" refer specifically to the number of atoms present in the ring; any "bridging" atoms are counted separately.

The term "heteroalkenyl" includes alkenyl groups in which up to three carbon atoms, or up to two carbon atoms, or one carbon atom, are each replaced independently by O, $S(O)_z$ or N, provided at least one of the alkenyl carbon atoms remains. The heteroalkenyl group may be C-linked or hetero-linked, i.e. it may be linked to the remainder of the molecule through a carbon atom or through O, $S(O)_z$ or N.

The term "hetercycloalkenyl" includes cycloalkenyl groups in which up to three carbon atoms, or up to two carbon atoms, or one carbon atom, are each replaced independently by O, $S(O)_z$ or N, provided at least one of the cycloalkenyl carbon atoms remains. Examples of hetercycloalkenyl groups include 3,4-dihydro-2H-pyranyl, 5-6-dihydro-2H-pyranyl, 2H-pyranyl, 1,2,3,4-tetrahydropyridinyl and 1,2,5,6-tetrahydropyridinyl. The hetercycloalkenyl group may be C-linked or N-linked, i.e. it may be linked to the remainder of the molecule through a carbon atom or through a nitrogen atom.

The term "heteroalkynyl" includes alkynyl groups in which up to three carbon atoms, or up to two carbon atoms, or one carbon atom, are each replaced independently by O, $S(O)_z$ or N, provided at least one of the alkynyl carbon atoms remains. The heteroalkynyl group may be C-linked or hetero-linked, i.e. it may be linked to the remainder of the molecule through a carbon atom or through O, $S(O)_z$ or N.

The term "heteroalkylene" includes alkylene groups in which up to three carbon atoms, or up to two carbon atoms, or one carbon atom, are each replaced independently by O, $S(O)_z$ or N, provided at least one of the alkylene carbon atoms remains.

The term "heteroalkenylene" includes alkenylene groups in which up to three carbon atoms, or up to two carbon atoms, or one carbon atom, are each replaced independently by O, $S(O)_z$ or N, provided at least one of the alkenylene carbon atoms remains.

The term "heterocycloalkoxy" means heterocycloalkyl-O—.

The term "heterocycloalkylalkyl" means alkyl substituted with a heterocycloalkyl group.

Aryl

The term "aryl" includes monovalent, aromatic, cyclic hydrocarbyl groups, such as phenyl or naphthyl (e.g. 1-naphthyl or 2-naphthyl). In general, the aryl groups may be monocyclic or polycyclic fused ring aromatic groups. Preferred aryl groups are $C_6$-$C_{14}$aryl.

Other examples of aryl groups are monovalent derivatives of aceanthrylene, acenaphthylene, acephenanthrylene, anthracene, azulene, chrysene, coronene, fluoranthene, fluorene, as-indacene, s-indacene, indene, naphthalene, ovalene, perylene, phenalene, phenanthrene, picene, pleiadene, pyrene, pyranthrene and rubicene.

The term "arylalkyl" means alkyl substituted with an aryl group, e.g. benzyl.

Heteroaryl

The term "heteroaryl" includes monovalent, heteroaromatic, cyclic hydrocarbyl groups additionally containing one or more heteroatoms independently selected from O, S, N and $NR^N$, where $R^N$ is selected from H, alkyl (e.g. $C_{1-6}$alkyl) and cycloalkyl (e.g. $C_{3-6}$cycloalkyl). In general, the heteroaryl groups are monocyclic or polycyclic (e.g. bicyclic) fused ring heteroaromatic groups. A heteroaryl groups may contain 5-13 ring members (preferably 5-10 members) and 1, 2, 3 or 4 ring heteroatoms independently selected from O, S, N and $NR^N$, or may be a 5, 6, 9 or 10 membered, e.g. 5-membered monocyclic, 6-membered monocyclic, 9-membered fused-ring bicyclic or 10-membered fused-ring bicyclic.

Monocyclic heteroaromatic groups include heteroaromatic groups containing 5-6 ring members and 1, 2, 3 or 4 heteroatoms selected from O, S, N or $NR^N$.

Examples of 5-membered monocyclic heteroaryl groups are pyrrolyl, furanyl, thiophenyl, pyrazolyl, imidazolyl, isoxazolyl, oxazolyl, isothiazolyl, thiazolyl, 1,2,3 triazolyl, 1,2,4 triazolyl, 1,2,3 oxadiazolyl, 1,2,4 oxadiazolyl, 1,2,5 oxadiazolyl, 1,3,4 oxadiazolyl, 1,3,4 thiadiazolyl, pyridyl, pyrimidinyl, pyridazinyl, pyrazinyl, 1,3,5 triazinyl, 1,2,4 triazinyl, 1,2,3 triazinyl and tetrazolyl.

Examples of 6-membered monocyclic heteroaryl groups are pyridinyl, pyridazinyl, pyrimidinyl and pyrazinyl.

Bicyclic heteroaromatic groups include fused-ring heteroaromatic groups containing 9-13 ring members and 1, 2, 3, 4 or more heteroatoms selected from O, S, N or $NR^N$.

Examples of 9-membered fused-ring bicyclic heteroaryl groups are benzofuranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolininyl, imidazo[1,2-a]pyridinyl, imidazo[1,5-a]pyridinyl, pyrazolo[1,2-a]pyridinyl, pyrrolo[1,2-b]pyridazinyl and imidazo[1,2-c]pyrimidinyl.

Examples of 10-membered fused-ring bicyclic heteroaryl groups are quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl and pyrimido[4,5-d]pyrimidinyl.

The term "heteroarylalkyl" means alkyl substituted with a heteroaryl group.

General

Unless indicated explicitly otherwise, where combinations of groups are referred to herein as one moiety, e.g. arylalkyl, the last mentioned group contains the atom by which the moiety is attached to the rest of the molecule.

Where reference is made to a carbon atom of an alkyl group or other group being replaced by O, S(O)$_z$ or N, what is intended is that:

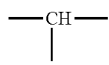

is replaced by

—CH= is replaced by —N=;
—C—H is replaced by —N; or
—CH$_2$— is replaced by —O—, —S(O)$_z$— or —NR$^N$—.

By way of clarification, in relation to the above mentioned heteroatom containing groups (such as heteroalkyl etc.), where a numerical of carbon atoms is given, for instance C$_{3-6}$heteroalkyl, what is intended is a group based on C$_{3-6}$alkyl in which one of more of the 3-6 chain carbon atoms is replaced by O, S(O)$_z$ or N. Accordingly, a C$_{3-6}$heteroalkyl group, for example, will contain less than 3-6 chain carbon atoms.

Substitution

Groups of the compounds of the invention (e.g. alkyl, cycloalkyl, alkoxy, alkenyl, cycloalkenyl, alkynyl, alkylene, alkenylene, heteroalkyl, heterocycloalkyl, heteroalkenyl, hetercycloalkenyl, heteroalkynyl, heteroalkylene, heteroalkenylene, heterocycloalkoxy, heterocycloalkylalkyl, aryl, arylalkyl, arylheteroalkyl, heteroaryl, heteroarylalkyl or heteroarylheteroalkyl groups etc.) may be substituted or unsubstituted. Typically, substitution involves the notional replacement of one or more hydrogen atoms on a designated atom (e.g. a carbon atom or a nitrogen atom) with one or more substituent groups (provided that the designated atom's normal valency is not exceeded), or two hydrogen atoms in the case of substitution by =O. Alternatively, in the case of bivalent substituent groups such as C$_{1-6}$alkylenedioxy, substitution involves the notional replacement of a hydrogen atom on a designated atom and a hydrogen atom on an adjacent atom with the substituent group.

Where an "optionally substituted" group is indeed substituted, there will generally be 1 to 5 substituents on the group, or 1 to 3 substituents, or 1 or 2 substituents, or 1 substituent. The substituents are independently selected from halo, trihalomethyl, trihaloethyl, trihalomethoxy, trihaloethoxy, —OH, —NO$_2$, —CN, —CO$_2$H, —CO$_2$C$_{1-6}$alkyl, —SO$_3$H, —SOC$_{1-6}$alkyl, —SO$_2$C$_{1-6}$alkyl, —NHSO$_2$C$_{1-6}$alkyl, —NC$_{1-6}$alkylSO$_2$C$_{1-6}$alkyl, —SO$_2$NH$_2$, —SO$_2$NHC$_{1-6}$alkyl, —SO$_2$N(C$_{1-6}$alkyl)$_2$, —NHSO$_2$NH$_2$, —NHSO$_2$NHC$_{1-6}$alkyl, —NHSO$_2$N(C$_{1-6}$alkyl)$_2$, —NC$_{1-6}$alkylSO$_2$NH$_2$, —NC$_{1-6}$alkylSO$_2$NHC$_{1-6}$alkyl, —NC$_{1-6}$alkylSO$_2$N(C$_{1-6}$alkyl)$_2$, —C(=O)H, —C(=O)C$_{1-6}$alkyl, —NHC(=O)C$_{1-6}$alkyl, —NC$_{1-6}$alkylC(=O)C$_{1-6}$alkyl, C$_{1-6}$alkylenedioxy, =O, —N(C$_{1-6}$alkyl)$_2$, —C(=O)NH$_2$, —C(=O)NHC$_{1-6}$alkyl, —C(=O)N(C$_{1-6}$alkyl)$_2$, —NHC(=O)NH$_2$, —NHC(=O)NHC$_{1-6}$alkyl, —NHC(=O)N(C$_{1-6}$alkyl)$_2$, —NC$_{1-6}$alkylC(=O)NH$_2$, —NC$_{1-6}$alkylC(=O)NHC$_{1-6}$alkyl, —NC$_{1-6}$alkylC(=O)N(C$_{1-6}$alkyl)$_2$, —C(=NH)NH$_2$, —C(=NH)NHC$_{1-6}$alkyl, —C(=NH)N(C$_{1-6}$alkyl)$_2$, —C(=NC$_{1-6}$alkyl)NH$_2$, —C(=NC$_{1-6}$alkyl)NHC$_{1-6}$alkyl, —C(=NC$_{1-6}$alkyl)N(C$_{1-6}$alkyl)$_2$, —C$_{1-6}$alkyl, —C$_{3-6}$cycloalkyl, —C$_{3-6}$heterocycloalkyl, 2-imidazolidinon-3-yl, 1-C$_{1-6}$alkyl-2-imidazolidinon-3-yl, C$_{1-6}$alkylC$_{3-6}$heterocycloalkyl, aryl, haloaryl, C$_{1-6}$alkoxyaryl, —C$_{1-6}$alkylene-NHSO$_2$C$_{1-6}$alkyl, —C$_{1-6}$alkylene-NC$_{1-6}$alkylSO$_2$C$_{1-6}$alkyl, —C$_{1-6}$alkylene-SO$_2$NH$_2$, —C$_{1-6}$alkylene-SO$_2$NHC$_{1-6}$alkyl, —C$_{1-6}$alkylene-SO$_2$N(C$_{1-6}$alkyl)$_2$, —Z$^t$H, —Z$^t$—C$_{1-6}$alkyl, —C$_{1-6}$alkylene-Z$^t$H, —Z$^t$—C$_{3-6}$cycloalkyl, or —C(=O)NHC$_{1-6}$alkylene-Z$^t$H wherein Z$^t$ is independently O, S, NH or N(C$_{1-6}$alkyl). "C$_{1-6}$alkyl" and "C$_{1-6}$alkylene" in the above substituents may optionally be replaced by "C$_{1-6}$heteroalkyl" and "C$_{1-6}$heteroalkylene" respectively.

In one embodiment, the substituents are independently selected from halo, trihalomethyl, trihaloethyl, trihalomethoxy, trihaloethoxy, —OH, —NO$_2$, —CN, —CO$_2$H, —CO$_2$C$_{1-6}$alkyl, —SO$_3$H, —SOC$_{1-6}$alkyl, —SO$_2$C$_{1-6}$alkyl, —NHSO$_2$C$_{1-6}$alkyl, —NC$_{1-6}$alkylSO$_2$C$_{1-6}$alkyl, —SO$_2$NH$_2$, —SO$_2$NHC$_{1-6}$alkyl, —SO$_2$N(C$_{1-6}$alkyl)$_2$, —NHSO$_2$NH$_2$, —NHSO$_2$NHC$_{1-6}$alkyl, —NHSO$_2$N(C$_{1-6}$alkyl)$_2$, —NC$_{1-6}$alkylSO$_2$NH$_2$, —NC$_{1-6}$alkylSO$_2$NHC$_{1-6}$alkyl, —NC$_{1-6}$alkylSO$_2$N(C$_{1-6}$alkyl)$_2$, —C(=O)H, —C(=O)C$_{1-6}$alkyl, —NHC(=O)C$_{1-6}$alkyl, —NC$_{1-6}$alkylC(=O)C$_{1-6}$alkyl, C$_{1-6}$alkylenedioxy, =O, —N(C$_{1-6}$alkyl)$_2$, —C(=O)NH$_2$, —C(=O)NHC$_{1-6}$alkyl, —C(=O)N(C$_{1-6}$alkyl)$_2$, —NHC(=O)NH$_2$, —NHC(=O)NHC$_{1-6}$alkyl, —NHC(=O)N(C$_{1-6}$alkyl)$_2$, —NC$_{1-6}$alkylC(=O)NH$_2$, —NC$_{1-6}$alkylC(=O)NHC$_{1-6}$alkyl, —NC$_{1-6}$alkylC(=O)N(C$_{1-6}$alkyl)$_2$, —C(=NH)NH$_2$, —C(=NH)NHC$_{1-6}$alkyl, —C(=NH)N(C$_{1-6}$alkyl)$_2$, —C(=NC$_{1-6}$alkyl)NH$_2$, —C(=NC$_{1-6}$alkyl)NHC$_{1-6}$alkyl, —C(=NC$_{1-6}$alkyl)N(C$_{1-6}$alkyl)$_2$, —C$_{1-6}$alkyl, —C$_{3-6}$cycloalkyl, —C$_{3-6}$heterocycloalkyl, 2-imidazolidinon-3-yl, 1-C$_{1-6}$alkyl-2-imidazolidinon-3-yl, C$_{1-6}$alkylC$_{3-6}$heterocycloalkyl, aryl, haloaryl, C$_{1-6}$alkoxyaryl, —Z$^t$H, —Z$^t$—C$_{1-6}$alkyl, —C$_{1-6}$alkylene-Z$^t$H, —Z$^t$—C$_{3-6}$cycloalkyl, or —C(=O)NHC$_{1-6}$alkylene-Z$^t$H wherein Z$^t$ is independently O, S, NH or N(C$_{1-6}$alkyl). "C$_{1-6}$alkyl" and "C$_{1-6}$alkylene" in the above substituents may optionally be replaced by "C$_{1-6}$heteroalkyl" and "C$_{1-6}$heteroalkylene" respectively.

In another embodiment, the substituents are independently selected from halo, trihalomethyl, trihaloethyl, —OH, —NO$_2$, —CN, —CO$_2$H, —CO$_2$C$_{1-6}$alkyl, —SO$_3$H, —SOC$_{1-6}$alkyl, —SO$_2$C$_{1-6}$alkyl, —NHSO$_2$C$_{1-6}$alkyl, —SO$_2$NH$_2$, —SO$_2$NHC$_{1-6}$alkyl, —SO$_2$N(C$_{1-6}$alkyl)$_2$, —C(=O)H, —C(=O)C$_{1-6}$alkyl, —NHC(=O)C$_{1-6}$alkyl, —NC$_{1-6}$alkylC(=O)C$_{1-6}$alkyl, =O, —N(C$_{1-6}$alkyl)$_2$, —C(=O)NH$_2$, —C(=O)NHC$_{1-6}$alkyl, —C(=O)N(C$_{1-6}$alkyl)$_2$, —C$_{1-6}$alkyl, —C$_{3-6}$cycloalkyl, —C$_{3-6}$heterocycloalkyl, aryl, haloaryl, —Z$^t$H, —Z$^t$—C$_{1-6}$alkyl, —C$_{1-6}$alkylene-Z$^t$H or —Z$^t$—C$_{3-6}$cycloalkyl, wherein Z$^t$ is independently O, S, NH or N(C$_{1-6}$alkyl).

Where a group has at least 2 positions which may be substituted, the group may be substituted by both ends of an alkylene or heteroalkylene chain to form a cyclic moiety.

The molecular weight of the compounds of the invention may, optionally, be less than 1000 g/mole, or less than 950 g/mole, or less than 900 g/mole, or less than 850 g/mole, or less than 800 g/mole, or less than 750 g/mole, or less than 700 g/mole, or less than 650 g/mole, or less than 600 g/mole, or less than 550 g/mole, or less than 500 g/mole.

The compounds of the invention may include any isotopes of the atoms comprised in the compounds. Examples include $^2$H and $^3$H, and $^{13}$C and $^{14}$C.

Pharmaceutically Acceptable Derivatives

The term "pharmaceutically acceptable derivative" includes any pharmaceutically acceptable salt, solvate, hydrate or prodrug of a compound of the invention. In one embodiment, the pharmaceutically acceptable derivatives are pharmaceutically acceptable salts, solvates or hydrates of a compound of the invention.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically Acceptable Salts

The term "pharmaceutically acceptable salt" includes a derivative of a compound of the invention that is a salt prepared from pharmaceutically acceptable non-toxic acids or bases including inorganic or organic acids and bases.

Compounds of the invention which contain basic, e.g. amino, groups are capable of forming pharmaceutically acceptable salts with acids. Pharmaceutically acceptable acid addition salts of the compounds of the invention may include, but are not limited to, those of inorganic acids such as hydrohalic acids (e.g. hydrochloric, hydrobromic and hydroiodic acid), sulfuric acid, sulfamic acid, nitric acid, and phosphoric acid. Pharmaceutically acceptable acid addition salts of the compounds of the invention may include, but are not limited to, those of organic acids such as aliphatic, aromatic, carboxylic and sulfonic classes of organic acids, examples of which include: aliphatic monocarboxylic acids such as formic acid, acetic acid, propionic acid or butyric acid; aliphatic hydroxy acids such as lactic acid, citric acid, tartaric acid or malic acid; dicarboxylic acids such as oxalic acid, maleic acid, hydroxymaleic acid, fumaric acid or succinic acid; aromatic carboxylic acids such as benzoic acid, p-chlorobenzoic acid, 2-acetoxybenzoic acid, phenylacetic acid, diphenylacetic acid or triphenylacetic acid; aromatic hydroxyl acids such as o-hydroxybenzoic acid, p-hydroxybenzoic acid, 1-hydroxynaphthalene-2-carboxylic acid or 3 hydroxynaphthalene-2-carboxylic acid; and sulfonic acids such as methanesulfonic acid, ethanesulfonic acid, ethanedisulfonic acid, isethionic acid, benzenesulfonic acid, toluenesulfonic acid. Other pharmaceutically acceptable acid addition salts of the compounds of the invention include, but are not limited to, those of ascorbic acid, glycolic acid, glucuronic acid, furoic acid, glutamic acid, anthranilic acid, salicylic acid, mandelic acid, embonic (pamoic) acid, pantothenic acid, stearic acid, sulfanilic acid, algenic acid, and galacturonic acid.

Compounds of the invention which contain acidic, e.g. carboxyl, groups are capable of forming pharmaceutically acceptable salts with bases. In one embodiment, pharmaceutically acceptable basic salts of the compounds of the invention include, but are not limited to, metal salts such as alkali metal or alkaline earth metal salts (e.g. sodium, potassium, magnesium or calcium salts) and zinc or aluminium salts. In one embodiment, pharmaceutically acceptable basic salts of the compounds of the invention include, but are not limited to, salts formed with ammonia or pharmaceutically acceptable organic amines or heterocyclic bases such as ethanolamines (e.g. diethanolamine), benzylamines, N-methyl-glucamine, amino acids (e.g. lysine) or pyridine.

Hemisalts of acids and bases may also be formed, e.g. hemisulphate salts.

Pharmaceutically acceptable salts of compounds of the invention may be prepared by methods well-known in the art. For instance, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. For a review of pharmaceutically acceptable salts, see Stahl and Wermuth, Handbook of Pharmaceutical Salts Properties, Selection and Use (Wiley-VCH, Weinheim, Germany, 2002).

Solvates & Hydrates

The compounds of the invention may exist in both unsolvated and solvated forms. The term "solvate" includes molecular complexes (e.g. crystals) comprising a compound of the invention and one or more pharmaceutically acceptable solvent molecules such as water or $C_{1-6}$ alcohols, e.g. ethanol. The term "hydrate" means a "solvate" where the solvent is water.

Prodrugs

The invention includes prodrugs of the compounds of the invention. Prodrugs are derivatives of compounds of the invention (which may have little or no pharmacological activity themselves), which can, when administered in vivo, be converted into compounds of the invention.

Prodrugs can, for example, be produced by replacing functionalities present in the compounds of the invention with appropriate moieties which are metabolized in vivo to form a compound of the invention. The design of prodrugs is well-known in the art, as discussed in Bundgaard, Design of Prodrugs 1985 (Elsevier), The Practice of Medicinal Chemistry 2003, 2nd Ed, 561-585 and Leinweber, Drug Metab. Res. 1987, 18: 379.

Examples of prodrugs of compounds of the invention are esters and amides of the compounds of the invention. For example, where the compound of the invention contains a carboxylic acid group (—COOH), the hydrogen atom of the carboxylic acid group may be replaced to form an ester (e.g. the hydrogen atom may be replaced by —$C_{1-6}$alkyl). Where the compound of the invention contains an alcohol group (—OH), the hydrogen atom of the alcohol group may be replaced in order to form an ester (e.g. the hydrogen atom may be replaced by —C(O)$C_{1-6}$alkyl. Where the compound of the invention contains a primary or secondary amino group, one or more hydrogen atoms of the amino group may be replaced in order to form an amide (e.g. one or more hydrogen atoms may be replaced by —C(O)$C_{1-6}$alkyl).

Amorphous & Crystalline Forms

The compounds of the invention may exist in solid states from amorphous through to crystalline forms. "Amorphous" refers to a solid form of a molecule, atom, and/or ions that is not crystalline. Different crystalline forms ("polymorphs") have the same chemical composition but different spatial arrangements of the molecules, atoms, and/or ions forming the crystal. All such solid forms are included within the invention.

Purity

The compounds of the invention may, subsequent to their preparation, be isolated and purified to obtain a composition containing an amount by weight equal to or greater than 99% of said compound ("substantially pure" compound), which is then used or formulated as described herein.

Isomeric Forms

Compounds of the invention may exist in one or more geometrical, optical, enantiomeric, diastereomeric and tautomeric forms, including but not limited to cis- and trans-forms, E- and Z-forms, R—, S— and meso-forms, keto-, and enol-forms. All such isomeric forms are included within the invention. The isomeric forms may be in isomerically pure or enriched form (e.g. one enantiomer may be present in excess, also known as a scalemic mixture), as well as in mixtures of isomers (e.g. racemic or diastereomeric mixtures).

If one enantiomer is present in a greater amount that its corresponding enantiomer, the enantiomeric excess may be expressed as a percentage of the whole. For instance, a 98:2 mixture of one enantiomer to another has a 96% enantiomeric excess of the first enantiomer. The enantiomeric excess may be at least 5%, 10%, 15%, 20%, 25%, 30%, 35%, 40%, 45%, 50%, 55%, 60%, 65%, 70%, 75%, 80%, 85%, 90%, 95% or up to 100% (i.e. enantiomerically pure, up to the detection limit of purity).

The invention therefore provides:
stereoisomeric mixtures of compounds of the invention;
a diastereomerically enriched or diastereomerically pure isomer of a compound of the invention; or
an enantiomerically enriched or enantiomerically pure isomer of a compound of the invention.

The processes for preparation can utilize racemates, enantiomers, or diastereomers as starting materials. Where appropriate, isomers can be prepared by the application or adaptation of known methods (e.g. asymmetric synthesis). When diastereomeric or enantiomeric products are prepared, they can be separated by conventional methods for example, chromatographic or fractional crystallization.

Isotopic Labeling

The invention includes pharmaceutically acceptable isotopically-labelled compounds of the invention wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}$H and $^{3}$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of the invention, for example, those incorporating a radioactive isotope, are useful in drug and/or substrate tissue distribution studies. The radioactive isotopes $^{3}$H and $^{14}$C are particularly useful for this purpose in view of their ease of incorporation and ready means of detection. Substitution with heavier isotopes such as $^{2}$H may afford certain therapeutic advantages resulting from greater metabolic stability, for example, increase in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of the invention can generally be prepared by conventional techniques known to those skilled in the art or by processes analogous to those described herein using an appropriate isotopically-labelled reagent in place of the non-labelled reagent previously employed.

Treatment of Diseases and Conditions

Compounds of the invention are inhibitors of $K_{ir}3.1$ and/or $K_{ir}3.4$.

The invention provides a compound of the invention for use in therapy. The invention further provides a pharmaceutical composition comprising a compound of the invention in combination with a pharmaceutically acceptable excipient.

The invention further provides a method for the treatment of a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof, comprising the step of administering a therapeutically effective amount of a compound of the invention to a patient. The invention also provides the use of a compound of the invention for the manufacture of a medicament for the treatment of a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof. The invention also provides a compound of the invention for use in a method for the treatment of a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof.

Preferred compounds of the invention have an $IC_{50}$ in the $K_{ir}3.1/3.4$ Electrophysiology Method (described below) of <100 µM, <10 µM, <3 µM, <1 µM, <100 nM, or <10 nM.

Diseases and Conditions Mediated by $K_{ir}3.1$ and/or $K_{ir}3.4$ or Heteromultimers Thereof/Requiring Inhibition of $K_{ir}3.1$ and/or $K_{ir}3.4$ or Heteromultimers Thereof The invention is useful for the treatment of a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof. In particular, the heteromultimer may be the heterotetramer $K_{ir}3.1/3.4$. The invention therefore has use in:

the treatment of cardiovascular diseases, such as atrial fibrillation (AF), atrial flutter (AFL), atrioventricular (AV) dysfunction and sinoatrial node (SAN) dysfunction;
the prevention of recurrence of supraventriclar arrhythmias including AF and AFL;
the maintenance of sinus rhythm;
the termination and cardioversion of supraventriclar arrhythmias;
the treatment of sinus node dysfunction;
the treatment of AV node dysfunction, including AV block;
the treatment of conduction dysfunction;
the prevention or reversal of atrial structural and ionic remodeling;
the prevention of thrombosis, thromboembolism and thromboembolic diseases, such as stroke, myocardial infarction, and peripheral vascular diseases;
the improvement of cardiac contractility;
the treatment of metabolic diseases, such as diabetes mellitus;
the modulation of neuro-endocrine function;
the modulation of the secretion of pituitary hormones;
the treatment of neurological and neuropsychiatric disorders, such as pain, depression, anxiety, attention deficit/hyperactivity disorder and epilepsy; and
the treatment of cancer, such as breast cancer.

Therapeutic Definitions

As used herein, "treatment" includes curative, modulative (i.e. arresting the development of a disease state) and prophylactic treatment. As used herein, a "patient" means an animal, such as a mammal, such as a human, in need of treatment.

The amount of the compound of the invention administered should be a therapeutically effective amount where the compound or derivative is used for the treatment of a disease or condition, or its modulation, and a prophylactically effective amount where the compound or derivative is used for the prevention of a disease or condition.

The term "therapeutically effective amount" used herein refers to the amount of compound needed to treat or ameliorate a targeted disease or condition. The term "prophylactically effective amount" used herein refers to the amount of compound needed to prevent a targeted disease or condition. The exact dosage will generally be dependent on the patient's status at the time of administration. Factors that may be taken into consideration when determining dosage include the severity of the disease state in the patient, the general health of the patient, the age, weight, gender, diet, time, frequency and route of administration, drug combinations, reaction sensitivities and the patient's tolerance or response to therapy.

The precise amount can be determined by routine experimentation, but may ultimately lie with the judgement of the clinician. Generally, an effective dose will be from 0.01 mg/kg/day (mass of drug compared to mass of patient) to 1000 mg/kg/day, e.g. 1 mg/kg/day to 100 mg/kg/day.

Compounds of the invention may be administered in a single daily dose, or the total daily dosage may be administered in divided doses of two, three, or four times daily. The daily oral dosage of the active ingredient may be between 3 and 600 mg either administered once daily or in divided doses administered twice daily. Alternatively, the active ingredient may be administered in doses of 10-20 mg administered twice daily or 40 to 100 mg administered once daily. Alternatively, the active ingredient may be administered a dose of 12.5 mg twice a day or 75 mg once a day. Alternatively, the active ingredient may be administered in doses of 3, 10, 30, 100, 300, and 600 mg administered either once or twice a day. Compositions may be administered individually to a patient or may be administered in combination with other agents, drugs or hormones.

Administration & Formulation

General

For pharmaceutical use, the compounds of the invention may be administered as a medicament by enteral or parenteral routes, including intravenous, intramuscular, subcutaneous, transdermal, airway (aerosol), oral, intranasal, rectal, vaginal and topical (including buccal and sublingual) administration. The compounds of the invention should be assessed for their biopharmaceutical properties, such as solubility and solution stability (across pH), permeability, etc., in order to select the most appropriate dosage form and route of administration for treatment of the proposed indication.

The compounds of the invention may be administered as crystalline or amorphous products. The compounds of the invention may be administered alone or in combination with one or more other compounds of the invention or in combination with one or more other drugs (or as any combination thereof). Generally, they will be administered as a formulation in association with one or more pharmaceutically acceptable excipients. The term "excipient" includes any ingredient other than the compound(s) of the invention which may impart either a functional (e.g. drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

Typical pharmaceutically acceptable excipients include:
diluents, e.g. lactose, dextrose, sucrose, mannitol, sorbitol, cellulose and/or glycine;
lubricants, e.g. silica, talcum, stearic acid, its magnesium or calcium salt and/or polyethyleneglycol;
binders, e.g. magnesium aluminium silicate, starch paste, gelatin, tragacanth, methylcellulose, sodium carboxymethylcellulose and/or polyvinylpyrrolidone;
disintegrants, e.g. starches, agar, alginic acid or its sodium salt, or effervescent mixtures; and/or
absorbants, colorants, flavors and/or sweeteners.

A thorough discussion of pharmaceutically acceptable excipients is available in Gennaro, Remington: The Science and Practice of Pharmacy 2000, 20th edition (ISBN: 0683306472). Accordingly, the present invention provides a pharmaceutical composition comprising a compound of the invention and a pharmaceutically acceptable excipient.

Compounds of the invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) may contain from about 1 milligram to about 500 milligrams of active ingredient per dosage unit. In these pharmaceutical compositions the active ingredient will typically be present in an amount of about 0.5-95% by weight based on the total weight of the composition.

Oral Administration

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions, or solutions in a digestible oil, such as soybean oil, cottonseed oil or olive oil), emulsions or powders; lozenges (including liquid-filled); chews; gels; fast dispersing dosage forms; powders; granules; films; ovules; sprays; and buccal/mucoadhesive patches.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, suspensions, solutions, syrups, tinctures and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, Expert Opinion in Therapeutic Patents 2001, 11(6): 981-986.

The formulation of tablets is discussed in H. Lieberman and L. Lachman, Pharmaceutical Dosage Forms Tablets 1980, vol. 1 (Marcel Dekker, New York).

Parenteral Administration

The compounds of the invention can be administered parenterally.

The compounds of the invention may be administered directly into the blood stream, into subcutaneous tissue, into muscle, or into an internal organ. Suitable means for administration include intravenous, intraarterial, intraperitoneal, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions and may include, as carriers, water, a suitable oil, saline, aqueous dextrose (glucose) and related sugar solutions, and/or glycols such as propylene glycol or polyethylene glycols. Where the solution is aqueous, excipients such as sugars (including but restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Solutions for parenteral administration may contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Parenteral formulations may include implants derived from degradable polymers such as polyesters (i.e. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of the invention used in the preparation of parenteral solutions may be increased by the use of appropriate formulation techniques, such as the incorporation of co-solvents and/or solubility-enhancing agents such as surfactants, micelle structures and cyclodextrins.

Inhalation & Intranasal Administration

The compounds of the invention can be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as 1 leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Formulations for inhaled/intranasal administration may be formulated to be immediate and/or modified release using, for example, PGLA. Modified release formulations include delayed-, sustained-, pulsed-, controlled-, targeted and programmed release.

Transdermal Administration

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Combination Therapy

A compound of the invention may be administered alone, or may be administered in combination with another therapeutic agent (i.e. a different agent to the compound of the invention). The compound of the invention and the other therapeutic agent may be administered in a therapeutically effective amount.

The compound of the present invention may be administered either simultaneously with, or before or after, the other therapeutic agent. The compound of the present invention and the other therapeutic agent may be administered separately, by the same or different route of administration, or together in the same pharmaceutical composition.

In one embodiment, the invention provides a product comprising a compound of the invention and another therapeutic agent as a combined preparation for simultaneous, separate or sequential use in therapy. In one embodiment, the therapy is the treatment of a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof. Products provided as a combined preparation include a composition comprising the compound of the invention and the other therapeutic agent together in the same pharmaceutical composition, or the compound of the invention and the other therapeutic agent in separate form, e.g. in the form of a kit.

The invention provides a pharmaceutical composition comprising a compound of the invention and another therapeutic agent. Optionally, the pharmaceutical composition may comprise a pharmaceutically acceptable excipient, as described above in "Administration & Formulation".

The invention provides a kit comprising two or more separate pharmaceutical compositions, at least one of which contains a compound the invention. The kit may comprise means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. The compound of the invention and the other therapeutic agent may be combined in a single dosage unit. Optionally, they may be formulated such that although the active ingredients are combined in a single dosage unit, the physical contact between the active ingredients is minimized. For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach can involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Accordingly, the invention provides the use of a compound of the invention in the manufacture of a medicament for treating a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof, wherein the medicament is prepared for administration with another therapeutic agent. The invention also provides the use of another therapeutic agent in the manufacture of medicament for treating a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof, wherein the medicament is prepared for administration with a compound of the invention.

The invention also provides a compound of the invention for use in a method of treating a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof, wherein the compound of the invention is prepared for administration with another therapeutic agent. The invention also provides another therapeutic agent for use in a method of treating a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof, wherein the other therapeutic agent is prepared for administration with a compound of the invention. The invention also provides a compound of the invention for use in a method of treating a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof, wherein the compound of the invention is administered with another therapeutic agent. The invention also provides another therapeutic agent for use in a method of treating a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof, wherein the other therapeutic agent is administered with a compound of the invention.

The invention also provides the use of a compound of the invention in the manufacture of a medicament for treating a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof, wherein the patient has previously (e.g. within 24 hours) been treated with another therapeutic agent. The invention also provides the use of another therapeutic agent in the manufacture of a medicament for treating a disease or condition mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof, wherein the patient has previously (e.g. within 24 hours) been treated with a compound of the invention.

In one embodiment, the other therapeutic agent is selected from other antiarrhythmic agents, such as Vaughan-Williams class I, class II, class III, or class IV agents, or from other cardiovascular agents.

Synthesis

Compounds of formula (i) may be prepared by conventional routes, for example those set out in Schemes 1 to 21 shown below.

SCHEME 1

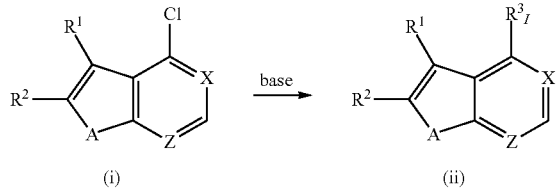

Compounds of formula (II) where $R^3_I$ is $NR^8R^9$, —$(NR^aR^b)$-J (e.g.

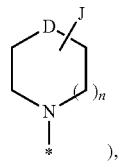

),

—CN, or alkoxy and where $R^1$, $R^2$, $R^8$, $R^9$, n, D and J are as defined above may be prepared according to scheme 1 from compounds of formula (i) via displacement of the 4-chloro substituent by a suitable nucleophilic species. Typically, this reaction is performed in the presence of a base, for example, triethylamine or potassium carbonate, utilising standard methods familiar to those skilled in the art such as reaction in solvents such as tetrahydrofuran, toluene, acetonitrile or dimethylformamide, at a range of temperatures from ambient to reflux temperature or via microwave irradiation.

SCHEME 2

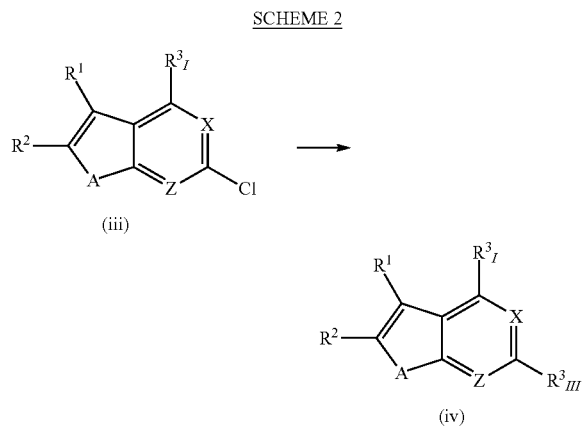

Compounds of formula (iv) where $R^3{}_{III}$ is $NR^{10}R^{11}$, —$(NR^cR^d)$-J (e.g.

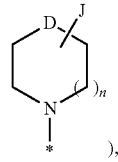

),

—CN, or alkoxy and where $R^1$, $R^2$, $R^3{}_I$, $R^{10}$, $R^{11}$, n, D and J are as defined above may be prepared according to scheme 2 from compounds of formula (iii) via displacement of the 2-chloro substituent by a suitable nucleophilic species. Typically, this reaction is performed in the presence of a base, for example, triethylamine or potassium carbonate, utilising standard methods familiar to those skilled in the art such as reaction in solvents such as tetrahydrofuran, toluene, acetonitrile or dimethylformamide, at a range of temperatures from ambient to reflux temperature or via microwave irradiation.

SCHEME 3

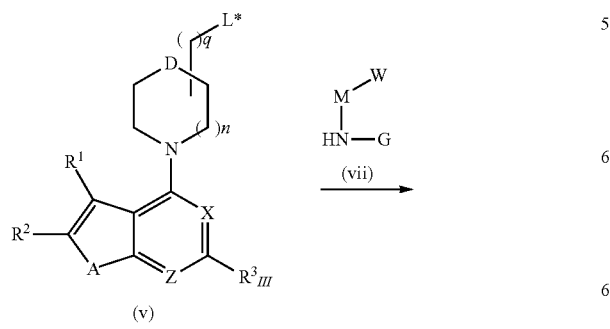

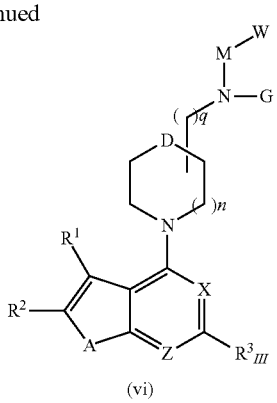

Compounds of formula (vi) may be prepared according to scheme 3 by reaction of compounds of formula (v) where L* is defined as a suitable leaving group, for example, bromine, chlorine, iodine, tosylate, or mesylate. Typically, this reaction is performed in the presence of a base, for example, triethylamine or potassium carbonate, utilising standard methods familiar to those skilled in the art such as reaction in solvent such as tetrahydrofuran, acetonitrile or dichloromethane at a range of temperatures from ambient to reflux temperature or via microwave irradiation. Compounds of formula (vii) are known compounds or may be prepared by standard published methods familiar to those skilled in the art.

SCHEME 4

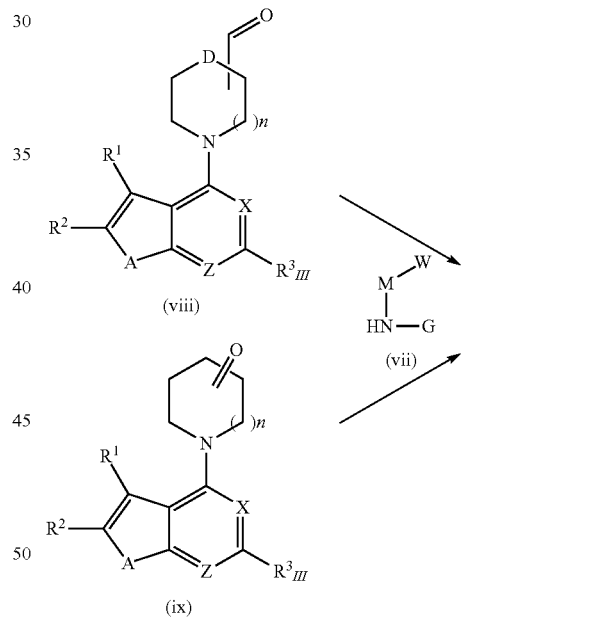

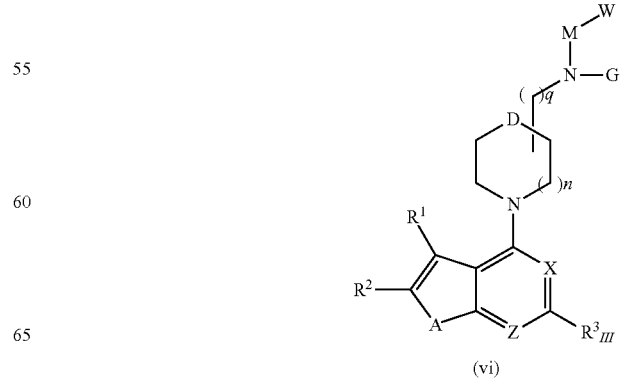

Compounds of formula (vi) where q is 0 or 1 may also be prepared from the corresponding aldehyde (viii) or ketone (ix) according to scheme 4 via a reductive amination. The reaction may be performed in a one pot procedure with in situ formation and reduction of the imine or via a two stage process where the imine is isolated and purified prior to reduction. Imine formation is performed under acid catalysis, suitable catalysts include acetic acid. The reduction may be performed using standard methods such as reaction in solvent such as tetrahydrofuran, acetonitrile, dichloromethane or toluene at a range of temperatures from −10° C. to reflux temperature with a suitable reductant such as sodium triacetoxyborohydride or sodium cyanoborohydride, the reduction may also be performed using catalytic hydrogenation or in the presence of phenylsilane and dibutyltin dichloride. Compounds of formula (vii) are known compounds or may be prepared by standard published methods familiar to those skilled in the art.

SCHEME 5

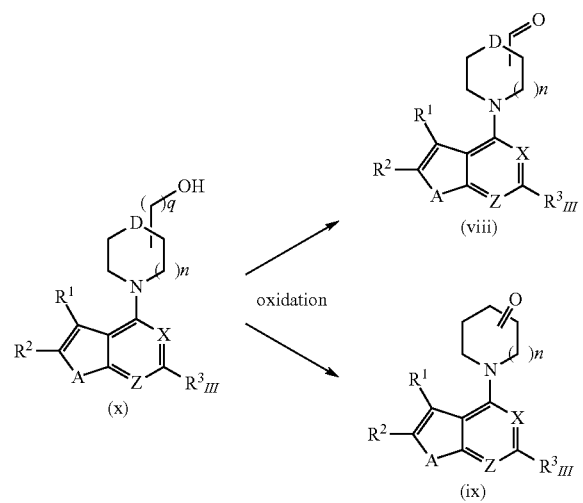

Compounds such as (viii) and (ix) may be prepared from the corresponding alcohols (x) according to scheme 5 via an oxidation. Typically, this reaction is performed in the presence of an oxidant, for example, pyridinium chlorochromate or Dess-Martin periodinane, utilising standard methods familiar to those skilled in the art such as reaction in solvent such as tetrahydrofuran, acetonitrile or dichloromethane at a range of temperatures from −10° C. to reflux temperature or via microwave irradiation.

SCHEME 6

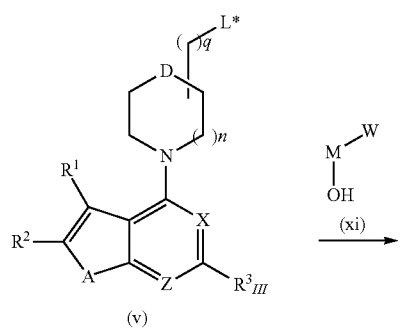

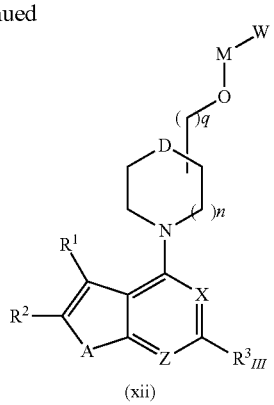

Compounds of formula (xii) may be prepared according to scheme 6 by reaction of compounds of formula (v) where L* is defined as a suitable leaving group, for example, bromine, chlorine, iodine, tosylate, or mesylate. It is understood that the reverse case also holds true in that (v) may bear the hydroxyl and (xi) the leaving group. Typically, this reaction is performed in the presence of a base, for example, sodium hydride, sodium hydroxide or potassium carbonate, utilising standard methods familiar to those skilled in the art such as reaction in solvent such as tetrahydrofuran, toluene, acetonitrile or dimethylformamide, or a mixture of solvents such as toluene/water in the presence of a phase-transfer catalyst such as tetrabutyl ammonium bromide, at a range of temperatures from ambient to reflux temperature or via microwave irradiation. Compounds of formula (xi) are known compounds or may be prepared by standard published methods familiar to those skilled in the art.

SCHEME 7

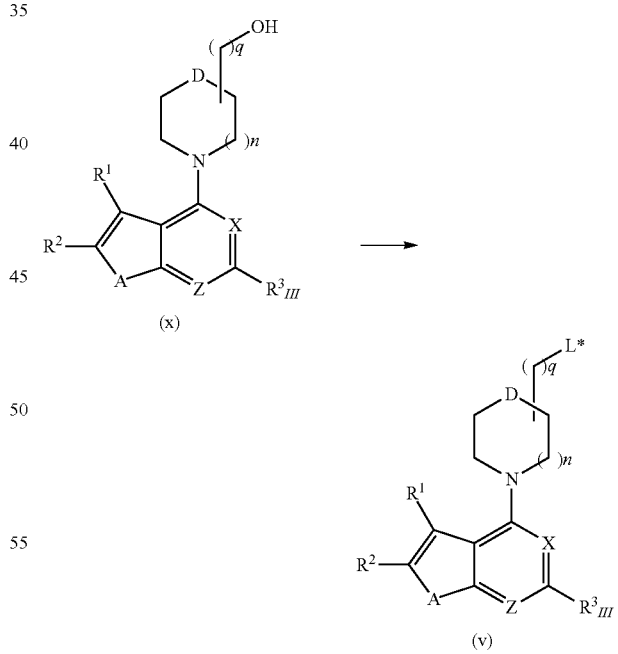

Compounds of formula (v) where L* is a halogen may be prepared according to scheme 7 from compounds of formula (x) via reaction with a suitable halogenating agent. For example, when L* is bromine, suitable reagents include phosphorous tribromide or phosphorous oxybromide or when L* is chlorine, suitable reagents include phosphorous pentachloride, phosphorous oxychloride or thionyl chloride. The halogenation reaction may also be performed using Appel (Appel R, 1975) conditions in the presence of carbontetrabromide and triphenylphosphine when L* is bromine, or carbontetrachloride and triphenylphosphine when L* is chlorine. The halogenation may be performed in solvent such as tetrahydrofuran, acetonitrile, dichloromethane or toluene, or in neat reagent, at a range of temperatures from −10° C. to reflux temperature.

Compounds of formula (v) where L* is an O-alkyl, or O-aryl sulfonyl leaving group may be synthesized from compounds of formula (x). Typically, this reaction is performed in the presence of a suitable sulfonylchloride such as toluenesulfonyl chloride or methanesulfonyl chloride and in the presence of base such as triethylamine or potassium carbonate utilising standard methods familiar to those skilled in the art such as reaction in solvent such as tetrahydrofuran, toluene, acetonitrile or dichloromethane at a range of temperatures from −10° C. to reflux temperature.

SCHEME 8

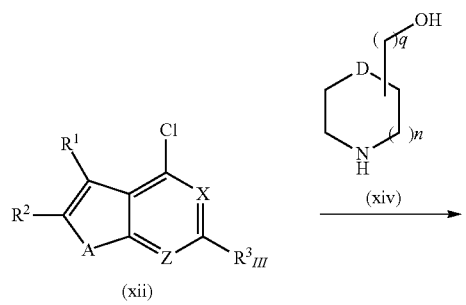

(xii)

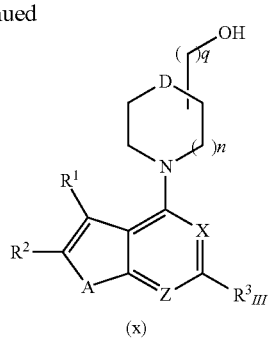

(x)

Compounds of formula (x) may be prepared according to scheme 8 from compounds of formula (xii). Typically, this reaction is performed in the presence of a base, for example, triethylamine or potassium carbonate, utilising standard methods familiar to those skilled in the art such as reaction in solvent such as tetrahydrofuran, toluene, acetonitrile or dimethylformamide, at a range of temperatures from ambient to reflux temperature or via microwave irradiation. Compounds of formula (xiv) are known compounds or may be prepared by standard published methods familiar to those skilled in the art.

SCHEME 9

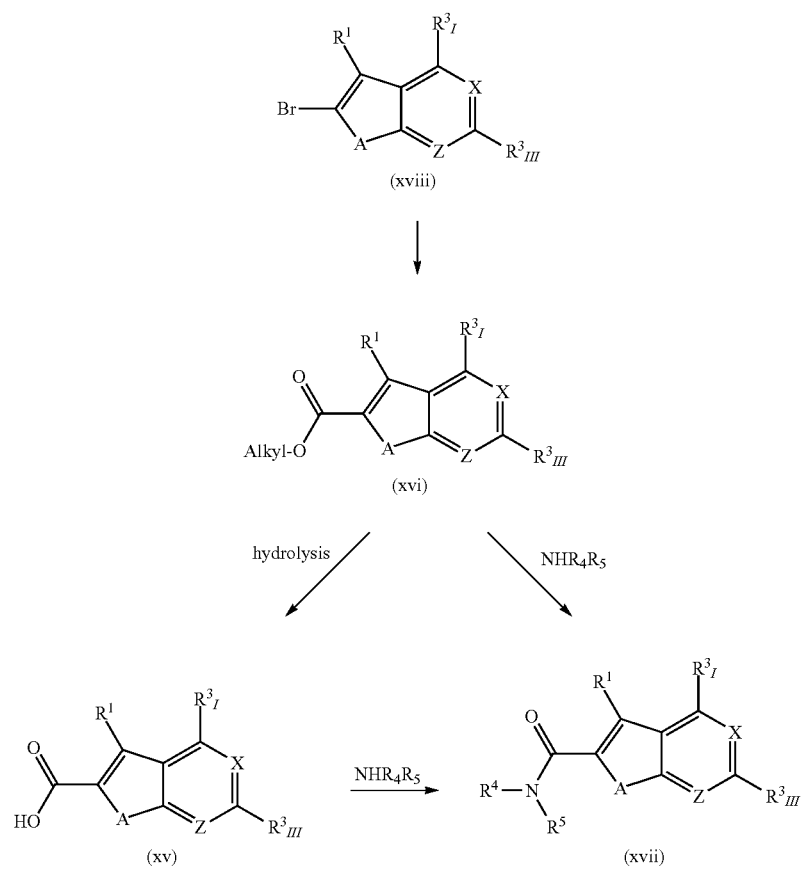

Compounds of formula (xvii) may be prepared according to scheme 9 via the reaction of compounds of formula (xv) with amines of formula $NHR^4R^5$. Typically, this reaction is carried out using a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods familiar to those skilled in the art such as reaction in solvent such as tetrahydrofuran, acetonitrile or dimethylformamide at a range of temperatures from ambient to reflux temperature.

Compounds of formula (xv) may be prepared according to scheme 9 via hydrolysis of an alkyl ester. Typically, this reaction is carried out using aqueous acid or base, at a range of temperatures from ambient to reflux temperature. Suitable acids include hydrochloric acid and suitable bases include sodium hydroxide or lithium hydroxide.

Compounds of formula (xvii) may also be synthesised directly from compounds of formula (xvi) and amines of formula $NHR^4R^5$. Typically this reaction is carried out using trimethylaluminium utilising standard methods familiar to those skilled in the art such as reaction in solvent such as tetrahydrofuran, toluene, acetonitrile or dimethylformamide, at a range of temperatures from ambient to reflux temperature or via microwave irradiation. Compounds of formula (xvi) may be synthesised from compounds of formula (xviii) via reaction with an organolithium base and reaction of the resulting anion derived from bromine/lithium exchange with a chlorocarbonate, preferably methyl chloroformate. Compounds of formula (xviii) may be synthesised by adapting procedures found in WO2004/111057.

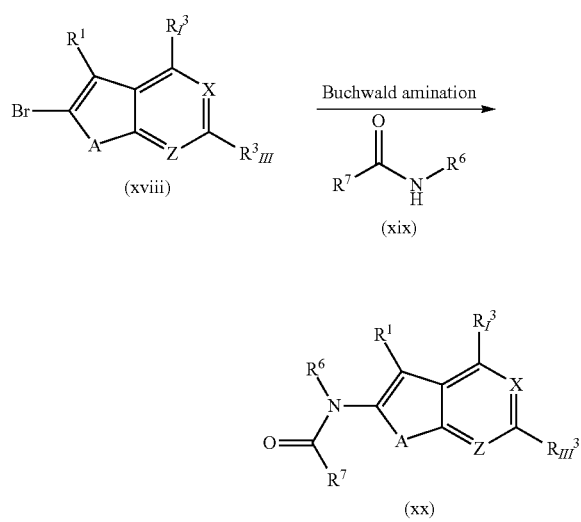

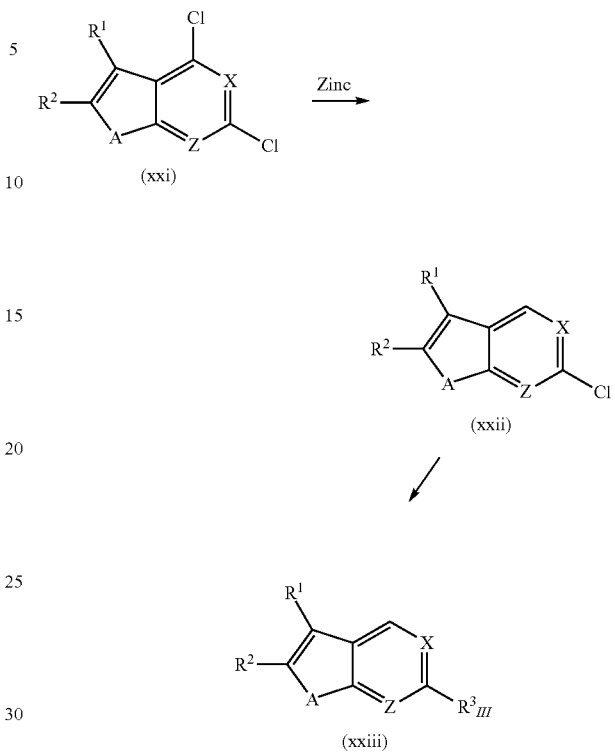

Compounds of formula (xx) may be prepared according to scheme 10 via the reaction of compounds of formula (xviii) and amides of form $HNC(O)R^7$ using the procedure of Buchwald et al. Typically, this reaction is carried out using a palladium coupling reagent such as tris(dibenzylideneacetone) dipalladium utilising standard methods familiar to those skilled in the art, such as reaction in solvent such as tetrahydrofuran, acetonitrile or dimethylformamide at a range of temperatures from ambient to reflux temperature or via microwave irradiation.

Compounds of formula (xxiii) where $R^3{}_{III}$ is $NR^{10}R^{11}$, $-(NR^cR^d)J$ (e.g

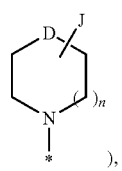

),

—CN, or alkoxy and where $R^1$, $R^2$, $R^{10}$, $R^{11}$, n, D and J are as defined above may be prepared according to scheme 11 from compounds of formula (xxi) via displacement of the 2-chloro substituent by a suitable nucleophilic species. Typically, this reaction is performed in the presence of a base, for example, triethylamine or potassium carbonate, utilising standard methods familiar to those skilled in the art such as reaction in solvents such as tetrahydrofuran, toluene, acetonitrile or dimethylformamide, at a range of temperatures from ambient to reflux temperature or via microwave irradiation.

Compounds of formula (xxii) may be prepared according to scheme 11 from compounds of formula (xxi) via selective reduction of the 4-chloro position. Typically, this reaction is performed in the presence of reducing metal, for example, Zinc, utilising standard methods familiar to those skilled in the art such as reaction in solvents such as ethanol in the presence of aqueous ammonia, at a range of temperatures from ambient to reflux temperature or via microwave irradiation.

SCHEME 12

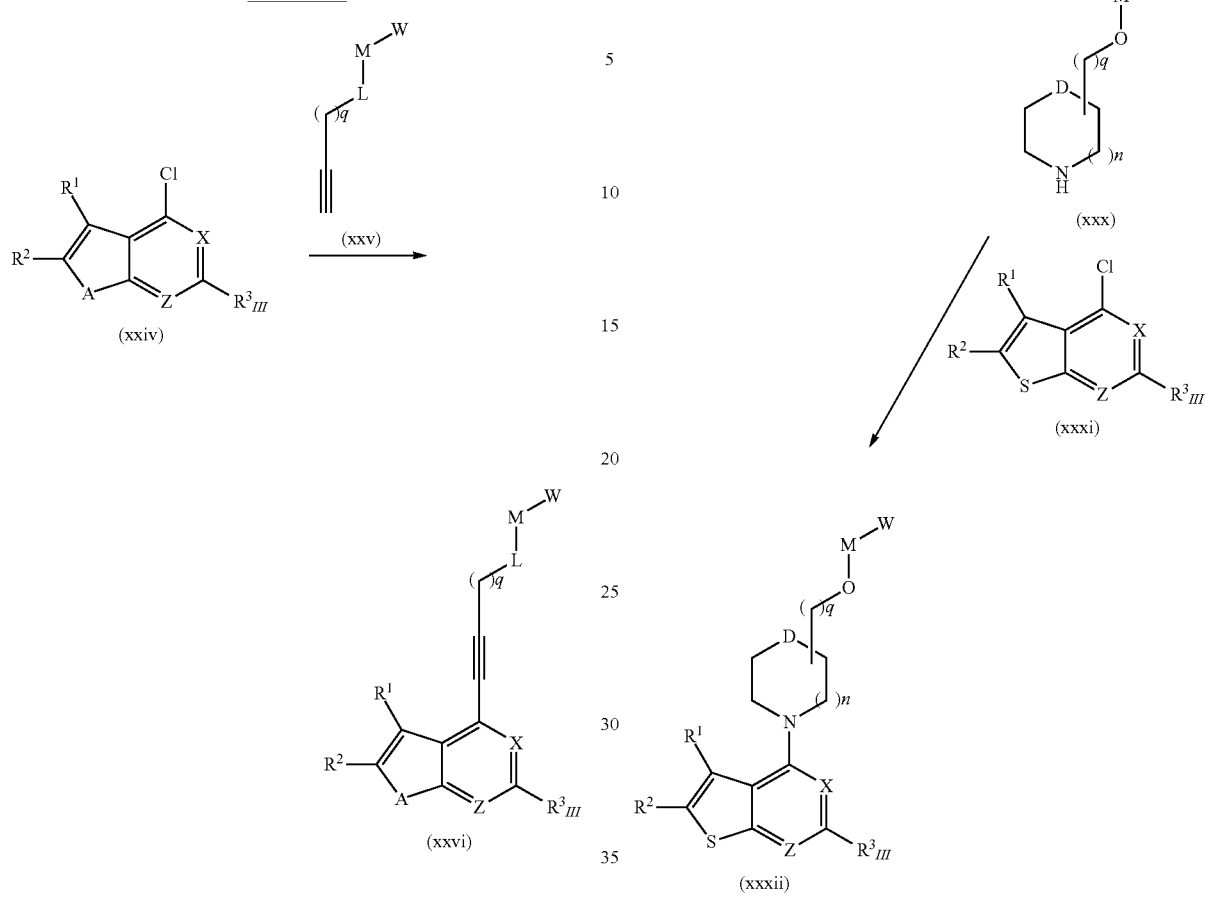

Compounds of formula (xxvi) may be prepared according to scheme 12 via reaction of compounds of formula (xxiv) with acetylene compounds of formula (xxv) using the method of Sonogashira coupling (Chinchilla et al, 2007; Berg et al, 2006). Typically, this reaction is carried out using a palladium coupling reagent such as tris(dibenzylideneacetone) dipalladium utilising standard methods familiar to those skilled in the art, such as reaction in solvent such as tetrahydrofuran, acetonitrile or dimethylformamide at a range of temperatures from ambient to reflux temperature or via microwave irradiation.

SCHEME 13

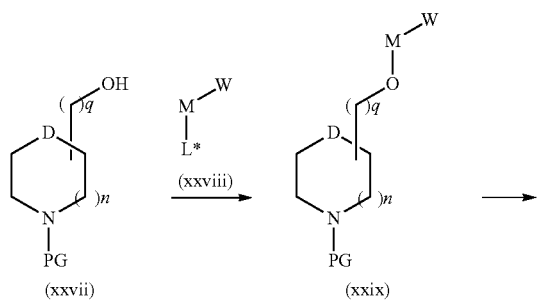

Compounds of formula (xxxii) may be prepared according to scheme 13 via reaction of compounds of formula (xxx) with compounds of formula (xxxi). Typically, this reaction is performed in the presence of a base, for example, triethylamine or potassium carbonate, utilising standard methods familiar to those skilled in the art such as reaction in solvents such as tetrahydrofuran, toluene, acetonitrile or dimethylformamide, at a range of temperatures from ambient to reflux temperature or via microwave irradiation.

Compounds of formula (xxx) may be prepared according to scheme 13 via the deprotection of nitrogen compounds of formula (xxix). Suitable nitrogen protecting groups (PG) are familiar to those skilled in the art and may include those removed by hydrogenation such as benzyl, and benzyloxycarbonyl (CBZ) or those removed by treatment with acid such as tert-butoxy carbonyl (BOC). A list of suitable protecting groups may be found in Greene et al (1999).

Compounds of formula (xxix) may be prepared according to scheme 13 by reaction of compounds of formula (xxvii) with compounds of formula (xxviii) where L* is defined as a suitable leaving group, for example, bromine, chlorine, iodine, tosylate, or mesylate. It is understood that the reverse case also holds true in that (xxviii) may bear the hydroxyl and (xxvii) the leaving group. Typically, this reaction is performed in the presence of a base, for example, sodium hydride, sodium hydroxide or potassium carbonate, utilising standard methods familiar to those skilled in the art such as reaction in solvent such as tetrahydrofuran, toluene, acetonitrile or dimethylformamide, or a mixture of solvents such as toluene/water in the presence of a phase-transfer catalyst such as tetrabutyl ammonium bromide, at a range of temperatures from ambient to reflux temperature or via microwave irradiation. Compounds of formula (xxviii) are known compounds or may be prepared by standard published methods familiar to those skilled in the art.

SCHEME 14

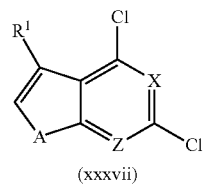

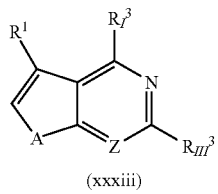
(xxxiii)

Compounds of formula (xxiii) where $R^1$ is aryl or heteroaryl may be prepared from compounds of formula (xxxiv) via an organometallic cross-coupling reaction. Suitable reactions for this transformation may include Suzuki couplings, where D* is a boronic acid, boronic acid ester, or borate salt; or Stille couplings where D* is a trialkyl tin moiety. Typically, the reaction is performed under catalysis in the presence of a palladium coupling reagent, for example tetrakis(triphenylphosphine) Palladium(0) and utilising standard methods familiar to those skilled in the art, such as reaction in solvent such as tetrahydrofuran, acetonitrile or dimethylformamide at a range of temperatures from ambient to reflux temperature or via microwave irradiation.

Compounds of formula (xxxiv) may be prepared from compounds of formula (xxxv) via a base-catalysed migration of a bromine atom using the method cited in WO2004/111057. Suitable bases include organolithium compounds such as lithium diisopropyl amide in a solvent such as diethyl ether or tetrahydrofuran. The reaction may be performed at a range of temperatures from −78° C. to 0° C.

SCHEME 15

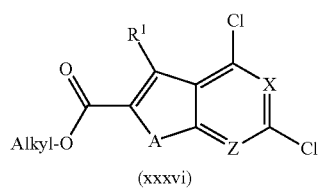

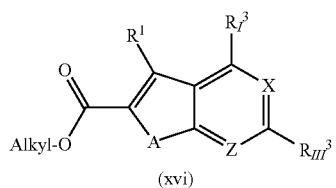

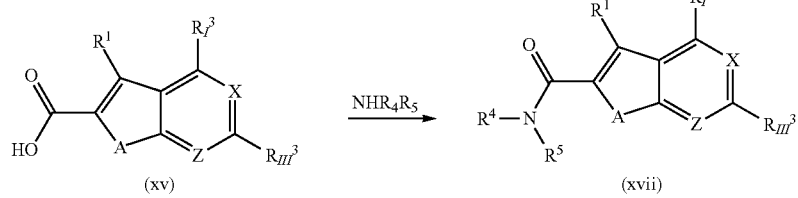

Compounds of formula (xvii) may be prepared according to scheme 15 via the reaction of compounds of formula (xv) with amines of formula $NHR^4R^5$. Typically, this reaction is carried out using a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods familiar to those skilled in the art such as reaction in solvent such as tetrahydrofuran, acetonitrile or dimethylformamide at a range of temperatures from ambient to reflux temperature in the presenceof an organic base, for example, N,N-diisopropylethylamine.

Compounds of formula (xv) may be prepared according to scheme 15 via hydrolysis of an alkyl ester. Typically, this reaction is carried out using aqueous acid or base, at a range of temperatures from ambient to reflux temperature. Suitable acids include hydrochloric acid and suitable bases include sodium hydroxide or lithium hydroxide. In the case where $R^3_{III}$ is a substituted alkoxy group and the substitution described in scheme 2 is performed under strongly basic conditions concomitant hydrolysis of the 6-ester may also occur to give (xv) directly. Compounds of formula (xvii) may also be synthesised directly from compounds of formula (xvi) and amines of formula $NHR^4R^5$. Typically this reaction is carried out using trimethylaluminium utilising standard methods familiar to those skilled in the art such as reaction in solvent such as tetrahydrofuran, toluene, acetonitrile or dimethylformamide, at a range of temperatures from ambient to reflux temperature or via microwave irradiation. Compounds of formula (xvi) may be prepared from compounds of formula (xxxvi) using the methods described in schemes 1 and 2.

Compounds of formula (xxxvi) may be prepared from compounds of formula (xxxvii) via treatment with an organlithium base, for example, lithium diisopropylamide in a solvent, for example, tetrahydrofuran at a range of temperature from −78° C. to 0° C. and quenching of the resulting anion with a chlorocarbonate typically methyl chloroformate. Compounds of formula (xxxvii) may be prepared according to the methods of WO2004/111057.

SCHEME 16

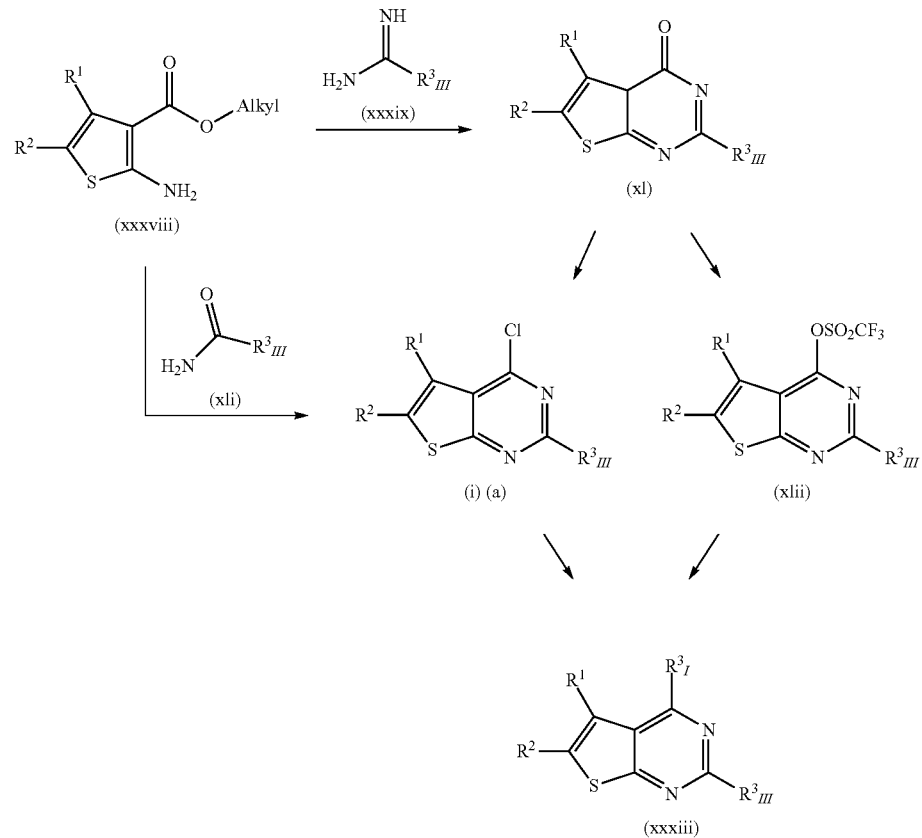

Compounds of formula (xliii) where $R^3{}_{III}$ is $NR^{10}R^{11}$, —$(NR^cR^d)$-J (e.g

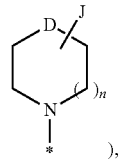

),

—CN, or alkoxy and where $R^1$, $R^2$, $R^{31}$, $R^{10}$, $R^{11}$, n, D and J are as defined above may be prepared according to scheme 16 from compounds of formula (i) or (xlii) via displacement of a suitable leaving-group such as a 4-chloro or 4-trifluorosulfonate substituent by a suitable nucleophilic species. Typically, this reaction is performed in the presence of a base, for example, triethylamine or potassium carbonate, utilising standard methods familiar to those skilled in the art such as reaction in solvents such as tetrahydrofuran, toluene, acetonitrile or dimethylformamide, at a range of temperatures from ambient to reflux temperature or via microwave irradiation.

Compounds of formula (xlii) may be prepared via the reaction of compounds of formula (xl) with trifluoromethanesulfonic anhydride in a solvent for example, dichloromethane or tetrahydrofuran and in the presence of a base, for example, pyridine. Compounds of formula (I)(a) may be prepared via the reaction of compounds of formula (xl) with a suitable chlorinating agent for example, phosphorous oxychloride or diphenylphosphoryl chloride. Typically, this reaction is performed in a neat solution of the chlorinating reagent at temperatures ranging from 50° C. to reflux temperature.

Compounds of formula (xl) may be prepared via cyclisation of compounds of formula (xxxviii) with an amidate of formula (xxxix). Typically, the reaction is performed in a suitable solvent, for example ethanol and at reflux temperature of the solvent.

Compounds of formula (i) may be prepared via cyclisation of compounds of formula (xxxviii) with primary amides of formula (xli) in the presence of a chlorinating agent for example, phosphorous trichloride. Typically, this reaction is performed in a solvent, for example toluene at temperatures ranging from 60° C. to reflux temperature.

SCHEME 17

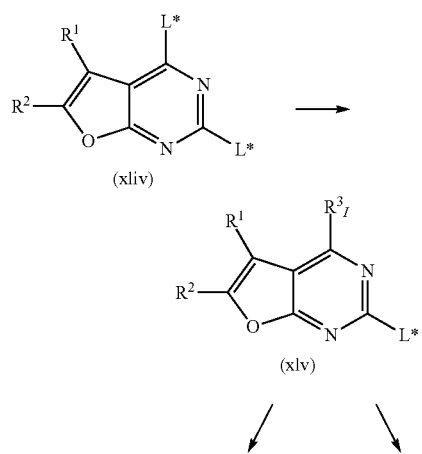

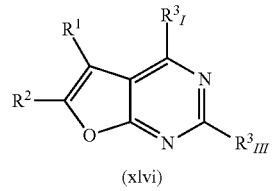
(xlvi)

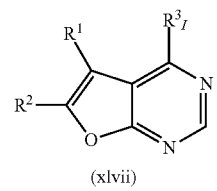
(xlvii)

Compounds of formula (xlvi) where $R^3{}_{III}$ is $NR^{10}R^{11}$, —$(NR^cR^d)$-J (e.g

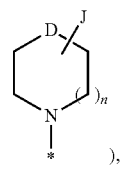

),

—CN, or alkoxy and where $R^1$, $R^2$, $R^3{}_I$, $R^{10}$, $R^{11}$, n, D and J are as defined above may be prepared according to scheme 17 from compounds of formula (xlv) via displacement of a suitable leaving-group (L*) for example, an alkyl sulfone, by a suitable nucleophilic species. Typically, this reaction is performed in the presence of a base, for example, triethylamine or potassium carbonate, utilising standard methods familiar to those skilled in the art such as reaction in solvents such as tetrahydrofuran, toluene, acetonitrile or dimethylformamide, at a range of temperatures from ambient to reflux temperature or via microwave irradiation. Compounds of formula (xlvii) may be prepared from compounds of formula (xlv) via treatment of compounds of formula (xlv) with a suitable reductant, for example, sodium borohydride in a solvent, for example, ethanol. Typically, this reaction is performed at a range of temperatures from 0° C. to 25° C.

Compounds of formula (xlv) where $R^3{}_I$ is $NR^8R^9$, —$(NR^aR^b)$-J (e.g.

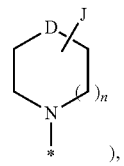

),

—CN, or alkoxy and where $R^1$, $R^2$, $R^8$, $R^9$, n, D and J are as defined above may be prepared according to scheme 17 from compounds of formula (xliv) via displacement of a suitable leaving-group (L) for example, and alkyl sulfone by a suitable nucleophilic species. Typically, this reaction is performed in the presence of a base, for example, triethylamine or potassium carbonate, utilising standard methods familiar to those skilled in the art such as reaction in solvents such as tetrahydrofuran, toluene, acetonitrile or dimethylformamide, at a range of temperatures from ambient to reflux temperature or via microwave irradiation. Compounds of formula (xliv) may be prepared according to the methods of WO2005/121149.

SCHEME 18

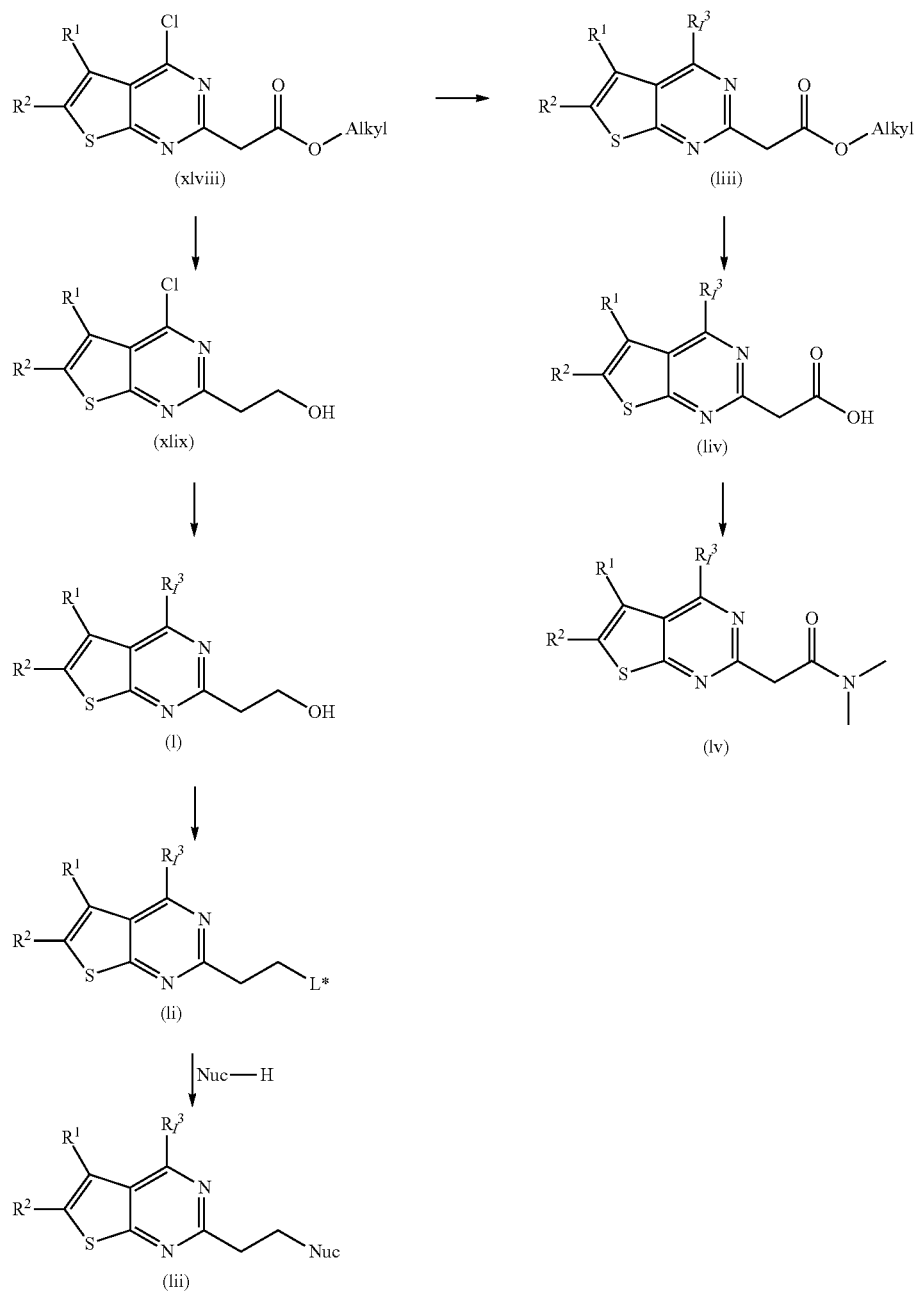

Compounds of formula (iii) may be prepared according to scheme 18 from compounds of formula (II) via displacement of a suitable leaving-group L* for example, a methansulfonyl, toluenesulfonyl, iodo, bromo or chloro group by a suitable nucleophile Nuc-H, for example, an amino or alkoxy group. Typically, this reaction is performed in the presence of a base, for example, triethylamine or potassium carbonate, utilising standard methods familiar to those skilled in the art such as reaction in solvents such as tetrahydrofuran, toluene, acetonitrile or dimethylformamide, at a range of temperatures from ambient to reflux temperature or via microwave irradiation. Compounds of formula (II) where L* is defined as a suitable leaving group, for example, methansulfonyl, toluenesulfonyl, iodo, bromo, or chloro, may be prepared from compounds of formula (i) using standard methods familiar to those skilled in the art, for example reaction with a sulfonyl chloride or a suitable halogenating agent such as thionyl chloride or phosphorous tribromide.

Compounds of formula (i) where $R^3{}_I$ is $NR^8R^9$, —$(NR^aR^b)$-J (e.g.,

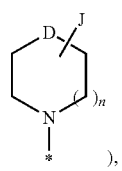

),

—CN, or alkoxy and where $R^1$, $R^2$, $R^8$, $R^9$, n, D and J are as defined above may be prepared according to scheme 18 from compounds of formula (xlix) via displacement of a suitable leaving-group, for example, an alkyl sulfone, by a suitable nucleophilic species. Typically, this reaction is performed in the presence of a base, for example, triethylamine or potassium carbonate, utilising standard methods familiar to those skilled in the art such as reaction in solvents such as tetrahydrofuran, toluene, acetonitrile or dimethylformamide, at a range of temperatures from ambient to reflux temperature or via microwave irradiation. Compounds of formula (xlix) may be prepared via reduction of compounds of formula (xlviii). Suitable reductants include lithium aluminium hydride in anhydrous solvent, typically tetrahydrofuran or diethyl ether at a range of temperatures from −78° C. to 0° C. Compounds of formula (xlviii) may be prepared according to the methods of WO2004/111057.

Compounds of formula (Iv) may be prepared from compounds of formula (liv) via an amide formation. Typically, this may be performed by conversion of compounds of formula (liv) to their corresponding acid chloride derivatives by treatment with a suitable chlorinating agent such as thionyl chloride or oxalyl chloride, optionally in the presence of a solvent for example dichloromethane. The acid chloride is then treated with an amine in the presence of base, typically pyridine, optionally the presence of solvent, for example dichloromethane to give the amide (lv). Alternatively, compounds of formula (lv) may be prepared via the reaction of compounds of formula (liv) with amines of formula $NHR^4R^5$. Typically, this reaction is carried out using a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods familiar to those skilled in the art such as reaction in solvent such as tetrahydrofuran, acetonitrile or dimethylformamide at a range of temperatures from ambient to reflux temperature in the presence of an organic base, for example, N,N-diisopropylethylamine.

Compounds of formula (liv) may be prepared according to scheme 18 via hydrolysis of an alkyl ester (liii). Typically, this reaction is carried out using aqueous acid or base, at a range of temperatures from ambient to reflux temperature. Suitable acids include hydrochloric acid and suitable bases include sodium hydroxide or lithium hydroxide.

Compounds of formula (liii) where $R^3_I$ is $NR^8R^9$, —$(NR^aR^b)$-J (e.g

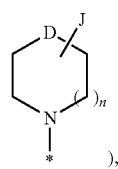

—CN, or alkoxy and where $R^1$, $R^2$, $R^8$, $R^9$, n, D and J are as defined above may be prepared according to scheme x from compounds of formula (xlviii) via displacement of a suitable leaving-group for example, a 4-chloro, by a suitable nucleophilic species. Typically, this reaction is performed in the presence of a base, for example, triethylamine or potassium carbonate, utilising standard methods familiar to those skilled in the art such as reaction in solvents such as tetrahydrofuran, toluene, acetonitrile or dimethylformamide, at a range of temperatures from ambient to reflux temperature or via microwave irradiation.

SCHEME 19

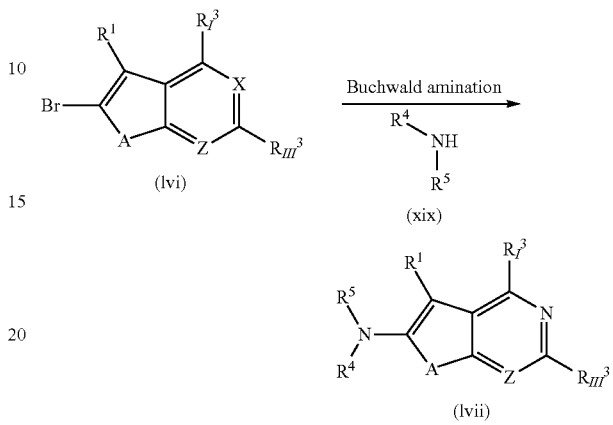

Compounds of formula (lvii) may be prepared according to scheme 19 via the reaction of compounds of formula (lxvi) and amines of form $NHR^4R^5$ using the procedure of Buchwald et al. Typically, this reaction is carried out in the presence of a palladium coupling reagent and using standard methods familiar to those skilled in the art, such as reaction in solvent such as tetrahydrofuran, acetonitrile or dimethylformamide at a range of temperatures from ambient to reflux temperature or via microwave irradiation.

SCHEME 20

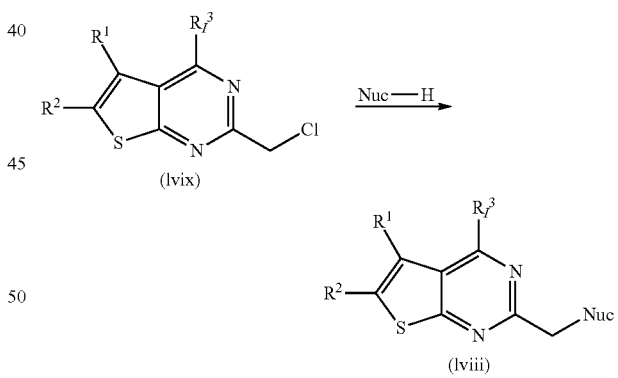

Compounds of formula (lviii) may be prepared according to scheme 20 from compounds of formula (lvix) via displacement of a suitable leaving-group for example, a chloro group, by a suitable nucleophile Nuc-H, for example, a substituted amino or alkoxy group. Typically, this reaction is performed in the presence of a base, for example, triethylamine or potassium carbonate, utilising standard methods familiar to those skilled in the art such as reaction in solvents such as tetrahydrofuran, toluene, acetonitrile or dimethylformamide, at a range of temperatures from ambient to reflux temperature or via microwave irradiation.

SCHEME 21

(lvi) (a) → (lx)

Compounds of formula (lx) may be prepared from compounds of formula (lvi)(a) via the introduction of a cyano group under catalytic conditions. Typically, the source of the cyanide group is zinc cyanide and the catalyst is formed from a palladium complex, for example, that formed from the combination of tris(dibenzylideneacetone) dipalladium with diphenylphosphino ferrocene. The reaction is performed in a solvent, preferably dimethylformamide at a range of temperatures from ambient to reflux temperature or via microwave irradiation.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

MODES FOR CARRYING OUT THE INVENTION

Experimental Section

Many of the starting materials referred to in the reactions described below are available from commercial sources or can be made by methods cited in the literature references. Synthetic methods can also be found in reviews; thieno[2,3-d]pyrimidines for example, can be found in references cited in WO2004/111057 and reference such as Han et al (2010).

Synthetic methods for thieno[2,3-d]pyridines may be found in WO2006/061642 and references such as Gewald et al (1979) Munchof et al (2004), Barker et al (1985), Charvát et al (1995) and articles cited therein.

The following starting materials were synthesized using the procedures described in WO2004/111057:
4-Chloro-5-phenyl-thieno[2,3-d]pyrimidine
4-Chloro-5-(3-fluorophenyl)-thieno[2,3-d]pyrimidine
4-Chloro-5-(4-fluorophenyl)-thieno[2,3-d]pyrimidine
2,4-Dichloro-5-phenyl-thieno[2,3-d]pyrimidine
Methyl 4-chloro-5-phenyl-thieno[2,3-d]pyrimidine-6-carboxylate
6-Bromo-4-chloro-5-phenyl-thieno[2,3-d]pyrimidine
4-chloro-5-isopropyl-thieno[2,3-d]pyrimidine
4-chloro-5,6-dimethyl-thieno[2,3-d]pyrimidine
2,4-dichloro-5-cyclohexyl-thieno[2,3-d]pyrimidine
4-chloro-2-ethyl-5-phenyl-thieno[2,3-d]pyrimidine
4-chloro-5-cyclohexyl-thieno[2,3-d]pyrimidine
2,4-dichloro-5-(4-fluorophenyl)thieno[2,3-d]pyrimidine
methyl 2-[4-chloro-5-(4-fluorophenyl)thieno[2,3-d]pyrimidin-2-yl]acetate The following starting materials were synthesized using the procedures described in WO2006/061642:
4-chloro-3-phenyl-thieno[2,3-b]pyridine The following starting materials were synthesized using the procedures described in WO2005/121149:
2,4-Bismethylsulphonyl)-5-phenyl-furo[2,3-d]-pyrimidine Analytical Methods HPLC analysis was conducted using the following methods:

AGILENT 6110/1200 LCMS system

Solvent: [$H_2O$-0.1% $HCO_2H$: MeCN-0.05% $HCO_2H$: $H_2O$-0.1% $HCO_2H$], 10-95% gradient 3 min, 95% 3-5 min, 5.5-5.8 min 95%-20% gradient; 6 min 5%; Column: Phenomenex Gemini 50×4.6 mm i.d., 3 micronC18 reverse phase; Flow rate: 0.75 mL/min. UV detection 220/254 nm, MS Electrospray (+ve and −ve mode).

Preparative HPLC purification was conducted in the following manner:

Solvent: [MeCN-0.05% $HCO_2H$: $H_2O$-0.1% $HCO_2H$], 5-95% gradient 12 min, 95% 3 min; Waters X-Bridge 100×19 mm i.d., C18 reverse phase; Flow rate: 16 mL/min unless otherwise indicated.

HPLC: Agilent HPLC with Waters XBridge C18, 5 μm, 100 mm×19 mm i.d. column and a flow rate of 16 ml/minute. With two G1361A prep pumps, a G2258A duel loop auto sampler, a G1315 diode array detector and a G3064B prep fraction collector. Analysed by ChemStation 3. Solvents, (acidic method) water with 0.01% formic acid and acetonitrile with 0.05% formic acid or (basic method) water with 0.1% ammonia and acetonitrile.

| Method a: | | | | | | |
|---|---|---|---|---|---|---|
| Time minutes | 0 | 12 | 15 | 15.5 | | |
| Acetonitrile concentration % | 5 | 95 | 95 | 5 | | |
| Method b: | | | | | | |
| Time minutes | 0 | 1.5 | 13.5 | 14 | 15 | 15.5 | 16 |
| Acetonitrile concentration % | 5 | 40 | 65 | 98 | 98 | 5 | 5 |
| Method c: | | | | | | |
| Time minutes | 0 | 1.5 | 14 | 14.5 | 15 | 15.5 |
| Acetonitrile concentration % | 5 | 50 | 75 | 95 | 95 | 5 |
| Method d: | | | | | | |
| Time minutes | 0 | 1.5 | 14 | 14.5 | 15 | 15.5 |
| Acetonitrile concentration % | 5 | 50 | 65 | 95 | 95 | 5 |
| Method e: | | | | | | |
| Time minutes | 0 | 11 | 12 | 15 | 15 | |
| Acetonitrile concentration % | 5 | 35 | 95 | 95 | 5 | |
| Method f: | | | | | | |
| Time minutes | 0 | 1.5 | 12 | 15 | 15.5 | |
| Acetonitrile concentration % | 5 | 50 | 95 | 95 | 5 | |
| Method g: | | | | | | |
| Time minutes | 0 | 11 | 11.5 | 14.5 | 15 | |
| Acetonitrile concentration % | 5 | 55 | 95 | 95 | 5 | |

HPLC: Agilent HPLC with Phenomenex Gemini-NX, 5 µm, 100 mm×30 mm i.d. column and a flow rate of 40 ml/minute. With two G1361A prep pumps, a G2258A duel loop auto sampler, a G1315 diode array detector and a G3064B prep fraction collector. Analysed by ChemStation 3. Solvents, (acidic method) water with 0.01% formic acid and acetonitrile with 0.05% formic acid or (basic method) water with 0.1% ammonia and acetonitrile.

| Method 1: | | | | | | |
|---|---|---|---|---|---|---|
| Time minutes | 0 | 12 | 15 | 15.5 | | |
| Acetonitrile concentration % | 5 | 95 | 95 | 5 | | |
| Method 2: | | | | | | |
| Time minutes | 0 | 1.5 | 13.5 | 14 | 15 | 15.5 | 16 |
| Acetonitrile concentration % | 5 | 40 | 65 | 98 | 98 | 5 | 5 |
| Method 3: | | | | | | |
| Time minutes | 0 | 1.5 | 14 | 14.5 | 15 | 15.5 | |
| Acetonitrile concentration % | 5 | 50 | 75 | 95 | 95 | 5 | |
| Method 4: | | | | | | |
| Time minutes | 0 | 1.5 | 14 | 14.5 | 15 | 15.5 | |
| Acetonitrile concentration % | 5 | 50 | 65 | 95 | 95 | 5 | |
| Method 5: | | | | | | |
| Time minutes | 0 | 11 | 12 | 15 | 15 | | |
| Acetonitrile concentration % | 5 | 35 | 95 | 95 | 5 | | |
| Method 6: | | | | | | |
| Time minutes | 0 | 1.5 | 12 | 15 | 15.5 | | |
| Acetonitrile concentration % | 5 | 50 | 95 | 95 | 5 | | |
| Method 7: | | | | | | |
| Time minutes | 0 | 11 | 11.5 | 14.5 | 15 | | |
| Acetonitrile concentration % | 5 | 55 | 95 | 95 | 5 | | |

Proton and carbon NMR were acquired on a Bruker Advance 300 at 300 and 75 mHz respectively.

Method A

Synthesis of 2-(1-methylpyrrolidin-2-yl)-N—[[1-(5-phenylthieno[2,3-d]pyrimidin-4-yl)-4-piperidyl]methyl]ethanamine Example 58 i) [4-(5-Phenyl-thieno[2,3-d]pyrimidin-4-yl)-piperidin-4-yl]-methanol

4-Chloro-5-phenyl-thieno[2,3-d]pyrimidine (1 g, 4.05 mmol) was dissolved in ethanol (15 ml) to give a yellow solution. To this was added triethylamine (1.7 ml, 12.2 mmol) and 4-piperidinemethanol (0.58 g, 5 mmol). The reaction mixture was heated to 50° C. and stirred for 1.5 hours until no 4-chloro-5-phenyl-thieno[2,3-d]pyrimidine was present by TLC. The reaction mixture was allowed to cool to room temperature before being poured over ice water (50:50 mix). The resultant precipitate was collected by filtration to give the product as a pale yellow solid (1.23 g, yield 90%). LCMS: RT=4.05 min, M+1=326.

The following compounds were synthesised according to the method described using the appropriate starting materials:
[3-[5-(4-fluorophenyl)thieno[2,3-d]pyrimidin-4-yl]-3-azabicyclo[3.1.0]hexan-6-yl]methanol
[1-[5-(4-nitrophenyl)thieno[2,3-d]pyrimidin-4-yl]-4-piperidyl]methanol
[3-(5-phenylthieno[2,3-d]pyrimidin-4-yl)-3-azabicyclo[3.1.0]hexan-6-yl]methanol
[1-[5-(3-fluorophenyl)thieno[2,3-d]pyrimidin-4-yl]-4-piperidyl]methanol
[1-(5-ethyl-6-methyl-thieno[2,3-d]pyrimidin-4-yl)-4-piperidyl]methanol
[1-(6-isopropylthieno[2,3-d]pyrimidin-4-yl)-4-piperidyl]methanol
[1-(5-methylthieno[2,3-d]pyrimidin-4-yl)-4-piperidyl]methanol
[1-(5-phenylthieno[2,3-d]pyrimidin-4-yl)azetidin-3-yl]methanol
[1-(5-phenylthieno[2,3-d]pyrimidin-4-yl)pyrrolidin-3-yl]methanol
[1-(5-phenylthieno[2,3-d]pyrimidin-4-yl)-3-piperidyl]methanol
[5-phenyl-1-(5-phenylthieno[2,3-d]pyrimnidin-4-yl)pyrrolidin-3-yl]methanol
[5-methyl-1-(5-phenylthieno[2,3-d]pyrimnidin-4-yl)pyrrolidin-3-yl]methanol
[1-(5,6-dimethylthieno[2,3-d]pyrimidin-4-yl)-4-piperidyl]methanol
[1-(5-isopropylthieno[2,3-d]pyrimidin-4-yl)-4-piperidyl]methanol
[8-(5-phenylthieno[2,3-d]pyrimidin-4-yl)-8-azabicyclo[3.2.1]octan-3-yl]methanol
1-(5-phenylthieno[2,3-d]pyrimidin-4-yl)piperidin-4-ol
1-(5-phenylthieno[2,3-d]pyrimidin-4-yl)piperidin-3-ol
1-(5-phenylthieno[2,3-d]pyrimidin-4-yl)pyrrolidin-3-ol
[3-[5-(4-fluorophenyl)thieno[2,3-d]pyrimidin-4-yl]-3-azabicyclo[3.1.0]hexan-6-yl]methanol
[(3R)-(5-phenylthieno[2,3-d]pyrimidin-4-yl)pyrrolidin-3-yl]methanol
2-(5-phenylthieno[2,3-d]pyrimidin-4-yl)-2-azabicyclo[2.2.1]heptan-5-ol
2-(5-cyclohexylthieno[2,3-d]pyrimidin-4-yl)-2-azabicyclo[2.2.1]heptan-5-ol
[(3S)-1-(5-phenylthieno[2,3-d]pyrimidin-4-yl)pyrrolidin-3-yl]methanol
[1-(5-methylthieno[2,3-d]pyrimidin-4-yl)pyrrolidin-3-yl]methanol ii) 4-(4-Bromomethyl-piperidin-1-yl)-5-phenyl-thieno[2,3-d]pyrimidine

[4-(5-Phenyl-thieno[2,3-d]pyrimidin-4-yl)-piperidin-4-yl]-methanol (8 g, 24.6 mmol) and tetrabromomethane (12.2 g, 36.9 mmol) were dissolved in dry dichloromethane (40 ml) at 0° C. to give a yellow solution. To this was added triphenylphosphine (0.089 g, 0.338 mmol) in portions. The reaction mixture was cooled with ice before the brown solution was left to stir for 2.5 hours. After this there was no [4-(5-phenyl-thieno[2,3-d]pyrimidin-4-yl)-piperidin-4-yl]-methanol present by LCMS or TLC. The reaction mixture was filtered through silica before solvent was removed in vacuo to give a crude mixture (14.24 g). This was purified through a plug of silica, eluted with diethyl ether before further purification by flash chromatography. The product was collected and concentrated to give a cream solid (7.63 g, yield 80%). LCMS: RT=5.3 min, M+1: 389.8.

The following compounds were synthesised according to the method described using the appropriate starting materials:
4-[3-(bromomethyl)-1-piperidyl]-5-phenyl-thieno[2,3-d]pyrimidine
4-[3-(bromomethyl)pyrrolidin-1-yl]-5-phenyl-thieno[2,3-d]pyrimidine 4-[3-(bromomethyl)azetidin-1-yl]-5-phenyl-thieno[2,3-d]pyrimidine 4-[4-(bromomethyl)-2-phenyl-pyrrolidin-1-yl]-5-phenyl-thieno[2,3-d]pyrimidine 4-[4-(bromomethyl)-1-piperidyl]-5,6-dimethyl-thieno[2,3-d]pyrimidine 4-[4-(bromomethyl)-1-piperidyl]-5-isopropyl-thieno[2,3-d]pyrimidine 4-[3-(bromomethyl)-8-azabicyclo[3.2.1]octan-8-yl]-5-phenyl-thieno[2,3-d]pyrimidine 4-[4-(bromomethyl)-1-piperidyl]-5-methyl-thieno[2,3-d]pyrimidine 4-[3-(bromomethyl)pyrrolidin-1-yl]-5-methyl-thieno[2,3-d]pyrimidine iii) 2-(1-methylpyrrolidin-2-yl)-N—[[1-(5-phenylthieno[2,3-d]pyrimidin-4-yl)-4-piperidyl]methyl]ethanamine Example 58

4-[4-(Bromomethyl)-1-piperidyl]-5-phenyl-thieno[2,3-d]pyrimidine (13.8 g, 35.5 mmol), 2-(1-methylpyrrolidin-2-yl)ethanamine (5.47 g, 42.6 mmol) and potassium carbonate (7.37 g, 53.3 mmol) were heated in acetonitrile (100 mL) in the microwave at 150° C. for 30 minutes in 8×20 mL microwave vials. The reaction mixtures were combined and diluted with DCM (250 mL). The organic was washed with water (250 mL) and concentrated at reduced pressure. The resulting residue was purified by flash chromatography, eluting with a gradient of DCM to 90:10:1 DCM/MeOH/NH$_4$OH to afford the target compound (4.0 g) and mixed fractions. LCMS [M+H]$^+$=436.0

Other compounds prepared by Method A as described for example (iii) using the appropriate starting materials are listed in TABLE 1.

Method B

Synthesis of 1-[4-[4-[[methyl-(1-methylpyrrolidin-3-yl)amino]methyl]-1-piperidyl]-5-phenyl-thieno[2,3-d]pyrimidin-2-yl]pyrrolidine-3-carboxamide Example 120 i) [1-(2-chloro-5-phenyl-thieno[2,3-d]pyrimidin-4-yl)-4-piperidyl]methanol

4-Piperidinemethanol (987 mg, 8.57 mmol) was added to a stirred suspension of 2,4-dichloro-5-phenyl-thieno[2,3-d]pyrimidine (2 g, 7.14 mmol) and triethylamine (2.18 ml, 15.7 mmol) in dry ethanol (ml) at room temperature. Reaction was warmed to 40° C. and the resulting solution stirred for ~2 h. Reaction was allowed to cool to room temperature and poured onto ice/water (50 ml). The resulting suspension was filtered and the solid dried in a vacuum oven at 40° C. The desired compound was obtained as a pale yellow solid (2.4 g, 93%). LCMS: (M+1) 360, RT=4.69 min.

The following compounds were synthesised according to the method described using the appropriate starting materials:

[1-(2-chloro-5,6-dimethyl-thieno[2,3-d]pyrimidin-4-yl)-4-piperidyl]methanol

[1-(2-chloro-5-isopropyl-thieno[2,3-d]pyrimidin-4-yl)-4-piperidyl]methanol ii) 1-(2-chloro-5-phenyl-thieno[2,3-d]pyrimidin-4-yl)piperidine-4-carbaldehyde Pyridinium chlorochromate (898 mg, 4.17 mmol) was added to a stirred solution of [1-(2-chloro-5-phenyl-thieno[2,3-d]pyrimidin-4-yl)-4-piperidyl]methanol (1 g, 2.78 mmol) in dry dichloromethane (ml) at room temperature. The resulting mixture was stirred for 2 h and then eluted through a pad of silica (eluting ethyl acetate). The solvent was evaporated to give the 1-(2-chloro-5-phenyl-thieno[2,3-d]pyrimidin-4-yl)piperidine-4-carbaldehyde as a pale yellow solid (1 g, quantitative yield). Product was used in the subsequent reaction without further purification. LCMS: (M+H)$^+$358, RT=4.98 min.

The following compounds were synthesised according to the method described using the appropriate starting materials:

1-(2-chloro-5-isopropyl-thieno[2,3-d]pyrimidin-4-yl)piperidine-4-carbaldehyde 1-(2-chloro-5,6-dimethyl-thieno[2,3-d]pyrimidin-4-yl)piperidine-4-carbaldehyde iii) N—[[1-(2-chloro-5-phenyl-thieno[2,3-d]pyrimidin-4-yl)-4-piperidyl]methyl]-N,1-dimethyl-pyrrolidin-3-amine Sodium triacetoxyborohydride (1.54 g, 7.28 mmol) was added to a stirred solution of 1-(2-chloro-5-phenyl-thieno[2,3-d]pyrimidin-4-yl)piperidine-4-carbaldehyde (1.3 g, 3.64 mmol), N,N'-dimethyl-3-aminopyrrolidine (519 ul, 4.00 mmol) and acetic acid (240 ul, 4.00 mmol) in dry dichloromethane (20 ml) at room temperature. The solution was stirred for ~2 h, after which time the reaction had reached completion. Water (20 ml) was added and the organic layer separated, the aqueous phase was extracted with dichloromethane (×3) and the combined organics washed with brine, then dried (MgSO$_4$) and evaporated. The crude residue was purified by flash column chromatography (0 to 5% 7.0M NH$_3$/MeOH in dichloromethane). N—[[1-(2-chloro-5-phenyl-thieno[2,3-d]pyrimidin-4-yl)-4-piperidyl]methyl]-N,1-dimethyl-pyrrolidin-3-amine was isolated as a pale yellow oil (1.25 g, 76%). LCMS: (M+H)$^+$ 456.2, RT=2.99.

The following compounds were synthesised according to the method described using the appropriate starting materials:

[1-[[1-(2-chloro-5-phenyl-thieno[2,3-d]pyrimidin-4-yl)-4-piperidyl]methylamino]cyclopentyl]methanol N—[[1-(2-chloro-5-phenyl-thieno[2,3-d]pyrimidin-4-yl)-4-piperidyl]methyl]-2-(1-methylpyrrolidin-2-yl)ethanamine N—[[1-(2-chloro-5-phenyl-thieno[2,3-d]pyrimidin-4-yl)-4-piperidyl]methyl]cyclobutanamine 1-[[1-(2-chloro-5-phenyl-thieno[2,3-d]pyrimidin-4-yl)-4-piperidyl]methyl]-N,N-dimethyl-piperidin-3-amine iv) 1-[4-[4-[[methyl-(1-methylpyrrolidin-3-yl)amino]methyl]-1-piperidyl]-5-phenyl-thieno[2,3-d]pyrimidin-2-yl]pyrrolidine-3-carboxamide Example 120

N—[[1-(2-chloro-5-phenyl-thieno[2,3-d]pyrimidin-4-yl)-4-piperidyl]methyl]-N,1-dimethyl-pyrrolidin-3-amine (100 mg, 0.219 mmol) and pyrrolidine-3-carboxamide (300 mg, 2.63 mmol) were stirred in dry acetonitrile (1.5 ml) and heated in a microwave at 140° C. for 0.5 h. The solvent was evaporated and the crude residue purified by flash column chromatography (0 to 5% 7.0M NH$_3$/MeOH in dichloromethane) to give 1-[4-[4-[[methyl-(1-methylpyrrolidin-3-yl)amino]methyl]-1-piperidyl]-5-phenyl-thieno[2,3-d]pyrimidin-2-yl]pyrrolidine-3-carboxamide as an off white solid (25 mg, 21%). m/z (M+H)$^+$534.3, RT=2.69 min.

Other compounds prepared by Method B as described for example (iv) using the appropriate starting materials are listed in TABLE 1.

Method C

Synthesis of N,N-dimethyl-5-phenyl-4-[4-(2-pyrrolidin-1-ylethoxymethyl)cyclohexyl]thieno[2,3-d]pyrimidine-6-carboxamide

Example 135 i) Methyl 5-phenyl-4-[4-(2-pyrrolidin-1-ylethoxymethyl)-1-piperidyl]thieno[2,3-d]pyrimidine-6-carboxylate To a stirred solution of methyl 4-chloro-5-phenyl-thieno[2,3-d]pyrimidine-6-carboxylate (0.850 g, 2.80 mmol) in THF (50 mL), was added diisopropylethylamine (0.73 mL, 4.20 mmol) and 4-(2-pyrrolidin-1-ylethoxymethyl)piperidine (0.890 g, 4.20 mmol) in one portion, and the reaction left to stir at room temperature for 2 hours. The reaction was diluted with water (50 mL) and extracted with ethyl acetate (3×50 mL). The reaction was dried over sodium sulphate, filtered and concentrated under reduced pressure. The crude material was purified by column chromatography using DCM: MeOH (0-25%) as eluent to afford the named product (1.012 g, 75%). m/z [M+H]$^+$481; RT=3.03 min.

The following compounds were synthesised according to the method described using the appropriate starting materials:

methyl 5-isopropyl-4-[4-(2-pyrrolidin-1-ylethoxymethyl)-1-piperidyl]thieno[2,3-d]pyrimidine-6-carboxylate methyl 5-phenyl-4-[3-(2-pyrrolidin-1-ylethoxymethyl)-8-azabicyclo[3.2.1]octan-8-yl]thieno[2,3-d]pyrimidine-6-carboxylate methyl 5-phenyl-4-[3-(2-pyrrolidin-1-ylethoxymethyl)-8-azabicyclo[3.2.1]octan-8-yl]thieno[2,3-d]pyrimidine-6-carboxylate ii) N,N-dimethyl-5-phenyl-4-[4-(2-pyrrolidin-1-ylethoxymethyl)cyclohexyl]thieno[2,3-d]pyrimidine-6-carboxamide

Example 135

To a stirred solution of methyl 5-phenyl-4-[4-(2-pyrrolidin-1-ylethoxymethyl)-1-piperidyl]thieno[2,3-d]pyrimidine-6-carboxylate (0.200 g, 0.42 mmol) in DCM (4 mL) was added trimethylaluminium (0.63 mL, 1.26 mmol, 2M solution in hexane) and the reaction stirred at room temperature for minutes. Dimethylamine (0.63 mL, 1.26 mmol, 2M solution in THF) was added and the reaction heated in a microwave at 100° C. for 2 hours. The reaction was diluted with DCM (20 mL) and water (20 mL) and the organic phase separated. The aqueous phase was further extracted with DCM (2×10 mL) and the combined extracts dried over sodium sulphate, filtered and concentrated under reduced pressure. The crude material was purified by high performance liquid chromatography and the pure fractions combined and evaporated under reduced pressure to afford the named product (0.044 g, 22%). m/z [M+H]$^+$494; RT=2.62 min.

Other compounds prepared by Method C as described for example (ii) using the appropriate starting materials are listed in TABLE 1.

Method D

Synthesis of N-isopropyl-5-phenyl-4-[4-(2-pyrrolidin-1-ylethoxymethyl)-1-piperidyl]thieno[2,3-d]pyrimidine-6-carboxamide

Example 139 i) 5-phenyl-4-[4-(2-pyrrolidin-1-ylethoxymethyl)-1-piperidyl]thieno[2,3-d]pyrimidine-256-carboxylic acid Lithium hydroxide monohydrate (0.08 g, 1.9 mmol) was added to a stirred solution of methyl 5-phenyl-4-[4-(2-pyrrolidin-1-ylethoxymethyl)-1-piperidyl]thieno[2,3-d]pyrimidine-6-carboxylate (0.44 g, 0.91 mmol) in THF (10 mL) and water (10 mL). The mixture was stirred for 2 hr. The organic solvent was evaporated and the remaining aqueous mixture was extracted with EtOAc (3×10 mL). The aqueous layer was acidified (to pH 3) with concentrated hydrochloric acid and then extracted with DCM/MeOH 4:1 (3×25 mL). The combined organic layers were dried (magnesium sulfate), filtered and evaporated to give the target compound (0.08 g) as a light orange solid. m/z [M+H]$^+$467.0. Retention time 2.80 min (LCMS method+ve 6 min).

The aqueous layer was evaporated to dryness. The residue was mixed with DCM and MeOH (1:1), sonicated and filtered. The filtrate was evaporated to give the target compound (424 mg) as a yellow solid.

The following compounds were synthesised according to the method described using the appropriate starting materials:

5-isopropyl-4-[4-(2-pyrrolidin-1-ylethoxymethyl)-1-piperidyl]thieno[2,3-d]pyrimidine-6-carboxylic acid 5-phenyl-4-[3-(2-pyrrolidin-1-ylethoxymethyl)-8-azabicyclo[3.2.1]octan-8-yl]thieno[2,3-d]pyrimidine-6-carboxylic acid ii) N-isopropyl-5-phenyl-4-[4-(2-pyrrolidin-1-ylethoxymethyl)-1-piperidyl]thieno[2,3-d]pyrimidine-6-carboxamide

Example 139

A mixture of 5-phenyl-4-[4-(2-pyrrolidin-1-ylethoxymethyl)-1-piperidyl]thieno[2,3-d]pyrimidine-6-carboxylic acid (70 mg, 0.15 mmol), HATU (114 mg, 0.30 mmol), isopropylamine (30 µL, 0.35 mmol) and triethylamine (63 µL, 0.45 mmol) in DMF (5 mL) was stirred at room temperature for 3 nights. The solvent was evaporated. The residue was dissolved in EtOAc (5 mL) and water (5 mL). The layers were separated and the aqueous was extracted with EtOAc (2×5 mL). The combined organic layers were dried (magnesium sulfate), filtered and evaporated to give a brown solid. This was purified by preparative HPLC. Fractions containing target compound were combined and evaporated to give the target compound (24.3 mg) as a brown solid. m/z [M+H]$^+$ 508; RT=2.94 min.

Other compounds prepared by Method D as described for example (ii) using the appropriate starting materials are listed in TABLE 1.

Method E

Synthesis of N-[5-phenyl-4-[4-(2-pyrrolidin-1-ylethoxymethyl)-1-piperidyl]thieno[2,3-d]pyrimidin-6-yl]acetamide

Example 162 i) 6-bromo-5-phenyl-4-[4-(2-pyrrolidin-1-ylethoxymethyl)-1-piperidyl]thieno[2,3-d]pyrimidine To a stirred solution of 6-bromo-4-chloro-5-phenyl-thieno[2,3-d]pyrimidine (0.820 g, 2.52 mmol) in THF (50 mL), was added diisopropylethylamine (0.65 mL, 3.78 mmol) and 4-(2-pyrrolidin-1-ylethoxymethyl)piperidine (0.801 g, 3.78 mmol) in one portion, and the reaction left to stir at room temperature overnight. The reaction was diluted with water (50 mL) and extracted with ethyl acetate (3×50 mL). The reaction was dried over sodium sulphate, filtered and concentrated under reduced pressure. The crude material was purified by column chromatography using DCM: MeOH (0-25%) as eluent to afford the named product (0.828 g, 66%).

ii) N-[5-phenyl-4-[4-(2-pyrrolidin-1-ylethoxymethyl)-1-piperidyl]thieno[2,3-d]pyrimidin-6-yl]acetamide

Example 162

To a stirred mixture of 6-bromo-5-phenyl-4-[4-(2-pyrrolidin-1-ylethoxymethyl)-1-piperidyl]thieno[2,3-d]pyrimidine (0.075 g, 0.15 mmol), cesium carbonate (0.102 g, 0.30 mmol), acetamide (0.019 g, 0.23 mmol), xantphos (0.014 g, 0.023 mmol) and tris(dibenzylideneacetone) dipalladium (0.007 g, 0.008 mmol) sealed in a microwave tube under an atmosphere of nitrogen, was added acetonitrile (2 mL) and 1,4-dioxane (2 mL). The reaction was placed in a microwave reactor at 150° C. for 1 hour. The reaction was concentrated under reduced pressure, diluted with ethyl acetate (20 mL) and water (20 mL), the organic layer washed with brine, dried over sodium sulphate, filtered and concentrated under reduced pressure. The crude material was purified by high performance liquid chromatography and the pure fractions combined and evaporated under reduced pressure to afford the named product (0.012 g, 17%). LCMS [M+H]$^+$=480; RT=2.82 min.

Other compounds prepared by Method E as described for example (ii) using the appropriate starting materials are listed in TABLE 1.

Method F

1) Synthesis of 5-phenyl-4-[4-(2-pyrrolidin-1-ylethoxymethyl)-1-piperidyl]thieno[2,3-d]pyrimidine

Example 5 i) 5-phenyl-4-[4-(2-pyrrolidin-1-ylethoxymethyl)-1-piperidyl]thieno[2,3-d]pyrimidine

Example 5

[1-(5-Phenylthieno[2,3-d]pyrimidin-4-yl)-4-piperidyl]methanol (100 mg, 0.31 mmol) was dissolved in anhydrous DMF (2 mL) under a nitrogen atmosphere. Sodium hydride (50 mg, 1.25 mmol, 60% w/w dispersion in mineral oil) was added and the mixture was stirred for 5 min. 1-(2-Chloroethyl)-pyrrolidine hydrochloride (105 mg, 0.62 mmol) was added and the mixture was stirred for two nights. Further portions of sodium hydride (50 mg, 1.25 mmol, 60% w/w dispersion in mineral oil) and 1-(2-chloroethyl)-pyrrolidine hydrochloride (105 mg, 0.62 mmol) were added and the mixture was stirred overnight. It was diluted with MeOH and then concentrated. The residue was dissolved in EtOAc (5 mL) and water (5 mL). The layers were separated and the aqueous was extracted with EtOAc (2×5 mL). The combined organic layers were dried (magnesium sulfate), filtered and evaporated to give a brown oil. This was purified by LCUV (basic method F). Collected fractions were analysed by LCMS and fractions containing the target compound were combined and evaporated to give the target compound (62 mg) as a white solid. m/z [M+H]$^+$423.0. RT=3.20 min. $^1$H NMR (CDCl$_3$): δ=0.64 (2H, qd), 1.38 (2H, d), 1.44-1.80 (5H, m), 2.38-2.53 (6H, m), 2.57 (2H, t), 3.04 (2H, d), 3.42 (2H, t), 3.75 (2H, d), 7.14 (1H, s), 7.25-7.42 (5H, m), 8.51 (1H, s)

Other compounds prepared by Method F as described for example (i) using the appropriate starting materials are listed in TABLE 1.

2) Synthesis of 5-[2-[[2-(5-isopropylthieno[2,3-d]pyrimidin-4-yl)-2-azabicyclo[2.2.1]heptan-5-yl]oxy]ethyl]-2-oxa-5-azabicyclo[2.2.1]heptane

Example 292 i) tert-butyl 5-(2-tetrahydropyran-2-yloxyethoxy)-2-azabicyclo[2.2.1]heptane-2-carboxylate Tert-butyl-5-hydroxy-2-azabicyclo[2.2.1]heptane-2-carboxylate (1.5 g, 7.0 mmol) and tetrabutylammonium bromide (0.35 g, 0.70 mmol) were stirred in sodium hydroxide (10 M) (30 mL, 1600 mmol)/toluene (30 mL) and heated to 60° C. 2-(2-Bromoethoxy)tetrahydropyran (4.4 g, 21 mmol) was added in 4 portions over 2 hours and heating continued overnight. Further 2-(2-bromoethoxy)tetrahydropyran (1 eq) was added and the reaction heated for a further 3 hours. The reaction mixture was diluted with DCM, washed with water, dried over Na$_2$SO$_4$ and concentrated in vacuo to afford a yellow oil. The reaction mixture was purified by flash chromatography, eluting with DCM then 90/10 DCM/MeOH to afford tert-butyl-5-(2-tetrahydropyran-2-yloxyethoxy)-2-azabicyclo[2.2.1]heptane-2-carboxylate (1.08 g).

ii) 2-(2-azabicyclo[2.2.1]heptan-5-yloxy)ethanol

Tert-butyl-5-(2-tetrahydropyran-2-yloxyethoxy)-2-azabicyclo[2.2.1]heptane-2-carboxylate (1.08 g, 3.16 mmol) was stirred overnight in 5 M hydrochloric acid (30 mL, 990 mmol)/THF (30 mL). The reaction mixture was basified with NaOH and washed with DCM. The organic was dried over Na$_2$SO$_4$ and concentrated in vacuo to afford 2-(2-azabicyclo[2.2.1]heptan-5-yloxy)ethanol (350 mg). LCMS RT=0.57 min. M+1=158.

iii) 2-[[2-(5-isopropylthieno[2,3-d]pyrimidin-4-yl)-2-azabicyclo[2.2.1]heptan-5-yl]oxy]ethanol 4-Chloro-5-isopropyl-thieno[2,3-d]pyrimidine (0.35 g, 1.6 mmol), 2-(2-azabicyclo[2.2.1]heptan-5-yloxy)ethanol (0.39 g, 2.5 mmol), triethylamine (0.50 g, 0.70 mL, 4.9 mmol) and ethanol (3.95 g, 5 mL, 85.6 mmol) were combined and heated to 50° C. overnight. The reaction mixture was concentrated in vacuo. The resulting residue was taken up in DCM, washed with water, dried over Na$_2$SO$_4$ and concentrated in vacuo to afford 2-[[2-(5-isopropylthieno[2,3-d]pyrimidin-4-yl)-2-azabicyclo[2.2.1]heptan-5-yl]oxy]ethanol (562 mg). LCMS RT: 3.47 min. M+1=334.

iv) 2-[[2-(5-isopropylthieno[2,3-d]pyrimidin-4-yl)-2-azabicyclo[2.2.1]heptan-5-yl]oxy]ethyl methanesulfonate 2-[[2-(5-Isopropylthieno[2,3-d]pyrimidin-4-yl)-2-azabicyclo[2.2.1]heptan-5-yl]oxy]ethanol (0.56 g, 1.7 mmol) was stirred in DCM (13.25 g, 10 mL, 156.0 mmol) at 0° C. Triethylamine (0.52 g, 0.71 mL, 5.0 mmol) was added. Methanesulfonyl chloride (0.29 g, 0.20 mL, 2.5 mmol) was added dropwise and the reaction allowed to warm slowly to room temperature and stirred for 1 hour. The reaction mixture was diluted with DCM, washed with water, dried over Na$_2$SO$_4$ and concentrated in vacuo to afford 2-[[2-(5-isopropylthieno[2,3-d]pyrimidin-4-yl)-2-azabicyclo[2.2.1]heptan-5-yl]oxy]ethyl methanesulfonate (0.747 g). LCMS RT=3.94 min. M+1=412.

(v) 5-[2-[[2-(5-isopropylthieno[2,3-d]pyrimidin-4-yl)-2-azabicyclo[2.2.1]heptan-5-yl]oxy]ethyl]-2-oxa-5-azabicyclo[2.2.1]heptane Example 292

2-[[2-(5-Isopropylthieno[2,3-d]pyrimidin-4-yl)-2-azabicyclo[2.2.1]heptan-5-yl]oxy]ethyl methanesulfonate (0.11 g, 0.27 mmol), 2-oxa-5-azabicyclo[2.2.1]heptane hydrochloride (0.072 g, 0.53 mmol) and potassium carbonate (0.11 g, 0.80 mmol) were combined in methyl ethyl ketone (2 mL)/DMF (1 mL, 12.8) and heated in the microwave for 30 minutes at 180° C. The reaction mixture was diluted with DCM, washed with water, dried over Na$_2$SO$_4$ and concentrated at reduced pressure. The resulting residue was purified by basic prep HPLC (method 2) to afford 5-[2-[[2-(5-isopropylthieno[2,3-d]pyrimidin-4-yl)-2-azabicyclo[2.2.1]heptan-5-yl]oxy]ethyl]-2-oxa-5-azabicyclo[2.2.1]heptane as a colourless gum (20 mg). LCMS RT=4.33 min. M+1=415.

Other compounds prepared by Method F as described for example (v) using the appropriate starting materials are listed in TABLE 1.

Method G

Synthesis of 5-phenyl-2-[4-(2-pyrrolidin-1-ylethoxymethyl)-1-piperidyl]thieno[2,3-d]pyrimidine Example 148 i) 2-chloro-5-phenyl-thieno[2,3-d]pyrimidine 2,4-Dichloro-5-phenyl-thieno[2,3-d]pyrimidine (1 g, 3.56 mmol) and zinc dust (2.34 g, 35.6 mmol) were combined and stirred in ethanol (10 mL). NH$_4$OH (1 mL) was added and the reaction heated to reflux for 2 hours. The reaction mixture was allowed to cool to room temperature, diluted with ethyl acetate (50 mL) and filtered through celite. The filtrate was washed with water (100 mL), dried over Na$_2$SO$_4$ and concentrated at reduced pressure. The resulting residue was purified by flash chromatography, eluting with a gradient of petroleum ether to 90/10 petroleum ether/ethyl acetate to afford 2-chloro-5-phenyl-thieno[2,3-d]pyrimidine (260 mg).

$^1$H NMR (250 MHz, CDCl$_3$) 9.12 (1H, d), 7.52 (5H, m).

The following compounds were synthesised according to the method described using the appropriate starting materials:
2-chloro-5-(4-fluorophenyl)thieno[2,3-d]pyrimidine
5-isopropyl-2-[4-(2-pyrrolidin-1-ylethoxymethyl)-1-piperidyl]thieno[2,3-d]pyrimidine
ii) 5-phenyl-2-[4-(2-pyrrolidin-1-ylethoxymethyl)-1-piperidyl]thieno[2,3-d]pyrimidine Example 148

2-Chloro-5-phenyl-thieno[2,3-d]pyrimidine (150 mg, 0.61 mmol), 4-(2-pyrrolidin-1-ylethoxymethyl)piperidine (293 mg, 0.92 mmol) and potassium carbonate (253 mg, 1.83 mmol) were combined in acetonitrile (2 mL) and heated in the microwave at 150° C. for 30 minutes. The reaction mixture was diluted with DCM (10 mL), washed with water (10 mL), dried over Na$_2$SO$_4$ and concentrated at reduced pressure. The resulting residue was purified by basic prep HPLC to afford 5-phenyl-2-[4-(2-pyrrolidin-1-ylethoxymethyl)-1-piperidyl]thieno[2,3-d]pyrimidine (67 mg). LCMS [M+H]$^+$=423.2.

Other compounds prepared by Method G as described for example (ii) using the appropriate starting materials are listed in TABLE 1.

Method H

Synthesis of 5-Phenyl-4-[3-(2-pyrrolidinyl-1-ylethoxy)prop-1-ynyl]thieno[2,3-d]pyrimidine Example 161 i) 1-(2-prop-2-ynoxyethyl)pyrrolidine

Propargyl alcohol (1.40 g, 25 mmol) in toluene (30 ml) was treated with 1-(2-chloroethyl)pyrrolidine hydrochloride (8.55 g, 50 mmol), 10 N aqueous sodium hydroxide solution (30 ml) and tetrabutylammonium bromide (150 mg, 1.2 mmol) and heated at 90° C. for 18 h. The layers were separated and the organic layer was dried over sodium sulphate and concentrated under reduced pressure to give a gum. The gum was distilled on a kugelrohr at 160° C. at 22 mbar to give two fractions. Fraction 1 (4.01 g, 25 mmol), the higher boiling, was found to be a mixture of the desired compound I-(2-prop-2-ynoxyethyl)pyrrolidine with some toluene and 2-pyrrolidine-1ylethanol. Fraction 2 (2.7 g) was found to be mainly the 2-pyrrolidine-1ylethanol and toluene and a trace of the desired compound I-(2-prop-2-ynoxyethyl)pyrrolidine. A portion of fraction 1 (1 g) was repurified by chromatography on silica in a gradient of 2-12% methanol in dichloromethane on a 100 g silica column collecting column volumes. 1-(2-Prop-2-ynoxyethyl)pyrrolidine was isolated as a yellow oil (0.419 g).

ii) 5-phenyl-4-[3-(2-pyrrolidinyl-1-ylethoxy)prop-1-ynyl]thieno[2,3-d]pyrimidine Example 161

Nitrogen gas was bubbled through a mixture of 4-chloro-5-phenyl-thieno[2,3-d]pyrimidine (1 g, 4.06 mmol), 1-(2-prop-2-ynoxyethyl)pyrrolidine (1.53 g, 10 mmol), bistriphenylphosphine palladium (II) dichloride (180 mg, 0.25 mmol), triethylamine (3.5 mL, 25 mmol), copper (I) iodide (75 mg, 0.4 mmol) in THF (20 mL) for 5 minutes. The reaction was then heated at 100° C. for 60 minutes in a microwave. The reaction was then diluted with ethyl acetate (50 ml) and water (50 ml) and shaken. The ethyl acetate layer was then separated, dried over sodium sulphate and concentrated in vacuum to a gum. The gum was chromatographed on silica in a gradient of $_2$-15% methanol in dichloromethane. A peak eluted in about 8-12% methanol in dichloromethane to give 5-phenyl-4-[3-(2-pyrrolidine-1-ylethoxy)prop-1-ynyl]thieno[2,3-d]pyrimidine as a gum. (55 mg, 0.15 mmol, 3.7%). LCMS [M+H]$^+$=364; RT=3.04 min.

Other compounds prepared by Method H as described for example (ii) using the appropriate starting materials are listed in TABLE 1.

Method I

1) Synthesis of 3-phenyl-4-[4-(2-pyrrolidin-1-ylethoxymethyl)-1-piperidyl]thieno[2,3-b]pyridine

Example 142 i) Synthesis of tert-butyl 4-(2-pyrrolidin-1-ylethoxymethyl)piperidine-1-carboxylate Tert-butyl 4-(hydroxymethyl)piperidine-1-carboxylate (5 g, 0.023 moles), 1-(2-chloroethyl)pyrrolidine (7.82 g, 0.046 moles) and tetrabutylammonium bromide (0.741 g, 2.3 mmol) were heated in toluene/water (1:1, 60 mL) to 90° C. overnight. The reaction mixture was diluted with DCM (100 mL), washed with water (100 mL), dried over $Na_2SO_4$ and concentrated at reduced pressure. The resulting residue was purified by flash chromatography, eluting with a gradient from DCM to 90/10 DCM/methanol to afford tert-butyl 4-(2-pyrrolidin-1-ylethoxymethyl)piperidine-1-carboxylate (5.28 g). LCMS $[M+H]^+=313.2$ The following compounds were synthesised according to the method described using the appropriate starting materials:
tert-butyl 5-(2-pyrrolidin-1-ylethoxy)-2-azabicyclo[2.2.1]heptane-2-carboxylate benzyl
3-(2-pyrrolidin-1-ylethoxymethyl)-8-azabicyclo[3.2.1]octane-8-carboxylate
tert-butyl 4-[2-(1-methylpyrrolidin-2-yl)ethoxymethyl]piperidine-1-carboxylate
tert-butyl 3-(2-pyrrolidin-1-ylethoxymethyl)pyrrolidine-1-carboxylate
tert-butyl 4-(2-morpholinoethoxymethyl)piperidine-1-carboxylate
benzyl 3-(methoxymethyl)-8-azabicyclo[3.2.1]octane-8-carboxylate tert-butyl 3-methoxy-8-azabicyclo[3.2.1]octane-1-carboxylate ii) 4-(2-pyrrolidin-1-ylethoxymethyl)piperidine Tert-butyl 4-(2-pyrrolidin-1-ylethoxymethyl)piperidine-1-carboxylate (5.28 g, 0.017 moles) was stirred at room temperature in TFA/DCM (1:1, 40 mL) for 1 hour. The solvent was removed at reduced pressure. The resulting residue was purified using an SCX column to afford 4-(2-pyrrolidin-1-ylethoxymethyl)piperidine (2.63 g). LCMS $[M+H]^+=213.2$ The following compounds were synthesised according to the method described using the appropriate starting materials:
5-(2-pyrrolidin-1-ylethoxy)-2-azabicyclo[2.2.1]heptane
3-(2-pyrrolidin-1-ylethoxymethyl)-8-azabicyclo[3.2.1]octane
1-[2-(pyrrolidin-3-ylmethoxy)ethyl]pyrrolidine
4-[2-(1-methylpyrrolidin-2-yl)ethoxyethyl]piperidine
4-(2-morpholinoethoxymethyl)piperidine
3-(methoxymethyl)-8-azabicyclo[3.2.1]octane
3-methoxy-8-azabicyclo[3.2.1]octane iii) Synthesis of 3-phenyl-4-[4-(2-pyrrolidin-1-ylethoxymethyl)-1-piperidyl]thieno[2,3-b]pyridine

Example 142 iv) 4-Chloro-3-phenyl-thieno[2,3-b]pyridine (150 mg, 0.462 mmol) and 4-(2-pyrrolidin-1-ylethoxymethyl)piperidine (150 mg, 0.706 mmol) were combined and heated in a Reactivial at 170° C. overnight. The reaction mixture was allowed to cool to room temperature and purified by basic prep HPLC to afford 3-phenyl-4-[4-(2-pyrrolidin-1-ylethoxymethyl)-1-piperidyl]thieno[2,3-b]pyridine (21 mg). LCMS [M+H]=422.2

1H NMR (250 MHz, $CDCl_3$) 8.39 (1H, d), 7.39 (5H, m), 7.24 (1H, s), 6.80 (2H, d), 3.55 (2H, t), 3.22 (2H, d), 3.06 (2H, d), 2.82 (7H, m), 2.52 (2H, t), 1.90 (4H, m), 1.49 (1H, m), 1.34 (2H, d), 0.47 (2H, q).

Other compounds prepared by Method I as described for example (iii) using the appropriate starting materials are listed in TABLE 1.

v) 5-phenyl-4-[(1S,5R)-3-(2-pyrrolidin-1-ylethoxymethyl)-8-azabicyclo[3.2.1]octan-8-yl]thieno[2,3-d]pyrimidine

Example 164

To a microwave vial was added 3-(2-pyrrolidin-1-ylethoxymethyl)-8-azabicyclo[3.2.1]octane (0.145 g, 0.608 mmol), 4-chloro-5-phenyl-thieno[2,3-d]pyrimidine (100 mg, 0.405 mmol) and N-ethyldiisopropylamine (0.0794 g, 0.608 mmol). The reaction was heated to 150° C. for 30 min. Solvents were removed and the residue was dissolved in DCM (50 mL). The solution was washed with water (2×50 mL), dried ($MgSO_4$) and concentrated. The residue was purified by prep HPLC to give the target compound as a brown oil. Yield=43 mg; LCMS $[M+H]^+=449$; RT=3.09 min.

Other compounds prepared by Method I as described for example (iv) using the appropriate starting materials are listed in TABLE 1.

2) Synthesis of 5-phenyl-4-[2-(1-piperidyl)ethoxy]thieno[2,3-d]pyrimidine

Example 369

Sodium hydride (8 mg, 0.16 mmol) was suspended in dry THF (0.5 mL). To this was added 2-(1-piperidyl)ethanol (16 μL, 0.12 mmol) and the reaction stirred for 10 min until effervescence had ceased. Then 4-chloro-5-phenyl-thieno[2,3-d]pyrimidine (20 mg, 0.08 mmol) in dry THF (0.5 mL) was added and the reaction left to stir at room temperature for 72 hrs. The reaction mixture was diluted with water and extracted with DCM. The organic layers were concentrated and the residue purified by preparative TLC (eluent 10% MeOH in DCM) to give 5-phenyl-4-[2-(1-piperidyl)ethoxy]thieno[2,3-d]pyrimidine as a yellow oil (19.4 mg, 72%). LCMS RT=3.03 min. M+1=340.

Method J

1) Synthesis of [8-(4-morpholino-5-phenyl-thieno[2,3-d]pyrimidin-2-yl)-8-azabicyclo[3.2.1]octan-3-yl]methanol

Example 165 i) 4-(2-chloro-5-phenyl-thieno[2,3-d]pyrimidin-4-yl)morpholine 2,4-Dichloro-5-phenyl-thieno[2,3-d]pyrimidine (2 g, 7.112 mmol), morpholine (0.9294 g, 10.67 mmol) and triethylamine (1.454 g, 2.00 mL, 14.22 mmol) were combined in ethanol (23.7 g, 30 mL, 493 mmol) and heated to 50° C. for 1 hour. The reaction mixture was allowed to cool to room temperature. The solvent volume was reduced by half and the resulting precipitate filtered off and washed with water and dried in vacuo overnight at 40° C. to afford 4-(2-chloro-5-phenyl-thieno[2,3-d]pyrimidin-4-yl)morpholine as a white solid.

Yield=2.31 g. LCMS $[M+H]^+=332.2$; RT=4.64 min.

The following compounds were synthesised according to the method described using the appropriate starting materials:

2-[1-[2-chloro-5-(4-fluorophenyl)thieno[2,3-d]pyrimidin-4-yl]-4-piperidyl]ethanol 1-(2-chloro-5-phenyl-thieno[2,3-d]pyrimidin-4-yl)-N,N-dimethyl-piperidin-4-amine 1-(2-chloro-5-phenyl-thieno[2,3-d]pyrimidin-4-yl)pyrrolidin-3-ol 1-(2-chloro-5-phenyl-thieno[2,3-d]pyrimidin-4-yl)pyrrolidine-3-carboxamide 2-chloro-N,N-dimethyl-5-phenyl-thieno[2,3-d]pyrimidin-4-amine 4-(2-chloro-5-phenyl-thieno[2,3-d]pyrimidin-4-yl)morpholine 4-(2-chloro-5-phenyl-thieno[2,3-d]pyrimidin-4-yl)morpholine-2-carboxamide

[8-(2-chloro-5-phenyl-thieno[2,3-d]pyrimidin-4-yl)-8-azabicyclo[3.2.1]octan-3-yl]methanol 5-(2-chloro-5-phenyl-thieno[2,3-d]pyrimidin-4-yl)-2-oxa-5-azabicyclo[2.2.1]heptane 2-chloro-4-[3-(methoxymethyl)-8-azabicyclo[3.2.]octan-8-yl]-5-phenyl-thieno[2,3-d]pyrimidine 2-chloro-4-(3-methoxy-8-azabicyclo[3.2.1]octan-8-yl)-5-phenyl-thieno[2,3-d]pyrimidine 8-(2-chloro-5-phenyl-thieno[2,3-d]pyrimidin-4-yl)-8-azabicyclo[3.2.1]octan-3-ol 8-(2-chloro-5-phenyl-thieno[2,3-d]pyrimidin-4-yl)-3-oxa-8-azabicyclo[3.2.1]octane 1-(2-chloro-5-phenyl-thieno[2,3-d]pyrimidin-4-yl)piperidine-3-carboxamide ii) [8-(4-morpholino-5-phenyl-thieno[2,3-d]pyrimidin-2-yl)-8-azabicyclo[3.2.1]octan-3-yl]methanol Example 165

4-(2-Chloro-5-phenyl-thieno[2,3-d]pyrimidin-4-yl)morpholine (0.2 g, 0.6028 mmol), 8-azabicyclo[3.2.1]octan-3-ylmethanol (0.1277 g, 0.9042 mmol) and potassium carbonate (0.2499 g, 1.808 mmol) were combined in acetonitrile (3 mL) and heated to 150° C. in the microwave for 30 minutes. The reaction was diluted with DCM, washed with water, dried over $Na_2SO_4$ and concentrated at reduced pressure. The resulting residue was purified by basic prep HPLC (method 6) to give the target compound. Yield=103 mg. LCMS [M+H]$^+$=437; RT=3.91 min.

2) Synthesis of 8-[2-(2-azabicyclo[2.2.1]heptan-5-yloxy)-5-phenyl-thieno[2,3-d]pyrimidin-4-yl]-3-oxa-8-azabicyclo[3.2.1]octane Example 349 i) 8-(2-chloro-5-phenyl-thieno[2,3-d]pyrimidin-4-yl)-3-oxa-8-azabicyclo[3.2.1]octane A slurry of 3-oxa-8-azabicyclo[3.2.1]octane hydrochloride (0.1064 g, 0.7112 mmol) in ethanol (2 mL) was added to 2,4-dichloro-5-phenyl-thieno[2,3-d]pyrimidine (0.1 g, 0.3556 mmol). triethylamine (0.250 mL, 1.778 mmol) was added and the mixture was stirred overnight at room temperature. DCM (2 mL) was added to form a complete solution and the mixture was stirred overnight at room temperature. The solvent was evaporated. The residue was dissolved in DCM (2 mL) and water (2 mL). The layers were separated and the aqueous was extracted with DCM (2×2 mL). The combined organic layers were evaporated to give a brown oil. Mass: 162 mg. This was purified by silica chromatography (10 g cartridge; eluent petrol/ethyl acetate 0 to 15%; all output collected) and the second eluting peak isolated to give 8-(2-chloro-5-phenyl-thieno[2,3-d]pyrimidin-4-yl)-3-oxa-8-azabicyclo[3.2.1]octane as a white solid (111 mg). LCMS: RT=4.95 min. M+1=358.

ii) tert-butyl 5-[4-(3-oxa-8-azabicyclo[3.2.1]octan-8-yl)-5-phenyl-thieno[2,3-d]pyrimidin-2-yl]oxy-2-azabicyclo[2.2.1]heptane-2-carboxylate Sodium hydride (0.02481 g, 0.6203 mmol, 60 mass %) was added to a solution of 5-hydroxy-2-aza-bicyclo[2.2.1]heptane-2-carboxylic acid tert-butyl ester (0.1023 g, 0.4652 mmol) in dry THF (2 mL). The mixture was stirred for 10 min and then a solution of 8-(2-chloro-5-phenyl-thieno[2,3-d]pyrimidin-4-yl)-3-oxa-8-azabicyclo[3.2.1]octane (0.111 g, 0.3101 mmol) in dry THF (3 mL) was added. The mixture was stirred overnight at room temperature. A second batch of sodium hydride (0.02481 g, 0.6203 mmol, 60 mass %) was added and the mixture was stirred overnight. Further batches of 5-hydroxy-2-aza-bicyclo[2.2.1]heptane-2-carboxylic acid tert-butyl ester (0.1023 g, 0.4652 mmol) and sodium hydride (0.02481 g, 0.6203 mmol, 60 mass %) were added and the mixture was stirred for 3 nights. It was poured into methanol to quench the reaction, and then the solvent was evaporated. The residue was dissolved in EtOAc (10 mL) and water (10 mL). The layers were separated and the aqueous was extracted with EtOAc (2×10 mL). The combined organic layers were washed with brine (1×10 mL), filtered through a hydrophobic frit and evaporated to give tert-butyl-5-[4-(3-oxa-8-azabicyclo[3.2.1]octan-8-yl)-5-phenyl-thieno[2,3-d]pyrimidin-2-yl]oxy-2-azabicyclo[2.2.1]heptane-2-carboxylate as a brown solid (269 mg) which was used in the next step without further purification. LCMS RT=4.23 min. M+1=535.

iii) 8-[2-(2-azabicyclo[2.2.1]heptan-5-yloxy)-5-phenyl-thieno[2,3-d]pyrimidin-4-yl]-3-oxa-8-azabicyclo[3.2.1]octane Example 349

Tert-butyl 5-[4-(3-oxa-8-azabicyclo[3.2.1]octan-8-yl)-5-phenyl-thieno[2,3-d]pyrimidin-2-yl]oxy-2-azabicyclo[2.2.1]heptane-2-carboxylate (269 mg, 0.503 mmol) was dissolved in DCM (2 mL) and trifluoroacetic acid (2 mL). The mixture was stirred at room temperature for 2 hrs and then evaporated. The residue was dissolved in water (2 mL) and DCM (2 mL). Solid sodium bicarbonate was added to neutralize the remaining acid. The layers were separated and the aqueous was extracted with DCM (2×2 mL). The combined organic layers were evaporated to give a brown solid. This was purified by preparative HPLC (acidic method 1). Fractions containing the target compound (by LCMS) were combined and evaporated. The residue was dissolved in methanol and applied to an SCX cartridge (2 g, equilibrated with methanol). The cartridge was washed with methanol (2 column volumes) then 0.5 M ammonia in methanol (2 column volumes). The ammonia solution was evaporated to give 8-[2-(2-azabicyclo[2.2.1]heptan-5-yloxy)-5-phenyl-thieno[2,3-d]pyrimidin-4-yl]-3-oxa-8-azabicyclo[3.2.1]octane as a white solid (6 mg). LCMS RT=3.16 min. M+1=435.

3) Synthesis of 5-phenyl-4-[4-(2-pyrrolidin-1-ylethoxymethyl)-1-piperidyl]thieno[2,3-d]pyrimidin-2-amine Example 314

2-Chloro-5-phenyl-4-[4-(2-pyrrolidin-1-ylethoxymethyl)-1-piperidyl]thieno[2,3-d]pyrimidine (0.4 g, 0.9 mmol) was dissolved in NMP (2 mL). Sodium azide (0.3 g, 4 mmol)

was added and the reaction heated to 150° C. in the microwave for 30 minutes. The reaction mixture was diluted with DCM, washed with water, dried over $Na_2SO_4$ and concentrated at reduced pressure. The resulting residue was purified by basic prep HPLC (method 6) to afford 5-phenyl-4-[4-(2-pyrrolidin-1-ylethoxymethyl)-1-piperidyl]thieno[2,3-d]pyrimidin-2-amine as a brown gum (81 mg). LCMS RT=2.8 min. M+1=438.

Other compounds prepared by Method J as described for examples 1, 2 or 3 using the appropriate starting materials are listed in TABLE 1.

Method K

Synthesis of N-[2-(1-methylpyrrolidin-2-yl)ethyl]-1-(5-phenylthieno[2,3-d]pyrimidin-4-yl)piperidine-4-carboxamide Example 166 i) 1-(5-phenylthieno[2,3-d]pyrimidin-4-yl)piperidine-4-carboxylic acid

4-Chloro-5-phenylthieno[2,3-d]pyrimidine (1.5 g, 6.1 mmol), piperidine-4-carboxylic acid (0.86 g, 6.7 mmol) and triethylamine (2.6 mL, 18 mmol) were suspended in dry ethanol (15 mL). The reaction was heated at 140° C. in a microwave for 10 min. The reaction was partitioned between water and DCM. The product was purified by column chromatography using a gradient of 10% methanol in DCM to 100% methanol to give the target compound as an off-white solid (yield=2.1 g). LCMS $[M+H]^+$=440; RT=4.04 min.

The following compounds were synthesised according to the method described using the appropriate starting materials:
1-(5-phenylthieno[2,3-d]pyrimidin-4-yl)piperidine-3-carboxylic acid
1-(5-phenylthieno[2,3-d]pyrimidin-4-yl)pyrrolidine-3-carboxylic acid ii) N-[2-(1-methylpyrrolidin-2-yl)ethyl]-1-(5-phenylthieno[2,3-d]pyrimidin-4-yl)piperidine-4-carboxamide Thionyl chloride (26 µL, 0.35 mmol) was added to (1-(5-phenylthieno[2,3-d]pyrimidin-4-yl)piperidine-4-carboxylic acid (100 mg, 0.294 mmol) in dry DCM at 0° C. The reaction was stirred for 30 min then 2-(1-methylpyrrolidin-2-yl)ethanamine (173 µL, 0.294 mmol) and triethylamine (82 µL, 0.588 mmol) were added and the reaction stirred for a further 10 min at 0° C. and then stirred at room temperature for 1 hr. The reaction was reduced to dryness in vacuo and the residue purified by prep HPLC (Basic, method F) to give the desired compound as an off-white solid. Yield=70 mg. LCMS $[M+H]^+$=450; RT=3.01 min iii) N-(2-morpholinoethyl)-1-(5-phenylthieno[2,3-d]pyrimidin-4-yl)piperidine-3-carboxamide O-(7-Azabenzotriazol-1-yl)-N,N,N',N'-tetramethyluronium hexafluorophosphate (0.23099 g, 0.58928 mmol) was added to a suspension of 1-(5-phenylthieno[2,3-d]pyrimidin-4-yl)piperidine-3-carboxylic acid (0.1 g, 0.29464 mmol) in acetonitrile (2 mL). Triethylamine (0.123 mL, 0.089443 g, 0.88391 mmol) and 2-morpholinoethanamine (0.0773 mL, 0.076718 g, 0.58928 mmol) were added and the mixture was stirred for 4 hr at room temperature. The solvent was evaporated and the residue was diluted with ethyl acetate (2 mL) and water (2 mL). The layers were separated and the aqueous was extracted with ethyl acetate (2×2 mL). The combined organic layers were washed with saturated aqueous sodium hydrogencarbonate (1×10 mL), dried (magnesium sulfate), filtered and evaporated to give a brown oil. Mass: 0.275 g. This was purified by prep HPLC (basic method 1). Fractions corresponding to the main peak were combined and evaporated to give a yellow oil. Yield=92 mg. LCMS $[M+H]^+$=452; RT=2.89 min Other compounds prepared by Method K using the appropriate starting materials are listed in TABLE 1.

Method L

Synthesis of N-[5-phenyl-2-[4-(2-pyrrolidin-1-ylethoxymethyl)-1-piperidyl]thieno[2,3-d]pyrimidin-6-yl]acetamide Example 155 i) 6-bromo-2-chloro-5-phenyl-thieno[2,3-d]pyrimidine
2-Chloro-5-phenyl-thieno[2,3-d]pyrimidine (0.5 g, 2.03 mmol) was stirred in acetic acid (10 mL). Bromine (0.65 g, 0.21 mL, 4.06 mmol) was added dropwise and the reaction allowed to stir at room temperature over the weekend. The reaction mixture was poured into saturated aqueous ascorbic acid solution. The resulting solid was filtered off and dried in vacuo at 40° C. to afford 6-bromo-2-chloro-5-phenyl-thieno[2,3-d]pyrimidine (567 mg).
LCMS $[M+H]^+$=323.3

The following compounds were synthesised according to the method described using the appropriate starting materials:
2-chloro-5-cyclohexyl-thieno[2,3-d]pyrimidine ii) 6-bromo-5-phenyl-2-[4-(2-pyrrolidin-1-ylethoxymethyl)-1-piperidyl]thieno[2,3-d]pyrimidine 4-(2-Pyrrolidin-1-ylethoxymethyl)piperidine (0.567 g, 1.74 mmol), 6-bromo-2-chloro-5-phenyl-thieno[2,3-d]pyrimidine (0.554 g, 2.61 mmol) and potassium carbonate (7.21 g, 7.7 mmol) were combined and heated in acetonitrile for 30 minutes to 150° C. in the microwave. The reaction mixture was diluted with DCM, washed with water, dried over $Na_2SO_4$ and concentrated at reduced pressure. The resulting residue was purified by flash chromatography, eluting with DCM—92/8/2 DCM/MeOH/$NH_4OH$ gradient to afford 6-bromo-5-phenyl-2-[4-(2-pyrrolidin-1-ylethoxymethyl)-1-piperidyl]thieno[2,3-d]pyrimidine (374 mg). LCMS $[M+H]^+$=501.1 iii) N-[5-phenyl-2-[4-(2-pyrrolidin-1-ylethoxymethyl)-1-piperidyl]thieno[2,3-d]pyrimidin-6-yl]acetamide Example 155

6-Bromo-5-phenyl-2-[4-(2-pyrrolidin-1-ylethoxymethyl)-1-piperidyl]thieno[2,3-d]pyrimidine (0.125 g, 0.25 mmol), acetamide (0.022 g, 0.37 mmol), cesium carbonate (0.163 g, 0.5 mmol), xantphos (0.022 g, mol %), $Pd_2(dba)_3$ (0.010 g, 5 mol %) and MeCN (2 mL) were combined and heated to 150° C. for 30 minutes. The reaction was diluted with DCM (10 mL), washed with water (10 mL), passed through a hydrophobic frit and concentrated at reduced pressure. The resulting residue was purified by basic prep HPLC to afford N-[5-phenyl-2-[4-(2-pyrrolidin-1-ylethoxymethyl)-1-piperidyl]thieno[2,3-d]pyrimidin-6-yl]acetamide (22 mg). LCMS $[M+H]^+$=480.2

Other compounds prepared by Method L using the appropriate starting materials are listed in TABLE 1.

Method M

Synthesis of 5-phenyl-4-[4-(2-pyrrolidin-1-ylethoxymethyl)-1-piperidyl]thieno[2,3-d]pyrimidine-6-carbonitrile Example 167

In a sealed microwave tube nitrogen was bubbled through a stirred solution of 6-bromo-5-phenyl-4-[4-(2-pyrrolidin-1- ylethoxymethyl)-1-piperidyl]thieno[2,3-d]pyrimidine (0.150 g, 0.30 mmol), zinc cyanide (0.035 mg, 0.30 mmol), and diphenylphosphino ferrocene (0.031 g, 0.042 mmol) in DMF (2 mL) for 30 minutes at room temperature. To the stirred reaction was added tris(dibenzylideneacetone)dipalladium (0.019 g, 0.021 mmol), the vessel sealed and heated in a microwave reactor at 180° C. for 20 minutes. The reaction was diluted with ethyl acetate (20 mL) and water (20 mL), the organic layer washed with brine, dried over sodium sulphate, filtered and concentrated under reduced pressure. The crude material was purified by high performance liquid chromatography and the pure fractions combined and evaporated under reduced pressure to afford the named product contaminated with diphenylphosphino ferrocene ligand. The contaminated product was dissolved in methanol and placed on an SCX-SAX catch and release cartridge and eluted with methanol followed by 7N methanolic ammonia. The ammonia fractions were concentrated under reduced pressure to afford the pure named product (0.0214 g, 16%).

Other compounds prepared by Method M using the appropriate starting materials are listed in TABLE 1.

Method N

Synthesis of N-benzyl-5-phenyl-4-[4-(2-pyrrolidin-1-ylethoxymethyl)-1-piperidyl]thieno[2,3-d]pyrimidin-6-amine Example 168

To a stirred mixture of 6-bromo-5-phenyl-4-[4-(2-pyrrolidin-1-ylethoxymethyl)-1-piperidyl]thieno[2,3-d]pyrimidine (0.300 g, 0.60 mmol), cesium carbonate (0.390 g, 1.20 mmol), benzylamine (0.10 mL, 0.90 mmol), xantphos (0.042 g, 0.072 mmol) and tris(dibenzylideneacetone)dipalladium (0.022 g, 0.036 mmol) sealed in a microwave tube under an atmosphere of nitrogen, was added acetonitrile (5 mL) and 1,4-dioxane (5 mL). The reaction was placed in a microwave reactor at 150° C. for 1 hour. The reaction was concentrated under reduced pressure, diluted with ethyl acetate (20 mL) and water (20 mL), the organic layer washed with brine, dried over sodium sulphate, filtered and concentrated under reduced pressure. The crude material was part-purified by column chromatography eluting with DCM: methanol (0-25%) as eluent and the product-containing fractions combined and evaporated under reduced pressure to afford the named product and minor impurities (0.435 g). A small proportion of the part purified product (0.100 g) was further purified by high performance liquid chromatography to give an analytically pure sample (0.006 g).

Other compounds prepared by Method N using the appropriate starting materials are listed in TABLE 1.

Method O

1) Synthesis of 5-(2-methoxy-3-pyridyl)-4-[4-(2-pyrrolidin-1-ylethoxymethyl)-1-piperidyl]thieno[2,3-d]Pyrimidine Example 316 i) 5-bromo-4-[4-(2-pyrrolidin-1-ylethoxymethyl)-1-piperidyl]thieno[2,3-d]pyrimidine
5-Bromo-4-chlorothieno[2,3-d]pyrimidine (828 mg 3.33 mmol) in dry acetonitrile (13 mL) was treated with 4-(2-pyrrolidin-1-ylethoxymethyl)piperidine (1.057 g, 5.0 mmol,) and potassium carbonate (687 mg, 5.0 mmol) and heated at 110° C. for 30 min in a microwave. The reaction was then poured into ethyl acetate (50 mL) and water (30 mL) and the ethyl acetate layer separated, dried over sodium sulphate and concentrated in vacuum to give 5-bromo-4-[4-(2-pyrrolidin-1-ylethoxymethyl)-1-piperidyl]thieno[2,3-d]pyrimidine (1.322 g, 3.11 mmol, 93%). LCMS RT=2.91 min. M+1=427.

The following compounds were synthesised according to the method described using the appropriate starting materials:
5-bromo-4-[(1S,5R)-3-(2-pyrrolidin-1-ylethoxymethyl)-8-azabicyclo[3.2.1]octan-8-yl]thieno[2,3-d]pyrimidine
(ii) 5-(2-methoxy-3-pyridyl)-4-[4-(2-pyrrolidin-1-ylethoxymethyl)-1-piperidyl]thieno[2,3-d]pyrimidine Example 316

5-Bromo-4-[4-(2-pyrrolidin-1-ylethoxymethyl)-1-piperidyl]thieno[2,3-d]pyrimidine, (100 mg, 0.23 mmol) in dimethoxyethane (3.5 mL) was treated with 2-methoxy-3-pyridyl)boronic acid (89 mg, 0.7 mmol), palladium (II) acetate (12 mg), triphenylphosphine (12 mg), and sodium carbonate solution (1.5 mL of a 2 M solution) and the mixture was heated in a microwave reactor with vigorous stirring at 85° C. for 1 h. The reaction was then partitioned between ethyl acetate and water. The ethyl acetate layer was separated, dried over sodium sulphate and concentrated in vacuum to a gum. The gum was dissolved in DMSO/methanol 1:1, purified by preparative HPLC. The main peak was collected and concentrated in vacuum to give 5-(2-methoxy-3-pyridyl)-4-[4-(2-pyrrolidin-1-ylethoxymethyl)-1-piperidyl]thieno[2,3-d]pyrimidine as a colourless gum (49 mg, 46%). $^1$H NMR (CDCl$_3$) δ: 0.6 (2H, m), 1.45 (2H, d, J=12 Hz), 1.6 (1H, br m), 1.8 (4H, br s), 2.2 (1H, br s), 2.52 (6H, br s), 2.65 (2H, t, J=4 Hz), 3.1 (2H, d, J=4 Hz), 3.5 (2H, t, J=4 Hz), 3.7 (2H, br d, J=12 Hz), 3.9 (3H, s), 7.0 (1H, dd, J=4 Hz, J'=8 Hz), 7.3 (1H, s), 7.5 (d, J=4 Hz), 8.2 (1H, d, J=4 Hz), 8.55 (1H, s).

Other compounds prepared by Method O using the appropriate starting materials are listed in TABLE 1.

Method P

1) Synthesis of N-isopropyl-8-(5-phenylthieno[2,3-d]pyrimidin-4-yl)-8-azabicyclo[3.2.1]octan-3-amine Example 327 i) 8-(5-phenylthieno[2,3-d]pyrimidin-4-yl)-8-azabicyclo[3.2.1]octan-3-one
A mixture of 4-chloro-5-phenyl-thieno[2,3-d]pyrimidine (1.00 g, 4.05 mmol), nortropinone hydrochloride (0.983 g, 6.08 mmol) and triethylamine (1.71 mL, 12.2 mmol) in THF (20 mL) was heated to 70° C. overnight. Ethanol (20 mL) was added and the mixture was heated to 70° C. for 3 hr. Further batches of nortropinone hydrochloride (0.983 g, 6.08 mmol) and triethylamine (1.71 mL, 12.2 mmol) were added and the mixture was heated to 70° C. overnight. Further batches of nortropinone hydrochloride (0.983 g, 6.08 mmol) and triethylamine (1.71 mL, 12.2 mmol) were added and the mixture was heated to 70° C. over 3 nights. It was cooled to room temperature and diluted with dichloromethane (40 mL) and water (40 mL). The layers were separated and the aqueous was extracted with dichloromethane (2×40 mL). The combined organic layers were washed with brine (1×40 mL), filtered through a hydrophobic frit and evaporated to give a brown oil. Mass: 3.21 g. This was purified by silica chromatography (100 g cartridge; eluent petrol/ethyl acetate 0 to 40%). Fractions corresponding to the main peak were combined and evaporated to give 8-(5-phenylthieno[2,3-d]pyrimidin-4-yl)-8-azabicyclo[3.2.1]octan-3-one as a white solid (0.99 g).

LCMS RT=4.43 min. M+1=336.

The following compounds were synthesised according to the method described using the appropriate starting materials:
1-(5-phenylthieno[2,3-d]pyrimidin-4-yl)piperidin-4-one
  ii) N-isopropyl-8-(5-phenylthieno[2,3-d]pyrimidin-4-yl)-8-azabicyclo[3.2.1]octan-3-amine Example 327

Isopropylamine (0.0385 mL, 0.4472 mmol) was added to a solution of 8-(5-phenylthieno[2,3-d]pyrimidin-4-yl)-8-azabicyclo[3.2.1]octan-3-one (0.05 g, 0.1491 mmol) in DCM (2 mL). Sodium triacetoxyborohydride (0.1663 g, 0.7454 mmol) was added and the mixture was stirred at room temperature overnight. A second batch of isopropylamine (0.0385 mL, 0.4472 mmol) and sodium triacetoxyborohydride (0.1663 g, 0.7454 mmol) was added and the mixture was stirred overnight. A third batch of isopropylamine (0.0385 mL, 0.4472 mmol) and sodium triacetoxyborohydride (0.1663 g, 0.7454 mmol) was added and the mixture was stirred over three nights. Methanol (2 mL) was added to quench the reaction. The solvent was evaporated and the residue was dissolved in dichloromethane (2 mL) and water (2 mL). The layers were separated and the aqueous was extracted with dichloromethane (2×2 mL). The combined organic layers were evaporated to give a colourless oil. Mass: 77 mg. This was purified by silica chromatography (10 g cartridge; eluent dichloromethane/0.5 M ammonia in methanol 0 to 10%; all output collected). Fractions containing the target compound (by TLC and LCMS; broad peak) were combined and evaporated to give N-isopropyl-8-(5-phenylthieno[2,3-d]pyrimidin-4-yl)-8-azabicyclo[3.2.1]octan-3-amine a white solid. (19 mg). LCMS RT=3.04 min. M+1=379.

Other compounds prepared by Method P using the appropriate starting materials are listed in TABLE 1.

Method Q

1) Synthesis of 2-cyclopropyl-5-(2-methoxyphenyl)-4-[4-(2-pyrrolidin-1-ylethoxymethyl)-1-piperidyl]thieno[2,3-d]pyrimidine Example 358 i) 4-chloro-2-cyclopropyl-5-(2-methoxyphenyl)thieno[2,3-d]pyrimidine
Ethyl 2-amino-4-(2-methoxyphenyl)thiophene-3-carboxylate (1 g, 3.606 mmol), cyclopropanecarboxamide (0.3069 g, 3.606 mmol) and phosphorous (V) trichloride (0.6723 mL, 7.212 mmol) were combined and heated to 100° C. over the weekend in a Reactivial. The reaction mixture was diluted with DCM (25 mL), washed with water (2×25 mL), dried over $Na_2SO_4$ and concentrated at reduced pressure. The resulting residue was purified by flash chromatography, eluting with a gradient of petroleum ether to 50/50 petroleum ether/ethyl acetate to afford 4-chloro-2-cyclopropyl-5-(2-methoxyphenyl)thieno[2,3-d]pyrimidine (0.51 g). LCMS: purity 100%, RT=4.63 min, M+1=317.0
  ii) 2-cyclopropyl-5-(2-methoxyphenyl)-4-[4-(2-pyrrolidin-1-ylethoxymethyl)-1-piperidyl]thieno[2,3-d]pyrimidine Example 358

4-(2-Pyrrolidin-1-ylethoxymethyl)piperidine (0.10 g, 0.47 mmol), triethylamine (0.089 mL, 0.63 mmol) and 4-chloro-2-cyclopropyl-5-(2-methoxyphenyl)thieno[2,3-d]pyrimidine (0.10 g, 0.32 mmol) were combined and heated to 50° C. in ethanol (10 mL) overnight. The solvent was removed at reduced pressure. The residue was taken up in DCM (20 mL), washed with water (20 mL) and the organic dried over $Na_2SO_4$ and concentrated at reduced pressure. The resulting residue was purified by flash chromatography, eluting with a gradient of DCM to 90/10/1 DCM/MeOH/$NH_4OH$ to afford 2-cyclopropyl-5-(2-methoxyphenyl)-4-[4-(2-pyrrolidin-1-ylethoxymethyl)-1-piperidyl]thieno[2,3-d]pyrimidine (0.03 g). LCMS: purity 100%, RT=3.62 min, M+1=493.1

2) Synthesis of 5-phenyl-4-[4-(2-pyrrolidin-1-ylethoxymethyl)-1-piperidyl]-2-(trifluoromethyl)thieno[2,3-d]pyrimidine Example 340

(i) 5-phenyl-2-(trifluoromethyl)-3H-thieno[2,3-d]pyrimidin-4-one
Ethyl 2-amino-4-phenyl-thiophene-3-carboxylate (2 g, 8.087 mmol) and trifluoroacetamidine (4.531 g, 40.44 mmol) were combined in ethanol (20 mL) and heated to reflux overnight. Further trifluoroacetamidine (4.531 g, 40.44 mmol) was added and the reaction heated to reflux for a further 18 hours. The reaction mixture was allowed to cool to room temperature. The resulting precipitate was filtered off, washed with ethanol (5 mL) and dried in vacuo at 40° C. to afford 5-phenyl-2-(trifluoromethyl)-3H-thieno[2,3-d]pyrimidin-4-one (1.195 g). LCMS: purity 99%, RT=4.11 min, M+1=297.
  (ii) 5-phenyl-4-[4-(2-pyrrolidin-1-ylethoxymethyl)-1-piperidyl]-2-(trifluoromethyl)thieno[2,3-d]pyrimidine Example 340

5-Phenyl-2-(trifluoromethyl)thieno[2,3-d]pyrimidin-4-one (0.20 g, 0.67 mmol) was stirred in dichloromethane (5 mL) at 0° C. Pyridine (0.11 mL, 1.3 mmol) was added, followed by trifluoromethanesulfonic anhydride (0.14 mL, 0.81 mmol) and stirring continued for 30 mins and the mixture allowed to warm to room temperature. 4-(2-Pyrrolidin-1-ylethoxymethyl)piperidine (0.29 g, 1.3 mmol) was added and the reaction stirred for 1 hour at room temperature. The reaction mixture was diluted with DCM (20 mL), washed with water (20 mL), dried over $Na_2SO_4$ and concentrated at reduced pressure. The resulting residue was purified by flash chromatography, eluting with a gradient of petroleum ether to 50/50 petroleum ether/ethyl acetate to afford 5-phenyl-4-[4-(2-pyrrolidin-1-ylethoxymethyl)-1-piperidyl]-2-(trifluoromethyl)thieno[2,3-d]pyrimidine (0.16 g). LCMS: purity 98%, RT=4.28 min, M+1=491.2

3) Synthesis of N-cyclobutyl-8-(2-cyclopropyl-5-phenyl-thieno[2,3-d]pyrimidin-4-yl)-8-azabicyclo[3.2.1]octan-3-amine Example 321 i) 8-(2-cyclopropyl-5-phenyl-thieno[2,3-d]pyrimidin-4-yl)-8-azabicyclo[3.2.1]octan-3-one
A mixture of 4-chloro-2-cyclopropyl-5-phenyl-thieno[2,3-d]pyrimidine (0.30 g, 1.05 mmol, ex Enamine), nortropinone hydrochloride (0.25 g, 1.57 mmol) and triethylamine (0.44 mL, 3.14 mmol) in ethanol (4 mL) was heated to 140° C. for 30 min in a microwave. Heating was repeated. Further portions of triethylamine (0.44 mL, 3.14 mmol) and nortropinone hydrochloride (0.25 g, 1.57 mmol) were added and the mixture was stirred at room temperature for 3 nights. It was diluted with ethyl acetate (20 mL) and water (20 mL). The layers were separated and the aqueous was extracted with ethyl acetate (2×20 mL). The combined organic layers were washed with brine (1×20 mL), dried (magnesium sulfate, filtered and evaporated to give a brown oil (512 mg). This was purified by silica chromatography (10 g cartridge; eluent petroleum ether 40-60/ethyl acetate 0 to 100%; all output collected) to give 8-(2-cyclopropyl-5-phenyl-thieno[2,3-d]pyrimidin-4-yl)-8-azabicyclo[3.2.1]octan-3-oneas a yellow solid (0.15 g). m/z [M+H]$^+$ 376.0. Retention time 4.98 min (LCMS method+ve 6 min).

ii) N-cyclobutyl-8-(2-cyclopropyl-5-phenyl-thieno[2,3-d]pyrimidin-4-yl)-8-azabicyclo[3.2.1]octan-3-amine Example 321

Cyclobutylamine (0.023 mL, 0.27 mmol) was added to a solution of 8-(2-cyclopropyl-5-phenyl-thieno[2,3-d]pyrimidin-4-yl)-8-azabicyclo[3.2.1]octan-3-one (50 mg, 0.133 mmol) in dichloromethane (2.5 mL). Sodium triacetoxyborohydride (89 mg, 0.40 mmol) was added and the mixture was stirred overnight at room temperature. Further portions of cyclobutylamine (0.023 mL, 0.27 mmol) and sodium triacetoxyborohydride (89 mg, 0.40 mmol) were added and the mixture was stirred for 3 nights at room temperature. Methanol (2 mL) was added to quench the reaction. The solvent was evaporated and the residue was dissolved in water (2 mL) and ethyl acetate (2 mL). The layers were separated and the aqueous was extracted with ethyl acetate (3×2 mL). The combined organic layers were dried (magnesium sulfate), filtered and evaporated to give a yellow oil (70 mg). This was purified by LCUV (acidic method 1). The relevant fractions were combined and evaporated.

The residue was dissolved in methanol and applied to an SCX cartridge (2 g, wetted with methanol), then washed with methanol (2 column volumes) and eluted with 7 M ammonia in methanol (2 column volumes). The ammonia solution was evaporated to give the target compound as a white solid (38 mg). m/z [M+H]$^+$431.1. Retention time 3.29 min (LCMS method+ve 6 min).

Other compounds prepared by Method Q using the appropriate starting materials are listed in TABLE 1.

Method R

1) Synthesis of N,N-dimethyl-5-phenyl-4-(3-pyrrolidin-1-yl-8-azabicyclo[3.2.1]octan-8-yl)thieno[2,3-d]pyrimidine-6-carboxamide Example 353 i) Methyl 4-(3-hydroxy-8-azabicyclo[3.2.1]octan-8-yl)-5-phenyl-thieno[2,3-d]pyrimidine-6-carboxylate To a stirred solution of methyl 4-chloro-5-phenyl-thieno[2,3-d]pyrimidine-6-carboxylate (3.231 g, 10.59 mmol) and DIPEA (2.39 mL, 15.89 mmol) in THF (60 mL) at room temperature was added nortropine (1.682 g, 15.89 mmol) and the reaction left to stir overnight. The reaction was diluted with water (60 mL) and the layers separated. The aqueous layer was acidified to pH 3 and extracted repeatedly with 3:1 chloroform/IPA. The combined organic layers were dried over sodium sulphate, filtered and concentrated under reduced pressure to afford methyl 4-(3-hydroxy-8-azabicyclo[3.2.1]octan-8-yl)-5-phenyl-thieno[2,3-d]pyrimidine-6-carboxylate (1.839 g, 44%). LCMS: R$_t$=4.23, 396 (M+1).

ii) Methyl 4-(3-oxo-8-azabicyclo[3.2.1]octan-8-yl)-5-phenyl-thieno[2,3-d]pyrimidine-6-carboxylate To a stirred solution of methyl 4-(3-hydroxy-8-azabicyclo[3.2.1]octan-8-yl)-5-phenyl-thieno[2,3-d]pyrimidine-6-carboxylate (0.940 g, 2.38 mmol) in DCM (100 mL) at room temperature was added Dess-Martin Periodinane (1.310 g, 3.094 mmol) in one portion and the reaction left to stir overnight. The reaction was filtered and the filtrate washed with saturated sodium bicarbonate and brine, the organic layer dried over sodium sulphate, filtered and concentrated under reduced pressure to afford methyl 4-(3-oxo-8-azabicyclo[3.2.1]octan-8-yl)-5-phenyl-thieno[2,3-d]pyrimidine-6-carboxylate which was used without further purification (0.935 g, 100%). LCMS: R$_t$=4.46, 394 (M+1).

iii) 5-Phenyl-4-(3-pyrrolidin-1-yl-8-azabicyclo[3.2.1]octan-8-yl)thieno[2,3-d]pyrimidine-6-carboxylic acid To a stirred solution of methyl 4-(3-oxo-8-azabicyclo[3.2.1]octan-8-yl)-5-phenyl-thieno[2,3-d]pyrimidine-6-carboxylate (0.935 g, 2.38 mmol), pyrrolidine (0.40 mL, 4.758 mmol) and dibutyltin dichloride (0.072 g, 0.238 mmol) in THF (10 mL) in a microwave vial was added phenylsilane (0.366 mL, 2.975 mmol) in one portion. The reaction was sealed and heated in a microwave at 100° C. for 1 hour. The reaction was diluted with water (20 mL) and ethyl acetate (30 mL), the aqueous further extracted with ethyl acetate (3×15 mL) and the combined organics dried over sodium sulphate, filtered and concentrated under reduced pressure. The reaction was purified by column chromatography using DCM:MeOH (0-25%) as eluent to afford the intermediate methyl ester (R$_t$=3.12, 449 M+1). The combined and concentrated intermediate was dissolved in THF (10 mL) and water (10 mL), lithium hydroxide (0.201 g, 4.758 mmol) added and the reaction stirred at room temperature for 1 hour. The THF was removed under reduced pressure, the aqueous acidified to pH 3 using concentrated hydrochloric acid and extracted repeatedly using 3:1 chloroform/IPA. The combined extracts were dried over sodium sulphate, filtered and concentrated to afford the crude acid which was used without further purification (0.984 g, 95%). LCMS: R$_t$=2.93, 435 (M+1).

iv) N,N-Dimethyl-5-phenyl-4-(3-pyrrolidin-1-yl-8-azabicyclo[3.2.1]octan-8-yl)thieno[2,3-d]pyrimidine-6-carboxamide Example 353

To a stirred solution of 5-phenyl-4-(3-pyrrolidin-1-yl-8-azabicyclo[3.2.1]octan-8-yl)thieno[2,3-d]pyrimidine-6-carboxylic acid (0.150 g, 0.346 mmol), HATU (0.262 g, 0.691 mmol) and DIPEA (0.12 mL, 0.691 mmol) in DMF (2 mL) was added a 2 M solution of dimethylamine in THF (0.52 mL, 1.037 mmol) in one portion. The reaction was stirred at room temperature over a weekend, filtered and purified by preparative chromatography using basic eluent to afford major (0.0294 g, 19%), LCMS: R$_t$=2.95, 462 (M+1); and minor (0.0125 g, 8%) LCMS: R$_t$=2.96, 462 (M+1) isomers of the named product.

Other compounds prepared by Method R using the appropriate starting materials are listed in TABLE 1.

Method S

1) Synthesis of N-cyclobutyl-8-[5-(2-methoxy-3-pyridyl)thieno[2,3-d]pyrimidin-4-yl]-N-methyl-8-azabicyclo[3.2.1]octan-3-amine Example 351 i) 8-(5-bromothieno[2,3-d]pyrimidin-4-yl)-8-azabicyclo[3.2.1]octan-3-ol

5-Bromo-4-chlorothieno[2,3-d]pyrimidine (2.11 g, 8.5 mmol) in dry acetonitrile (100 mL) was treated with 8-azabicyclo[3.2.1]octan3-ol (1.34 g, 10.6 mmol) and potassium carbonate (3.519 g, 25.5 mmol) and stirred and heated at reflux for 4 h. The reaction was diluted with ethyl acetate (200 mL) and dichloromethane (100 mL) and washed with water (100 mL). The organic layer was separated, dried over sodium sulphate and concentrated in vacuum to give 8-(5-bromothieno[2,3-d]pyrimidin-4-yl)-8-azabicyclo[3.2.1]octan-3-ol as a yellow solid (2.890 g, 8.5 mmol, 100%). This was used directly in the next step without further purification. $^1$H NMR (CDCl$_3$) δ: 1.83 (2H, d, J=12 Hz), 2.0 (2H, br s) 2.28 (2H, d, J=6 Hz), 2.45 (2H, d, J=8 Hz), 4.15 (1H, br s), 4.7 (2H, br s), 7.35 (1H, s), 8.45 (1H, s).

ii) 8-(5-bromothieno[2,3-d]pyrimidin-4-yl)-8-azabicyclo[3.2.1]octan-3-one 8-(5-Bromothieno[2,3-d]pyrimidin-4-yl)-8-azabicyclo[3.2.1]octan-3-ol (1.87 g, 5.5 mmol) in dichloromethane (60 mL) was treated with Dess Martin Periodane (3.5 g, 8.25 mmol) and stirred at room temperature for 1 h. The reaction was washed with 10% potassium carbonate solution (25 mL), the dichloromethane layer was separated, dried over sodium sulphate and concentrated in vacuum to give a gummy solid. This was dissolved in dichloromethane (15 mL) and applied to two 100 g silica column samplets and then chromatographed on 2×100 g silica columns in a gradient of 25-50% ethyl acetate in petrol. The first peak was collected and concentrated in vacuum to give a colourless crystalline solid that was dried in vacuum (1.4833 g, 4.388 mmol, 79%) of 8-(5-bromothieno[2,3-d]pyrimidin-4-yl)-8-azabicyclo[3.2.1]octan-3-one. $^1$H NMR (CDCl$_3$) δ: 1.82 (2H, dd, J=6 Hz, J'=4 Hz), 2.1 (2H, brs), 2.35 (2H, d, J=12 Hz), 2.97 (2H, dd, J=12 hz, J'=3 Hz), 4.85 (2H, br s), 7.35 (2H, s), 8.5 (1H, s).

iii) 8-(5-bromothieno[2,3-d]pyrimidin-4-yl)-N-cyclobutyl-8-azabicyclo[3.2.1]octan-3-amine 8-(5-Bromothieno[2,3-d]pyrimidin-4-yl)-8-azabicyclo[3.2.1]octan-3-one (1.5 g, 4.43 mmol) in toluene (60 mL) was treated with cyclobutylamine (3.145 g, 44.3 mmol) and heated with stirring to reflux for 2 h. Ethanol (100 mL) and sodium triacetoxyborohydride (9.347 g, 44.3 mmol) were added and the reaction stirred and warmed at 30° C. over 3 days. The reaction was then concentrated in vacuum to a gum, diluted with ethyl acetate (100 mL) and saturated sodium hydrogen carbonate solution (50 mL) and shaken. The ethyl acetate layer was then separated, dried over sodium sulphate and concentrated in vacuum to give 8-(5-bromothieno[2,3-d]pyrimidin-4-yl)-N-cyclobutyl-8-azabicyclo[3.2.1]octan-3-amine as a yellow solid (1.799 g, 3.97 mmol, 89%). $^1$H NMR (CDCl$_3$) δ: 1.5 (3H, d, J=12 Hz), 1.65 (3H, br s), 1.93 (2H, br s), 2.1 (2H, d, J=6 Hz), 2.22 (2H, m), 2.4 (2H, m), 3.0 (1H, br s), 3.3 (1H, m), 4.63 (2H, br s), 7.3 (1H, s), 8.45 (1H, s).

iv) 8-(5-bromothieno[2,3-d]pyrimidin-4-yl)-N-cyclobutyl-N-methyl-8-azabicyclo[3.2.1]octan-3-amine 8-(5-Bromothieno[2,3-d]pyrimidin-4-yl)-N-cyclobutyl-8-azabicyclo[3.2.1]octan-3-amine (200 mg, 0.5 mmol) in formalin solution (5 mL) and formic acid (5 mL) was heated to 80° C. for 1 h. The reaction was then concentrated in vacuum to a gum, diluted with ethyl acetate (50 mL) and 10% potassium carbonate solution (10 mL) and shaken. The ethyl acetate layer was then separated, dried over sodium sulphate and concentrated in vacuum to give a colourless gum. The gum was chromatographed on a 25 g silica column in a gradient of 2-15% methanol in dichloromethane. The slower running peak was collected to give 8-(5-bromothieno[2,3-d]pyrimidin-4-yl)-N-cyclobutyl-N-methyl-8-azabicyclo[3.2.1]octan-3-amine (165 mg, 0.405 mmol, 81%). $^1$H NMR (CDCl$_3$) δ: 1.35 (2H, t, J=12 Hz), 1.5-1.7 (4H, m), 1.8-2.0 (6H, m), 2.1 (3H, s), 2.5 (2H, br m), 3.1 (2H, br m), 4.7 (2H, br m), 7.3 (1H, s), 8.4 (1H, s).

v) N-cyclobutyl-8-[5-(2-methoxy-3-pyridyl)thieno[2,3-d]pyrimidin-4-yl]-N-methyl-8-azabicyclo[3.2.1]octan-3-amine Example 351

8-(5-Bromothieno[2,3-d]pyrimidin-4-yl)-N-cyclobutyl-N-methyl-8-azabicyclo[3.2.1]octan-3-amine (82.5 mg, 0.20 mmol) in dimethoxyethane (4 mL) and 2 M sodium carbonate solution (1 mL) was treated with (2-methoxy-3-pyridyl)boronic acid (134 mg, 0.75 mmol) and palladium (II) acetate (12 mg, 0.053 mmol), triphenylphosphine (12 mg) and the reaction was stirred in a microwave at 85° C. over 1 h. The reaction was then diluted with ethyl acetate (25 mL) and saturated aqueous sodium bicarbonate solution (25 mL) and shaken. The ethyl acetate layer was then separated, dried over sodium sulphate and concentrated in vacuum to give a gum. The gum was dissolved in DMSO/water 1:1 (2.5 mL) and purified by reverse phase HPLC. The main peak was collected and concentrated in vacuum to give N-cyclobutyl-8-[5-(2-methoxy-3-pyridyl)thieno[2,3-d]pyrimidin-4-yl]-N-methyl-8-azabicyclo[3.2.1]octan-3-amine as a gum (32 mg, 0.073 mmol, 36%). LCMS RT=4.76 min. M+1=436. $^1$H NMR (CDCl$_3$) δ: 1.1 (2H, t, J=12 Hz), 1.3-1.9 (1H, m), 1.9 (3H, s), 2.2 (1H, br m), 2.9 (1H, br m), 3.9 (3H, s), 4.3 (2H, br s), 7.0 (1H, q, J=6 Hz, J'=4 Hz), 7.25 (1H, s), 7.55 (1H, d, J=6 Hz), 8.2 (1H, d, J=4 Hz), 8.5 (1H, s).

2) Synthesis of N—[[8-[5-(2-methoxy-3-pyridyl)thieno[2,3-d]pyrimidin-4-yl]-8-azabicyclo[3.2.1]octan-3-yl]methyl]cyclobutanamine Example 427 i) 3-[8-(5-bromothieno[2,3-d]pyrimidin-4-yl)-8-azabicyclo[3.2.1]octan-3-yl]methanol 5-Bromo-4-chloro-thieno[2,3-d]pyrimidine (1.0 g, 4.0 mmol) in acetonitrile (25 mL) was treated with 8-azabicyclo[3.2.1]octan-3-ylmethanol (705 mg, 16 mmol) and potassium carbonate (2.208 g, 16 mmol) at reflux for 4 h. The reaction was then concentrated in vacuum to a gum and partitioned between ethyl acetate (100 mL) and water (50 mL). The ethyl acetate was separated, dried over sodium sulphate and concentrated in vacuum to give a yellow gum. The gum was columned on silica in a gradient of 2-8% methanol in dichloromethane on a 100 g column. The main first fraction was collected and concentrated in vacuum to a gum. The gum was triturated with diethyl ether (20 mL) and crystallized on standing for a few minutes. The diethyl ether was decanted off and the crystals dried in vacuum to yield 3 [8-(5-bromothieno[2,3-d]pyrimidin-4-yl)-8-azabicyclo[3.2.1]octan-3-yl]methanol (1.297 g, 3.66 mmol, 91%). $^1$H NMR (CDCl$_3$) δ: 1.42 (2H, dd, J=12 Hz, J'=4 Hz), 1.67 (2H, d, J=4 Hz), 1.82 (1H, br s), 1.98 (3H, br m), 2.48 (2H, quintet, J=4 Hz), 3.64 (2H, d, J=4 Hz), 4.7 (2H, br s), 7.32 (1H, s), 8.45 (1H, s).

ii) 3-[8-[5-(2-methoxy-3-pyridyl)thieno[2,3-d]pyrimidin-4-yl]-8-azabicyclo[3.2.1]octan-3-yl]methanol 3 [8-(5-Bromothieno[2,3-d]pyrimidin-4-yl)-8-azabicyclo[3.2.1]octan-3-yl]methanol (350 mg, 1.0 mmol) in 1,2-dimethoxyethane (12 mL) was treated with 2 M aqueous sodium carbonate (3 mL), (2-methoxy-3-pyridyl)boronic acid (612 mg, 4.0 mmol), palladium acetate (40 mg) and triphenylphosphine (40 mg) and heated in a microwave at 85° C. for 1 h. The reaction was then poured into ethyl acetate (100 mL) and water (50 mL) and shaken. The ethyl acetate layer was separated, dried over sodium sulphate and concentrated in vacuum to give a gum. The gum was purified by preparative HPLC method 6a). The main peak was collected to give 3[8-[5-(2-methoxy-3-pyridyl)thieno[2,3-d]pyrimidin-4-yl]-8-azabicyclo[3.2.1]octan-3-yl]methanol as a gum (352 mg, 0.93 mmol, 93%). $^1$H NMR (CDCl$_3$) δ: 1.18 (2H, d, J=6 Hz), 1.4 (2H, d, J=6 Hz), 1.56 (2H, m), 3.45 (2H, J=4 Hz), 3.9 (3H, s), 4.2 (2H, m), 7.0 (1H dd, J=4 Hz, J'=4 Hz), 7.27 (1H, s), 7.55 (1H, d, J=4 Hz), 8.15 (1H, d, J=4 Hz,), 8.5 (1H, s).

iii) 8-[5-(2-methoxy-3-pyridyl)thieno[2,3-d]pyrimidin-4-yl]-8-azabicyclo[3.2.1]octane-3-carbaldehyde To a stirred solution of [8-[5-(2-methoxy-3-pyridyl)thieno[2,3-d]pyrimidin-4-yl]-8-azabicyclo[3.2.1]octan-3-yl]methanol (0.20 g, 0.52 mmol) in dichloromethane (20 mL) was added in one portion Dess-Martin Periodiane (0.26 g, 0.62 mmol) at room temperature and the resulting suspension stirred at room temperature for 48 h. The reaction was diluted with dichloromethane (20 mL), filtered and the resulting filtrate washed with saturated sodium hydrogen carbonate solution (10 mL). The organic phase was washed with brine (10 mL), separated, dried (MgSO$_4$), filtered and concentrated under reduced pressure to give a pale yellow gum (0.22 g). The residue was subjected to flash column chromatography (silica gel, 10 g SNAP, gradient elution 20% ethyl acetate/petroleum ether to 50% ethyl acetate/petroleum ether) to give the desired product as a colourless gum (0.086 g, 0.23 mmol, 43%).

LCMS: $R_t$=5.95, 381 (M+1).

iv) N—[[8-[5-(2-methoxy-3-pyridyl)thieno[2,3-d]pyrimidin-4-yl]-8-azabicyclo[3.2.1]octan-3-yl]methyl]cyclobutanamine To a stirred solution of 8-[5-(2-methoxy-3-pyridyl)thieno[2,3-d]pyrimidin-4-yl]-8-azabicyclo[3.2.1]octane-3-carbaldehyde (0.086 g, 0.23 mmol) in anhydrous tetrahydrofuran (4.0 mL) and under an atmosphere of nitrogen was added neat cyclobutylamine (0.046 mL, 0.53 mmol) followed by a solution of dibutyltin dichloride (0.008 g, 0.03 mmol) in anhydrous tetrahydrofuran (0.5 mL) and neat phenylsilane (0.04 mL, 0.27 mmol). The reaction mixture was heated at 105° C. for 1 h using a microwave reactor. The reaction mixture was partitioned between water (10 mL) and ethyl acetate (10 mL). The aqueous phase was separated and extracted with ethyl acetate (3×10 mL). The combined organic phases were washed with brine (10 mL), separated, dried (MgSO$_4$), filtered and concentrated under reduced pressure to give a very pale yellow gum (0.25 g). The impure product was purified by preparative HPLC(P Method 1) to give the formate salt of the desired product as a light brown gum (52 mg). The material was dissolved in 10% MeOH/DCM and loaded onto a SCX cartridge, washed with dichloromethane (5 mL), methanol (5 mL) and 2 M NH$_3$ in methanol to obtain the free base of the desired product as a colourless gum (47.8 mg, 0.11 mmol, 49%). LCMS: $R_t$=3.61, 436 (M+1).

Other compounds prepared by Method S using the appropriate starting materials are listed in TABLE 1.

Method T

1) Synthesis of 5-phenyl-4-[4-(2-pyrrolidin-1-ylethoxymethyl)-1-piperidyl]furo[2,3-d]pyrimidine Example 308 i) 2-methylsulfonyl-5-phenyl-4-[4-(2-pyrrolidin-1-ylethoxymethyl)-1-piperidyl]furo[2,3-d]pyrimidine 2,4-Bis(methylsulphonyl)-5-phenyl-furo[2,3-d]-pyrimidine (400 mg, 1.14 mmol) in acetonitrile (10.0 mL) was treated with 4-(2-pyrrolidine-1-ylethyloxymethyl)piperidine (360 mg, 1.7 mmol) and potassium carbonate (219 mg, 1.71 mmol) and heated in a microwave at 120° C. for 30 min. The reaction was concentrated in vacuum to a gum and the residue was partitioned between ethyl acetate and water. The ethyl acetate layer was separated, dried over sodium sulphate and concentrated in vacuum to a gum. The gum was purified by preparative HPLC (basic method 6) to yield methylsulfonyl-5-phenyl-4-[4-(2-pyrrolidin-1-ylethoxymethyl)-1-piperidyl]furo[2,3-d]pyrimidine (96 mg, 0.198 mmol, 17%). $^1$H NMR (CDCl$_3$) δ: 1.07 (2H, m), 1.52 (2H, br d, J=8 Hz), 1.75 (5H, br s), 2.5 (4H, b s), 2.6 (2H, t, J=5 Hz), 2.8 (2H, t, J=8 Hz), 3.18 (2H, d, J=4 Hz), 3.35 (3H, s), 3.5 (2H, t, J=4 Hz), 4.05 (2H, d, J=8 Hz), 7.4 (5H, m), 7.6 (1H, s).

ii) 5-phenyl-4-[4-(2-pyrrolidin-1-ylethoxymethyl)-1-piperidyl]furo[2,3-d]pyrimidine Example 308

2-Methylsulphonyl-5-phenyl-4 [4-2-pyrrolidin-1-ylethoxymethyl-1-piperidyl]furo[2,3-d]-pyrimidine pyrimidine (75 mg, 0.15 mmol) in ethanol (5.0 mL) was treated with sodium borohydride (15 mg, 0.38 mmol) at 20° C. with continuous stirring for 30 min. A further 30 mg of sodium borohydride was added and the reaction was stirred at 20° C. for a further 1 h. A further 60 mg of sodium borohydride was added and the reaction was stirred at 20° C. for a further 1 hr then concentrated in vacuum to a gum and the residue partitioned between dichloromethane and water. The dichloromethane layer was separated, dried over sodium sulphate and concentrated in vacuum to a gum. The gum was purified by preparative HPLC to give 5-phenyl-4-[4-(2-pyrrolidin-1-ylethoxymethyl)-1-piperidyl]furo[2,3-d]pyrimidine (53 mg, 0.13 mmol, 84%). $^1$H NMR (CDCl$_3$) δ: 1.02 (2H, m), 1.5 (2H, m), 1.75 (6H, m), 2.45-2.8 (9H, m), 3.2 (2H, d, J=8 Hz), 3.5 (2H, t, J=8 Hz), 3.95 (2H, d, J=12 Hz), 7.35-7.45 (5H, m), 7.52 (1H, s), 8.45 (1H, s). LCMS RT=5.14 min. M+1=407.

Other compounds prepared by Method T using the appropriate starting materials are listed in TABLE 1.

Method U

1) Synthesis of 2-(2-azabicyclo[2.2.1]heptan-5-yloxy)-4-[(1S,5R)-3-(methoxymethyl)-8-azabicyclo[3.2.1]octan-8-yl]-N,N-dimethyl-5-phenyl-thieno[2,3-d]pyrimidine-6-carboxamide Example 366 i) methyl 2,4-dichloro-5-phenyl-thieno[2,3-d]pyrimidine-6-carboxylate

A solution of diisopropylamine (0.755 mL, 5.33 mmol) in dry tetrahydrofuran (10 mL) was cooled with an acetone/cardice bath to −55° C. under a nitrogen atmosphere. Butyllithium in hexanes (2.0 mL, 4.98 mmol, 2.5 M) was added and the temperature was allowed to rise to 0° C. for 10 min. The mixture was cooled to −55° C. and a solution of 2,4-dichloro-5-phenyl-thieno[2,3-d]pyrimidine (1.00 g, 3.56 mmol) in dry tetrahydrofuran (10 mL) was added. The mixture was stirred for 1 hr, maintaining the temperature at −55° C. Methyl chloroformate (0.561 mL, 7.11 mmol) was added and the mixture was allowed to rise to room temperature. It was stirred for 4 hr. Water (20 mL) was added to quench the reaction. The layers were separated and the aqueous was extracted with ethyl acetate (2×20 mL). The combined organic layers were dried (magnesium sulfate), filtered and evaporated to give a brown solid. (1.63 g). This was purified by silica chromatography (50 g cartridge; eluent petroleum ether 40-60/ethyl acetate 0 to 10%; collection by UV trigger). Fractions corresponding to the main peak were combined and evaporated to give the target compound as a yellow solid (1.24 g). m/z [M+H]$^+$338.9/340.9. Retention time 4.89 min (LCMS method+ve 6 min).

ii) Methyl-2-chloro-4-[3-(methoxymethyl)-8-azabicyclo[3.2.1]octan-8-yl]-5-phenyl-thieno[2,3-d]pyrimidine-6-carboxylate 3-(Methoxymethyl)-8-azabicyclo[3.2.1]octane (0.106 g, 0.683 mmol) was dissolved in ethanol (2 mL) and dichloromethane (2 mL). Triethylamine (0.166 mL, 1.18 mmol) and methyl 2,4-dichloro-5-phenyl-thieno[2,3-d]pyrimidine-6-carboxylate (0.200 g, 0.590 mmol) were added and the mixture was stirred at room temperature for 5 hr. It was diluted with dichloromethane (2 mL) and water (2 mL). The layers were separated and the aqueous was extracted with dichloromethane (2×2 mL). The combined organic layers were evaporated to give a yellow oil (281 mg). This was purified by silica chromatography (10 g cartridge; eluent petroleum ether 40-60/ethyl acetate 0 to 20%; all output collected). Fractions corresponding to the main peak were combined and evaporated to give the target compound as a yellow solid (0.177 g). m/z [M+H]$^+$458.0/460.0. Retention time 5.30 min (LCMS method+ve 6 min).

iii) 2-(2-azabicyclo[2.2.1]heptan-5-yloxy)-4-[3-(methoxymethyl)-8-azabicyclo[3.2.1]octan-8-yl]-N,N-dimethyl-5-phenyl-thieno[2,3-d]pyrimidine-6-carboxamide Example 366

Sodium hydride (62 mg, 1.54 mmol, 60% w/w in mineral oil) was added to a stirred solution of tert-butyl 5-hydroxy-2-azabicyclo[2.2.1]heptane-2-carboxylate (165 mg, 0.773 mmol) in tetrahydrofuran (2 mL) under a nitrogen atmosphere. The mixture was stirred for 3 min and then a solution of methyl 2-chloro-4-[3-(methoxymethyl)-8-azabicyclo[3.2.1]octan-8-yl]-5-phenyl-thieno[2,3-d]pyrimidine-6-carboxylate (177 mg, 0.387 mmol) in tetrahydrofuran (4 mL) was added. The mixture was heated to reflux (70° C.) for 1.5 hr and then cooled to room temperature. Methanol (5 mL) was added to quench the reaction. Dichloromethane (10 mL) and water (10 mL) were added. The layers were separated and the aqueous was extracted with dichloromethane (2×10 mL). The combined organic layers were washed with brine (1×10 mL)—intractable emulsion formed. The mixture was concentrated under vacuum to remove the organic solvents. Ethyl acetate (20 mL) and water (10 mL) were added. The layers were separated and the aqueous was extracted with ethyl acetate (2×20 mL). The combined organic layers were dried (magnesium sulfate), filtered and evaporated to give a yellow solid. Mass: 0.358 g. This was dissolved in methanol and applied to a Biotage KP—NH$_2$ cartridge (10 g, equilibrated with methanol). The cartridge was treated with methanol (2 column volumes) then 0.5 M formic acid in methanol (2 column volumes). The acid solution was evaporated to give a yellow solid. This was purified by silica chromatography (10 g cartridge; eluent dichloromethane/methanol 0 to 10%; all output collected). Fractions corresponding to the main peak (broad) were combined and evaporated to give a yellow solid. Mass: 170 mg. Analysed by LCMS: mixture containing 2-[(2-tert-butoxycarbonyl-2-azabicyclo[2.2.1]heptan-5-yl)oxy]-4-[(3-(methoxymethyl)-8-azabicyclo[3.2.1]octan-8-yl]-5-phenyl-thieno[2,3-d]pyrimidine-6-carboxylic acid. m/z [M+H]$^+$ 621.1. Retention time 5.10 min (LCMS method+ve 6 min).

Triethylamine (0.116 mL, 0.8215 mmol) and O-(7-azabenzotriazol-1-yl)-N,N,N',N'-tetramethyluronium hexafluorophosphate (0.215 g, 0.5477 mmol) were added to a suspension of impure 2-[(2-tert-butoxycarbonyl-2-azabicyclo[2.2.1]heptan-5-yl)oxy]-4-[3-(methoxymethyl)-8-azabicyclo[3.2.1]octan-8-yl]-5-phenyl-thieno[2,3-d]pyrimidine-6-carboxylic acid (170 mg) in acetonitrile (4 mL). Dimethylamine in tetrahydrofuran (0.7 mL, 2 M) was added and the mixture was stirred overnight at room temperature. The solvent was evaporated and the residue was dissolved in ethyl acetate (4 mL) and saturated aqueous ammonium chloride solution (4 mL). The layers were separated and the aqueous was extracted with ethyl acetate (2×2 mL). The combined organic layers were dried (magnesium sulfate), filtered and evaporated to give a brown solid (239 mg). This was purified by silica chromatography (10 g cartridge; eluent petroleum ether 40-60/ethyl acetate 20 to 70%; collection by UV trigger). Several peaks were observed, all containing tert-butyl 5-[6-(dimethylcarbamoyl)-4-[3-(methoxymethyl)-8-azabicyclo[3.2.1]octan-8-yl]-5-phenyl-thieno[2,3-d]pyrimidin-2-yl]oxy-2-azabicyclo[2.2.1]heptane-2-carboxylate by LCMS. All collected fractions were combined to give a mixture containing tert-butyl 5-[6-(dimethylcarbamoyl)-4-[3-(methoxymethyl)-8-azabicyclo[3.2.1]octan-8-yl]-5-phenyl-thieno[2,3-d]pyrimidin-2-yl]oxy-2-azabicyclo[2.2.1]heptane-2-carboxylate as a yellow solid (200 mg).

Dichloromethane (2 mL) and trifluoroacetic acid (2 mL) were added to a mixture containing tert-butyl 5-[6-(dimethylcarbamoyl)-4-[3-(methoxymethyl)-8-azabicyclo[3.2.1]octan-8-yl]-5-phenyl-thieno[2,3-d]pyrimidin-2-yl]oxy-2-azabicyclo[2.2.1]heptane-2-carboxylate (200 mg) and the mixture was stirred for 2 hr. The solvent was evaporated. The residue was dissolved in methanol and applied to an SCX cartridge (10 g, equilibrated with methanol). The cartridge was washed with methanol (2 column volumes) and 0.5 M ammonia in methanol (2 column volumes). The ammonia solution was evaporated to give a yellow oil. Mass: 136 mg. This was purified by LCUV (acidic method 1). The peak corresponding to the target compound was identified by LCMS and the corresponding fractions were combined and evaporated. The residue was dissolved in methanol and applied to an MP-TsOH cartridge (1 g, equilibrated with methanol). The cartridge was washed with methanol (2 column volumes) then 0.5 M ammonia in methanol (2 column volumes). The ammonia solution was evaporated to give the target compound (22 mg) as a yellow oil. m/z [M+H]$^+$548.2. Retention time 3.07 min (LCMS method+ve 6 min).

Other compounds prepared by Method U using the appropriate starting materials are listed in TABLE 1.

Method V

1) Synthesis of 1-[[4-[4-[[methyl-(1-methylpyrrolidin-3-yl)amino]methyl]-piperidyl]-5-phenyl-thieno[2,3-d]pyrimidin-2-yl]methyl]pyrrolidin-2-one Example 244 i) 4-chloro-2-(chloromethyl)-5-phenyl-thieno[2,3-d]pyrimidine

A suspension of 2-(chloromethyl)-5-phenyl-3H-thieno[2,3-d]pyrimidin-4-one (1.50 g, ex Enamine) in phosphorus oxychloride (23 mL) was heated to reflux (105° C.) overnight. The reaction was cooled and the solvent was evaporated. Toluene (30 mL) was added and the mixture was evaporated again. The residue was dissolved in dichloromethane (100 mL). It was washed with water (1×100 mL) and saturated aqueous sodium bicarbonate solution (1×100 mL), dried (sodium sulfate), filtered and evaporated to give the target compound as a yellow solid (1.45 g). m/z [M+H]$^+$ 294.8/296.8. Retention time 4.99 min (LCMS method+ve 6 min). It was used in the next step without further purification.

ii) [1-[2-(chloromethyl)-5-phenyl-thieno[2,3-d]pyrimidin-4-yl]-4-piperidyl]methanol 4-Piperidinemethanol (0.85 g) was added to a suspension of 4-chloro-2-(chloromethyl)-5-phenyl-thieno[2,3-d]pyrimidine (1.45 g) in ethanol (70 mL). Triethylamine (1.4 mL) was added and the mixture was stirred at room temperature for 24 hr. The solvent was evaporated and the residue was dissolved in water (100 mL) and ethyl acetate (100 mL). The layers were separated and the aqueous was extracted with ethyl acetate (2×100 mL). The combined organic layers were washed with brine (1×100 mL), dried (sodium sulfate), filtered and evaporated to give an off-white foam (1.76 g). This was purified by silica chromatography (50 g cartridge; eluent petroleum ether 40-60/ethyl acetate 0 to 50%; collection by UV trigger). Fractions corresponding to the main peak were combined and evaporated to give the target compound as a white foam (1.10 g). m/z [M+H]+373.9/375.9. Retention time 4.67 min (LCMS method+ve 6 min).

iii) 1-[[4-[4-(hydroxymethyl)-1-piperidyl]-5-phenyl-thieno[2,3-d]pyrimidin-2-yl]methyl]pyrrolidin-2-one Sodium hydride (25 mg, 60% w/w in mineral oil) was added to a solution of 2-pyrrolidinone in dry N,N-dimethyl-formamide (2 mL) under a nitrogen atmosphere. The mixture was stirred for 10 min then [1-[2-(chloromethyl)-5-phenyl-thieno[2,3-d]pyrimidin-4-yl]-4-piperidyl]methanol (100 mg) was added. The mixture was stirred for 2 hr at room temperature. The solvent was evaporated and the residue was dissolved in ethyl acetate (10 mL) and water (10 mL). The layers were separated and the aqueous was extracted with ethyl acetate (2×10 mL). The combined organic layers were washed with brine (1×10 mL), dried (sodium sulfate), filtered and evaporated to give the target compound (96 mg) as a yellow solid. m/z [M+H]+ 424.0. Retention time 3.95 min (LCMS method+ve 6 min). It was used in the next reaction without purification.

iv) 1-[[4-[4-(bromomethyl)-1-piperidyl]-5-phenyl-thieno[2,3-d]pyrimidin-2-yl]methyl]pyrrolidin-2-one Tetrabromomethane (120 mg) was added to a solution of 1-[[4-[4-(hydroxymethyl)-1-piperidyl]-5-phenyl-thieno[2,3-d]pyrimidin-2-yl]methyl]pyrrolidin-2-one (102 mg) in dichloromethane (10 mL). Polystyrene-supported triph-enylphosphine (0.35 g, 2.04 mmol g-1) was added and the mixture was stirred overnight at room temperature. The solid material was filtered off and the solvent was evaporated to give the target compound as a yellow solid (160 mg). m/z [M+H]+ 484.9/486.9. Retention time 4.97 min (LCMS method+ve 6 min).

It was used in the next reaction without purification.

v) 1-[[4-[4-[[methyl-(1-methylpyrrolidin-3-yl)amino]methyl]-1-piperidyl]-5-phenyl-thieno[2,3-d]pyrimidin-2-yl]methyl]pyrrolidin-2-one Example 244

A solution of 1-[[4-[4-(bromomethyl)-1-piperidyl]-5-phenyl-thieno[2,3-d]pyrimidin-2-yl]methyl]pyrrolidin-2-one (160 mg) in N,N'-dimethylaminopyrrolidine (0.5 mL) was heated to 150° C. for 30 min in a microwave (twice). An unsuccessful attempt was made to dissolve the resulting dark brown solid in ethyl acetate and water. The solvent was evaporated and the residue was dissolved in dimethyl sulfoxide and methanol (1:1), and then purified by LCUV (basic method F). Fractions containing the target compound (by LCMS) were combined and evaporated. The resulting brown oil was purified again by LCUV (basic method A) to give the target compound (12 mg) as a brown glass. m/z [M+H]+ 519.0. Retention time 2.88 min (LCMS method+ve 6 min).

Other compounds prepared by Method V using the appropriate starting materials are listed in TABLE 1.

Method W

1) Synthesis of 2-[cyclobutyl-[[1-(5-phenylthieno[2,3-d]pyrimidin-4-yl)-4-piperidyl]methyl]amino]-N-methyl-acetamide Example 252 i) Methyl-2-[cyclobutyl-[[1-(5-phenylthieno[2,3-d]pyrimidin-4-yl)-4-piperidyl]methyl]amino]acetate Methyl bromoacetate (15 µL, 0.158 mmol) was added dropwise to a stirred suspension of N—[[1-(5-phenylthieno[2,3-d]pyrimidin-4-yl)-4-piperidyl]methyl]cyclobutanamine (50 mg, 0.132 mmol) and cesium carbonate (51 mg, 0.158 mmol) in dry DMF (4 mL) at room temperature. The reaction was allowed to stir for 2 h, then water and ethyl acetate were added and the organic layer separated. The aqueous layer was further extracted with ethyl acetate (×3). The organic layers were combined, washed with water, dried by passage through a hydrophobic frit and concentrated in vacuo to give methyl 2-[cyclobutyl-[[1-(5-phenylthieno[2,3-d]pyrimidin-4-yl)-4-piperidyl]methyl]amino]acetate as a colourless oil (37 mg). LCMS RT=3.20. M+1=451.

ii) 2-[cyclobutyl-[[1-(5-phenylthieno[2,3-d]pyrimidin-4-yl)-4-piperidyl]methyl]amino]-N-methyl-acetamide Example 252

Trimethylaluminium solution (2 M in hexanes, 123 µL, 0.246 mmol) was added to a stirred solution of methylamine (2 M in THF, 123 µL, 0.246 mmol) in DCM at 0° C. under nitrogen.

The reaction was stirred for min and then allowed to warm to room temperature. After stirring for 30 minutes, methyl-2-[cyclobutyl-[[1-(5-phenylthieno[2,3-d]pyrimidin-4-yl)-4-piperidyl]methyl]amino]acetate (37 mg, 0.082 mmol) in DCM (0.5 mL) was added dropwise and the reaction stirred for 2 h. A further 123 µL of trimethylaluminium and a further 123 µL of methylamine were added and the reaction stirred overnight at room temperature. The solvents were then evaporated and the residue purified by column chromatography eluting 0 to 5% v/v of 7 M ammonia/methanol in DCM to give 2-[cyclobutyl-[[1-(5-phenylthieno[2,3-d]pyrimidin-4-yl)-4-piperidyl]methyl]amino]-N-methyl-acetamide as a colourless solid (6 mg). LCMS RT=3.01. M+1=450.

Other compounds prepared by Method W using the appropriate starting materials are listed in TABLE 1.

Method X

1) Synthesis of [5-phenyl-4-[4-(2-pyrrolidin-1-ylethoxymethyl)-1-piperidyl]thieno[2,3-d]pyrimidin-6-yl]methanol Example 281

To a stirred solution of methyl 5-phenyl-4-[4-(2-pyrrolidin-1-ylethoxymethyl)-1-piperidyl]thieno[2,3-d]pyrimidine-6-carboxylate (0.170 g, 0.354 mmol) in dry THF (20 mL) under an atmosphere of nitrogen at 0° C. was added DIBAL-H 1 M solution in THF (1.42 mL, 1.42 mmol) dropwise via syringe. The reaction was stirred for 30 mins before being allowed to warm to room temperature. The reaction was quenched with saturated Rochelle's salt (10 mL) and extracted with ethyl acetate (3×10 mL). The combined organics were dried over sodium sulphate, filtered and concentrated in vacuo. The reaction was purified using preparatory chromatography using basic eluent to afford the named product (0.0043 g, 3%). LCMS: $R_t$=2.76, 453 (M+1).

Other compounds prepared by Method X using the appropriate starting materials are listed in TABLE 1.

Method Y

1) Synthesis of 5-(4-fluorophenyl)-4-[4-(methoxymethyl)-1-piperidyl]-2-(2-pyrrolidin-1-ylethyl)thieno[2,3-d]pyrimidine Example 184 i) ethyl 2-[4-chloro-5-(4-fluorophenyl)thieno[2,3-d]pyrimidin-2-yl]acetate

Ethyl 2-[5-(4-fluorophenyl)-4-oxo-4-H-thieno[2,3-d]pyrimidin-2-yl]acetate (10 g, 0.0301 mol) in N,N-diethylaniline (50 mL) and phosphorous oxychloride (150 mL) was heated to 115° C. for 4.5 hrs. The mixture was concentrated in vacuo and the residue poured into ice-water and allowed to stand overnight. The aqueous solution was neutralized with sodium bicarbonate, filtered, then extracted with DCM. The reaction was repeated on a further 10 g of ethyl 2-[5-(4-fluorophenyl)-4-oxo-4-H-thieno[2,3-d]pyrimidin-2-yl]acetate and the DCM extract combined with that of the first batch. The solvent was removed in vacuo and the residue purified by silica column chromatography eluting first with petroleum ether/DCM 50:50 v/v, then petroleum ether/DCM 25:75 v/v, followed by DCM (100%). Further fractions were eluted from the column with 25% diethyl ether in DCM. Fractions were analysed by TLC, combined and concentrated to give ethyl 2-[4-chloro-5-(4-fluorophenyl)thieno[2,3-d]pyrimidin-2-yl]acetate as a brown solid (14 g). LCMS RT=4.83 min, M+1=351.

ii) 2-[4-chloro-5-(4-fluorophenyl)thieno[2,3-d]pyrimidin-2-yl]ethanol

Ethyl 2-[4-chloro-5-(4-fluorophenyl)thieno[2,3-d]pyrimidin-2-yl]acetate (9.98 g, 0.285 mol) was dissolved in dry THF (100 mL) under nitrogen. To this was added diisobutyl aluminium hydride (1 M in THF, 95 mL). The reaction was stirred at room temperature for 5.5 hrs before being quenched by careful addition to a saturated solution of Rochelle's salt. The mixture was stirred for 1 hr then allowed to stand overnight. The mixture was extracted with DCM (3×700 mL), the extracts were then combined, dried and concentrated in vacuo. The residue was purified by silica column chromatography eluting with DCM, then 3:1 v/v DCM/ethyl Acetate. Fractions were analysed by TLC, combined and concentrated to give 2-[4-chloro-5-(4-fluorophenyl)thieno[2,3-d]pyrimidin-2-yl]ethanol as a brown solid (4 g). LCMS RT=4.25 min, M+1=309.

iii) 2-[5-(4-fluorophenyl)-4-[4-(methoxymethyl)-1-piperidyl]thieno[2,3-d]pyrimidin-2-yl]ethanol 2-[4-Chloro-5-(4-fluorophenyl)thieno[2,3-d]pyrimidin-2-yl]ethanol (150 mg, 0.0005 mol), triethylamine (0.214 mL, 0.00154 mol) and 4-(methoxymethyl)piperidine hydrochloride (0.091 g, 0.00055 mol) were dissolved in ethanol (5 mL) and warmed to 55° C. for 2 hrs. The reaction was then poured over ice and extracted with DCM. The organics were dried by passage through a PTFE frit and concentrated in vacuo to give 2-[5-(4-fluorophenyl)-4-[4-(methoxymethyl)-1-piperidyl]thieno[2,3-d]pyrimidin-2-yl]ethanol (180 mg). LCMS RT=4.33 min. M+1=402.

iv) 5-(4-fluorophenyl)-4-[4-(methoxymethyl)-1-piperidyl]-2-(2-pyrrolidin-1-ylethyl)thieno[2,3-d]pyrimidine Example 184

2-[5-(4-Fluorophenyl)-4-[4-(methoxymethyl)-1-piperidyl]thieno[2,3-d]pyrimidin-2-yl]ethanol (20 mg, 0.05 mmol) was dissolved in THF (1 mL) to which was added triethylamine (0.021 mL, 0.15 mmol) and methanesulfonyl chloride (0.1 mmol). The reaction was stirred at 50° C. for 2 hrs then pyrrolidine (18 mg, 0.25 mmol) was added and the reaction stirred at 50° C. overnight. The reaction was partitioned between water and DCM. The organics wre concentrated in vacuo and the residue purified by preparative TLC, eluting with 7.5% 7M ammonia in methanol/DCM v/v to give 5-(4-fluorophenyl)-4-[4-(methoxymethyl)-1-piperidyl]-2-(2-pyrrolidin-1-ylethyl)thieno[2,3-d]pyrimidine (10 mg). LCMS RT=3.28 min. M+1=455.

2) Synthesis of 2-[4-[4-(methoxymethyl)-1-piperidyl]-5-phenyl-thieno[2,3-d]pyrimidin-2-yl]-1-pyrrolidin-1-yl-ethanone Example 183 i) 2-[4-[4-(methoxymethyl)-1-piperidyl]-5-phenyl-thieno[2,3-d]pyrimidin-2-yl]acetic acid Ethyl 2-(4-chloro-5-phenyl-thieno[2,3-d]pyrimidin-2-yl)acetate (100 mg, 0.285 mmol), 4-(methoxymethyl)piperidine hydrochloride (52 mg, 0.314 mmol) and triethylamine (0.12 mL, 0.85 mmol) were dissolved in ethanol (4 mL) and heated to 65° C. for 6 hrs. The reaction was then heated to 150° C. in a microwave for 10 min. The reaction was poured over ice and extracted with DCM. The extracts were combined and concentrated in vacuo. The residue was dissolved in non-dry THF (2 mL) and lithium hydroxide monohydrate (48 mg) was added. The reaction was stirred at room temperature overnight then another portion of lithium hydroxide monohydrate was added (10 mg) and the reaction stirred for a further 2 hrs. The reaction mixture was purified on an Isolute NH$_2$ SPE column (eluting ammonia in methanol) to give 2-[4-[4-(methoxymethyl)-1-piperidyl]-5-phenyl-thieno[2,3-d]pyrimidin-2-yl]acetic acid (107 mg).

ii) Synthesis of 2-[4-[4-(methoxymethyl)-1-piperidyl]-5-phenyl-thieno[2,3-d]pyrimidin-2-yl]-1-pyrrolidin-1-yl-ethanone Example 183

2-[4-[4-(Methoxymethyl)-1-piperidyl]-5-phenyl-thieno[2,3-d]pyrimidin-2-yl]acetic acid (24 mg, 0.06 mmol), pyrrolidine (5 mg, 0.067 mmol), HATU (26 mg) and triethylamine (0.025 mL) were stirred in acetonitrile (2 mL) at 50° C. for 20 hrs. The reaction was partitioned between water and DCM. The organics were separated and concentrated in vacuo. The residue was purified by preparative TLC, eluting 10% methanol in DCM. The isolated band was repurified by preparative TLC, eluting ethyl acetate to give 2-[4-[4-(methoxymethyl)-1-piperidyl]-5-phenyl-thieno[2,3-d]pyrimidin-2-yl]-1-pyrrolidin-1-yl-ethanone (3 mg). LCMS RT=4.61 min. M+1=451.

Other compounds prepared by Method Y using the appropriate starting materials are listed in TABLE 1.

Method Z

1) Synthesis of 1-[4-[3-(cyclobutylamino)-8-azabicyclo[3.2.1]octan-8-yl]-5-phenyl-thieno[2,3-d]pyrimidin-2-yl]pyrrolidine-3-carboxamide Example 337 i) 8-(2-chloro-5-phenyl-thieno[2,3-d]pyrimidin-4-yl)-8-azabicyclo[3.2.1]octan-3-ol Tetrahydrofuran (2 mL) and triethylamine (0.10 mL, 0.71 mmol) were added to 2,4-dichloro-5-phenyl-thieno[2,3-d]pyrimidine (100 mg, 0.356 mmol) and 8-azabicyclo[3.2.1]

octan-3-ol (68 mg, 0.53 mmol). The mixture was stirred overnight at room temperature. Ethyl acetate (2 mL) and water (2 mL) were added and the layers were separated. The aqueous was extracted with ethyl acetate (2×2 mL). The combined organic layers were dried (magnesium sulfate), filtered and evaporated to give a brown solid (127 mg). This was purified by silica chromatography (10 g cartridge; eluent petroleum ether 40-60/ethyl acetate 0 to 30%; all output collected). One set of fractions was identified and the relevant fractions were combined and evaporated to give a brown solid (83 mg). This was purified again by LCUV (acidic method 1) to give the target compound as a white solid (44 mg). m/z [M+H]$^+$372.0/373.9. Retention time 4.74 min (LCMS method+ve 6 min).

ii) 1-[4-[3-hydroxy-8-azabicyclo[3.2.1]octan-8-yl]-5-phenyl-thieno[2,3-d]pyrimidin-2-yl]pyrrolidine-3-carboxamide 8-(2-Chloro-5-phenyl-thieno[2,3-d]pyrimidin-4-yl)-8-azabicyclo[3.2.1]octan-3-ol (44 mg, 0.12 mmol) was suspended in acetonitrile (3 mL). Pyrrolidine-3-carboxamide hydrochloride (36 mg, 0.24 mmol) and triethylamine (0.067 mL, 0.47 mmol) were added and the mixture was heated to 150° C. for 30 min in a microwave (twice). Further batches of pyrrolidine-3-carboxamide hydrochloride (36 mg, 0.24 mmol) and triethylamine (0.067 mL, 0.47 mmol) were added and the mixtures were heated to 150° C. for 30 min in a microwave. The solvent was evaporated and the residue was purified by LCUV (acidic method 1) to give the target compound as a white solid (44 mg). m/z [M+H]$^+$450.1. Retention time 3.75 min (LCMS method+ve 6 min).

iii) 1-[4-[3-oxo-8-azabicyclo[3.2.1]octan-8-yl]-5-phenyl-thieno[2,3-d]pyrimidin-2-yl]pyrrolidine-3-carboxamide Dess-Martin Periodinane (50 mg, 0.12 mmol) was added to a suspension of 1-[4-[3-hydroxy-8-azabicyclo[3.2.1]octan-8-yl]-5-phenyl-thieno[2,3-d]pyrimidin-2-yl]pyrrolidine-3-carboxamide (40 mg, 0.089 mmol) in dichloromethane (4 mL). The mixture was stirred overnight at room temperature. Saturated aqueous sodium thiosulfate solution (2 mL) was added and the layers were separated. The aqueous was extracted with dichloromethane (2×2 mL). The combined organic layers were washed with saturated aqueous sodium bicarbonate solution (1×2 mL), filtered through a hydrophobic frit and evaporated to give the target compound as a white solid (46 mg). m/z [M+H]$^+$448.1. Retention time 3.59 min (LCMS method+ve 6 min).

iv) 1-[4-[3-(cyclobutylamino)-8-azabicyclo[3.2.1]octan-8-yl]-5-phenyl-thieno[2,3-d]pyrimidin-2-yl]pyrrolidine-3-carboxamide Example 337

Dibutyltin dichloride (5 mg, 0.016 mmol) was added to a solution of 1-[4-(3-oxo-8-azabicyclo[3.2.1]octan-8-yl)-5-phenyl-thieno[2,3-d]pyrimidin-2-yl]pyrrolidine-3-carboxamide (40 mg, 0.089 mmol) in tetrahydrofuran (2 mL). Cyclobutylamine (0.02 mL, 0.23 mmol) was added, followed by phenylsilane (0.03 mL, 0.24 mmol) and the mixture was heated to 100° C. for 2 hr in a microwave. The reaction was quenched with methanol then applied to an SCX cartridge (10 g, equilibrated with methanol). It was washed with methanol (2 column volumes) then eluted with 0.5 M ammonia in methanol (2 column volumes). The ammonia solution was evaporated to give an off-white solid (35 mg). This was purified by LCUV (acidic method 1). Fractions containing the target compound were combined and evaporated to give a white solid, which was dissolved in methanol and applied to an SCX cartridge (2 g, equilibrated with methanol). It was washed with methanol (2 column volumes) and eluted with 0.5 M ammonia in methanol (2 column volumes). The ammonia solution was evaporated to give the target compound as a white solid (16 mg). m/z [M+H]$^+$503.1. Retention time 2.99 min (LCMS method+ve 6 min).

Method AA

1) Synthesis of N-isopropyl-4-[3-[2-(methanesulfonamido)ethoxymethyl]-8-azabicyclo[3.2.1]octan-8-yl]-5-phenyl-thieno[2,3-d]pyrimidine-6-carboxamide i) 4-[3-(2-hydroxyethoxymethyl)-8-azabicyclo[3.2.1]octan-8-yl]-N-isopropyl-5-phenyl-thieno[2,3-d]pyrimidine-6-carboxamide 4-[3-(2-hydroxyethoxymethyl)-8-azabicyclo[3.2.1]octan-8-yl]-N-isopropyl-5-phenyl-thieno[2,3-d]pyrimidine-6-carboxamide (1.87 g, 3.89 mmol) was stirred in DMF (20 mL) at 0° C. Triethylamine (0.795 g, 1.10 mL, 7.78 mmol) was added followed by methanesulfonyl chloride (0.682 g, 0.461 mL, 5.84 mmol). The reaction mixture was allowed to warm to room temperature and stirred for 1 hour. The solvent was removed at reduced pressure. The resulting residue was taken up in DCM (100 mL), washed with water (2×100 mL), dried over $Na_2SO_4$ and concentrated at reduced pressure to afford 4-[3-(2-hydroxyethoxymethyl)-8-azabicyclo[3.2.1]octan-8-yl]-N-isopropyl-5-phenyl-thieno[2,3-d]pyrimidine-6-carboxamide (2.67 g).

LCMS: purity 97%, RT=4.27 min, M+1=559.20 ii) 4-[3-(2-aminoethoxymethyl)-8-azabicyclo[3.2.1]octan-8-yl]-N-isopropyl-5-phenyl-thieno[2,3-d]pyrimidine-6-carboxamide 2-[[8-[6-(isopropylcarbamoyl)-5-phenyl-thieno[2,3-d]pyrimidin-4-yl]-8-azabicyclo[3.2.1]octan-3-yl]methoxy]ethyl methanesulfonate (0.3 g, 0.5 mmol) was dissolved in NMP (2 mL). Sodium azide (0.2 g, 3 mmol) was added and the reaction heated to 150° C. in the microwave for 30 minutes. The reaction mixture was diluted with DCM (20 mL), washed with water (2×20 mL), dried over $Na_2SO_4$ and concentrated in vacuo. The resulting residue was dissolved in THF (5 mL). Triphenylphosphine (0.2 g, 0.8 mmol) was added and the reaction stirred overnight at room temperature. It was heated to reflux for 5 hours. The solvent was removed at reduced pressure. The resulting residue was taken up in DCM, washed with water, dried over $Na_2SO_4$ and concentrated at reduced pressure. The resulting residue was purified by flash chromatography, eluting with a gradient of DCM to 90/10/1 DCM/MeOH/NH$_4$OH to afford 4-[(1R,5S)-3-(2-aminoethoxymethyl)-8-azabicyclo[3.2.1]octan-8-yl]-N-isopropyl-5-phenyl-thieno[2,3-d]pyrimidine-6-carboxamide (100 mg).

LCMS: purity 100%, RT=3.45 min, M+1=480.20 iii) N-isopropyl-4-[3-[2-(methanesulfonamido)ethoxymethyl]-8-azabicyclo[3.2.1]octan-8-yl]-5-phenyl-thieno[2,3-d]pyrimidine-6-carboxamide 4-[3-(2-aminoethoxymethyl)-8-azabicyclo[3.2.1]octan-8-yl]-N-isopropyl-5-phenyl-thieno[2,3-d]pyrimidine-6-carboxamide (0.1 g, 0.2 mmol) and was stirred in DCM (10 mL) at 0° C. Triethylamine (0.04 g, 0.06 mL, 0.4 mmol) was added followed by methanesulfonyl chloride (0.04 g, 0.02 mL, 0.3 mmol). The reaction mixture was allowed to warm to room temperature and stirred for 1 hour. The solvent was removed at reduced pressure. The resulting residue was taken up in DCM, washed with water, dried over $Na_2SO_4$ and concentrated at reduced pressure. The resulting residue was purified by acidic prep HPLC (method 1). Desired fractions were combined and concentrated at reduced pressure. The residue was taken up in DCM, washed with sat. NaHCO$_3$ solution, the organic dried over Na₂SO₄ and concentrated at reduced pressure to afford N-isopropyl-4-[3-[2-(methanesulfonamido)ethoxymethyl]-8-azabicyclo[3.2.1]octan-8-yl]-5-phenyl-thieno[2,3-d]pyrimidine-6-carboxamide (41 mg).

LCMS: purity 100%, RT=4.10 min, M+1=558.20 Other compounds prepared by Method Z using the appropriate starting materials are listed in TABLE 1.

Biological Testing

Compound activity against the recombinant G-protein activated inward rectifier current encoded by the heterotetramer Kir3.1/3.4 was assessed using manual whole-cell patch technique. The heterotetramer forms the pore-forming channel that conducts the acetylcholine/adenosine-activated potassium current in the heart.

Kir3.1/3.4 Electrophysiology Method

For whole-cell patch-clamp studies, cells (Human Embryonic Kidney 293 stably transfected with rat Kir3.1/3.4) were seeded onto glass coverslips before recordings were made. Cells were seeded in sterile 30 mm Petri dishes at a density to enable isolated cells to be selected for patch clamp experiments. The dishes were stored in a humidified, gassed (5% $CO_2$) incubator at 37° C. until use.

Whole-cell patch-clamp recordings of membrane currents were made following gigaohm seal formation between the patch electrode and the cell using HEKA EPC-9/10 amplifiers controlled by Pulse Software (Ver8.5x/8.6x/8.7x, HEKA, Germany). Coverslips seeded with cells were placed in a recording chamber mounted on the stage of an inverted microscope. During the experiment, the cell of interest was continuously superfused with bather solution delivered via a cannula placed in close proximity to the cell to enable control of the extracellular solution environment. Only those cells with a current <-500 pA (current at -140 mV) were used for experiments. During experiments, series resistance was compensated by a minimum of 70%.

Electrophysiology voltage-step protocols and analysis of data were performed as follows. Data was sampled at 5 kHz, and filtered with a -3 dB bandwidth of 2.5 kHz. Cells were held at a voltage of -60 mV. Currents were evoked by a depolarising voltage step to +60 mV (100 ms) before a ramp-repolarisation (0.4 V·s$^{-1}$) to -140 mV (100 ms) before returning to -60 mV. The command waveform was repeatedly applied every 10 s throughout the experiment. Mean currents during 1-99% of the time at -140 mV were analysed using Pulsefit software (v8.x, HEKA, Germany). The voltage protocol was repeatedly applied to achieve a stable current baseline in bather before the test substance was superfused via the cannula in close proximity to the cell under investigation. The test substance was allowed to equilibrate during which time voltage protocol was repeatedly applied and recorded. On reaching steady-state inhibition, the cell was superfused with an identical bather solution containing zero external potassium chloride (replaced by equimolar NaCl). The identical current measurement was made in the absence of potassium to assess the passive leak at -140 mV. The leak current was subtracted from the control and steady-state drug current values. The percentage inhibition of the leak-subtracted current in the presence of test substance was calculated relative to the control leak-subtracted pre-drug value. Internal patch-pipette solution contained in mM: 110 KCl, 20 NaCl, 0.9 GTPγS, 5 Mg-ATP, 5 EGTA, 10 HEPES, pH7.2 corrected with KOH. The external superfusate composition in mM was: 150 (or 160) NaCl, 10 (or 0) KCl, 3 $CaCl_2$, 1 $MgCl$, 10 HEPES, pH 7.4 corrected with NaOH.

Kir3.1/3.4 Q-patch Method

For automated patch-clamp studies using the Sophion Q-patch, accumulative concentration-responses experiments were conducted to determine compound activity against the ion channel target. Voltage-clamp experiments were performed using HEK293 cells stably-expressing Kir3.1/3.4 using either a QPatch-16 or QPatch-48 (Sophion Bioscience A/S). A voltage waveform ($V_{Hold}$ -20 mV, step to 60 mV for 100 ms, ramp to -120 mV over 500 ms, hold at -120 mV for 100 ms before returning to $V_{Hold}$) was repeatedly applied to the cells under voltage-clamp at a frequency of 0.1 Hz to elicit Kir3.1/3.4 currents. Mean current at -120 mV was measured in the absence ($I_{control}$) and presence of drug ($I_{Drug}$). Assessment of passive leak was performed by removal of external potassium ($I_{Zero}$). Leak current was subtracted from control and drug recordings. Current inhibition (%) was calculated as $\{1-[(I_{Drug}-I_{Zero})/(I_{Control}-I_{Zero})]\}*100$. Data were fitted with a sigmoidal function to yield an $IC_{50}$ and Hill coefficient. Composition of external experimental buffer was (in mM): 40 NaCl, 100 KCl, 5 $CaCl_2$, 1 $MgCl_2$, 10 HEPES pH 7.4. Composition of internal solution was (in mM). 40 K-gluconate, 60 KF, 20 NaCl, 5 Mg-ATP, 0.9 GTPgS, 20 EGTA, pH 7.2. Compounds were formulated in DMSO and diluted in buffer to give a final drug concentration of between 0.03-10 M and a final DMSO concentration of 0.1-0.3%.

$IC_{50}$ data obtained via the Electrophysiology Method are provided in TABLE 1 and $IC_{50}$ data obtained via the Q-patch Method are provided in TABLE 2:

A corresponds to an $IC_{50}$ of less than 500 nM;

B corresponds to an $IC_{50}$ of greater than 500 nM but less than 3000 nM; and

C corresponds to an $IC_{50}$ of greater than 3000 nM but less than 10,000 nM.

A compound is considered to be "active" if its $IC_{50}$ is below 10,000 nM.

TABLE 1

Summary of synthesis methods and biological activity

| Example | Chemical name | Synthetic Method | $IC_{50}$ |
|---|---|---|---|
| Example 1 | 4-[4-[2-(1-methylpyrrolidin-2-yl)ethoxymethyl]-1-piperidyl]-5-phenyl-thieno[2,3-d]pyrimidine | F | A |
| Example 2 | 5-methyl-4-[4-[2-(1-methylpyrrolidin-2-yl)ethoxymethyl]-1-piperidyl]thieno[2,3-d]pyrimidine | F | B |
| Example 3 | 4-[4-[2-(1-methylpyrrolidin-2-yl)ethoxymethyl]-1-piperidyl]thieno[2,3-d]pyrimidine | F | C |
| Example 4 | 5,6-dimethyl-4-[4-[2-(1-methylpyrrolidin-2-yl)ethoxymethyl]-1-piperidyl]thieno[2,3-d]pyrimidine | F | A |
| Example 5 | 5-phenyl-4-[4-(2-pyrrolidin-1-ylethoxymethyl)-1-piperidyl]thieno[2,3-d]pyrimidine | F | A |
| Example 6 | 4-[2-[[1-(5-phenylthieno[2,3-d]pyrimidin-4-yl)-4-piperidyl]methoxy]ethyl]morpholine | F | A |

TABLE 1-continued

Summary of synthesis methods and biological activity

| Example | Chemical name | Synthetic Method | IC$_{50}$ |
|---|---|---|---|
| Example 7 | 4-[4-[(1-methylpyrrolidin-2-yl)methoxymethyl]-1-piperidyl]-5-phenyl-thieno[2,3-d]pyrimidine | F | A |
| Example 8 | N,N-dimethyl-3-[[1-(5-phenylthieno[2,3-d]pyrimidin-4-yl)-4-piperidyl]methoxy]propan-1-amine | F | A |
| Example 9 | 4-[4-(cyclobutoxymethyl)-1-piperidyl]-5-phenyl-thieno[2,3-d]pyrimidine | F | A |
| Example 10 | 4-[4-[2-(1-methyl-2-piperidyl)ethoxymethyl]-1-piperidyl]-5-phenyl-thieno[2,3-d]pyrimidine | F | A |
| Example 11 | N,N-dimethyl-2-[[1-(5-phenylthieno[2,3-d]pyrimidin-4-yl)-4-piperidyl]methoxy]ethanamine | F | A |
| Example 12 | 4-[4-[(1-methylpyrrolidin-3-yl)oxymethyl]-1-piperidyl]-5-phenyl-thieno[2,3-d]pyrimidine | F | A |
| Example 13 | 4-[4-[(1-methyl-4-piperidyl)oxymethyl]-1-piperidyl]-5-phenyl-thieno[2,3-d]pyrimidine | F | A |
| Example 14 | 1-[4-[4-(2-dimethylaminoethyloxymethyl)-1-piperidyl]-5-phenyl-thieno[2,3-d]pyrimidin-2-yl]pyrrolidine-3-carboxamide | F | A |
| Example 15 | 4-[4-(isopropoxymethyl)-1-piperidyl]-5-phenyl-thieno[2,3-d]pyrimidine | F | B |
| Example 16 | 5-phenyl-4-[4-(tetrahydrofuran-3-yloxymethyl)-1-piperidyl]thieno[2,3-d]pyrimidine | F | B |
| Example 17 | 5-(3-fluorophenyl)-4-[4-(2-pyrrolidin-1-ylethoxymethyl)-1-piperidyl]thieno[2,3-d]pyrimidine | F | A |
| Example 18 | 5-ethyl-6-methyl-4-[4-(2-pyrrolidin-1-ylethoxymethyl)-1-piperidyl]thieno[2,3-d]pyrimidine | F | A |
| Example 19 | 4-[2-[[1-(6-isopropylthieno[2,3-d]pyrimidin-4-yl)-4-piperidyl]methoxy]ethyl]morpholine | F | B |
| Example 20 | 5-(4-fluorophenyl)-4-[4-(2-pyrrolidin-1-ylethoxymethyl)-1-piperidyl]thieno[2,3-d]pyrimidine | F | A |
| Example 21 | 4-[2-[[1-[5-(4-fluorophenyl)thieno[2,3-d]pyrimidin-4-yl]-4-piperidyl]methoxy]ethyl]morpholine | F | A |
| Example 22 | 4-[4-[2-(3-fluoropyrrolidin-1-yl)ethoxymethyl]-1-piperidyl]-5-phenyl-thieno[2,3-d]pyrimidine | F | A |
| Example 23 | 4-[2-[[1-(5-ethyl-6-methyl-thieno[2,3-d]pyrimidin-4-yl)-4-piperidyl]methoxy]ethyl]morpholine | F | A |
| Example 24 | 5-ethyl-6-methyl-4-[4-[2-(1-methylpyrrolidin-2-yl)ethoxymethyl]-1-piperidyl]thieno[2,3-d]pyrimidine | F | A |
| Example 25 | 6-isopropyl-4-[4-[2-(1-methyl-2-piperidyl)ethoxymethyl]-1-piperidyl]thieno[2,3-d]pyrimidine | F | A |
| Example 26 | 4-[4-[2-(3,3-difluoropyrrolidin-1-yl)ethoxymethyl]-1-piperidyl]-5-phenyl-thieno[2,3-d]pyrimidine | F | A |
| Example 27 | 5-[2-[[1-(5-phenylthieno[2,3-d]pyrimidin-4-yl)-4-piperidyl]methoxy]ethyl]-2-oxa-5-azabicyclo[2.2.1]heptane | F | A |
| Example 28 | 4-[2-[[1-(5-phenylthieno[2,3-d]pyrimidin-4-yl)-4-piperidyl]methoxy]ethyl]piperazin-2-one | F | B |
| Example 29 | 1-[2-[[1-(5-phenylthieno[2,3-d]pyrimidin-4-yl)-4-piperidyl]methoxy]ethyl]pyrrolidine-3-carboxamide | F | A |
| Example 30 | N-[1-[2-[[1-(5-phenylthieno[2,3-d]pyrimidin-4-yl)-4-piperidyl]methoxy]ethyl]pyrrolidin-3-yl]acetamide | F | A |
| Example 31 | 1-[2-[[1-(5-phenylthieno[2,3-d]pyrimidin-4-yl)-4-piperidyl]methoxy]ethyl]pyrrolidine-2-carboxamide | F | A |
| Example 32 | 4-[4-[2-[(3R)-3-fluoropyrrolidin-1-yl]ethoxymethyl]-1-piperidyl]-5-phenyl-thieno[2,3-d]pyrimidine | F | A |
| Example 33 | 4-[4-[2-[(3S)-3-fluoropyrrolidin-1-yl]ethoxymethyl]-1-piperidyl]-5-phenyl-thieno[2,3-d]pyrimidine | F | A |
| Example 34 | 5-ethyl-6-methyl-4-[4-[2-(1-methyl-2-piperidyl)ethoxymethyl]-1-piperidyl]thieno[2,3-d]pyrimidine | F | A |
| Example 35 | 5-(3-fluorophenyl)-4-[4-[2-(1-methylpyrrolidin-2-yl)ethoxymethyl]-1-piperidyl]thieno[2,3-d]pyrimidine | F | A |
| Example 36 | 5-(3-fluorophenyl)-4-[4-[2-(1-methyl-2-piperidyl)ethoxymethyl]-1-piperidyl]thieno[2,3-d]pyrimidine | F | A |
| Example 37 | 5-phenyl-4-[6-(2-pyrrolidin-1-ylethoxymethyl)-3-azabicyclo[3.1.0]hexan-3-yl]thieno[2,3-d]pyrimidine | F | A |
| Example 38 | 4-[2-[[3-(5-phenylthieno[2,3-d]pyrimidin-4-yl)-3-azabicyclo[3.1.0]hexan-6-yl]methoxy]ethyl]morpholine | F | B |
| Example 39 | 4-[6-[2-(1-methylpyrrolidin-2-yl)ethoxymethyl]-3-azabicyclo[3.1.0]hexan-3-yl]-5-phenyl-thieno[2,3-d]pyrimidine | F | A |
| Example 40 | 4-[6-[2-[(3S)-3-fluoropyrrolidin-1-yl]ethoxymethyl]-3-azabicyclo[3.1.0]hexan-3-yl]-5-phenyl-thieno[2,3-d]pyrimidine | F | A |

TABLE 1-continued

Summary of synthesis methods and biological activity

| Example | Chemical name | Synthetic Method | IC$_{50}$ |
|---|---|---|---|
| Example 41 | 4-[6-[2-[(3R)-3-fluoropyrrolidin-1-yl]ethoxymethyl]-3-azabicyclo[3.1.0]hexan-3-yl]-5-phenyl-thieno[2,3-d]pyrimidine | F | A |
| Example 42 | (2R)-1-[2-[[3-(5-phenylthieno[2,3-d]pyrimidin-4-yl)-3-azabicyclo[3.1.0]hexan-6-yl]methoxy]ethyl]pyrrolidine-2-carboxamide | F | A |
| Example 43 | (2S)-1-[2-[[3-(5-phenylthieno[2,3-d]pyrimidin-4-yl)-3-azabicyclo[3.1.0]hexan-6-yl]methoxy]ethyl]pyrrolidine-2-carboxamide | F | A |
| Example 44 | N,N-dimethyl-4-[4-[4-(2-pyrrolidin-1-ylethoxymethyl)-1-piperidyl]thieno[2,3-d]pyrimidin-5-yl]benzenesulfonamide | F | B |
| Example 45 | (2R)-1-[2-[[3-[5-(4-fluorophenyl)thieno[2,3-d]pyrimidin-4-yl]-3-azabicyclo[3.1.0]hexan-6-yl]methoxy]ethyl]pyrrolidine-2-carboxamide | F | A |
| Example 46 | 5-(4-nitrophenyl)-4-[4-(2-pyrrolidin-1-ylethoxymethyl)-1-piperidyl]thieno[2,3-d]pyrimidine | F | A |
| Example 47 | 5-(4-fluorophenyl)-4-[6-[2-[(3S)-3-fluoropyrrolidin-1-yl]ethoxymethyl]-3-azabicyclo[3.1.0]hexan-3-yl]thieno[2,3-d]pyrimidine | F | A |
| Example 48 | 5-[2-[[3-[5-(4-fluorophenyl)thieno[2,3-d]pyrimidin-4-yl]-3-azabicyclo[3.1.0]hexan-6-yl]methoxy]ethyl]-2-oxa-5-azabicyclo[2.2.1]heptane | F | A |
| Example 49 | 1-cyclopropyl-N-[[1-(5-phenylthieno[2,3-d]pyrimidin-4-yl)-4-piperidyl]methyl]methanamine | A | A |
| Example 50 | 4-[4-[(3-methylpyrrolidin-1-yl)methyl]-1-piperidyl]-5-phenyl-thieno[2,3-d]pyrimidine | A | B |
| Example 51 | N-[[1-(5-phenylthieno[2,3-d]pyrimidin-4-yl)-4-piperidyl]methyl]propan-1-amine | A | B |
| Example 52 | 2,2-difluoro-N-[[1-(5-phenylthieno[2,3-d]pyrimidin-4-yl)-4-piperidyl]methyl]ethanamine | A | B |
| Example 53 | 2-methoxy-N-(2-methoxyethyl)-N-[[1-(5-phenylthieno[2,3-d]pyrimidin-4-yl)-4-piperidyl]methyl]ethanamine | A | A |
| Example 54 | [1-[[1-(5-phenylthieno[2,3-d]pyrimidin-4-yl)-4-piperidyl]methylamino]cyclopentyl]methanol | A | A |
| Example 55 | 1-[[1-(5-phenylthieno[2,3-d]pyrimidin-4-yl)-4-piperidyl]methyl]piperidin-3-ol | A | B |
| Example 56 | 2-phenyl-4-[[1-(5-phenylthieno[2,3-d]pyrimidin-4-yl)-4-piperidyl]methyl]morpholine | A | A |
| Example 57 | 3-phenyl-2-[[1-(5-phenylthieno[2,3-d]pyrimidin-4-yl)-4-piperidyl]methylamino]propan-1-ol | A | A |
| Example 58 | 2-(1-methylpyrrolidin-2-yl)-N-[[1-(5-phenylthieno[2,3-d]pyrimidin-4-yl)-4-piperidyl]methyl]ethanamine | A | A |
| Example 59 | 2-methyl-2-morpholino-N-[[1-(5-phenylthieno[2,3-d]pyrimidin-4-yl)-4-piperidyl]methyl]propan-1-amine | A | A |
| Example 60 | N,N-dimethyl-1-[[1-(5-phenylthieno[2,3-d]pyrimidin-4-yl)-4-piperidyl]methyl]piperidin-3-amine | A | A |
| Example 61 | 1-(2-furyl)-N-[[1-(5-phenylthieno[2,3-d]pyrimidin-4-yl)-4-piperidyl]methyl]methanamine | A | A |
| Example 62 | N',N'-diisopropyl-N-[[1-(5-phenylthieno[2,3-d]pyrimidin-4-yl)-4-piperidyl]methyl]ethane-1,2-diamine | A | A |
| Example 63 | N'-[[1-(5-phenylthieno[2,3-d]pyrimidin-4-yl)-4-piperidyl]methyl]ethane-1,2-diamine | A | A |
| Example 64 | N-[[1-(5-phenylthieno[2,3-d]pyrimidin-4-yl)-4-piperidyl]methyl]cyclobutanamine | A | A |
| Example 65 | [1-[[1-(5-phenylthieno[2,3-d]pyrimidin-4-yl)-4-piperidyl]methyl]pyrrolidin-2-yl]methanol | A | A |
| Example 66 | N-[[1-(5-phenylthieno[2,3-d]pyrimidin-4-yl)-4-piperidyl]methyl]-1-(2-pyridyl)methanamine | A | A |
| Example 67 | (3S,4S)-1-[[1-(5-phenylthieno[2,3-d]pyrimidin-4-yl)-4-piperidyl]methyl]-4-pyrrolidin-1-yl-pyrrolidin-3-ol | A | A |
| Example 68 | 4-[4-[(3-methoxypyrrolidin-1-yl)methyl]-1-piperidyl]-5-phenyl-thieno[2,3-d]pyrimidine | A | A |
| Example 69 | N-[[1-(5-phenylthieno[2,3-d]pyrimidin-4-yl)-4-piperidyl]methyl]-1-(2-thienyl)methanamine | A | A |
| Example 70 | 4-[4-[[3-(4-fluorophenyl)pyrrolidin-1-yl]methyl]-1-piperidyl]-5-phenyl-thieno[2,3-d]pyrimidine | A | A |
| Example 71 | N,N,N'-trimethyl-N'-[[1-(5-phenylthieno[2,3-d]pyrimidin-4-yl)-4-piperidyl]methyl]ethane-1,2-diamine | A | A |
| Example 72 | N,N,N'-trimethyl-N'-[[1-(5-phenylthieno[2,3-d]pyrimidin-4-yl)-4-piperidyl]methyl]propane-1,3-diamine | A | A |

TABLE 1-continued

Summary of synthesis methods and biological activity

| Example | Chemical name | Synthetic Method | IC$_{50}$ |
|---|---|---|---|
| Example 73 | 4-[4-(azetidin-1-ylmethyl)-1-piperidyl]-5-phenyl-thieno[2,3-d]pyrimidine | A | B |
| Example 74 | N-[[1-(5-phenylthieno[2,3-d]pyrimidin-4-yl)-4-piperidyl]methyl]cyclopropanamine | A | A |
| Example 75 | N,N-dimethyl-1-[[1-(5-phenylthieno[2,3-d]pyrimidin-4-yl)-4-piperidyl]methyl]piperidin-4-amine | A | A |
| Example 76 | 5-phenyl-4-[4-[(3-pyrrolidin-1-ylpyrrolidin-1-yl)methyl]-1-piperidyl]thieno[2,3-d]pyrimidine | A | A |
| Example 77 | N-[[1-[5-(4-fluorophenyl)thieno[2,3-d]pyrimidin-4-yl]-4-piperidyl]methyl]cyclopropanamine | A | B |
| Example 78 | N-[[1-[5-(4-fluorophenyl)thieno[2,3-d]pyrimidin-4-yl]-4-piperidyl]methyl]cyclobutanamine | A | B |
| Example 79 | 1-[[1-[5-(4-fluorophenyl)thieno[2,3-d]pyrimidin-4-yl]-4-piperidyl]methyl]-N,N-dimethyl-piperidin-3-amine | A | A |
| Example 80 | 2-(1-methyl-2-piperidyl)-N-[[1-(5-phenylthieno[2,3-d]pyrimidin-4-yl)-4-piperidyl]methyl]ethanamine | A | A |
| Example 81 | (3R)-N,N-dimethyl-1-[[1-(5-phenylthieno[2,3-d]pyrimidin-4-yl)-4-piperidyl]methyl]pyrrolidin-3-amine | A | A |
| Example 82 | tert-butyl 2-[2-[[1-(5-phenylthieno[2,3-d]pyrimidin-4-yl)-4-piperidyl]methylamino]ethyl]pyrrolidine-1-carboxylate | A | A |
| Example 83 | N-methyl-1-[1-(5-phenylthieno[2,3-d]pyrimidin-4-yl)-4-piperidyl]-N-(pyrrolidin-2-ylmethyl)methanamine | A | A |
| Example 84 | N-[(1-methylpyrrolidin-2-yl)methyl]-1-[1-(5-phenylthieno[2,3-d]pyrimidin-4-yl)-4-piperidyl]methanamine | A | A |
| Example 85 | N-[[1-(5-phenylthieno[2,3-d]pyrimidin-4-yl)-4-piperidyl]methyl]-2-pyrrolidin-2-yl-ethanamine | A | B |
| Example 86 | N-methyl-N-[[1-(5-phenylthieno[2,3-d]pyrimidin-4-yl)-4-piperidyl]methyl]-2-pyrrolidin-2-yl-ethanamine | A | A |
| Example 87 | 2-(1-ethylpyrrolidin-2-yl)-N-methyl-N-[[1-(5-phenylthieno[2,3-d]pyrimidin-4-yl)-4-piperidyl]methyl]ethanamine | A | A |
| Example 88 | 2-(1-isopropylpyrrolidin-2-yl)-N-methyl-N-[[1-(5-phenylthieno[2,3-d]pyrimidin-4-yl)-4-piperidyl]methyl]ethanamine | A | A |
| Example 89 | 1-[2-[2-[methyl-[[1-(5-phenylthieno[2,3-d]pyrimidin-4-yl)-4-piperidyl]methyl]amino]ethyl]pyrrolidin-1-yl]ethanone | A | B |
| Example 90 | (3S)-1-[[1-(5-phenylthieno[2,3-d]pyrimidin-4-yl)-4-piperidyl]methyl]piperidin-3-amine | A | A |
| Example 91 | 1-methyl-4-[[1-(5-phenylthieno[2,3-d]pyrimidin-4-yl)-4-piperidyl]methylamino]pyrrolidin-2-one | A | B |
| Example 92 | 4-[4-[[(3S)-3-fluoropyrrolidin-1-yl]methyl]-1-piperidyl]-5-phenyl-thieno[2,3-d]pyrimidine | A | B |
| Example 93 | 2-[methyl-[[1-(5-phenylthieno[2,3-d]pyrimidin-4-yl)-4-piperidyl]methyl]amino]-1-pyrrolidin-1-yl-ethanone | A | B |
| Example 94 | N-[[1-(5-phenylthieno[2,3-d]pyrimidin-4-yl)-4-piperidyl]methyl]prop-2-en-1-amine | A | A |
| Example 95 | [1-[[1-(5-phenylthieno[2,3-d]pyrimidin-4-yl)-4-piperidyl]methyl]pyrrolidin-3-yl]methanol | A | B |
| Example 96 | N-[1-[1-(5-phenylthieno[2,3-d]pyrimidin-4-yl)-4-piperidyl]ethyl]cyclopropanamine | A | A |
| Example 97 | 1-methyl-N-[[1-(5-phenylthieno[2,3-d]pyrimidin-4-yl)-4-piperidyl]methyl]piperidin-4-amine | A | A |
| Example 98 | 4-[4-[(2,5-dimethylpyrrolidin-1-yl)methyl]-1-piperidyl]-5-phenyl-thieno[2,3-d]pyrimidine | A | B |
| Example 99 | 5-phenyl-4-[4-[[4-(trifluoromethyl)-1-piperidyl]methyl]-1-piperidyl]thieno[2,3-d]pyrimidine | A | B |
| Example 100 | 2-[(2S)-1-methylpyrrolidin-2-yl]-N-[[1-(5-phenylthieno[2,3-d]pyrimidin-4-yl)-4-piperidyl]methyl]ethanamine | A | A |
| Example 101 | N-methyl-2-(1-methylpyrrolidin-2-yl)-N-[[1-(5-phenylthieno[2,3-d]pyrimidin-4-yl)-4-piperidyl]methyl]ethanamine | A | A |
| Example 102 | N-[[1-(5-phenylthieno[2,3-d]pyrimidin-4-yl)-4-piperidyl]methyl]-2-tetrahydrofuran-2-yl-ethanamine | A | A |
| Example 103 | 2-cyclopropyl-N-[[1-(5-phenylthieno[2,3-d]pyrimidin-4-yl)-4-piperidyl]methyl]ethanamine | A | A |
| Example 104 | 2-(1-methylpyrrolidin-3-yl)-N-[[1-(5-phenylthieno[2,3-d]pyrimidin-4-yl)-4-piperidyl]methyl]ethanamine | A | A |
| Example 105 | 2-[[1-(5-phenylthieno[2,3-d]pyrimidin-4-yl)-4-piperidyl]methylamino]-1-pyrrolidin-1-yl-ethanone | A | A |

TABLE 1-continued

Summary of synthesis methods and biological activity

| Example | Chemical name | Synthetic Method | IC$_{50}$ |
|---|---|---|---|
| Example 106 | (2S)-1-[[1-(5-phenylthieno[2,3-d]pyrimidin-4-yl)-4-piperidyl]methyl]pyrrolidine-2-carboxamide | A | A |
| Example 107 | 2-[2-hydroxyethyl-[[1-[2-(4-methylpiperazin-1-yl)-5-phenyl-thieno[2,3-d]pyrimidin-4-yl]-4-piperidyl]methyl]amino]ethanol | A | B |
| Example 108 | 4-[4-[(isopropylamino)methyl]-1-piperidyl]-5-phenyl-N-(2-pyrrolidin-1-ylethyl)thieno[2,3-d]pyrimidin-2-amine | B | B |
| Example 109 | 4-[4-[(2-methoxyethylamino)methyl]-1-piperidyl]-5-phenyl-N-(2-pyrrolidin-1-ylethyl)thieno[2,3-d]pyrimidin-2-amine | B | B |
| Example 110 | 4-[4-[[methyl-(1-methylpyrrolidin-3-yl)amino]methyl]-1-piperidyl]-5-phenyl-N-(2-pyrrolidin-1-ylethyl)thieno[2,3-d]pyrimidin-2-amine | B | A |
| Example 111 | N,1-dimethyl-N-[[1-[2-(4-methylpiperazin-1-yl)-5-phenyl-thieno[2,3-d]pyrimidin-4-yl]-4-piperidyl]methyl]pyrrolidin-3-amine | B | A |
| Example 112 | N,1-dimethyl-N-[[1-(5-phenyl-2-piperazin-1-yl-thieno[2,3-d]pyrimidin-4-yl)-4-piperidyl]methyl]pyrrolidin-3-amine | B | A |
| Example 113 | [1-[[1-[2-(4-methylpiperazin-1-yl)-5-phenyl-thieno[2,3-d]pyrimidin-4-yl]-4-piperidyl]methylamino]cyclopentyl]methanol | B | B |
| Example 114 | N-[[1-[2-(4-methylpiperazin-1-yl)-5-phenyl-thieno[2,3-d]pyrimidin-4-yl]-4-piperidyl]methyl]-2-(1-methylpyrrolidin-2-yl)ethanamine | B | B |
| Example 115 | N,N-dimethyl-1-[[1-[2-(4-methylpiperazin-1-yl)-5-phenyl-thieno[2,3-d]pyrimidin-4-yl]-4-piperidyl]methyl]piperidin-3-amine | B | A |
| Example 116 | N-[[1-[2-(4-methylpiperazin-1-yl)-5-phenyl-thieno[2,3-d]pyrimidin-4-yl]-4-piperidyl]methyl]cyclobutanamine | B | A |
| Example 117 | 4-[4-[[3-(dimethylamino)-1-piperidyl]methyl]-1-piperidyl]-5-phenyl-N-(2-pyrrolidin-1-ylethyl)thieno[2,3-d]pyrimidin-2-amine | B | A |
| Example 118 | N-(2-methoxyethyl)-4-[4-[[methyl-(1-methylpyrrolidin-3-yl)amino]methyl]-1-piperidyl]-5-phenyl-thieno[2,3-d]pyrimidin-2-amine | B | A |
| Example 119 | N-(cyclopropylmethyl)-4-[4-[[methyl-(1-methylpyrrolidin-3-yl)amino]methyl]-1-piperidyl]-5-phenyl-thieno[2,3-d]pyrimidin-2-amine | B | A |
| Example 120 | 1-[4-[4-[[methyl-(1-methylpyrrolidin-3-yl)amino]methyl]-1-piperidyl]-5-phenyl-thieno[2,3-d]pyrimidin-2-yl]pyrrolidine-3-carboxamide | B | A |
| Example 121 | 2-[methyl-[4-[4-[[methyl-(1-methylpyrrolidin-3-yl)amino]methyl]-1-piperidyl]-5-phenyl-thieno[2,3-d]pyrimidin-2-yl]amino]acetamide | B | A |
| Example 122 | N-[[1-[2-[4-(2-methoxyethyl)piperazin-1-yl]-5-phenyl-thieno[2,3-d]pyrimidin-4-yl]-4-piperidyl]methyl]-N,1-dimethyl-pyrrolidin-3-amine | B | A |
| Example 123 | 1-[4-[4-[[3-(dimethylamino)-1-piperidyl]methyl]-1-piperidyl]-5-phenyl-thieno[2,3-d]pyrimidin-2-yl]pyrrolidine-3-carboxamide | B | A |
| Example 124 | 4-[4-[[3-(dimethylamino)-1-piperidyl]methyl]-1-piperidyl]-N-(2-methoxyethyl)-5-phenyl-thieno[2,3-d]pyrimidin-2-amine | B | A |
| Example 125 | 4-[4-[4-[(cyclobutylamino)methyl]-1-piperidyl]-5-phenyl-thieno[2,3-d]pyrimidin-2-yl]piperazin-2-one | B | B |
| Example 126 | 4-[4-[(cyclobutylamino)methyl]-1-piperidyl]-N-(2-methoxyethyl)-5-phenyl-thieno[2,3-d]pyrimidin-2-amine | B | A |
| Example 127 | 4-[4-[(cyclobutylamino)methyl]-1-piperidyl]-5-phenyl-N-(2-pyrrolidin-1-ylethyl)thieno[2,3-d]pyrimidin-2-amine | B | A |
| Example 128 | 1-[4-[4-[(cyclobutylamino)methyl]-1-piperidyl]-5-phenyl-thieno[2,3-d]pyrimidin-2-yl]pyrrolidine-3-carboxamide | B | B |
| Example 129 | 1-[4-[4-[[methyl-(1-methylpyrrolidin-3-yl)amino]methyl]-1-piperidyl]-5-phenyl-thieno[2,3-d]pyrimidin-2-yl]piperidine-2-carboxamide | B | B |
| Example 130 | 1-[4-[4-[[methyl-(1-methylpyrrolidin-3-yl)amino]methyl]-1-piperidyl]-5-phenyl-thieno[2,3-d]pyrimidin-2-yl]pyrrolidine-2-carboxamide | B | B |
| Example 131 | N-methyl-4-[4-[[methyl-(1-methylpyrrolidin-3-yl)amino]methyl]-1-piperidyl]-5-phenyl-thieno[2,3-d]pyrimidine-6-carboxamide | B | C |

TABLE 1-continued

Summary of synthesis methods and biological activity

| Example | Chemical name | Synthetic Method | IC$_{50}$ |
|---|---|---|---|
| Example 132 | N-isopropyl-4-[4-[[methyl-(1-methylpyrrolidin-3-yl)amino]methyl]-1-piperidyl]-5-phenyl-thieno[2,3-d]pyrimidine-6-carboxamide | B | A |
| Example 133 | 5-isopropyl-N,N-dimethyl-4-[4-(2-pyrrolidin-1-ylethoxymethyl)-1-piperidyl]thieno[2,3-d]pyrimidine-6-carboxamide | C | B |
| Example 134 | 5-isopropyl-N-methyl-4-[4-(2-pyrrolidin-1-ylethoxymethyl)-1-piperidyl]thieno[2,3-d]pyrimidine-6-carboxamide | C | B |
| Example 135 | N,N-dimethyl-5-phenyl-4-[4-(2-pyrrolidin-1-ylethoxymethyl)-1-piperidyl]thieno[2,3-d]pyrimidine-6-carboxamide | D | A |
| Example 136 | N,N-dimethyl-4-[4-[[methyl-(1-methylpyrrolidin-3-yl)amino]methyl]-1-piperidyl]-5-phenyl-thieno[2,3-d]pyrimidine-6-carboxamide | D | B |
| Example 137 | 5-(3-fluorophenyl)-N-isopropyl-4-[4-(2-pyrrolidin-1-ylethoxymethyl)-1-piperidyl]thieno[2,3-d]pyrimidine-6-carboxamide | D | A |
| Example 138 | 5-(3-fluorophenyl)-N,N-dimethyl-4-[4-(2-pyrrolidin-1-ylethoxymethyl)-1-piperidyl]thieno[2,3-d]pyrimidine-6-carboxamide | D | A |
| Example 139 | [5-phenyl-4-[4-(2-pyrrolidin-1-ylethoxymethyl)-1-piperidyl]thieno[2,3-d]pyrimidin-6-yl]-pyrrolidin-1-yl-methanone | D | A |
| Example 140 | N-isopropyl-5-phenyl-4-[4-(2-pyrrolidin-1-ylethoxymethyl)-1-piperidyl]thieno[2,3-d]pyrimidine-6-carboxamide | D | A |
| Example 141 | N-methyl-5-phenyl-4-[4-(2-pyrrolidin-1-ylethoxymethyl)-1-piperidyl]thieno[2,3-d]pyrimidine-6-carboxamide | D | A |
| Example 142 | 3-phenyl-4-[4-(2-pyrrolidin-1-ylethoxymethyl)-1-piperidyl]thieno[2,3-b]pyridine | I | A |
| Example 143 | 2-bromo-3-phenyl-4-[4-(2-pyrrolidin-1-ylethoxymethyl)-1-piperidyl]thieno[2,3-b]pyridine | I | A |
| Example 144 | 3-phenyl-4-[4-(2-pyrrolidin-1-ylethoxymethyl)-1-piperidyl]thieno[2,3-b]pyridine-2-carbonitrile | M | A |
| Example 145 | 5-phenyl-2-[4-(2-pyrrolidin-1-ylethyl)piperazin-1-yl]thieno[2,3-d]pyrimidine | G | A |
| Example 146 | 2-(1-methylpyrrolidin-2-yl)-N-[[1-(5-phenylthieno[2,3-d]pyrimidin-2-yl)-4-piperidyl]methyl]ethanamine | G | A |
| Example 147 | (2R)-1-[2-[4-(5-phenylthieno[2,3-d]pyrimidin-2-yl)piperazin-1-yl]ethyl]pyrrolidine-2-carboxamide | G | A |
| Example 148 | 5-phenyl-2-[4-(2-pyrrolidin-1-ylethoxymethyl)-1-piperidyl]thieno[2,3-d]pyrimidine | G | A |
| Example 149 | 5-phenyl-2-[3-(2-pyrrolidin-1-ylethoxymethyl)pyrrolidin-1-yl]thieno[2,3-d]pyrimidine | G | A |
| Example 150 | (3R)-1-[2-[4-(5-phenylthieno[2,3-d]pyrimidin-2-yl)piperazin-1-yl]ethyl]pyrrolidine-3-carboxamide | G | B |
| Example 151 | 2-[4-[2-[(3R)-3-fluoropyrrolidin-1-yl]ethoxymethyl]-1-piperidyl]-5-phenyl-thieno[2,3-d]pyrimidine | G | A |
| Example 152 | 5-(4-fluorophenyl)-2-[4-(2-pyrrolidin-1-ylethoxymethyl)-1-piperidyl]thieno[2,3-d]pyrimidine | G | A |
| Example 153 | 1-[2-[[1-(5-phenylthieno[2,3-d]pyrimidin-2-yl)-4-piperidyl]methoxy]ethyl]pyrrolidine-3-carboxamide | G | A |
| Example 154 | 5-[2-[[1-(5-phenylthieno[2,3-d]pyrimidin-2-yl)-4-piperidyl]methoxy]ethyl]-2-oxa-5-azabicyclo[2.2.1]heptane | G | A |
| Example 155 | N-[5-phenyl-2-[4-(2-pyrrolidin-1-ylethoxymethyl)-1-piperidyl]thieno[2,3-d]pyrimidin-6-yl]acetamide | L | B |
| Example 156 | 1-[5-phenyl-2-[4-(2-pyrrolidin-1-ylethoxymethyl)-1-piperidyl]thieno[2,3-d]pyrimidin-6-yl]pyrrolidin-2-one | L | A |
| Example 157 | 5-isopropyl-2-[4-(2-pyrrolidin-1-ylethoxymethyl)-1-piperidyl]thieno[2,3-d]pyrimidine | G | A |
| Example 158 | 1-[5-phenyl-2-[4-(2-pyrrolidin-1-ylethoxymethyl)-1-piperidyl]thieno[2,3-d]pyrimidin-6-yl]pyrrolidin-2-one | L | A |
| Example 159 | 5-isopropyl-2-[4-(2-pyrrolidin-1-ylethoxymethyl)-1-piperidyl]thieno[2,3-d]pyrimidine | G | A |
| Example 160 | 4-[3-[(1-methylpyrrolidin-3-yl)methoxy]prop-1-ynyl]-5-phenyl-thieno[2,3-d]pyrimidine | H | A |
| Example 161 | 5-phenyl-4-[3-(2-pyrrolidin-1-ylethoxy)prop-1-ynyl]thieno[2,3-d]pyrimidine | H | A |
| Example 162 | N-[5-phenyl-4-[4-(2-pyrrolidin-1-ylethoxymethyl)-1-piperidyl]thieno[2,3-d]pyrimidin-6-yl]acetamide | E | A |

TABLE 1-continued

Summary of synthesis methods and biological activity

| Example | Chemical name | Synthetic Method | IC$_{50}$ |
|---|---|---|---|
| Example 163 | 1-[5-phenyl-4-[4-(2-pyrrolidin-1-ylethoxymethyl)-1-piperidyl]thieno[2,3-d]pyrimidin-6-yl]pyrrolidin-2-one | E | A |
| Example 164 | 5-phenyl-4-[(1S,5R)-3-(2-pyrrolidin-1-ylethoxymethyl)-8-azabicyclo[3.2.1]octan-8-yl]thieno[2,3-d]pyrimidine | I | A |
| Example 165 | [8-(4-morpholino-5-phenyl-thieno[2,3-d]pyrimidin-2-yl)-8-azabicyclo[3.2.1]octan-3-yl]methanol | J | B |
| Example 166 | N-[2-(1-methylpyrrolidin-2-yl)ethyl]-1-(5-phenylthieno[2,3-d]pyrimidin-4-yl)piperidine-4-carboxamide | K | B |
| Example 167 | 5-phenyl-4-[4-(2-pyrrolidin-1-ylethoxymethyl)-1-piperidyl]thieno[2,3-d]pyrimidine-6-carbonitrile | M | A |
| Example 168 | N-benzyl-5-phenyl-4-[4-(2-pyrrolidin-1-ylethoxymethyl)-1-piperidyl]thieno[2,3-d]pyrimidin-6-amine | N | A |
| Example 169 | N,N-dimethyl-1-(5-phenylthieno[2,3-d]pyrimidin-4-yl)piperidin-4-amine | I | B |
| Example 170 | 1-(2-ethyl-5-phenyl-thieno[2,3-d]pyrimidin-4-yl)-N,N-dimethyl-piperidin-4-amine | I | B |
| Example 171 | 2-[1-[5-(4-fluorophenyl)-2-(2-hydroxyethylamino)thieno[2,3-d]pyrimidin-4-yl]-4-piperidyl]ethanol | J | B |
| Example 172 | 4-[4-(methoxymethyl)-1-piperidyl]-5-phenyl-thieno[2,3-d]pyrimidine | I | B |
| Example 173 | N-[4-[4-(methoxymethyl)-1-piperidyl]-5-phenyl-thieno[2,3-d]pyrimidin-2-yl]-N',N'-dimethyl-ethane-1,2-diamine | J | A |
| Example 174 | 4-[4-(methoxymethyl)-1-piperidyl]-2-(4-methylpiperazin-1-yl)-5-phenyl-thieno[2,3-d]pyrimidine | J | A |
| Example 175 | 4-[4-(methoxymethyl)-1-piperidyl]-5-phenyl-N-(2-pyrrolidin-1-ylethyl)thieno[2,3-d]pyrimidin-2-amine | J | A |
| Example 176 | 4-[4-(4-methoxyphenyl)-1-piperidyl]-5-phenyl-thieno[2,3-d]pyrimidine | I | B |
| Example 177 | 5-cyclohexyl-4-[4-(methoxymethyl)-1-piperidyl]-N-[2-(1-methylpyrrolidin-2-yl)ethyl]thieno[2,3-d]pyrimidin-2-amine | J | B |
| Example 178 | 4-(3-benzyloxypyrrolidin-1-yl)-5-phenyl-thieno[2,3-d]pyrimidine | I | B |
| Example 179 | 4-[4-(dimethylamino)-1-piperidyl]-5-phenyl-N-(2-pyrrolidin-1-ylethyl)thieno[2,3-d]pyrimidin-2-amine | J | B |
| Example 180 | 5-phenyl-4-[4-(3-pyridyloxymethyl)-1-piperidyl]thieno[2,3-d]pyrimidine | I | A |
| Example 181 | 5-phenyl-4-[3-(1-piperidyl)pyrrolidin-1-yl]thieno[2,3-d]pyrimidine | I | B |
| Example 182 | 2-[4-[4-(methoxymethyl)-1-piperidyl]-5-phenyl-thieno[2,3-d]pyrimidin-2-yl]-N-(2-pyrrolidin-1-ylethyl)acetamide | Y | A |
| Example 183 | 2-[4-[4-(methoxymethyl)-1-piperidyl]-5-phenyl-thieno[2,3-d]pyrimidin-2-yl]-1-pyrrolidin-1-yl-ethanone | Y | B |
| Example 184 | 5-(4-fluorophenyl)-4-[4-(methoxymethyl)-1-piperidyl]-2-(2-pyrrolidin-1-ylethyl)thieno[2,3-d]pyrimidine | Y | A |
| Example 185 | 2-[[4-[4-(methoxymethyl)-1-piperidyl]-5-phenyl-thieno[2,3-d]pyrimidin-2-yl]-(2-pyrrolidin-1-ylethyl)amino]ethanol | J | A |
| Example 186 | 2-[2-hydroxyethyl-[[1-(5-phenylthieno[2,3-d]pyrimidin-4-yl)-4-piperidyl]methyl]amino]ethanol | I | B |
| Example 187 | N-[[1-(5-phenylthieno[2,3-d]pyrimidin-4-yl)-4-piperidyl]methyl]propan-2-amine | I | A |
| Example 188 | 1-[4-[4-(dimethylamino)-1-piperidyl]-5-phenyl-thieno[2,3-d]pyrimidin-2-yl]pyrrolidin-3-ol | J | B |
| Example 189 | 1-[5-phenyl-2-(2-pyrrolidin-1-ylethylamino)thieno[2,3-d]pyrimidin-4-yl]pyrrolidin-3-ol | J | B |
| Example 190 | (3S)-1-[[1-(5-phenylthieno[2,3-d]pyrimidin-4-yl)-4-piperidyl]methyl]pyrrolidin-3-ol | A | A |
| Example 191 | [1-[4-[4-(methoxymethyl)-1-piperidyl]-5-phenyl-thieno[2,3-d]pyrimidin-2-yl]-4-piperidyl]methanol | J | A |
| Example 192 | 2-methoxy-N-[[1-[4-[4-(methoxymethyl)-1-piperidyl]-5-phenyl-thieno[2,3-d]pyrimidin-2-yl]-4-piperidyl]methyl]ethanamine | J | A |
| Example 193 | 4-[4-(methoxymethyl)-1-piperidyl]-N-methyl-N-(1-methylpyrrolidin-3-yl)-5-phenyl-thieno[2,3-d]pyrimidin-2-amine | J | A |

TABLE 1-continued

Summary of synthesis methods and biological activity

| Example | Chemical name | Synthetic Method | IC$_{50}$ |
|---|---|---|---|
| Example 194 | 5-cyclohexyl-4-[4-(methoxymethyl)-1-piperidyl]-2-piperazin-1-yl-thieno[2,3-d]pyrimidine | J | A |
| Example 195 | 1-(5-phenylthieno[2,3-d]pyrimidin-4-yl)-4-(pyrrolidin-1-ylmethyl)piperidin-4-ol | I | A |
| Example 196 | N-[[1-(5-cyclohexylthieno[2,3-d]pyrimidin-4-yl)-4-piperidyl]methyl]propan-2-amine | A | A |
| Example 197 | 4-[[1-(5-cyclohexylthieno[2,3-d]pyrimidin-4-yl)-4-piperidyl]methyl]-2,6-dimethyl-morpholine | A | A |
| Example 198 | 4-[4-[(3-methylpyrrolidin-1-yl)methyl]-2-phenyl-pyrrolidin-1-yl]-5-phenyl-thieno[2,3-d]pyrimidine | A | A |
| Example 199 | 2-[5-(4-fluorophenyl)-4-(2-phenylpyrrolidin-1-yl)thieno[2,3-d]pyrimidin-2-yl]-N-(2-pyrrolidin-1-ylethyl)acetamide | Y | A |
| Example 200 | 1-[[1-(5-cyclohexylthieno[2,3-d]pyrimidin-4-yl)-4-piperidyl]methyl]pyrrolidin-3-ol | A | A |
| Example 201 | 2-[[1-(5-cyclohexylthieno[2,3-d]pyrimidin-4-yl)-4-piperidyl]methyl-(2-hydroxyethyl)amino]ethanol | A | A |
| Example 202 | N,1-dimethyl-N-[[1-(5-phenylthieno[2,3-d]pyrimidin-4-yl)-4-piperidyl]methyl]pyrrolidin-3-amine | A | A |
| Example 203 | N-methyl-N-[[1-(5-phenylthieno[2,3-d]pyrimidin-4-yl)-4-piperidyl]methyl]tetrahydrofuran-3-amine | A | B |
| Example 204 | 2-(1-methylpyrrolidin-2-yl)-N-[[1-(5-phenylthieno[2,3-d]pyrimidin-4-yl)pyrrolidin-3-yl]methyl]ethanamine | A | A |
| Example 205 | N,1-dimethyl-N-[[1-(5-phenylthieno[2,3-d]pyrimidin-4-yl)pyrrolidin-3-yl]methyl]pyrrolidin-3-amine | A | A |
| Example 206 | N-[[1-(5-phenylthieno[2,3-d]pyrimidin-4-yl)-4-piperidyl]methyl]-2-pyrrolidin-1-yl-ethanamine | A | A |
| Example 207 | N-[[1-(5-phenylthieno[2,3-d]pyrimidin-4-yl)-3-piperidyl]methyl]cyclobutanamine | A | B |
| Example 208 | N,N-dimethyl-1-[[1-(5-phenylthieno[2,3-d]pyrimidin-4-yl)-3-piperidyl]methyl]piperidin-3-amine | A | A |
| Example 209 | N-[[5-methyl-1-(5-phenylthieno[2,3-d]pyrimidin-4-yl)pyrrolidin-3-yl]methyl]-2-(1-methylpyrrolidin-2-yl)ethanamine | A | A |
| Example 210 | 2-(1-methylpyrrolidin-2-yl)-N-[[1-(5-methylthieno[2,3-d]pyrimidin-4-yl)-5-phenyl-pyrrolidin-3-yl]methyl]ethanamine | A | A |
| Example 211 | 1-[[1-(5-phenylthieno[2,3-d]pyrimidin-4-yl)-4-piperidyl]methyl]piperidin-3-amine | A | A |
| Example 212 | 5-phenyl-4-[4-[[3-(trifluoromethyl)-1-piperidyl]methyl]-1-piperidyl]thieno[2,3-d]pyrimidine | A | A |
| Example 213 | 4-[[1-(5-phenylthieno[2,3-d]pyrimidin-4-yl)-4-piperidyl]methyl]piperazin-2-one | A | B |
| Example 214 | 4-[4-[(4-methylpiperazin-1-yl)methyl]-1-piperidyl]-5-phenyl-thieno[2,3-d]pyrimidine | A | A |
| Example 215 | (3S)-N,N-dimethyl-1-[[1-(5-phenylthieno[2,3-d]pyrimidin-4-yl)-4-piperidyl]methyl]piperidin-3-amine | A | A |
| Example 216 | (3R)-N,N-dimethyl-1-[[1-(5-phenylthieno[2,3-d]pyrimidin-4-yl)-4-piperidyl]methyl]piperidin-3-amine | A | A |
| Example 217 | N',N'-dimethyl-N-[[1-(5-phenylthieno[2,3-d]pyrimidin-4-yl)-4-piperidyl]methyl]propane-1,3-diamine | A | A |
| Example 218 | 5-phenyl-4-[4-[[3-(1-piperidyl)pyrrolidin-1-yl]methyl]-1-piperidyl]thieno[2,3-d]pyrimidine | A | A |
| Example 219 | 2-(1-methylpyrrolidin-2-yl)-N-[[1-(5-phenylthieno[2,3-d]pyrimidin-4-yl)azetidin-3-yl]methyl]ethanamine | A | A |
| Example 220 | N-[[1-(5,6-dimethylthieno[2,3-d]pyrimidin-4-yl)-4-piperidyl]methyl]-2-(1-methylpyrrolidin-2-yl)ethanamine | A | A |
| Example 221 | 2-(1-methylimidazol-2-yl)-N-[[1-(5-phenylthieno[2,3-d]pyrimidin-4-yl)-4-piperidyl]methyl]ethanamine | A | A |
| Example 222 | N,N-dimethyl-1-[1-(5-phenylthieno[2,3-d]pyrimidin-4-yl)-4-piperidyl]piperidin-4-amine | P | A |
| Example 223 | 1-methyl-N-[1-(5-phenylthieno[2,3-d]pyrimidin-4-yl)-4-piperidyl]piperidin-4-amine | P | A |
| Example 224 | N-[2-(1-methylpyrrolidin-2-yl)ethyl]-1-(5-phenylthieno[2,3-d]pyrimidin-4-yl)piperidine-4-carboxamide | K | B |
| Example 225 | 1-[4-[[2-dimethylaminoethyl(methyl)amino]methyl]-1-piperidyl]-5-phenyl-thieno[2,3-d]pyrimidin-2-yl]pyrrolidine-3-carboxamide | B | A |
| Example 226 | N-[1-[4-[[methyl-(1-methylpyrrolidin-3-yl)amino]methyl]-1-piperidyl]-5-phenyl-thieno[2,3-d]pyrimidin-2-yl]pyrrolidin-3-yl]acetamide | B | A |

TABLE 1-continued

Summary of synthesis methods and biological activity

| Example | Chemical name | Synthetic Method | IC$_{50}$ |
|---|---|---|---|
| Example 227 | N-methyl-1-[4-[4-[[methyl-(1-methylpyrrolidin-3-yl)amino]methyl]-1-piperidyl]-5-phenyl-thieno[2,3-d]pyrimidin-2-yl]piperidine-3-carboxamide | B | A |
| Example 228 | N,N-diethyl-1-[4-[4-[[methyl-(1-methylpyrrolidin-3-yl)amino]methyl]-1-piperidyl]-5-phenyl-thieno[2,3-d]pyrimidin-2-yl]piperidine-3-carboxamide | B | A |
| Example 229 | (2R)-1-[4-[4-[[methyl-(1-methylpyrrolidin-3-yl)amino]methyl]-1-piperidyl]-5-phenyl-thieno[2,3-d]pyrimidin-2-yl]pyrrolidine-2-carboxamide | B | A |
| Example 230 | 4-[4-(4-methylpiperazin-1-yl)-1-piperidyl]-5-phenyl-thieno[2,3-d]pyrimidine | P | A |
| Example 231 | N-methyl-N-(1-methylpyrrolidin-3-yl)-1-(5-phenylthieno[2,3-d]pyrimidin-4-yl)piperidin-4-amine | P | A |
| Example 232 | N-[[1-(5,6-dimethylthieno[2,3-d]pyrimidin-4-yl)-4-piperidyl]methyl]-1-methyl-piperidin-4-amine | A | A |
| Example 233 | N-[[1-(5,6-dimethylthieno[2,3-d]pyrimidin-4-yl)-4-piperidyl]methyl]-2-(1-methyl-2-piperidyl)ethanamine | A | A |
| Example 234 | 1-[[1-(5,6-dimethylthieno[2,3-d]pyrimidin-4-yl)-4-piperidyl]methyl]-N,N-dimethyl-piperidin-3-amine | A | A |
| Example 235 | 1-[4-[4-[[4-(dimethylamino)-1-piperidyl]methyl]-1-piperidyl]-5-phenyl-thieno[2,3-d]pyrimidin-2-yl]pyrrolidine-3-carboxamide | B | A |
| Example 236 | 1-[4-[4-[[(3R)-3-(dimethylamino)pyrrolidin-1-yl]methyl]-1-piperidyl]-5-phenyl-thieno[2,3-d]pyrimidin-2-yl]pyrrolidine-3-carboxamide | B | A |
| Example 237 | 1-[4-[4-[[methyl-(1-methylpyrrolidin-3-yl)amino]methyl]-1-piperidyl]-5-phenyl-thieno[2,3-d]pyrimidin-2-yl]azetidine-3-carboxamide | B | A |
| Example 238 | 1-[4-[4-[[methyl-(1-methylpyrrolidin-3-yl)amino]methyl]-1-piperidyl]-5-phenyl-thieno[2,3-d]pyrimidin-2-yl]piperidine-3-carboxamide | B | A |
| Example 239 | 1-[4-[4-[[methyl-(1-methylpyrrolidin-3-yl)amino]methyl]-1-piperidyl]-5-phenyl-thieno[2,3-d]pyrimidin-2-yl]piperidine-4-carboxamide | B | A |
| Example 240 | 1-[5,6-dimethyl-4-[4-[[2-(1-methyl-2-piperidyl)ethylamino]methyl]-1-piperidyl]thieno[2,3-d]pyrimidin-2-yl]pyrrolidine-3-carboxamide | B | A |
| Example 241 | N-methyl-N-[1-[4-[4-[[methyl-(1-methylpyrrolidin-3-yl)amino]methyl]-1-piperidyl]-5-phenyl-thieno[2,3-d]pyrimidin-2-yl]-4-piperidyl]acetamide | B | A |
| Example 242 | N-[[1-(5-isopropylthieno[2,3-d]pyrimidin-4-yl)-4-piperidyl]methyl]-2-(1-methylpyrrolidin-2-yl)ethanamine | A | A |
| Example 243 | 2-(1-methylpyrrolidin-2-yl)-N-[[1-(5-methylthieno[2,3-d]pyrimidin-4-yl)-4-piperidyl]methyl]ethanamine | A | A |
| Example 244 | 1-[[4-[4-[[methyl-(1-methylpyrrolidin-3-yl)amino]methyl]-1-piperidyl]-5-phenyl-thieno[2,3-d]pyrimidin-2-yl]methyl]pyrrolidin-2-one | V | A |
| Example 245 | 1-[5-isopropyl-4-[4-[[methyl-(1-methylpyrrolidin-3-yl)amino]methyl]-1-piperidyl]thieno[2,3-d]pyrimidin-2-yl]pyrrolidine-3-carboxamide | B | A |
| Example 246 | N,N-diethyl-1-[[1-(5-phenylthieno[2,3-d]pyrimidin-4-yl)-4-piperidyl]methyl]piperidine-3-carboxamide | A | A |
| Example 247 | 1-[[1-(5-phenylthieno[2,3-d]pyrimidin-4-yl)-4-piperidyl]methyl]pyrrolidine-2-carboxamide | A | A |
| Example 248 | N-methyl-N-[1-[[1-(5-phenylthieno[2,3-d]pyrimidin-4-yl)-4-piperidyl]methyl]pyrrolidin-3-yl]acetamide | A | A |
| Example 249 | N-methyl-N-(1-methylpyrrolidin-3-yl)-1-(5-phenylthieno[2,3-d]pyrimidin-4-yl)piperidine-4-carboxamide | K | A |
| Example 250 | 1-methyl-4-[methyl-[[1-(5-phenylthieno[2,3-d]pyrimidin-4-yl)-4-piperidyl]methyl]amino]pyrrolidin-2-one | A | B |
| Example 251 | N-methyl-N-[[1-(5-phenylthieno[2,3-d]pyrimidin-4-yl)-4-piperidyl]methyl]cyclobutanamine | W | A |
| Example 252 | 2-[cyclobutyl-[[1-(5-phenylthieno[2,3-d]pyrimidin-4-yl)-4-piperidyl]methyl]amino]-N-methyl-acetamide | W | B |
| Example 253 | N-[1-[[1-(5-phenylthieno[2,3-d]pyrimidin-4-yl)-4-piperidyl]methyl]pyrrolidin-3-yl]acetamide | A | A |
| Example 254 | (2S)-N,N-dimethyl-2-[[1-(5-phenylthieno[2,3-d]pyrimidin-4-yl)-4-piperidyl]methoxy]propan-1-amine | F | A |
| Example 255 | 1-[4-[4-[2-(1-methylpyrrolidin-2-yl)ethoxymethyl]-1-piperidyl]-5-phenyl-thieno[2,3-d]pyrimidin-2-yl]pyrrolidine-3-carboxamide | J | A |

TABLE 1-continued

Summary of synthesis methods and biological activity

| Example | Chemical name | Synthetic Method | IC$_{50}$ |
|---|---|---|---|
| Example 256 | 1-[5-phenyl-4-[4-(2-pyrrolidin-1-ylethoxymethyl)-1-piperidyl]thieno[2,3-d]pyrimidin-2-yl]pyrrolidine-3-carboxamide | J | A |
| Example 257 | N-[1-[5-phenyl-4-[4-(2-pyrrolidin-1-ylethoxymethyl)-1-piperidyl]thieno[2,3-d]pyrimidin-2-yl]pyrrolidin-3-yl]acetamide | J | A |
| Example 258 | 1-[4-[4-(2-morpholinoethoxymethyl)-1-piperidyl]-5-phenyl-thieno[2,3-d]pyrimidin-2-yl]pyrrolidine-3-carboxamide | J | A |
| Example 259 | N-[1-[4-[4-(2-morpholinoethoxymethyl)-1-piperidyl]-5-phenyl-thieno[2,3-d]pyrimidin-2-yl]pyrrolidin-3-yl]acetamide | J | A |
| Example 260 | N-methyl-1-[[1-(5-phenylthieno[2,3-d]pyrimidin-4-yl)-4-piperidyl]methylamino]cyclobutanecarboxamide | A | A |
| Example 261 | 1-[4-[2-[[1-(5-phenylthieno[2,3-d]pyrimidin-4-yl)-4-piperidyl]methoxy]ethyl]piperazin-1-yl]ethanone | F | A |
| Example 262 | 5-phenyl-4-[(3R)-3-(2-pyrrolidin-1-ylethoxymethyl)pyrrolidin-1-yl]thieno[2,3-d]pyrimidine | F | A |
| Example 263 | 5-phenyl-4-[(3S)-3-(2-pyrrolidin-1-ylethoxymethyl)pyrrolidin-1-yl]thieno[2,3-d]pyrimidine | F | A |
| Example 264 | N,5-diisopropyl-4-[4-(2-pyrrolidin-1-ylethoxymethyl)-1-piperidyl]thieno[2,3-d]pyrimidine-6-carboxamide | C | B |
| Example 265 | 5-isopropyl-4-[4-(2-pyrrolidin-1-ylethoxymethyl)-1-piperidyl]thieno[2,3-d]pyrimidine | F | A |
| Example 266 | N-[[1-(6-bromo-5-phenyl-thieno[2,3-d]pyrimidin-4-yl)-4-piperidyl]methyl]-N,1-dimethyl-pyrrolidin-3-amine | I | A |
| Example 267 | 1-(5-phenylthieno[2,3-d]pyrimidin-4-yl)-N-(2-pyrrolidin-1-ylethyl)piperidine-4-carboxamide | K | B |
| Example 268 | 1-(5-phenylthieno[2,3-d]pyrimidin-4-yl)-N-(2-pyrrolidin-1-ylethyl)piperidine-3-carboxamide | K | A |
| Example 269 | 5-phenyl-4-[3-(2-pyrrolidin-1-ylethoxy)pyrrolidin-1-yl]thieno[2,3-d]pyrimidine | F | A |
| Example 270 | 1-(5-phenylthieno[2,3-d]pyrimidin-4-yl)-N-(2-pyrrolidin-1-ylethyl)pyrrolidine-3-carboxamide | K | B |
| Example 271 | 5-phenyl-4-[4-(2-pyrrolidin-1-ylethoxy)-1-piperidyl]thieno[2,3-d]pyrimidine | F | A |
| Example 272 | 5-phenyl-4-[3-(2-pyrrolidin-1-ylethoxy)-1-piperidyl]thieno[2,3-d]pyrimidine | F | A |
| Example 273 | 5-phenyl-4-[3-(2-pyrrolidin-1-ylethoxymethyl)azetidin-1-yl]thieno[2,3-d]pyrimidine | F | B |
| Example 274 | 1-[5-phenyl-2-[4-(2-pyrrolidin-1-ylethoxymethyl)-1-piperidyl]thieno[2,3-d]pyrimidin-4-yl]pyrrolidine-3-carboxamide | J | A |
| Example 275 | N,N-dimethyl-5-phenyl-2-[4-(2-pyrrolidin-1-ylethoxymethyl)-1-piperidyl]thieno[2,3-d]pyrimidin-4-amine | J | A |
| Example 276 | 4-[5-phenyl-2-[4-(2-pyrrolidin-1-ylethoxymethyl)-1-piperidyl]thieno[2,3-d]pyrimidin-4-yl]morpholine | J | A |
| Example 277 | (2S)-1-[2-[[3-[5-(4-fluorophenyl)thieno[2,3-d]pyrimidin-4-yl]-3-azabicyclo[3.1.0]hexan-6-yl]methoxy]ethyl]pyrrolidine-2-carboxamide | F | A |
| Example 278 | 5-(4-fluorophenyl)-4-[6-[2-[(3R)-3-fluoropyrrolidin-1-yl]ethoxymethyl]-3-azabicyclo[3.1.0]hexan-3-yl]thieno[2,3-d]pyrimidine | F | A |
| Example 279 | 2-chloro-5-(4-fluorophenyl)-4-[4-(2-pyrrolidin-1-ylethoxymethyl)-1-piperidyl]thieno[2,3-d]pyrimidine | I | A |
| Example 280 | N-(2-hydroxyethyl)-5-phenyl-4-[4-(2-pyrrolidin-1-ylethoxymethyl)-1-piperidyl]thieno[2,3-d]pyrimidine-6-carboxamide | D | B |
| Example 281 | [5-phenyl-4-[4-(2-pyrrolidin-1-ylethoxymethyl)-1-piperidyl]thieno[2,3-d]pyrimidin-6-yl]methanol | X | A |
| Example 282 | N-methyl-N-(1-methylpyrrolidin-3-yl)-1-(5-phenylthieno[2,3-d]pyrimidin-4-yl)piperidine-3-carboxamide | K | B |
| Example 283 | 5-cyclohexyl-2-[4-(2-pyrrolidin-1-ylethoxymethyl)-1-piperidyl]thieno[2,3-d]pyrimidine | G | A |
| Example 284 | 5-phenyl-4-[5-(2-pyrrolidin-1-ylethoxy)-2-azabicyclo[2.2.1]heptan-2-yl]thieno[2,3-d]pyrimidine | I | A |
| Example 285 | N-(2-morpholinoethyl)-1-(5-phenylthieno[2,3-d]pyrimidin-4-yl)piperidine-3-carboxamide | K | B |
| Example 286 | 5-phenyl-4-[3-(2-pyrrolidin-1-ylethoxymethyl)-8-azabicyclo[3.2.1]octan-8-yl]thieno[2,3-d]pyrimidine | I | A |

TABLE 1-continued

Summary of synthesis methods and biological activity

| Example | Chemical name | Synthetic Method | IC$_{50}$ |
|---|---|---|---|
| Example 287 | 5-isopropyl-4-[3-(2-pyrrolidin-1-ylethoxymethyl)-8-azabicyclo[3.2.1]octan-8-yl]thieno[2,3-d]pyrimidine | I | A |
| Example 288 | 5-isopropyl-4-[5-(2-pyrrolidin-1-ylethoxy)-2-azabicyclo[2.2.1]heptan-2-yl]thieno[2,3-d]pyrimidine | I | A |
| Example 289 | 5-phenyl-4-[3-(2-pyrrolidin-1-ylethoxy)-8-azabicyclo[3.2.1]octan-8-yl]thieno[2,3-d]pyrimidine | I | A |
| Example 290 | 1-[2-[[2-(5-phenylthieno[2,3-d]pyrimidin-4-yl)-2-azabicyclo[2.2.1]heptan-5-yl]oxy]ethyl]pyrrolidine-3-carboxamide | F | A |
| Example 291 | 4-[5-[2-[(3S)-3-fluoropyrrolidin-1-yl]ethoxy]-2-azabicyclo[2.2.1]heptan-2-yl]-5-phenyl-thieno[2,3-d]pyrimidine | F | A |
| Example 292 | 5-[2-[[2-(5-isopropylthieno[2,3-d]pyrimidin-4-yl)-2-azabicyclo[2.2.1]heptan-5-yl]oxy]ethyl]-2-oxa-5-azabicyclo[2.2.1]heptane | F | B |
| Example 293 | (2R)-1-[2-[[2-(5-phenylthieno[2,3-d]pyrimidin-4-yl)-2-azabicyclo[2.2.1]heptan-5-yl]oxy]ethyl]pyrrolidine-2-carboxamide | F | A |
| Example 294 | 4-[5-[2-[(3S)-3-fluoropyrrolidin-1-yl]ethoxy]-2-azabicyclo[2.2.1]heptan-2-yl]-5-isopropyl-thieno[2,3-d]pyrimidine | F | A |
| Example 295 | 4-[5-[2-[(3R)-3-fluoropyrrolidin-1-yl]ethoxy]-2-azabicyclo[2.2.1]heptan-2-yl]-5-isopropyl-thieno[2,3-d]pyrimidine | F | A |
| Example 296 | 5-phenyl-4-[4-(3-pyrrolidin-1-ylpropoxy)-1-piperidyl]thieno[2,3-d]pyrimidine | F | A |
| Example 297 | 5-isopropyl-4-[3-(2-pyrrolidin-1-ylethoxy)-8-azabicyclo[3.2.1]octan-8-yl]thieno[2,3-d]pyrimidine | I | A |
| Example 298 | [8-(4-morpholino-5-phenyl-thieno[2,3-d]pyrimidin-2-yl)-8-azabicyclo[3.2.1]octan-3-yl]methanol | J | B |
| Example 299 | 8-[4-[4-(methoxymethyl)-1-piperidyl]-5-phenyl-thieno[2,3-d]pyrimidin-2-yl]-8-azabicyclo[3.2.1]octan-3-ol | J | B |
| Example 300 | 4-[2-[3-(methoxymethyl)-8-azabicyclo[3.2.1]octan-8-yl]-5-phenyl-thieno[2,3-d]pyrimidin-4-yl]morpholine | J | B |
| Example 302 | 8-[2-[4-(2-pyrrolidin-1-ylethoxymethyl)-1-piperidyl]thieno[2,3-d]pyrimidin-4-yl]-3-oxa-8-azabicyclo[3.2.1]octane | J | A |
| Example 303 | 3-methyl-N-[5-phenyl-2-[4-(2-pyrrolidin-1-ylethoxymethyl)-1-piperidyl]thieno[2,3-d]pyrimidin-6-yl]butanamide | L | A |
| Example 304 | 2-methyl-N-[5-phenyl-2-[4-(2-pyrrolidin-1-ylethoxymethyl)-1-piperidyl]thieno[2,3-d]pyrimidin-6-yl]propanamide | L | A |
| Example 305 | 4-[5-phenyl-2-[4-(2-pyrrolidin-1-ylethoxymethyl)-1-piperidyl]thieno[2,3-d]pyrimidin-4-yl]morpholine-2-carboxamide | J | A |
| Example 306 | 1-(4-morpholino-5-phenyl-thieno[2,3-d]pyrimidin-2-yl)pyrrolidine-3-carboxamide | J | C |
| Example 307 | 2-(2-azabicyclo[2.2.1]heptan-5-yloxy)-4-[4-(methoxymethyl)-1-piperidyl]-5-phenyl-thieno[2,3-d]pyrimidine | J | A |
| Example 308 | 5-phenyl-4-[4-(2-pyrrolidin-1-ylethoxymethyl)-1-piperidyl]furo[2,3-d]pyrimidine | T | A |
| Example 309 | 1-[4-(2-oxa-5-azabicyclo[2.2.1]heptan-5-yl)-5-phenyl-thieno[2,3-d]pyrimidin-2-yl]pyrrolidine-3-carboxamide | J | C |
| Example 310 | 1-[4-[3-(hydroxymethyl)-8-azabicyclo[3.2.1]octan-8-yl]-5-phenyl-thieno[2,3-d]pyrimidin-2-yl]pyrrolidine-3-carboxamide | J | B |
| Example 311 | 5-(4-pyridyl)-4-[4-(2-pyrrolidin-1-ylethoxymethyl)-1-piperidyl]thieno[2,3-d]pyrimidine | O | B |
| Example 312 | 5-(3-methoxyphenyl)-4-[4-(2-pyrrolidin-1-ylethoxymethyl)-1-piperidyl]thieno[2,3-d]pyrimidine | O | A |
| Example 313 | 4-[4-(2-pyrrolidin-1-ylethoxymethyl)-1-piperidyl]-5-[3-(trifluoromethoxy)phenyl]thieno[2,3-d]pyrimidine | O | A |
| Example 314 | 5-phenyl-4-[4-(2-pyrrolidin-1-ylethoxymethyl)-1-piperidyl]thieno[2,3-d]pyrimidin-2-amine | J | A |
| Example 315 | 5-(3-furyl)-4-[4-(2-pyrrolidin-1-ylethoxymethyl)-1-piperidyl]thieno[2,3-d]pyrimidine | O | A |
| Example 316 | 5-(2-methoxy-3-pyridyl)-4-[4-(2-pyrrolidin-1-ylethoxymethyl)-1-piperidyl]thieno[2,3-d]pyrimidine | O | A |
| Example 317 | 4-[4-(2-pyrrolidin-1-ylethoxymethyl)-1-piperidyl]-5-(3-thienyl)thieno[2,3-d]pyrimidine | O | A |
| Example 318 | N-tert-butyl-2-methyl-4-(5-phenylthieno[2,3-d]pyrimidin-4-yl)but-3-yn-2-amine | H | A |

TABLE 1-continued

Summary of synthesis methods and biological activity

| Example | Chemical name | Synthetic Method | IC$_{50}$ |
|---|---|---|---|
| Example 319 | 5-(1,3-benzodioxol-5-yl)-4-[4-(2-pyrrolidin-1-ylethoxymethyl)-1-piperidyl]thieno[2,3-d]pyrimidine | O | A |
| Example 320 | 5-(2-pyridyl)-4-[4-(2-pyrrolidin-1-ylethoxymethyl)-1-piperidyl]thieno[2,3-d]pyrimidine | O | B |
| Example 321 | N-cyclobutyl-8-(2-cyclopropyl-5-phenyl-thieno[2,3-d]pyrimidin-4-yl)-8-azabicyclo[3.2.1]octan-3-amine | Q | A |
| Example 322 | 4-[3-(azetidin-1-yl)-8-azabicyclo[3.2.1]octan-8-yl]-2-cyclopropyl-5-phenyl-thieno[2,3-d]pyrimidine | Q | A |
| Example 323 | N-[[8-(5-phenylthieno[2,3-d]pyrimidin-4-yl)-8-azabicyclo[3.2.1]octan-3-yl]methyl]cyclobutanamine | A | A |
| Example 324 | 5-(3-pyridyl)-4-[4-(2-pyrrolidin-1-ylethoxymethyl)-1-piperidyl]thieno[2,3-d]pyrimidine | O | B |
| Example 325 | N-cyclobutyl-8-(5-phenylthieno[2,3-d]pyrimidin-4-yl)-8-azabicyclo[3.2.1]octan-3-amine | P | A |
| Example 326 | 4-[3-(azetidin-1-yl)-8-azabicyclo[3.2.1]octan-8-yl]-5-phenyl-thieno[2,3-d]pyrimidine | P | A |
| Example 327 | N-isopropyl-8-(5-phenylthieno[2,3-d]pyrimidin-4-yl)-8-azabicyclo[3.2.1]octan-3-amine | P | A |
| Example 328 | 5-(2-isopropoxy-3-pyridyl)-4-[4-(2-pyrrolidin-1-ylethoxymethyl)-1-piperidyl]thieno[2,3-d]pyrimidine | O | A |
| Example 329 | 5-(2-methoxyphenyl)-4-[4-(2-pyrrolidin-1-ylethoxymethyl)-1-piperidyl]thieno[2,3-d]pyrimidine | O | A |
| Example 330 | N,N-dimethyl-2-[4-[4-(2-pyrrolidin-1-ylethoxymethyl)-1-piperidyl]thieno[2,3-d]pyrimidin-5-yl]benzamide | O | C |
| Example 331 | 5-(2-ethoxy-3-pyridyl)-4-[4-(2-pyrrolidin-1-ylethoxymethyl)-1-piperidyl]thieno[2,3-d]pyrimidine | O | A |
| Example 332 | N,N-dimethyl-3-[4-[4-(2-pyrrolidin-1-ylethoxymethyl)-1-piperidyl]thieno[2,3-d]pyrimidin-5-yl]benzamide | O | B |
| Example 333 | 2-methyl-N-[[8-(5-phenylthieno[2,3-d]pyrimidin-4-yl)-8-azabicyclo[3.2.1]octan-3-yl]methyl]propan-2-amine | A | A |
| Example 334 | N-[[8-(5-phenylthieno[2,3-d]pyrimidin-4-yl)-8-azabicyclo[3.2.1]octan-3-yl]methyl]propan-2-amine | A | A |
| Example 335 | 5-phenyl-4-[3-(pyrrolidin-1-ylmethyl)-8-azabicyclo[3.2.1]octan-8-yl]thieno[2,3-d]pyrimidine | A | A |
| Example 336 | 4-[5-phenyl-2-(trifluoromethyl)thieno[2,3-d]pyrimidin-4-yl]morpholine | Q | B |
| Example 337 | 1-[4-[3-(cyclobutylamino)-8-azabicyclo[3.2.1]octan-8-yl]-5-phenyl-thieno[2,3-d]pyrimidin-2-yl]pyrrolidine-3-carboxamide | Z | B |
| Example 338 | 4-[3-(cyclobutylamino)-8-azabicyclo[3.2.1]octan-8-yl]-5-phenyl-thieno[2,3-d]pyrimidine-2-carbonitrile | Z | A |
| Example 339 | 4-[3-(cyclobutylamino)-8-azabicyclo[3.2.1]octan-8-yl]-N,N-dimethyl-5-phenyl-thieno[2,3-d]pyrimidine-6-carboxamide | R | A |
| Example 340 | 5-phenyl-4-[4-(2-pyrrolidin-1-ylethoxymethyl)-1-piperidyl]-2-(trifluoromethyl)thieno[2,3-d]pyrimidine | Q | A |
| Example 341 | N-cyclobutyl-8-[5-[2-(trifluoromethoxy)phenyl]thieno[2,3-d]pyrimidin-4-yl]-8-azabicyclo[3.2.1]octan-3-amine | S | A |
| Example 342 | N-cyclobutyl-8-[5-(2-methoxyphenyl)thieno[2,3-d]pyrimidin-4-yl]-8-azabicyclo[3.2.1]octan-3-amine | S | A |
| Example 343 | 4-[3-(cyclobutylamino)-8-azabicyclo[3.2.1]octan-8-yl]-N-methyl-5-phenyl-thieno[2,3-d]pyrimidine-6-carboxamide | R | B |
| Example 344 | N-cyclobutyl-8-[5-(o-tolyl)thieno[2,3-d]pyrimidin-4-yl]-8-azabicyclo[3.2.1]octan-3-amine | S | A |
| Example 345 | N-cyclobutyl-8-[5-(2-methoxy-3-pyridyl)thieno[2,3-d]pyrimidin-4-yl]-8-azabicyclo[3.2.1]octan-3-amine | S | A |
| Example 346 | N-cyclobutyl-8-[5-(5-fluoro-2-methoxy-3-pyridyl)thieno[2,3-d]pyrimidin-4-yl]-8-azabicyclo[3.2.1]octan-3-amine | S | B |
| Example 347 | 4-[3-[cyclobutyl(methyl)amino]-8-azabicyclo[3.2.1]octan-8-yl]-N,N-dimethyl-5-phenyl-thieno[2,3-d]pyrimidine-6-carboxamide | R | A |
| Example 348 | 2-(2-azabicyclo[2.2.1]heptan-5-yloxy)-4-[3-methoxy-8-azabicyclo[3.2.1]octan-8-yl]-5-phenyl-thieno[2,3-d]pyrimidine | J | A |
| Example 349 | 8-[2-(2-azabicyclo[2.2.1]heptan-5-yloxy)-5-phenyl-thieno[2,3-d]pyrimidin-4-yl]-3-oxa-8-azabicyclo[3.2.1]octane | J | A |
| Example 350 | N-cyclobutyl-8-[5-(2-methoxyphenyl)thieno[2,3-d]pyrimidin-4-yl]-N-methyl-8-azabicyclo[3.2.1]octan-3-amine | S | A |

TABLE 1-continued

Summary of synthesis methods and biological activity

| Example | Chemical name | Synthetic Method | IC$_{50}$ |
|---|---|---|---|
| Example 351 | N-cyclobutyl-8-[5-(2-methoxy-3-pyridyl)thieno[2,3-d]pyrimidin-4-yl]-N-methyl-8-azabicyclo[3.2.1]octan-3-amine | S | A |
| Example 352 | 2-(2-azabicyclo[2.2.1]heptan-5-yloxy)-4-[3-(methoxymethyl)-8-azabicyclo[3.2.1]octan-8-yl]-5-phenyl-thieno[2,3-d]pyrimidine | J | A |
| Example 353 | N,N-dimethyl-5-phenyl-4-[3-pyrrolidin-1-yl-8-azabicyclo[3.2.1]octan-8-yl]thieno[2,3-d]pyrimidine-6-carboxamide | R | A |
| Example 354 | N-isopropyl-5-phenyl-4-[3-pyrrolidin-1-yl-8-azabicyclo[3.2.1]octan-8-yl]thieno[2,3-d]pyrimidine-6-carboxamide | R | A |
| Example 355 | N-isopropyl-5-phenyl-4-[3-pyrrolidin-1-yl-8-azabicyclo[3.2.1]octan-8-yl]thieno[2,3-d]pyrimidine-6-carboxamide | R | A |
| Example 356 | N,N-dimethyl-5-phenyl-4-[3-(2-pyrrolidin-1-ylethoxymethyl)-8-azabicyclo[3.2.1]octan-8-yl]thieno[2,3-d]pyrimidine-6-carboxamide | D | A |
| Example 357 | N-isopropyl-5-phenyl-4-[3-(2-pyrrolidin-1-ylethoxymethyl)-8-azabicyclo[3.2.1]octan-8-yl]thieno[2,3-d]pyrimidine-6-carboxamide | D | A |
| Example 358 | 2-cyclopropyl-5-(2-methoxyphenyl)-4-[4-(2-pyrrolidin-1-ylethoxymethyl)-1-piperidyl]thieno[2,3-d]pyrimidine | Q | A |
| Example 359 | N-cyclobutyl-8-[5-phenyl-2-(trifluoromethyl)thieno[2,3-d]pyrimidin-4-yl]-8-azabicyclo[3.2.1]octan-3-amine | Q | A |
| Example 360 | 2-cyclopropyl-5-phenyl-4-[4-(2-pyrrolidin-1-ylethoxymethyl)-1-piperidyl]thieno[2,3-d]pyrimidine | Q | A |
| Example 361 | N-methyl-5-phenyl-4-[3-(2-pyrrolidin-1-ylethoxymethyl)-8-azabicyclo[3.2.1]octan-8-yl]thieno[2,3-d]pyrimidine-6-carboxamide | D | A |
| Example 362 | 5-(2-methoxyphenyl)-4-[3-(2-pyrrolidin-1-ylethoxymethyl)-8-azabicyclo[3.2.1]octan-8-yl]thieno[2,3-d]pyrimidine | O | A |
| Example 363 | 5-(2-methoxy-3-pyridyl)-4-[3-(2-pyrrolidin-1-ylethoxymethyl)-8-azabicyclo[3.2.1]octan-8-yl]thieno[2,3-d]pyrimidine | O | A |
| Example 364 | N,N-dimethyl-2-[4-[3-(2-pyrrolidin-1-ylethoxymethyl)-8-azabicyclo[3.2.1]octan-8-yl]thieno[2,3-d]pyrimidin-5-yl]benzamide | O | A |
| Example 365 | [8-[5-(2-methoxy-3-pyridyl)thieno[2,3-d]pyrimidin-4-yl]-8-azabicyclo[3.2.1]octan-3-yl]methanol | S | B |
| Example 366 | 2-(2-azabicyclo[2.2.1]heptan-5-yloxy)-4-[3-(methoxymethyl)-8-azabicyclo[3.2.1]octan-8-yl]-N,N-dimethyl-5-phenyl-thieno[2,3-d]pyrimidine-6-carboxamide | U | B |
| Example 367 | N-[[8-[5-(2-methoxyphenyl)thieno[2,3-d]pyrimidin-4-yl]-8-azabicyclo[3.2.1]octan-3-yl]methyl]cyclobutanamine | S | A |
| Example 368 | 1-[5-phenyl-4-[4-(2-pyrrolidin-1-ylethoxymethyl)-1-piperidyl]thieno[2,3-d]pyrimidin-6-yl]imidazolidin-2-one | E | A |
| Example 369 | 2-[5-phenyl-4-[4-(2-pyrrolidin-1-ylethoxymethyl)-1-piperidyl]thieno[2,3-d]pyrimidin-6-yl]-1,2-thiazolidine 1,1-dioxide | E | A |
| Example 370 | 1-(2-ethyl-5-phenyl-thieno[2,3-d]pyrimidin-4-yl)-N,N-dimethyl-piperidin-4-amine | AA | A |

TABLE 2

Summary of synthesis methods and biological activity

| Example | Chemical name | Synthetic Method | IC$_{50}$ Q-Patch |
|---|---|---|---|
| Example 371 | [8-[4-(3-methoxy-8-azabicyclo[3.2.1]octan-8-yl)-5-(2-methoxyphenyl)thieno[2,3-d]pyrimidin-2-yl]-8-azabicyclo[3.2.1]octan-3-yl]methanol | J | B |
| Example 372 | 8-[4-[3-(methoxymethyl)-8-azabicyclo[3.2.1]octan-8-yl]-5-(2-methoxyphenyl)thieno[2,3-d]pyrimidin-2-yl]-8-azabicyclo[3.2.1]octan-3-ol | J | A |

TABLE 2-continued

Summary of synthesis methods and biological activity

| Example | Chemical name | Synthetic Method | IC$_{50}$ Q-Patch |
|---|---|---|---|
| Example 373 | 1-[5-(2-chlorophenyl)-4-(3-methoxy-8-azabicyclo[3.2.1]octan-8-yl)thieno[2,3-d]pyrimidin-2-yl]piperidine-3-carboxamide | J | A |
| Example 374 | 1-[5-(2-chlorophenyl)-2-(3-methoxy-8-azabicyclo[3.2.1]octan-8-yl)thieno[2,3-d]pyrimidin-4-yl]piperidine-3-carboxamide | J | A |
| Example 375 | 8-[5-(2-chlorophenyl)-4-(3-methoxy-8-azabicyclo[3.2.1]octan-8-yl)thieno[2,3-d]pyrimidin-2-yl]-8-azabicyclo[3.2.1]octan-3-ol | J | B |
| Example 376 | 1-[4-[3-(methoxymethyl)-8-azabicyclo[3.2.1]octan-8-yl]-5-(2-methoxyphenyl)thieno[2,3-d]pyrimidin-2-yl]pyrrolidine-3-carboxamide | J | B |
| Example 377 | 8-[4-(3-methoxy-8-azabicyclo[3.2.1]octan-8-yl)-5-(2-methoxyphenyl)thieno[2,3-d]pyrimidin-2-yl]-8-azabicyclo[3.2.1]octan-3-ol | J | B |
| Example 378 | 4-[4-[3-(methoxymethyl)-8-azabicyclo[3.2.1]octan-8-yl]-5-(2-methoxyphenyl)thieno[2,3-d]pyrimidin-2-yl]piperazin-2-one | J | B |
| Example 379 | 8-[4-(3-methoxy-8-azabicyclo[3.2.1]octan-8-yl)-5-(2-methoxyphenyl)thieno[2,3-d]pyrimidin-2-yl]-3-oxa-8-azabicyclo[3.2.1]octane | J | B |
| Example 380 | 4-[4-(3-methoxy-8-azabicyclo[3.2.1]octan-8-yl)-5-(2-methoxyphenyl)thieno[2,3-d]pyrimidin-2-yl]piperazin-2-one | J | A |
| Example 390 | 1-[4-(3-methoxy-8-azabicyclo[3.2.1]octan-8-yl)-5-(2-methoxyphenyl)thieno[2,3-d]pyrimidin-2-yl]piperidine-3-carboxamide | J | B |
| Example 391 | 4-[5-(2-chlorophenyl)-4-(3-methoxy-8-azabicyclo[3.2.1]octan-8-yl)thieno[2,3-d]pyrimidin-2-yl]piperazin-2-one | J | B |
| Example 392 | 4-[5-(2-chlorophenyl)-4-(3-methoxy-8-azabicyclo[3.2.1]octan-8-yl)thieno[2,3-d]pyrimidin-2-yl]piperazine-2-carboxamide | J | A |
| Example 393 | 1-[5-(2-chlorophenyl)-2-[3-(hydroxymethyl)-8-azabicyclo[3.2.1]octan-8-yl]thieno[2,3-d]pyrimidin-4-yl]piperidine-3-carboxamide | J | A |
| Example 394 | 4-[4-(3-methoxy-8-azabicyclo[3.2.1]octan-8-yl)-5-(2-methoxyphenyl)thieno[2,3-d]pyrimidin-2-yl]piperazine-2-carboxamide | J | A |
| Example 395 | 8-[2-[3-(methoxymethyl)-8-azabicyclo[3.2.1]octan-8-yl]-5-(2-methoxyphenyl)thieno[2,3-d]pyrimidin-4-yl]-3-oxa-8-azabicyclo[3.2.1]octane | J | B |
| Example 396 | 1-[4-(3-methoxy-8-azabicyclo[3.2.1]octan-8-yl)-5-(2-methoxyphenyl)thieno[2,3-d]pyrimidin-2-yl]pyrrolidine-3-carboxamide | J | A |
| Example 397 | 8-[2-(3-methoxy-8-azabicyclo[3.2.1]octan-8-yl)-5-(2-methoxyphenyl)thieno[2,3-d]pyrimidin-4-yl]-3-oxa-8-azabicyclo[3.2.1]octane | J | A |
| Example 398 | 4-[5-(2-methoxyphenyl)-4-(3-oxa-8-azabicyclo[3.2.1]octan-8-yl)thieno[2,3-d]pyrimidin-2-yl]piperazine-2-carboxamide | J | A |
| Example 399 | 1-[5-(2-methoxyphenyl)-4-(3-oxa-8-azabicyclo[3.2.1]octan-8-yl)thieno[2,3-d]pyrimidin-2-yl]piperidine-3-carboxamide | J | B |
| Example 400 | 8-[5-(2-methoxyphenyl)-4-(3-oxa-8-azabicyclo[3.2.1]octan-8-yl)thieno[2,3-d]pyrimidin-2-yl]-8-azabicyclo[3.2.1]octan-3-ol | J | B |
| Example 401 | 1-[5-(2-methoxyphenyl)-4-(3-oxa-8-azabicyclo[3.2.1]octan-8-yl)thieno[2,3-d]pyrimidin-2-yl]pyrrolidine-3-carboxamide | J | B |
| Example 402 | 8-[5-(2-methoxyphenyl)-2-(3-oxa-8-azabicyclo[3.2.1]octan-8-yl)thieno[2,3-d]pyrimidin-4-yl]-3-oxa-8-azabicyclo[3.2.1]octane | J | B |
| Example 403 | 4-[5-(2-methoxyphenyl)-4-(3-oxa-8-azabicyclo[3.2.1]octan-8-yl)thieno[2,3-d]pyrimidin-2-yl]piperazin-2-one | J | A |
| Example 404 | 1-[5-(2-methoxyphenyl)-4-(3-oxa-8-azabicyclo[3.2.1]octan-8-yl)thieno[2,3-d]pyrimidin-2-yl]pyrrolidin-3-ol | J | A |
| Example 405 | 4-(3-methoxy-8-azabicyclo[3.2.1]octan-8-yl)-5-(2-methoxyphenyl)thieno[2,3-d]pyrimidine-2-carbonitrile | J | B |
| Example 406 | 4-[3-(methoxymethyl)-8-azabicyclo[3.2.1]octan-8-yl]-5-(2-methoxyphenyl)thieno[2,3-d]pyrimidine-2-carbonitrile | J | A |

TABLE 2-continued

Summary of synthesis methods and biological activity

| Example | Chemical name | Synthetic Method | IC$_{50}$ Q-Patch |
|---|---|---|---|
| Example 407 | 2,4-bis(3-methoxy-8-azabicyclo[3.2.1]octan-8-yl)-5-(2-methoxyphenyl)thieno[2,3-d]pyrimidine | J | B |
| Example 408 | 4-[5-(2-chlorophenyl)-4-(3-methoxy-8-azabicyclo[3.2.1]octan-8-yl)thieno[2,3-d]pyrimidin-2-yl]morpholine-2-carboxamide | J | A |
| Example 409 | 4-[4-(3-methoxy-8-azabicyclo[3.2.1]octan-8-yl)-5-(2-methoxyphenyl)thieno[2,3-d]pyrimidin-2-yl]morpholine-2-carboxamide | J | B |
| Example 410 | 1-[5-(2-chlorophenyl)-4-(3-oxa-8-azabicyclo[3.2.1]octan-8-yl)thieno[2,3-d]pyrimidin-2-yl]piperidine-3-carboxamide | J | B |
| Example 411 | 1-[5-(2-chlorophenyl)-2-(3-oxa-8-azabicyclo[3.2.1]octan-8-yl)thieno[2,3-d]pyrimidin-4-yl]piperidine-3-carboxamide | J | B |
| Example 412 | 1-[5-(2-chlorophenyl)-2-(3-hydroxy-8-azabicyclo[3.2.1]octan-8-yl)thieno[2,3-d]pyrimidin-4-yl]pyrrolidine-3-carboxamide | J | B |
| Example 413 | 4-[2-[3-(hydroxymethyl)-8-azabicyclo[3.2.1]octan-8-yl]-5-(2-methoxyphenyl)thieno[2,3-d]pyrimidin-4-yl]piperazin-2-one | J | A |
| Example 414 | 1-[2-(3-hydroxy-8-azabicyclo[3.2.1]octan-8-yl)-5-(2-methoxyphenyl)thieno[2,3-d]pyrimidin-4-yl]pyrrolidine-3-carboxamide | J | B |
| Example 415 | 1-[5-(2-chlorophenyl)-2-(3-oxa-8-azabicyclo[3.2.1]octan-8-yl)thieno[2,3-d]pyrimidin-4-yl]pyrrolidine-3-carboxamide | J | B |
| Example 416 | 4-[5-(2-chlorophenyl)-4-(3-oxa-8-azabicyclo[3.2.1]octan-8-yl)thieno[2,3-d]pyrimidin-2-yl]piperazine-2-carboxamide | J | A |
| Example 417 | 4-[5-(2-chlorophenyl)-2-(3-oxa-8-azabicyclo[3.2.1]octan-8-yl)thieno[2,3-d]pyrimidin-4-yl]piperazine-2-carboxamide | J | B |
| Example 418 | 4-[5-(2-methoxyphenyl)-4-(3-oxa-8-azabicyclo[3.2.1]octan-8-yl)thieno[2,3-d]pyrimidin-2-yl]morpholine-2-carboxamide | J | B |
| Example 419 | 4-[5-(2-methoxyphenyl)-2-(3-oxa-8-azabicyclo[3.2.1]octan-8-yl)thieno[2,3-d]pyrimidin-4-yl]morpholine-2-carboxamide | J | A |
| Example 420 | 4-[5-(2-chlorophenyl)-4-(3-oxa-8-azabicyclo[3.2.1]octan-8-yl)thieno[2,3-d]pyrimidin-2-yl]morpholine-2-carboxamide | J | A |
| Example 421 | 8-[5-(2-chlorophenyl)-4-(3-oxa-8-azabicyclo[3.2.1]octan-8-yl)thieno[2,3-d]pyrimidin-2-yl]-8-azabicyclo[3.2.1]octan-3-ol | J | A |
| Example 422 | 1-[5-(2-chlorophenyl)-4-(3-oxa-8-azabicyclo[3.2.1]octan-8-yl)thieno[2,3-d]pyrimidin-2-yl]pyrrolidine-3-carboxamide | J | B |
| Example 423 | 8-[5-(2-chlorophenyl)-2-(3-oxa-8-azabicyclo[3.2.1]octan-8-yl)thieno[2,3-d]pyrimidin-4-yl]-3-oxa-8-azabicyclo[3.2.1]octane | J | B |
| Example 424 | 4-[5-(2-chlorophenyl)-4-(3-oxa-8-azabicyclo[3.2.1]octan-8-yl)thieno[2,3-d]pyrimidin-2-yl]piperazin-2-one | J | A |
| Example 425 | 8-[5-(2-chlorophenyl)-2-morpholino-thieno[2,3-d]pyrimidin-4-yl]-3-oxa-8-azabicyclo[3.2.1]octane | J | A |
| Example 426 | 1-[5-(2-chlorophenyl)-4-(3-oxa-8-azabicyclo[3.2.1]octan-8-yl)thieno[2,3-d]pyrimidin-2-yl]pyrrolidin-3-ol | J | A |
| Example 427 | N-[[8-[5-(2-methoxy-3-pyridyl)thieno[2,3-d]pyrimidin-4-yl]-8-azabicyclo[3.2.1]octan-3-yl]methyl]cyclobutanamine | S | A |

REFERENCES

Berg, Tom Christian; Bakken, Vebjoern; Gundersen, Lise-Lotte; Petersen, Dirk Cyclization and rearrangement products from coupling reactions between terminal o-alkynylphenols or o-ethynyl(hydroxymethyl)benzene and 6-halopurinesTetrahedron, 2006, vol. 62, #25 p. 6121-6131.

Jingjun yin, Buchwald, Stephen L.; Palladium-Catalyzed Intermolecular Coupling of Aryl Halides and Amides; Org. Lett. 2000, Vol. 2, (8), p. 1101-1104. Munchof et al., Design and SAR of thienopyrimidine and thienopyridine inhibitors of VEGFR-2 kinase activity. Bioorganic & Medicinal Chemistry Letters, 14(1), 21-24, 2004.

Barker et al., Thienopyridines Part 6. Synthesis and nucleophilic substitution of some chlorothieno[2,3b]pyridine derivatives and comparison with the analogous quinoline compounds. J. Chem. Res. (Miniprint), 1985, 2501-2509.

Charvát et al., Diethyl Acetonedicarboxylate—a Precursor for the Synthesis of new Substituted 4-Aminoquinolines and Fused 4-Aminopyridines. Monatsheft. Chem. 126, 333-340, 1995.

Gewald et al., Synthesen von 4-Amino-thieno[2,3-b]pyridinen, Monatsheft. Chem. 110, 1189-1196, 1979.

Chinchilla, Rafael, and Njera, Carmen, The Sonogashira Reaction: A Booming Methodology in Synthetic Organic Chemistry; Chem. Rev., 2007, 107 (3), pp 874-922.

Greene et al., Protective groups in organic synthesis, 3$^{rd}$ edn, Wiley & Sons, 1999.

Han et al, Efficient and library-friendly synthesis of furo- and thieno[2,3-d]pyrimidin-4-amine derivatives by microwave irradiation, Tett. Lett., 51, 629-632, 2010.

Jang et al, Synthesis immunosuppressive activity and structure-activity relationship study of a new series of 4-N-piperazinyl-thieno[2,3-d]pyrimidine analogues, Bioorg. Med. Chem. Lett., 20, 844-847, 2010.

Modica et al., Synthesis and binding properties of novel selective 5HT$_3$ receptor ligands, Bioorg. Med. Chem. Lett., 12, 3891-3901, 2004.

Tasler et al., Thienopyrimidines as β-adrenoreceptor agonists: Hit to lead optimization, Bioorg. Med. Chem. Lett., 20, 6108-6115, 2010.

Gorja et al., C≡C (alkynylation) vs C—O (ether) bond formation under Pd/C≡Cu catalysis: synthesis andpharmacological evaluation of 4-alkynylthieno[2,3-d]pyrimidines, Beilstein J. Org. Chem., 7, 338-345, 2011.

(1973). The sick sinus syndrome. Br Med J2, 677-678.

ALANIS J, GONZALEZ H, & LOPEZ E (1958). The electrical activity of the bundle of His. *J Physiol* 142, 127-140.

ALANIS J, LOPEZ E, MANDOKI J J, & Pilar G (1959). Propagation of impulses through the atrioventricular node. *Am J Physiol* 197, 1171-1174.

Altomare C, Barbuti A, Viscomi C, Baruscotti M, & DiFrancesco D (2000). Effects of dronedarone on Acetylcholine-activated current in rabbit SAN cells. *Br J Pharmacol* 130, 1315-1320.

Appel, Rolf (1975). Tertiary phosphane/tetrachloroethane, a versatile reagent for chlorination, dehydration and P—N linkage, *Angew. Chem. Intl. Ed. Eng.*, 14 (12), 801-811.

Armstrong C M & Hille B (1998). Voltage-gated ion channels and electrical excitability. *Neuron* 20, 371-380.

Belardinelli L, Shryock J C, Song Y, Wang D, & Srinivas M (1995). Ionic basis of the electrophysiological actions of adenosine on cardiomyocytes. *FASEB J* 9, 359-365.

Borchard R, Van B M, Wickenbrock I, Prull M W, Pott L, & Trappe H J. [Inhibition of the muscarinic potassium current by KB130015, a new antiarrhythmic agent to treat atrial fibrillation]. Med. Klin. (Munich) 100[1,1], 697-703. 2005.
Ref Type: Abstract Bosch R F, Zeng X, Grammer J B, Popovic K, Mewis C, & Kuhlkamp V (1999). Ionic mechanisms of electrical remodeling in human atrial fibrillation. *Cardiovascular Research* 44, 121-131.

Brodde O E & Michel M C (1999). Adrenergic and muscarinic receptors in the human heart. *Pharmacol Rev* 51, 651-690.

Brundel B J, Van Gelder I C, Henning R, Tieleman R G, Tuinenburg A E, Wietses M, Grndjean J G, Van Gilst W H, & Crijns H J (2001a). Alterations in potassium channel gene expression in atria of patients with persistent and paroxysmal atrial fibrillation: differential regulation of protein and mRNA levels for K+ channels. *ACC Current Journal Review* 10, 71-72.

Brundel B J, Van G, Henning R H, Tieleman R G, Tuinenburg A E, Wietses M, Grandjean J G, Van G, & Crijns H J (2001b). Ion channel remodeling is related to intraoperative atrial effective refractory periods in patients with paroxysmal and persistent atrial fibrillation. *Circulation* 103, 684-690.

Brundel B J J M, Ausma J, van Gelder I C, Van Der Want J J L, Van Gilst W H, Crijns H J G M, & Henning R H (2002a). Activation of proteolysis by calpains and structural changes in human paroxysmal and persistent atrial fibrillation. *Cardiovascular Research* 54, 380-389.

Brundel B J J M, Henning R H, Kamping a HH, van Gelder I C, & Crijns H J G M (2002b). Molecular mechanisms of remodeling in human atrial fibrillation. *Cardiovascular Research* 54, 315-324.

Burashnikov A & Antzelevitch C (2006). Late-phase 3 EAD. A unique mechanism contributing to initiation of atrial fibrillation. *Pacing Clin Electrophysiol* 29, 290-295.

Burashnikov A, Sicouri S, Di Diego J M, Belardinelli L, & Antzelevitch C (2010). Synergistic effect of the combination of ranolazine and dronedarone to suppress atrial fibrillation. *J Am Coll Cardiol* 56, 1216-1224.

Camerino D C, Desaphy J F, Tricarico D, Pierno S, & Liantonio A (2008). Therapeutic approaches to ion channel diseases. *Adv Genet.* 64, 81-145.

Cha T J, Ehrlich J R, Chartier D, Qi X Y, Xiao L, & Nattel S (2006). Kir3-based inward rectifier potassium current: potential role in atrial tachycardia remodeling effects on atrial repolarization and arrhythmias. *Circulation* 113, 1730-1737.

Chan K W, Langan M N, Sui J L, Kozak J A, Pabon A, Ladias J A, & Logothetis D E (1996). A recombinant inwardly rectifying potassium channel coupled to GTP— binding proteins. *The Journal Of General Physiology* 107, 381-397.

Chiou C W, Eble J N, & Zipes D P (1997). Efferent vagal innervation of the canine atria and sinus and atrioventricular nodes. The third fat pad. *Circulation* 95, 2573-2584.

Colatsky T J, Follmer C H, & Starmer C F (1990). Channel specificity in antiarrhythmic drug action. Mechanism of potassium channel block and its role in suppressing and aggravating cardiac arrhythmias. *Circulation* 82, 2235-2242.

Corey S & CLAPHAM D E (1998). Identification of native atrial G-protein-regulated inwardly rectifying K$^+$ (GIRK4) channel homomultimers. *J Biol Chem* 273, 27499-27504.

Corey S, Krapivinsky G, Krapivinsky L, & CLAPHAM D E (1998). Number and stoichiometry of subunits in the native atrial G-protein-gated K$^+$ channel, I$_{KACh}$. *J Biol Chem* 273, 5271-5278.

Coumel P (1994). Paroxysmal atrial fibrillation: a disorder of autonomic tone?*Eur Heart J* 15 Suppl A, 9-16.

Coumel P (1996). Autonomic influences in atrial tachyarrhythmias. *J Cardiovasc Electrophysiol* 7, 999-1007.

Dhar M S & Plummer H K, III (2006). Protein expression of G-protein inwardly rectifying potassium channels (GIRK) in breast cancer cells. *BMC Physiol* 6, 8.

Dobrev D, Friedrich A, Voigt N, Jost N, Wettwer E, Christ T, Knaut M, & Ravens U (2005). The G protein-gated potassium current I($_{K,ACh}$) is constitutively active in patients with chronic atrial fibrillation. *Circulation* 112, 3697-3706.

Dobrev D, Graf E, Wettwer E, Himmel H M, Hala O, Doerfel C, Christ T, Schuler S, & Ravens U (2001). Molecular basis of downregulation of G-protein-coupled inward rectifying K$^+$ current (I$_{K,ACh}$) in chronic human atrial fibrillation: decrease in GIRK4 mRNA correlates with reduced I$_{K,ACh}$ and muscarinic receptor-mediated shortening of action potentials. *Circulation* 104, 2551-2557.

Dobrzynski H, Boyett M R, & Anderson R H (2007). New insights into pacemaker activity: promoting understanding of sick sinus syndrome. *Circulation* 115, 1921-1932.

Drici M D, Diochot S, Terrenoire C, Romey G, & Lazdunski M (2000). The bee venom peptide tertiapin underlines the role of IKACh in acetylcholine-induced atrioventricular blocks. *Br J Pharmacol* 131, 569-577.

Duprat F, Lesage F, Guillemare E, Fink M, Hugnot J P, Bigay J, Lazdunski M, Romey G, & Barhanin J (1995). Heterologous multimeric assembly is essential for $K^+$ channel activity of neuronal and cardiac G-protein-activated inward rectifiers. *Biochem Biophys Res Commun* 212, 657-663.

Ehrlich J R (2008). Inward rectifier potassium currents as a target for atrial fibrillation therapy. *J Cardiovasc Pharmacol* 52, 129-135.

Ehrlich J R, Cha T J, Zhang L, Chartier D, Villeneuve L, Hebert T E, & Nattel S (2004). Characterization of a hyperpolarization-activated time-dependent potassium current in canine cardiomyocytes from pulmonary vein myocardial sleeves and left atrium. *J Physiol* 557, 583-597.

Ehrlich J R, Nattel S, & Hohnloser S H (2007). Novel antiarrhythmic drugs for atrial fibrillation management. *Curr Vasc Pharmacol* 5, 185-195.

Ezekowitz M D, Aikens T H, Brown A, & Ellis Z (2010). The evolving field of stroke prevention in patients with atrial fibrillation. *Stroke* 41, S17-S20.

Ferrer J, Nichols C G, Makhina E N, SALKOFF L, Bernstein J, Gerhard D, Wasson J, Ramanadham S, & Permutt A (1995). Pancreatic Islet Cells Express a Family of Inwardly Rectifying K Channel Subunits Which Interact to Form G-protein-activated Channels. *J Biol Chem* 270, 26086-26091.

Ferrer M I (1968). The sick sinus syndrome in atrial disease. *JAMA* 206, 645-646.

Ford J W, Stevens E B, Treherne J M, Packer J, & Bushfield M (2002). Potassium channels: gene family, therapeutic relevance, high-throughput screening technologies and drug discovery. *Prog Drug Res* 58, 133-168.

Gaborit N, Le B S, Szuts V, Varro A, Escande D, Nattel S, & Demolombe S (2007a). Regional and Tissue Specific Transcript Signatures of Ion Channel Genes in the Non-diseased Human Heart. *J Physiol*.

Gaborit N, Le B S, Szuts V, Varro A, Escande D, Nattel S, & Demolombe S (2007b). Regional and tissue specific transcript signatures of ion channel genes in the non-diseased human heart. *J Physiol* 582, 675-693.

Geibel J P (2005). Role of potassium in acid secretion. *World J Gastroenterol* 11, 5259-5265.

Gögelein H, Brendel J, Steinmeyer K, Strubing C, Picard N, Rampe D, Kopp K, Busch A E, & Bleich M (2004). Effects of the atrial antiarrhythmic drug AVE0118 on cardiac ion channels. *Naunyn Schmiedebergs Arch Pharmacol* 370, 183-192.

Gomes J A, Kang P S, Matheson M, Gough W B, Jr., & El-Sherif N (1981). Coexistence of sick sinus rhythm and atrial flutter-fibrillation. *Circulation* 63, 80-86.

Gregerson K A, Flagg T P, O'Neill T J, Anderson M, Lauring O, Horel J S, & Welling P A (2001). Identification of G protein-coupled, inward rectifier potassium channel gene products from the rat anterior pituitary gland. *Endocrinology* 142, 2820-2832.

Guillemare E, Marion A, Nisato D, & Gautier P (2000). Inhibitory effects of dronedarone on muscarinic $K^+$ current in guinea pig atrial cells. *J Cardiovasc Pharmacol* 36, 802-805.

Gutman G A, Chandy K G, Adelman J P, Aiyar J, Bayliss D A, Clapham D E, Covarriubias M, Desir G V, Furuichi K, & Ganetzky et a (2003). International Union of Pharmacology. XLI. Compendium of voltage-gated ion channels: potassium channels. *Pharmacological Reviews* 55, 583-586.

Haissaguerre M, Jais P, Shah D C, Takahashi A, Hocini M, Quiniou G, Garrigue S, Le M A, Le M P, & Clementy J (1998). Spontaneous initiation of atrial fibrillation by ectopic beats originating in the pulmonary veins. *N Engl J Med* 339, 659-666.

Han S Y & Bolter C P (2011). The muscarinic-activated potassium channel always participates in vagal slowing of the guinea-pig sinoatrial pacemaker. *Auton Neurosci* 164, 96-100.

Hara Y & Kizaki K (2002). Antimalarial drugs inhibit the acetylcholine-receptor-operated potassium current in atrial myocytes. *Heart Lung Circ* 11, 112-116.

Hashimoto N, Yamashita T, Fujikura N, & Tsuruzoe N (2007). NIP-141, a multiple ion channel blocker, terminates aconitine-induced atrial fibrillation and prevents the rapid pacing-induced atrial effective refractory period shortening in dogs. *Europace* 9, 246-251.

Hashimoto N, Yamashita T, & Tsuruzoe N (2006). Tertiapin, a selective $I_{KACh}$ blocker, terminates atrial fibrillation with selective atrial effective refractory period prolongation. *Pharmacol Res* 54, 136-141.

Hashimoto N, Yamashita T, & Tsuruzoe N (2008). Characterization of In Vivo and In Vitro Electrophysiological and Antiarrhythmic Effects of a Novel $I_{KACh}$ Blocker, NIP-151: A Comparison With an $I_{Kr}$-Blocker Dofetilide. *J Cardiovasc Pharmacol* 51, 162-169.

Hedin K E, Lim N F, & CLAPHAM D E (1996). Cloning of a *Xenopus laevis* inwardly rectifying K+ channel subunit that permits GIRK1 expression of IKACh currents in oocytes. *Neuron* 16, 423-429.

Hibino H, Inanobe A, Furutani K, Murakami S, Findlay I, & Kurachi Y (2010). Inwardly rectifying potassium channels: their structure, function, and physiological roles. *Physiol Rev* 90, 291-366.

Hille B, Armstrong C M, & MacKinnon R (1999). Ion channels: from idea to reality. *Nat Med* 5, 1105-1109.

Hollopeter G, Jantzen H M, Vincent D, Li G, England L, Ramakrishnan V, Yang R B, Nurden P, Nurden A, Julius D, & Conley P B (2001). Identification of the platelet ADP receptor targeted by antithrombotic drugs. *Nature* 409, 202-207.

Hong C M, Zheng Q S, Liu X T, Shang F J, Wang H T, & Jiang W R (2009). Effects of autoantibodies against M2 muscarinic acetylcholine receptors on rabbit atria in vivo. *Cardiology* 112, 180-187.

Horikawa-Tanami T, Hirao K, Furukawa T, & Isobe M (2007). Mechanism of the conversion of a pulmonary vein tachycardia to atrial fibrillation in normal canine hearts: role of autonomic nerve stimulation. *J Cardiovasc Electrophysiol* 18, 534-541.

Huang J L, Wen Z C, Lee W L, Chang M S, & Chen S A (1998). Changes of autonomic tone before the onset of paroxysmal atrial fibrillation. *Int J Cardiol* 66, 275-283.

Iwanir S & Reuveny E (2008). Adrenaline-induced hyperpolarization of mouse pancreatic islet cells is mediated by G protein-gated inwardly rectifying potassium (GIRK) channels. *Pflugers Arch*.

Jayachandran J V, Sih H J, Winkle W, Zipes D P, Hutchins G D, & Olgin J E (2000). Atrial fibrillation produced by prolonged rapid atrial pacing is associated with heterogeneous changes in atrial sympathetic innervation. *Circulation* 101, 1185-1191.

Jin W, Klem A M, Lewis J H, & Lu Z (1999). Mechanisms of inward-rectifier K+ channel inhibition by tertiapin-Q. *Biochemistry* 38, 14294-14301.

Jin W & Lu Z (1998). A novel high-affinity inhibitor for inward-rectifier K+ channels. *Biochemistry* 37, 13291-13299.

Jin W & Lu Z (1999). Synthesis of a Stable Form of Tertiapin: A High-Affinity Inhibitor for Inward-Rectifier K+ Channels. *Biochemistry* 38, 14286-14293.

Kabell G, Buchanan L V, Gibson J K, & Belardinelli L (1994). Effects of adenosine on atrial refractoriness and arrhythmias. *Cardiovasc Res* 28, 1385-1389.

Kent K M, Epstein S E, Cooper T, & Jacobowitz D M (1974). Cholinergic innervation of the canine and human ventricular conducting system. Anatomic and electrophysiologic correlations. *Circulation* 50, 948-955.

Kobayashi T, Hirai H, Iino M, Fuse I, Mitsumura K, Washiyama K, Kasai S, & Ikeda K (2009). Inhibitory effects of the antiepileptic drug ethosuximide on G protein-activated inwardly rectifying $K^+$ channels. *Neuropharmacology* 56, 499-506.

Kobayashi T & Ikeda K (2006). G protein-activated inwardly rectifying potassium channels as potential therapeutic targets. *Curr Pharm Des* 12, 4513-4523.

Kobayashi T, Washiyama K, & Ikeda K (2003). Inhibition of G protein-activated inwardly rectifying K+ channels by fluoxetine (Prozac). *Br J Pharmacol* 138, 1119-1128.

Kobayashi T, Washiyama K, & Ikeda K (2004). Inhibition of G protein-activated inwardly rectifying $K^+$ channels by various antidepressant drugs. *Neuropsychopharmacology* 29, 1841-1851.

Kobayashi T, Washiyama K, & Ikeda K (2006). Inhibition of G protein-activated inwardly rectifying $K^+$ channels by the antidepressant paroxetine. *J Pharmacol Sci* 102, 278-287.

Kobayashi T, Washiyama K, & Ikeda K (2010). Inhibition of G-protein-activated inwardly rectifying K+ channels by the selective norepinephrine reuptake inhibitors atomoxetine and reboxetine. *Neuropsychopharmacology* 35, 1560-1569.

Koo S H, Wakili R, Heo J H, Chartier D, Kim H S, Kim S J, Lee J W, Qi X Y, Nattel S, & Cha T J (2010). Role of constitutively active acetylcholine-mediated potassium current in atrial contractile dysfunction caused by atrial tachycardia remodelling. *Europace* 12, 1490-1497.

Koumi S, Arentzen C E, Backer C L, & Wasserstrom J A (1994). Alterations in muscarinic K+ channel response to acetylcholine and to G protein-mediated activation in atrial myocytes isolated from failing human hearts. *Circulation* 90, 2213-2224.

Koumi S & Wasserstrom J A (1994). Acetylcholine-sensitive muscarinic K+ channels in mammalian ventricular myocytes. *Am J Physiol* 266, H1812-H1821.

Kovoor P, Wickman K, Maguire C T, Pu W, Gehrmann J, Berul C I, & Clapham D E (2001). Evaluation of the role of IKACh in atrial fibrillation using a mouse knockout model. *Journal of the American College of Cardiology* 37, 2136-2143.

Krapivinsky G, Gordon E A, Wickman K, Velimirovic B, Krapivinsky L, & Clapham D (1995). The G-protein-gated atrial $K^+$ channel $I_{KACh}$ is a heteromultimer of two inwardly rectifying $K^+$-channel proteins. *Nature* 374, 135-141.

Kurachi Y, Nakajima T, & Sugimoto T (1987). Quinidine inhibition of the muscarine receptor-activated K+ channel current in atrial cells of guinea pig. *Naunyn Schmiedebergs Arch Pharmacol* 335, 216-218.

Liu L & Nattel S (1997). Differing sympathetic and vagal effects on atrial fibrillation in dogs: role of refractoriness heterogeneity. *The American Journal Of Physiology* 273, H805-H816.

Lo L W, Chen Y C, Chen Y J, Wongcharoen W, Lin C I, & Chen S A (2007). Calmodulin kinase II inhibition prevents arrhythmic activity induced by alpha and beta adrenergic agonists in rabbit pulmonary veins. *Eur J Pharmacol* 571, 197-208.

Lomax A E, Rose R A, & Giles W R (2003). Electrophysiological evidence for a gradient of G protein-gated K+ current in adult mouse atria. *Br J Pharmacol* 140, 576-584.

Luscher C & Slesinger P A (2010). Emerging roles for G protein-gated inwardly rectifying potassium (GIRK) channels in health and disease. *Nat Rev Neurosci* 11, 301-315.

Machida T, Hashimoto N, Kuwahara I, Ogino Y, Matsuura J, Yamamoto W, Itano Y, Zamma A, Matsumoto R, Kamon J, Kobayashi T, Ishiwata N, Yamashita T, Ogura T, & Nakaya H (2011). Effects of a highly selective acetylcholine-activated K+ channel blocker on experimental atrial fibrillation. *Circ Arrhythm Electrophysiol* 4, 94-102.

Makary S, Voigt N, Maguy A, Wakili R, Nishida K, Harada M, Dobrev D, & Nattel S (2011). Differential Protein Kinase C Isoform Regulation and Increased Constitutive Activity of Acetylcholine-Regulated Potassium Channels in Atrial Remodeling. *Circ Res*.

Marban E (2002). Cardiac channelopathies. *Nature* 415, 213-218.

Mark M D & Herlitze S (2000). G-protein mediated gating of inward-rectifier K+ channels. *Eur J Biochem* 267, 5830-5836.

Martin P (1977). The influence of the parasympathetic nervous system on atrioventricular conduction. *Circ Res* 41, 593-599.

Mathie A & Veale E L (2007). Therapeutic potential of neuronal two-pore domain potassium-channel modulators. *Curr Opin Investig Drugs* 8, 555-562.

Matsuda T, Ito M, Ishimaru S, Tsuruoka N, Saito T, Iida-Tanaka N, Hashimoto N, Yamashita T, Tsuruzoe N, Tanaka H, & Shigenobu K (2006). Blockade by NIP-142, an Antiarrhythmic Agent, of Carbachol-Induced Atrial Action Potential Shortening and GIRK1/4 Channel. *Journal of Pharmacological Sciences* 101, 303-310.

Miyauchi M, Kobayashi Y, Miyauchi Y, Abe J, Morita N, Iwasaki Y K, Hayashi M, & Takano T (2004). Parasympathetic blockade promotes recovery from atrial electrical remodeling induced by short-term rapid atrial pacing. *Pacing Clin Electrophysiol* 27, 33-37.

Nagasawa H, Fujiki A, Fujikura N, Matsuda T, Yamashita T, & Inoue H (2002). Effects of a novel class III antiarrhythmic agent, NIP-142, on canine atrial fibrillation and flutter. *Circulation Journal: Official Journal Of The Japanese Circulation Society* 66, 185-191.

Novelli G, Predazzi I M, Mango R, Romeo F, Mehta J L, Ezekowitz M D, Aikens T H, Brown A, Ellis Z, Rorsman P, Bokvist K, Ammala C, Arkhammar P, Berggren P O, Larsson O, & Wahlander K (2010). Role of genomics in cardiovascular medicine The evolving field of stroke prevention in patients with atrial fibrillation Activation by adrenaline of a low-conductance G protein-dependent $K^+$ channel in mouse pancreatic B cells. *World J Cardiol* 2, 428-436.

Ogawa M, Zhou S, Tan A Y, Song J, Gholmieh G, Fishbein M C, Luo H, Siegel R J, Karagueuzian H S, Chen L S, Lin S F, & Chen P S (2007). Left stellate ganglion and vagal nerve activity and cardiac arrhythmias in ambulatory dogs with pacing-induced congestive heart failure. *J Am Coil Cardiol* 50, 335-343.

Pappone C, Rosanio S, Oreto G, Tocchi M, Gugliotta F, Vicedomini G, Salvati A, Dicandia C, Mazzone P, Santinelli V, Gulletta S, & Chierchia S (2000). Circumferential radiofrequency ablation of pulmonary vein ostia: A new anatomic approach for curing atrial fibrillation. *Circulation* 102, 2619-2628.

Pappone C, Santinelli V, Manguso F, Vicedomini G, Gugliotta F, Augello G, Mazzone P, Tortoriello V, Landoni G, Zangrillo A, Lang C, Tomita T, Mesas C, Mastella E, & Alfieri O (2004). Pulmonary vein denervation enhances long-term benefit after circumferential ablation for paroxysmal atrial fibrillation. *Circulation* 109, 327-334.

Patterson E, Lazzara R, Szabo B, Liu H, Tang D, Li Y H, Scherlag B J, & Po S S (2006). Sodium-calcium exchange initiated by the Ca2+ transient: an arrhythmia trigger within pulmonary veins. *J Am Coll Cardiol* 47, 1196-1206.

Patterson E, Po S S, Scherlag B J, & Lazzara R (2005). Triggered firing in pulmonary veins initiated by in vitro autonomic nerve stimulation. *Heart Rhythm* 2, 624-631.

Philipson L H, Kuznetsov A, Toth P T, Murphy J F, Szabo G, Ma G H, & Miller R J (1995). Functional expression of an epitope-tagged G protein-coupled K+ channel (GIRK1). *J Biol Chem* 270, 14604-14610.

Plummer H K, III, Yu Q, Cakir Y, & Schuller H M (2004). Expression of inwardly rectifying potassium channels (GIRKs) and beta-adrenergic regulation of breast cancer cell lines. *BMC Cancer* 4, 93.

Po S S, Scherlag B J, Yamanashi W S, Edwards J, Zhou J, Wu R, Geng N, Lazzara R, & Jackman W M (2006). Experimental model for paroxysmal atrial fibrillation arising at the pulmonary vein-atrial junctions. *Heart Rhythm* 3, 201-208.

Rodriguez-Martinez M, rechiga-Figueroa I A, Moreno-Galindo E G, Navarro-Polanco R A, & Sanchez-Chapula J A (2011). Muscarinic-activated potassium current mediates the negative chronotropic effect of pilocarpine on the rabbit sinoatrial node. *Pflugers Arch* 462, 235-243.

Rorsman P, Bokvist K, Ammala C, Arkhammar P, Berggren P O, Larsson O, & Wahlander K (1991). Activation by adrenaline of a low-conductance G protein-dependent K+ channel in mouse pancreatic B cells. *Nature* 349, 77-79.

Sarmast F, Kolli A, Zaitsev A, Parisian K, Dhamoon A S, Guha P K, Warren M, Anumonwo J M, Taffet S M, Berenfeld O, & Jalife J (2003). Cholinergic atrial fibrillation: I(K,ACh) gradients determine unequal left/right atrial frequencies and rotor dynamics. *Cardiovasc Res* 59, 863-873.

Schauerte P, Scherlag B J, Pitha J, Scherlag M A, Reynolds D, Lazzara R, & Jackman W M (2000). Catheter ablation of cardiac autonomic nerves for prevention of vagal atrial fibrillation. *Circulation* 102, 2774-2780.

Scherlag B J, Yamanashi W, Patel U, Lazzara R, & Jackman W M (2005). Autonomically induced conversion of pulmonary vein focal firing into atrial fibrillation. *J Am Coil Cardiol* 45, 1878-1886.

Schotten U, Verheule S, Kirchhof P, & Goette A (2011). Pathophysiological mechanisms of atrial fibrillation: a translational appraisal. *Physiol Rev* 91, 265-325.

Shankar H, Murugappan S, Kim S, Jin J, Ding Z, Wickman K, & Kunapuli S P (2004). Role of G protein-gated inwardly rectifying potassium channels in P2Y12 receptor-mediated platelet functional responses. *Blood* 104, 1335-1343.

Sharifov O F, Fedorov V V, Beloshapko G G, Glukhov A V, Yushmanova A V, & Rosenshtraukh L V (2004). Roles of adrenergic and cholinergic stimulation in spontaneous atrial fibrillation in dogs. *J Am Coll Cardiol* 43, 483-490.

Shieh C C, Coghlan M, Sullivan J P, & Gopalakrishnan M (2000). Potassium channels: molecular defects, diseases, and therapeutic opportunities. *Pharmacol Rev* 52, 557-594.

Sicouri S, Burashnikov A, Belardinelli L, & Antzelevitch C (2009). Synergistic Electrophysiologic and Antiarrhythmic Effects of the Combination of Ranolazine and Chronic Amiodarone in Canine Atria. *Circ Arrhythm Electrophysiol*.

Steinberg J S (2004). Atrial fibrillation: an emerging epidemic? *Heart* 90, 239-240.

Sun H, Xing D, Lloyd J, Hennan J K, & Levesque P C. Abstract 21061: Mild I Kr inhibition Significantly Enhances IKur-induced Selective Prolongation of Atrial Refractoriness. *Circulation* 122, A21061. 2010.
Ref Type: Abstract Takahashi Y, Jais P, Hocini M, Sanders P, Rotter M, Rostock T, Hsu L F, Sacher F, Clementy J, & Haissaguerre M (2006). Shortening of fibrillatory cycle length in the pulmonary vein during vagal excitation. *J Am Coll Cardiol* 47, 774-780.

Tamargo J, Caballero R, Gomez R, Valenzuela C, & Delpon E (2004). Pharmacology of cardiac potassium channels. *Cardiovascular Research* 62, 9-33.

Tan A Y, Li H, Wachsmann-Hogiu S, Chen L S, Chen P S, & Fishbein M C (2006). Autonomic innervation and segmental muscular disconnections at the human pulmonary vein-atrial junction: implications for catheter ablation of atrial-pulmonary vein junction. *J Am Coll Cardiol* 48, 132-143.

Tanaka H & Hashimoto N (2007). A Multiple Ion Channel Blocker, NIP-142, for the Treatment of Atrial Fibrillation. *Cardiovasc Drug Rev* 25, 342-356.

Tellez J O, Dobrzynski H, Greener I D, Graham G M, Laing E, Honjo H, Hubbard S J, Boyett M R, & Billeter R (2006). Differential expression of ion channel transcripts in atrial muscle and sinoatrial node in rabbit. *Circ Res* 99, 1384-1393.

Thery C, Gosselin B, Lekieffre J, & Warembourg H (1977). Pathology of sinoatrial node. Correlations with electrocardiographic findings in 111 patients. *Am Heart J* 93, 735-740.

Voigt N, Maguy A, Yeh Y, Qi X, Ravens U, Dobrev D, & Nattel S (2008). Changes in $I_{K,ACh}$ single-channel activity with atrial tachycardia remodelling in canine atrial cardiomyocytes. *Cardiovascular Research* 77, 35-43.

Voigt N, Rozmaritsa N, Trausch A, Zimniak T, Christ T, Wettwer E, Matschke K, Dobrev D, & Ravens U (2010a). Inhibition of IK,ACh current may contribute to clinical efficacy of class I and class III antiarrhythmic drugs in patients with atrial fibrillation. *Naunyn Schmiedebergs Arch Pharmacol* 381, 251-259.

Voigt N, Trausch A, Knaut M, Matschke K, Varro A, Van Wagoner D R, Nattel S, Ravens U, & Dobrev D (2010b). Left-to-Right Atrial Inward-Rectifier Potassium Current Gradients in Patients with Paroxysmal Versus Chronic Atrial Fibrillation. *Circ Arrhythm Electrophysiol*.

Wagner V, Stadelmeyer E, Riederer M, Regitnig P, Gorischek A, Devaney T, Schmidt K, Tritthart H A, Hirschberg K, Bauernhofer T, & Schreibmayer W (2010). Cloning and characterisation of GIRK1 variants resulting from alternative RNA editing of the KCNJ3 gene transcript in a human breast cancer cell line. *J Cell Biochem* 110, 598-608.

Watanabe Y, Hara Y, Tamagawa M, & Nakaya H (1996). Inhibitory effect of amiodarone on the muscarinic acetylcholine receptor-operated potassium current in guinea pig atrial cells. *J Pharmacol Exp Ther* 279, 617-624.

Wettwer E, Hala O, Christ T, Heubach J F, Dobrev D, Knaut M, Varro A, & Ravens U (2004). Role of $I_{Kur}$ in controlling action potential shape and contractility in the human atrium: influence of chronic atrial fibrillation. *Circulation* 110, 2299-2306.

Wickman K, Karschin C, Karschin A, Picciotto M R, & CLAPHAM D E (2000). Brain localization and behavioral impact of the G-protein-gated K+ channel subunit GIRK4. *J Neurosci* 20, 5608-5615.

Wickman K, NEMEC J, Gendler S J, & CLAPHAM D E (1998). Abnormal heart rate regulation in GIRK4 knockout mice. *Neuron* 20, 103-114.

Wongcharoen W, Chen Y C, Chen Y J, Chen S Y, Yeh H I, Lin C I, & Chen S A (2007). Aging increases pulmonary veins arrhythmogenesis and susceptibility to calcium regulation agents. *Heart Rhythm* 4, 1338-1349.

Woodward R, Stevens E B, & Murrell-Lagnado R D (1997). Molecular determinants for assembly of G-protein-activated inwardly rectifying K+ channels. *J Biol Chem* 272, 10823-10830.

Workman A J, Kane K A, & Rankin A C (2008). Cellular bases for human atrial fibrillation. *Heart Rhythm* 5, S1-S6.

Wulff H, Castle N A, & Pardo L A (2009). Voltage-gated potassium channels as therapeutic targets. *Nat Rev Drug Discov* 8, 982-1001.

Wulff H & Zhorov B S (2008). K+ Channel Modulators for the Treatment of Neurological Disorders and Autoimmune Diseases. *Chem. Rev* 108, 1744-1773.

Wulfsen I, Hauber H P, Schiemann D, Bauer C K, & Schwarz J R (2000). Expression of mRNA for voltage-dependent and inward-rectifying K channels in GH3/B6 cells and rat pituitary. *J Neuroendocrinol* 12, 263-272.

Yamashita T, Murakawa Y, Sezaki K, Inoue M, Hayami N, Shuzui Y, & Omata M (1997). Circadian variation of paroxysmal atrial fibrillation. *Circulation* 96, 1537-1541.

Yang D, Xi Y, Ai T, Wu G, Sun J, Razavi M, Delapasse S, Shurail M, Gao L, Mathuria N, Elayda M, & Cheng J (2011). Vagal stimulation promotes atrial electrical remodeling induced by rapid atrial pacing in dogs: evidence of a noncholinergic effect. *Pacing Clin Electrophysiol* 34, 1092-1099.

Yoshimoto Y, Fukuyama Y, Horio Y, Inanobe A, Gotoh M, & Kurachi Y (1999). Somatostatin induces hyperpolarization in pancreatic islet alpha cells by activating a G protein-gated K+ channel. *FEBS Lett* 444, 265-269.

Zhang C, Yuan G H, Cheng Z F, Xu M W, Hou L F, & Wei F P (2009). The Single Nucleotide Polymorphisms of Kir3.4 Gene and Their Correlation with Lone Paroxysmal Atrial Fibrillation in Chinese Han Population. *Heart Lung Circ*.

The invention claimed is:
1. A compound of formula (I)

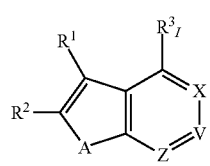

(I)

or a pharmaceutically acceptable salt, solvate, or hydrate thereof, wherein:
A is S;
X is N;
V is $CR^3{}_{III}$;
Z is N;

$R^1$ is selected from optionally substituted alkyl, optionally substituted cycloalkyl, optionally substituted aryl, and optionally substituted heteroaryl;

$R^2$ is selected from H, halo, —CN, trifluoromethyl, optionally substituted alkyl, optionally substituted alkoxy, $NR^4R^5$, —$NR^6C(O)R^7$, —$NR^6S(O)_2R^7$, —$S(O)_2NR^4R'$, —$CONR^4R^5$, —$CO_2R^7$, optionally substituted oxazolinyl, —$SR^{14}$, —$S(O)R^{14}$ and —$S(O)_2R^{14}$;

$R^3{}_I$ is $(NR^aR^b)$-J;

$R^3{}_{III}$ is selected from H, halo, —CN, trifluoromethyl, optionally substituted alkyl, optionally substituted alkoxy, optionally substituted heterocycloalkoxy, optionally substituted heterocycloalkylalkyl, —$NR^6C(O)R^7$, —$NR^6S(O)_2R^7$, —$S(O)_2NR^4R^5$, —$CONR^4R^5$, optionally substituted -alkylene-$CONR^4R^5$, —$CO_2R^7$, —$NR^{10}R^{11}$, —C≡C-J, optionally substituted cycloalkyl-J and —$(NR^cR^d)$-J;

wherein $R^a$ and $R^b$ are linked to form an optionally substituted 4 to 7 membered heterocycloalkyl ring, which is optionally bridged by a bond, optionally substituted $C_{1-2}$alkylene, —$NR^6$—, —O—, or —$S(O)_z$—, wherein the optionally bridged, optionally substituted heterocycloalkyl ring is selected from the group consisting of azetidinyl, pyrrolidinyl, piperidinyl, morpholinyl, tetrahydro-1,3-oxazinyl, hexahydropyrimidinyl, 1,4-thiazanyl, azepanyl, 1,4-oxaazepanyl, and 1,4-thieazepanyl;

wherein $R^c$ and $R^d$ are linked to form an optionally substituted 4 to 7 membered heterocycloalkyl ring, which is optionally bridged by a bond, optionally substituted $C_{1-2}$alkylene, —$NR^6$—, —O—, or —$S(O)_z$—;

J is —$(CR^{12}R^{13})_q$-L-M-W,
wherein
q is 0, 1 or 2;
L is —O—;
M is —$(CR^{12}R^{13})_t$;
t is 0, 1, 2 or 3;
W is selected from the group consisting of optionally substituted alkoxy, optionally substituted alkenyl, optionally substituted cycloalkyl, optionally substituted heterocycloalkyl and —$NR^8R^9$,
wherein when W is optionally substituted cycloalkyl it may optionally be bridged by a bond or optionally substituted $C_{1-2}$alkylene, and
wherein when W is optionally substituted heterocycloalkyl it may optionally be bridged by a bond, optionally substituted $C_{1-2}$alkylene, —$NR^6$—, —O—, or —$S(O)_z$—;
z is 0, 1 or 2;

$R^4$ and $R^5$ are, at each instance, independently selected from H, optionally substituted alkyl, optionally substituted aryl, optionally substituted heteroaryl, and optionally substituted cycloalkyl, or are linked to form an optionally substituted heterocycloalkyl;

$R^6$ and $R^7$ are, at each instance, independently selected from H and optionally substituted alkyl, or are linked to form an optionally substituted heterocycloalkyl;

$R^8$ and $R^9$ are, at each instance, independently selected from optionally substituted alkyl, optionally substituted aryl, optionally substituted heterocycloalkyl, optionally substituted heteroaryl, and optionally substituted cycloalkyl;

$R^{10}$ and $R^{11}$ are, at each instance, independently selected from H, optionally substituted alkyl, optionally substituted aryl, optionally substituted heterocycloalkyl, optionally substituted heteroaryl, and optionally substituted cycloalkyl;

$R^{12}$ and $R^{13}$ are, at each instance, independently selected from H, hydroxy, and optionally substituted alkyl, or may be linked to form an optionally substituted cycloalkyl ring, or may together form =O; and
$R^{14}$ is optionally substituted alkyl,
wherein the optional substituents are independently selected from halo, trihalomethyl, trihaloethyl, trihalomethoxy, trihaloethoxy, —OH, —NO$_2$, —CN, —CO$_2$H, —CO$_2$C$_{1-6}$alkyl, —SO$_3$H, —SOC$_{1-6}$alkyl, —SO$_2$C$_{1-6}$alkyl, —NHSO$_2$C$_{1-6}$alkyl, —NC$_{1-6}$alkylSO$_2$C$_{1-6}$alkyl, —SO$_2$NH$_2$, —SO$_2$NHC$_{1-6}$alkyl, —SO$_2$N(C$_{1-6}$alkyl)$_2$, —NHSO$_2$NH$_2$, —NHSO$_2$NHC$_{1-6}$alkyl, —NHSO$_2$N(C$_{1-6}$alkyl)$_2$, —NC$_{1-6}$alkylSO$_2$NH$_2$, —NC$_{1-6}$alkylSO$_2$NHC$_{1-6}$alkyl, —NC$_{1-6}$alkylSO$_2$N(C$_{1-6}$alkyl)$_2$, —C(=O)H, —C(=O)C$_{1-6}$alkyl, —NHC(=O)C$_{1-6}$alkyl, —NC$_{1-6}$alkylC(=O)C$_{1-6}$alkyl, C$_{1-6}$alkylenedioxy, =O, —N(C$_{1-6}$alkyl)$_2$, —C(=O)NH$_2$, —C(=O)NHC$_{1-6}$alkyl, —C(=O)N(C$_{1-6}$alkyl)$_2$, —NHC(=O)NH$_2$, —NHC(=O)NHC$_{1-6}$alkyl, —NHC(=O)N(C$_{1-6}$alkyl)$_2$, —NC$_{1-6}$alkylC(=O)NH$_2$, —NC$_{1-6}$alkylC(=O)NHC$_{1-6}$alkyl, —NC$_{1-6}$alkyl C(=O)N(C$_{1-6}$alkyl)$_2$, —C(=NH)NH$_2$, —C(=NH)NHC$_{1-6}$alkyl, —C(=NH)N(C$_{1-6}$alkyl)$_2$, —C(=NC$_{1-6}$alkyl)NH$_2$, —C(=NC$_{1-6}$alkyl)NHC$_{1-6}$alkyl, —C(=NC$_{1-6}$alkyl)N(C$_{1-6}$alkyl)$_2$, —C$_{1-6}$alkyl, —C$_{3-6}$cycloalkyl, —C$_{3-6}$heterocycloalkyl, 2-imidazolidinon-3-yl, 1-C$_{1-6}$alkyl-2-imidazolidinon-3-yl, C$_{1-6}$alkylC$_{3-6}$heterocycloalkyl, aryl, haloaryl, C$_{1-6}$alkoxyaryl, —C$_{1-6}$alkylene-NHSO$_2$C$_{1-6}$alkyl, —C$_{1-6}$alkylene-NC$_{1-6}$alkylSO$_2$C$_{1-6}$alkyl, —C$_{1-6}$alkylene-SO$_2$NH$_2$, —C$_{1-6}$alkylene-SO$_2$NHC$_{1-6}$alkyl, —C$_{1-6}$alkylene-SO$_2$N(C$_{1-6}$alkyl)$_2$, —Z$^t$H, —Z$^t$—C$_{1-6}$alkyl, —C$_{1-6}$alkylene-Z$^t$H, —Z$^t$—C$_{3-6}$cycloalkyl, or —C(=O)NHC$_{1-6}$alkylene-Z$^t$H wherein Z$^t$ is independently O, S, NH or N(C$_{1-6}$alkyl).

2. The compound of claim 1, wherein $R^1$ is phenyl.

3. The compound of claim 1, wherein $R^2$ is selected from H, trifluoromethyl, substituted alkyl, optionally substituted alkoxy, —NR$^4$R$^5$, —NR$^6$C(O)R$^7$, —S(O)$_2$NR$^4$R$^5$, —CONR$^4$R$^5$, CO$_2$R$^7$, optionally substituted oxazolinyl, —SR$^{14}$, —S(O)R$^{14}$ and —S(O)$_2$R$^{14}$.

4. The compound of claim 1, wherein $R^3_{III}$ is selected from H, halo, —CN, trifluoromethyl, optionally substituted alkyl, optionally substituted alkoxy, optionally substituted heterocycloalkoxy, optionally substituted heterocycloalkylalkyl, —NR$^6$C(O)R$^7$, —NR$^6$S(O)$_2$R$^7$, —S(O)$_2$NR$^4$R$^5$, —CONR$^4$R$^5$, optionally substituted -alkylene-CONR$^4$R$^5$, —CO$_2$R$^7$, —NR$^{10}$R$^{11}$, optionally substituted cycloalkyl-J and —(NR$^c$R$^d$)-J.

5. The compound of claim 1, wherein $R^3_I$ is —(NR$^a$R$^b$)-J, V is CR$^3_{III}$ and $R^3_{III}$ is H or —(NR$^c$R$^d$)-J.

6. The compound of claim 1, wherein q is 0 or 1.

7. The compound of claim 1, wherein q is 1.

8. The compound of claim 1, wherein t is 0, 1 or 2.

9. The compound of claim 1, wherein t is 2.

10. The compound of claim 1, wherein $R^{12}$ and $R^{13}$ are, at each instance, H.

11. The compound of claim 1, wherein W is optionally substituted heterocycloalkyl.

12. A pharmaceutical composition comprising one or more compounds as claimed in claim 1 and, optionally, one or more pharmaceutically acceptable excipients.

13. A method for the treatment of arrhythmia that is mediated by $K_{ir}3.1$ and/or $K_{ir}3.4$ or any heteromultimers thereof, or that requires inhibition of $K_{ir}3.1$ and/or $K_{ir}3.4$ or any heteromultimers thereof, comprising administering to a subject an effective amount of at least one compound as defined in claim 1 or a composition comprising one or more compounds as defined in claim 1 and, optionally, one or more pharmaceutically acceptable excipients.

14. The compound of claim 1, wherein NR$^a$R$^b$ is piperidinyl.

15. The compound of claim 1, wherein W is selected from pyrrolidinyl, and piperidinyl, wherein each of the pyrrolidinyl and piperidinyl is optionally substituted by one of -Me, -Et and -iPr.

16. The compound of claim 1, wherein $R^2$ is selected from H, halo, —CN, optionally substituted alkyl, —NR$^4$R$^5$, —NR$^6$C(O)R$^7$, and —CONR$^4$R$^5$.

17. The compound of claim 1, wherein $R^4$ and $R^5$ are, at each instance, independently selected from H and optionally substituted alkyl, or are linked to form an optionally substituted heterocycloalkyl.

* * * * *